United States Patent
Sennino et al.

(10) Patent No.: US 12,247,061 B2
(45) Date of Patent: Mar. 11, 2025

(54) COMPOSITIONS AND METHODS FOR THE TREATMENT OF CANCER USING A CD8 ENGINEERED T CELL THERAPY

(71) Applicant: ADOC SSF, LLC, South San Francisco, CA (US)

(72) Inventors: Barbara Sennino, San Francisco, CA (US); Kyle Jacoby, Emeryville, CA (US); Stefanie Mandl-Cashman, San Francisco, CA (US); Michael M. Dubreuil, Palo Alto, CA (US); John Gagnon, San Francisco, CA (US); Alex Franzusoff, El Granada, CA (US)

(73) Assignee: ADOC SSF, LLC, South San Francisco, CA (US)

( * ) Notice: Subject to any disclaimer, the term of this patent is extended or adjusted under 35 U.S.C. 154(b) by 246 days.

(21) Appl. No.: 17/691,565

(22) Filed: Mar. 10, 2022

(65) Prior Publication Data

US 2022/0193139 A1    Jun. 23, 2022

Related U.S. Application Data

(60) Division of application No. 17/100,223, filed on Nov. 20, 2020, now Pat. No. 11,304,978, which is a continuation of application No. PCT/US2020/030818, filed on Apr. 30, 2020.

(60) Provisional application No. 62/841,753, filed on May 1, 2019, provisional application No. 62/841,748, filed on May 1, 2019.

(51) Int. Cl.
| | |
|---|---|
| *A61K 35/17* | (2015.01) |
| *A61K 39/00* | (2006.01) |
| *C07K 14/705* | (2006.01) |
| *C07K 14/725* | (2006.01) |
| *C12N 5/0783* | (2010.01) |
| *C12N 9/22* | (2006.01) |
| *C12N 15/113* | (2010.01) |

(52) U.S. Cl.
CPC .......... *C07K 14/7051* (2013.01); *A61K 35/17* (2013.01); *A61K 39/4611* (2023.05); *A61K 39/4632* (2023.05); *A61K 39/4644* (2023.05); *C07K 14/70517* (2013.01); *C12N 5/0636* (2013.01); *C12N 9/22* (2013.01); *C12N 15/113* (2013.01); *C12N 2310/20* (2017.05)

(58) Field of Classification Search
None
See application file for complete search history.

(56) References Cited

U.S. PATENT DOCUMENTS

| | | | |
|---|---|---|---|
| 5,399,346 A | 3/1995 | Anderson et al. | |
| 6,355,412 B1 | 3/2002 | Stewart et al. | |
| 7,485,291 B2 | 2/2009 | Fang et al. | |
| 8,119,772 B2 | 2/2012 | Yang et al. | |
| 2004/0265970 A1 | 12/2004 | Gearing et al. | |
| 2015/0110760 A1 | 4/2015 | Zhang et al. | |
| 2015/0299656 A1 | 10/2015 | Gattinoni et al. | |
| 2017/0319722 A1 | 11/2017 | Agnew et al. | |
| 2018/0185463 A1 | 7/2018 | Borriello | |
| 2018/0258149 A1 | 9/2018 | Motz et al. | |
| 2018/0362926 A1 | 12/2018 | Conway et al. | |
| 2019/0038672 A1 | 2/2019 | Puléet al. | |
| 2020/0338128 A1 | 10/2020 | Zhong | |

FOREIGN PATENT DOCUMENTS

| | | |
|---|---|---|
| JP | 2017-538443 A | 12/2017 |
| JP | 2018-513683 A | 5/2018 |
| JP | 2018-531593 A | 11/2018 |
| WO | WO 2017/049166 A1 | 3/2017 |
| WO | WO 2017/106537 A2 | 6/2017 |
| WO | WO 2018/058002 A1 | 3/2018 |
| WO | 2018/175733 A1 | 9/2018 |
| WO | WO 2018/170338 A2 | 9/2018 |
| WO | WO 2018/175636 A2 | 9/2018 |
| WO | WO 2019/004831 A1 | 1/2019 |
| WO | WO 2019/051424 A2 | 3/2019 |
| WO | WO 2019/089610 A1 | 5/2019 |
| WO | WO 2019/195310 A1 | 10/2019 |
| WO | WO 2020/049496 A1 | 3/2020 |
| WO | WO 2020/109616 A1 | 6/2020 |
| WO | WO 2020/167918 A1 | 8/2020 |
| WO | WO 2020/243134 A1 | 12/2020 |

OTHER PUBLICATIONS

Van Loenen et al. (PLoS One. 2013;8(5):e65212). (Year: 2013).*
Bajwa et al., "Reprogramming CD4 T cells into cytotoxic CD8 cells by forced expression of CD8[alpha][beta] and class I restricted T cell receptors," EMBASE (2018).
Carty et al., "The Loss of TET2 Promotes CD8 + T Cell Memory Differentiation," The Journal of Immunology, 200(1):82-91 (2017).
Extended European Search Report dated Apr. 28, 2023 in Application No. 20798347.9.
Extended European Search Report dated Jun. 2, 2023 in Application No. 20798669.6.
Gros et al., "Prospective identification of neoantigen-specific lymphocytes in the peripheral blood of melanoma patients," Nature Medicine, 22(4):433-438 (2016).
Lee et al., "Disruption of TET2 Dioxygenase Enhances Antitumor Efficiency in CD8+ Tumor Infiltrating Lymphocytes," Blood, 132(Suppl_1):860 (2018) 3 pgs.
Bosselut et al., "Role of CD8B Domains in CD8 Coreceptor Function: Importance for MHC I Binding, Signaling, and Positive Selection of CD8+ T Cells in the Thymus," Immunity, 12:409-418 (2000).

(Continued)

*Primary Examiner* — Zachary S Skelding
(74) *Attorney, Agent, or Firm* — Baker Botts L.L.P.

(57) ABSTRACT

Compositions comprising and methods for the treatment of cancer using a neoTCR based cell therapy with a CD8 expression construct.

11 Claims, 51 Drawing Sheets

Specification includes a Sequence Listing.

(56) References Cited

OTHER PUBLICATIONS

Itano et al., "The Cytoplasmic Domain of CD4 Promotes the Development of CD4 Lineage T Cells," J. Exp. Med. 183:731-741 (1996).
U.S. Appl. No. 17/099,140 (US 2021/0085720), filed Nov. 16, 2020 (Mar. 25, 2021).
U.S. Appl. No. 17/100,223 (US 2021/0085721), filed Nov. 20, 2020 (Mar. 25, 2021).
U.S. Appl. No. 17/099,140, Feb. 15, 2022, Non-Final Office Action.
U.S. Appl. No. 17/099,140, Sep. 9, 2021 Amendment and Request for Continued Examination (RCE).
U.S. Appl. No. 17/099,140, Aug. 27, 2021 Advisory Action.
U.S. Appl. No. 17/099,140, Aug. 10, 2021 Response after Final Action.
U.S. Appl. No. 17/099,140, Jun. 10, 2021 Final Office Action.
U.S. Appl. No. 17/099,140, Jun. 1, 2021 Response to Non-Final Office Action.
U.S. Appl. No. 17/099,140, Mar. 2, 2021 Non-Final Office Action.
U.S. Appl. No. 17/099,140, Feb. 12, 2021 Response to Restriction Requirement.
U.S. Appl. No. 17/099,140, Feb. 2, 2021 Restriction Requirement.
U.S. Appl. No. 17/100,223, Mar. 8, 2022 Notice of Allowance.
U.S. Appl. No. 17/100,223, Feb. 22, 2022 Notice of Allowance.
U.S. Appl. No. 17/100,223, Aug. 13, 2021 Amendment and Request for Continued Examination (RCE).
U.S. Appl. No. 17/100,223, Aug. 9, 2021 Advisory Action.
U.S. Appl. No. 17/100,223, Jul. 28, 2021 Response after Final Action.
U.S. Appl. No. 17/100,223, May 28, 2021 Final Office Action.
U.S. Appl. No. 17/100,223, May 13, 2021 Response to Non-Final Office Action.
U.S. Appl. No. 17/100,223, Feb. 17, 2021 Non-Final Office Action.
U.S. Appl. No. 17/100,223, Jan. 25, 2021 Response to Restriction Requirement.
U.S. Appl. No. 17/100,223, Jan. 12, 2021 Restriction Requirement.
Albers et al. (Life Sci Alliance. Mar. 15, 2019;2(2):e201900367). (2019).
Anderson et al. ("Enhanced Activity of Second-Generation MAGE-A4 Spear T-Cells Through Co-Expression of a CD8a Homodimer," American Association for Cancer Research Annual Meeting, Mar. 29-Apr. 3, 2019, Atlanta, Georgia, USA, 1 page). (2019).
Anderson, "Prospects for Human Gene Therapy," Science 226:401-409 (1984).
Blomer et al., "Highly Efficient and Sustained Gene Transfer in Adult Neurons with a Lentivirus Vector," Journal of Virology 71:6641-6649 (1997).
Bregni, et al., "Human Peripheral Blood Hematopoietic Progenitors are Optimal Targets of Retroviral-Mediated Gene Transfer," Blood 80(6):1418-1422 (1992).
Brigham et al., "Rapid Communication: In vivo Transfection of Murine Lungs with a Functioning Prokaryotic Gene Using a Liposome Vehicle," Am. J. Med. Sci. 298(4):278-281 (1989).
Buenrostro et al., "Transposition of native chromatin for multimodal regulatory analysis and personal epigenomics," N. Methods, 10(12):1213-1218 (2013).
Cayouette et al., "Adenovirus-Mediated Gene Transfer of Ciliary Neurotrophic Factor Can Prevent Photoreceptor Degeneration in the Retinal Degeneration (rd ) Mouse," Human Gene Therapy 8:423-430 (1997).
Cornetta et al., "Gene Transfer into Primates and Prospects for Gene Therapy in Humans," Progress in Nucleic Acid Research and Molecular Biology 36:311-322 (1987).
Eglitis et al., "Retroviral Vectors for Introduction of Genes into Mammalian Cells," BioTechniques 6(7):608-614 (1988).
Epstein, "Crystalloids Fluids," NCBI Bookshelf, 2021 (6 pgs.).
Eyquem et al., "Targeting a CAR to the TRAC locus with CRISPR/Cas9 enhances tumour rejection," Nature 543:113-117 (2017).
Felgner et al., "Lipofection: A highly efficient, lipid-mediated DNA-transfection procedure," Proc. Natl. Acad. Sci. U.S.A. 84:7413-7417 (1987).
Fraietta et al., "Disruption of TET2 Promotes the Therapeutic Efficacy of CD19-targeted T-cells," Nature, 558(7709):307-312 (2018).
Friedman, "Progress toward Human Gene Therapy," Science 244:1275-1281 (1989).
Hughes et al., "Retroviral Gene Transfer to Primitive Normal and Leukemic Hematopoietic Cells Using Clinically Applicable Procedures," J. Clin. Invest. 89:1817-1824 (1992).
International Search Report mailed Aug. 12, 2020 in International Application No. PCT/US2020/030704.
International Search Report mailed Aug. 14, 2020 in International Application No. PCT/US2020/030818.
International Search Report mailed Oct. 1, 2020 in International Application No. PCT/US20/31007.
Irie et al., "The Cytoplasmic Domain of CD8b Regulates Lck Kinase Activation and CD8 T Cell Development," J. Immunol, 161:183-191 (1998).
Johnson, "Gene Therapy for Cystic Fibrosis," Chest 107:77S-83S (1995).
Kido et al., "Use of retroviral vector with an internal opsin promoter to direct gene expression to retinal photoreceptor cells," Current Eye Research 15:833-844 (1996).
Le Gal La Salle et al., "An Adenovirus Vector for Gene Transfer into Neurons and Glia in the Brain," Science 259:988-990 (1993).
Leisegang et al., "Enhanced functionality of T cell receptor-redirected T cells is defined by the transgene cassette," J. Mol. Med., 86:573-583 (2008).
Liu et al., "Systematic comparison of 2A peptides for cloning multi-genes in a polycistronic vector," Scientific Reports 7:2193 (2017), 9 pages.
Lu et al., "A Rapid Cell Expansion Process for Production of Engineered Autologous CAR-T Cell Therapies," Human Gene Therapy Methods 27(6):209-218 (2016).
Miller et al., "Improved Retroviral Vectors for Gene Transfer and Expression," Biotechnology 7:980-990 (1989).
Miller, "Retrovirus Packaging Cells," Human Gene Therapy 1:5-14 (1990).
Miyoshi et al., "Stable and efficient gene transfer into the retina using an HIV-based lentiviral vector," Proc. Natl. Acad. Sci. U.S.A. 94:10319-10323 (1997).
Moen, "Directions in Gene Therapy," Blood Cells 17:407-416 (1991).
Naldini et al., "In Vivo Gene Delivery and Stable Transduction of Nondividing Cells by a Lentiviral Vector," Science 272:263-267 (1996).
Nicolaou et al., "Calicheamicin $\theta^1$: A Rationally Designed Molecule with Extremely Potent and Selective DNA Cleaving Properties and Apoptosis Inducing Activity," Angew. Chem Intl. Ed. Engl., 33(2):183-186 (1994).
Ono et al., "Plasmid DNAs directly injected into mouse brain with lipofectin can be incorporated and expressed by brain cells," Neuroscience Letters 117:259-263 (1990).
Peng et al., "Neoantigen vaccine: an emerging tumor immunotherapy," Molecular Cancer, 18:128 (2019) 14 pages.
Rosenberg et al., "Gene Transfer Into Humans-Immunotherapy of Patients With Advanced Melanoma, Using Tumor-Infiltrating Lymphocytes Modified by Retroviral Gene Transduction," N. Engl. J. Med 323:570-578 (1990).
Roth et al., "Reprogramming human T cell function and specificity with non-viral genome targeting," Nature 559(7714):405-409 (2018).
Sequence Alignment, 2021 (Human TET2 exon3 targeting gRNA, SEQ:1323).
Serganova et al., "Enhancement of PSMA-Directed CAR Adoptive Immunotherapy by PD-1/PD-L1 Blockade," Molecular Therapy: Oncolytics, 4:41-54 (2017).
Sharp, "Gene Therapy," The Lancet 337:1277-1278 (1991).
Soto et al., Cancer Immunol Immunother (2013) 62:359-369. (2013).
Stepanek et al. (Cell. Oct. 9, 2014;159(2):333-45, supplementary pp. S1-S13 and Supplementary Tables 1-3). (2014).
Straubinger et al., "Liposomes as Carriers for Intracellular Delivery of Nucleic Acids," Methods in Enzymology 101:512-527 (1983).

(56) References Cited

OTHER PUBLICATIONS

Szymczak et al., "Correction of multi-gene deficiency in vivo using a single 'self-cleaving' 2A peptide-based retroviral vector," Nature Biotechnology 22(5):589-594 (2004).
Tolstoshev et al., "Gene expression using retroviral vectors," Current Opinion in Biotechnology 1:55-61 (1990).
Tubb et al. Journal for ImmunoTherapy of Cancer (2018) 6:70. (2018).
Wargo et al., "Recognition of NY-ESO4+ tumor cells by engineered lymphocytes is enhanced by improved vector design and epigenetic modulation of tumor antigen expression," Cancer Immunol. Immunother 58:383-394 (2009).
Wolff et al., "Direct Gene Transfer into Mouse Muscle in Vivo," Science 247(4949):1465-1468 (1990).
Wu et al., "Receptor-mediated Gene Delivery and Expression in Vivo," Journal of Biological Chemistry 263(29):14621-14624 (1988).
Wu et al., "Targeting Genes: Delivery and Persistent Expression of a Foreign Gene Driven by Mammalian Regulatory Elements in Vivo," Journal of Biological Chemistry 264(29):16985-16987 (1989).
Xu et al., "Correction of the enzyme deficiency in hematopoietic cells of Gaucher patients using a clinically acceptable retroviral supernatant transduction protocol," Exp. Hemat. 22:223-230 (1994).
Van Loenen et al., "Extracellular Domains of CD8a and β Subunits are Required and Sufficient for HLA Class I Restricted Helper Activity of TCR-Engineered CD4+ T Cells," Blood, 114(22):3574 (2009) 2 pgs.
Mouse Genome Informatics (MGI) (Tg(TcraTcrb)1100Mjb Transgene Detail), 2019 https://web.archive.org/web/20190409065757/https://www.informatics.jax.org/allele/MGI:3054907.
Odiba et al., "Modified T-cells (using TCR and CTAs), chimeric antigen receptor (CAR) and other molecular tools in recent gene therapy," Egyptian Journal of Medical Human Genetics, 19(3):153-157 (2017).

* cited by examiner (CD8alpha-P2A-CD8beta_CD8 Product 2)

FIGURE 5

NeoTCR Product Nucleic Acid Sequence

ACATTAAAAACACAAATCCTACGGAAATACTGAAGAATGAGTCTCAGCACTAAGGAAAAGC
CTCCAGCAGCTCCTGCTTTCTGAGGGTGAAGGATAGACGCTGTGGCTCTGCATGACTCACTA
GCACTCTATCACGGCCATATCTGGCAGGGTCAGTGGCTCCAACTAACATTTGTTGGTACTT
TACAGTTTATTAAATAGATGTTTATATGGAGAAGCTCCATTTCTTTCTCAGAAGAGCTGGCT
AGGAAGGTGGATGAGGCACCATATTCATTTTGCAGGTGAAATTCCTGAGATGTAAGGAGCT
GCTGTGACTTGCTCAAGGCCTTATATCGAGTAAACGTAGTGCTGGGGCTTAGACGCAGGTG
TTCTGATTTATAGTTCAAAACCTCTATCAATGAGAGAGCAATCTCCTGGTAATGTGATAGATTT
CCCAACTTAATGCCAACATACCATAAACCTCTGCTAATGCCCAGCTAAGCTAAGTTGGGGA
GACCACTCCAGATTCCAAGATGTACAGTTTGCTTTGCTGGCCCTTTTGCCCATGCCTGCCTTTA
CTCTGCCAGAGTTATATTGCTGCATTTCAGGTTTCCTTGAGTGGCAGGCCAGGCTGTGAACG
ATTATTAAGTAGCCCTGCATTTCAGGTTTCCTTGAGTGGCAGGCCAGGCCTGTGCCTGAACG
TTCACTGAAATCATGGCCTCTTGGCCAAGATTGATAGCTTATTTCCCGTATAAAGCATGAGACCGTGACTTGCC
CATCACGAGCAGCTGGTTTCTAAGATGCTATTTCCCGTATAAAGCATGAGACCGTGACTTGCC
AGCCCCAGAGAGCCCCGCTTGTCCTCATCACTGGACTCACTGGACTCACTCCAGCCTGGGTTGGGGCA
AAGAGGGAAATGAGATCATGTCCTAACCCTGATCCTCTTGTCCCACAG

Left HR Arm (SEQ ID NO:1)

ATATCCAGAACCCTGACCCTGCCGTGTACCAGCTGAGAGACTCTAAATCCAGTG
ACAAGTCTGTCTGCCTATTC

TRAC CDS (SEQ ID NO:2)

GAATTCGGCTCCGGA

GSG Linker 1 (SEQ ID NO:3)

GCCACTAACTTCTCCCTGTTGAAACAGGCTGGCGATGTTGAAGAAAACCCCGG
TCCT

P2A (SEQ ID NO:4)

FIGURE 5 Cont.

ATGGCCACCGGCTCTAGAACAAGCCTGCTGCTCGCTTTTGGCCTGCTCTGCCTCCCATGGCTC
AAGAAGGATCTGCT      HGH/SS/2 (SEQ ID NO:5)

[[TRB_VDJ Sequence, specific for the NeoTCR]]      Insertion site for neoTCR TRB_VDJ sequence CTGAAAAACGTGTTCCCTCCAAAAGTGGCGTGTTCGAGCCTTCTGAGGCCGAGATCAGCC
ACACAGAAAGCCACACTCGTGTGTCTGGCTACCGGCTTCTACCCGGATCACGTGGAACTG
TCTTGGTGGGTCAACGGCAAAGAGGTGCACAGCGGCGTCTGTCTAGCAGAGACTGAGAGTGCCGC
AAGAACAGCCCGCTCTGAACGACACCGGAAACCTTCAGATGCCAGGTCCAGTTCTACGGCCTGAGCG
CACCTTCTGGCAGAACCCCAGAACGACAGAGCCAAGCCTGTGACACAGATCGTGTCTGCCGAAG
AGAACGATGAGTGGACCCAGGACAGAGCCAAGCCTGTGACACAGATCGTGTCTGCCGAAG
CCTGGGGCAGAGCCGATTGTGGCTTTACCAGGAGTCATACCAGCAGGGCGTGTGTGCTGC
CACCATCCTGTATGATGGCTATGGTGTCTCCCGGGAGCCCATCCCCGAGGCC      TCR-beta/constant (SEQ ID NO:7)

CGGGCCAAGCGG      Furin Cleavage Site (SEQ ID NO:8)

GGCAGCGGC      GSG Linker (SEQ ID NO:9)

GCCACCAACTTCAGCCTGCTGAAGCAGGCCGGCGACGTGGAGGAGAACCCCGGCCCT      P2A (SEQ ID NO:10)

ATGGCCACAGGCAGCAGAGAACATCTCTGCTGCCTTGCCTGTGTCTGCCTTGGCT
GCAAGAGGGTTCCGCC      HGH SS (SEQ ID NO:11)

FIGURE 5 Cont.

[[TRA_VDJ Sequence, specific for the NeoTCR]]   Insertion site for neoTCR TRA_VDJ sequence ATATTCAGAACCCCGATCCTGCTGTGTATCAGCTGCCGGACAGCAAGAGCAGGGACAAGAGC
GTGTGTTTGTTC   TCR-alpha/constant (SEQ ID NO:13)

ACCGATTTTGATTCTCAAACAAATGTGTCACAAAGTAAGGATTCTGATGTGTATATCACAGAC
AAAACTGTGCTAGACATGAGGTCTATGGACTTCAAGAGCAACAGTGCTGTGGCCTGGAGCA
ACAAATCTGACTTTGCATGTGCAAACGCCTTCAACAACAGCATTATTCCAGAAGACACCTTCT
TCCCCAGCCCAGG   TRAC CDS/right HR arm(SEQ ID NO: 14)

TAAGGGCAGCTTTGGTGCCTTCGCAGGCTGTTTCCTTGCTTCAGGAATGGCCAGGTTCTGCC
CAGAGCTCTGGTCAATGATGTCTAAAACTCCTCTGATTGGTGGTCTCGGCCTTATCCATTGCC
ACCAAAACCCTCTTTTACTAAGAAAACAGTGAGCCTTGTTCTGGCAGTCAGGCGAGAATGACAC
GGGAAAAAGCAGATGAAGAGAAGGTGGCAGGAGAGGCACGTGGCCCAGCTCAGTCT
CTCCAACTGAGTCCTTCGCCTGCCTCTCCAAGTTGCCTCTCTCCTATTCTCCCTGTCTGCTCTTCTAGG
CCTCATTCTAAGCCCCTCACCTAAGTCAGTCTCACGCAGTCACTCATTAACCCACCAATCACTGATTGTGCCGG
CCCAGTCAATGACCAGGTGTTGAAGTGGAGGAGCCCATCTGCAGCTGGGAAAAGTCCAAATAACTT
CACATGAATGCACCATTCAGTTGGGGAGCCCATCTGCAGCTGGGAAAAGTCCAAATAACTT
GAGGAAGCACCATTCAGTTGGGGAGCCCATCTGCAGCTGGGAAAAGTCCAAATAACTT
CAGATTGGAATGTGTTTAACTCAGGGTTGAAGAAACAGTACCTTCAGGACAAAGTCAG
GGAAGGGCTCTCTGAAGAAATGCTACTTGAAGATACCAGCCCTACCAAGGCAGGGAGAG
GACCCTATAGAGGCCTGGGACAGGAGAGTCAATGAGAAAAGGAGAAGAGCAGCAGGCATGA
GTTGAATGAAGGAGGCAGGGCCGGGTCACAGGGCCTTCTAGGCCATGAGAGGTAGACAG   Right HR arm (SEQ ID NO:15)

GCTAGC   (SEQ ID NO:16)

FIGURE 5 Cont.

pBR322_origin (SEQ ID NO:17)

```
CGCGTTGCTGGCGTTTTTCCATAGGCTCCGCCCCCCTGACGAGCATCACAAAAATCGACGCT
CAAGTCAGAGGTGGCGAAACCCGACAGGACTATAAAGATACCAGGCGTTTCCCCCTGGAAG
CTCCCTCGTGCGCTCTCCTGTTCCGACCCTGCCGCTTACCGGATACCTGTCCGCCTTTCTCCCT
TCGGGAAGCGTGGCGCTTTCTCATAGCTCACGCTGTAGGTATCTCAGTTCGGTGTAGGTCGTT
CGCTCCAAGCTGGGCTGTGTGCACGAACCCCCCGTTCAGCCCGACCGCTGCGCCTTATCCGG
TAACTATCGTCTTGAGTCCAACCCGGTAAGACACGACTTATCGCCACTGGCAGCAGCCACTG
GTAACAGGATTAGCAGAGCGAGGTATGTAGGCGGTGCTACAGAGTTCTTGAAGTGGTGGCC
TAACTACGGCTACACTAGAAGAACAGTATTTGGTATCTGCGCTCTGCTGAAGCCAGTTACCTT
CGGAAAAAGAGTTGGTAGCTCTTGATCCGGCAAACAAACCACCGCTGGTAGCGGTGGTTTT
TTTGTTTGCAAGCAGCAGATTACGCGCAGAAAAAAAGGATCTCAAGAAGATCCTTTGATCT
```

Kanamycin resistant gene (KanR2) (SEQ ID NO:18)

```
TTAGAAAAACTCATCGAGCATCAAATGAAACTGCAATTTATTCATATCAGGATTATCAATACCA
TATTTTGAAAAGCCGTTTCTGTAATGAAGGAGAAAACTCACCGAGGCAGTTCCATAGGAT
GGCAAGATCCTGGTATCGGTCTGCGATTCCGACTCGTCCAACATCAATACAACCTATTAATTC
CCCTCGTCAAAAATAAGGTTATCATTTCTTCCAGATTGCATTTCAACAGGCCAGCCATTACGCTCGTC
GAATGGCAAAAGTTTATGCATTCAACCAAACCGTTATTCATTCGTGATTGCGCCTGAGCCAGACGAAA
ATCAAAATCACTCGCATCAACCAAACAATTACAAACAGGAATCGAATGCAACCGGCGCAGGAAC
ACTGCCAGCGCATCAACATGGGGGATCGTTTCATGGCGCGCATCAGCGAATCAGGATAT
TTTTCCGGGATCGCAGTGGTGAGTAACCATGCATCATCAGGAGTACGGATAAATGCTTG
ATGGTCGGAAGAGGCATAAATTCGTCAGCCAGTTTAGTCTGACCATCTCATCGTAACATCA
TGGCAACGCTACCTTTGCCATGTTTCAGAAACAACTCTGGCGCATCGGGCTTCCCATACAAG
CGATAGATTGTCGCACCTGATTGCCCGACATTATCCGGAGCCATTATACCCATATAAATCAG
CATCCATGTTGGAATTTAATCGCGGCCTCGAGCACGTTTCCCGGTTGAATATGGCTCAT
```

Kanamycin Promoter (SEQ ID NO:19)

```
AACACCCCTTGTATTACTGTTTATGTAAGCAGACAGTTTTATTGTTCATGATGATATTTTTATC
TTGTGCAATGTAACATCAGAGATTTTGAGACAC
```

FIGURE 6

CD8 Product 1 Product Nucleic Acid Sequence

ACATTAAAACACAAATCCTACGGAAATACTGAAGAATGAGTCTCAGCACTAAGGAAAAGC
CTCCAGCAGCTCCTGCTTTCTGAGGGTGAAGGATAGACGCTGTGGCTCTGCATGACTCACTA
GCACTCTATCACGGCCATATTCTGGCAGGGTCAGTGGCTCCAACTAACATTGTTTGGTACTT
TACAGTTTATTAAATAGATGTTTATATGGAGAAGCTCTCATTCTTTCTCAGAAGAGCTGGCT
AGGAAGGTGGATGAGGCACCATATTCATTTGCAGGTGAAATTCCTGAGATGTAAGGAGCT
GCTGTGACTTGCTCAAGGCCTTATATCGAGTAAACGTAGTGCTGGGCTTAGACGCAGGTG
TTCTGATTTATAGTTCAAAACCTCATCAATGAGAGAGCAATCTCCTGGTAATGTGATAGATTT
CCCAACTTAATGCCAACATACCATAAACCTCCCATTCTGCTAATGCCAGCCTAAGTTGGGGA
GACCACTCCAGATTCCAAGATGTACAGTTTGCTTTGCTGGCCCTTTTCCCATGCCTGCCTTA
CTCTGCCAGAGTTATATGCTGGGGTTTGAAGAAGATCCTATTAAAAAGAATAAAGCAGT
ATTATTAAGTAGCCCTGCATTTCAGTTTCCTTGAGTGGCAGGCCAGGCCTGGCGTGAACG
TTCACTGAAATCATGGCCTCTTGGCCAAGATTGATAGCTTGTGCCTGTCCCTGAGTCCAGTC
CATCGAGCAGCAGTGGTTTCTAAGATGTCTATTTCCCGTATAAAGCATGGACCTGACTTGCC
AGCCCCACAGAGCCCGCCCTTGTCCATCAGCCTGGCATCTGGACTCCAGCCTGGGGTTGGGGCA
AAGAGGGAAATGAGATCATGTCCTAACCCTGATCCTCCTTGTCCCACAG

Left HR Arm (SEQ ID NO:22)

ATATCCAGAACCCTGACCCTGCCGTGTACCAGCTGAGAGACTCTAAATCCAGTGACAAGTCTG
TCTGCCTATTC

TRAC CDS (SEQ ID NO:23)

GAATTCGGCTCCGGA

GSG Linker 1 (SEQ ID NO:24)

GCCACTAACTTCAGCCTGTTGAAGCAGGCCGGCGACGTTGAGGAAAACCCCGGTCCT

P2A (SEQ ID NO:25)

FIGURE 6 Cont.

| Sequence | Description |
|---|---|
| ATGGCCTTACCAGTGACCGCCTGCCTGCTCCTGCTGCTGCTCCACGCCGCCAGGCCG | CD8A Signal peptide (SEQ ID NO:26) |
| AGCCAGTTCCGGGTGTCGCCGCTGATCGGAACCTGGAACCTGGGAGACAGTGGAGCTGAAGTGCCAGGTGCTGCTGTCCAACCGCGAGTGCTGGGCGTGCTGCTCAGCGCGCGGCGCGCCAGTCCCACCTTCCTCCTATACCTCTCCAAACAAGCCAAGGGGGCCGAGGGGCTGGACACCCAGCGGTTCTCGGGCAAGAGAGGTTGGGGGACACCTTCGTCCTCACCCTGAGCGACTTCCGCCGAGAGAACGAGGCTACTATTTCTGCTGCCAACTCCATCATGTACTTCAGCCACTTCGTGCCGGTCTTCCTGCCAGCCCCACCACGACGCCAGCGCGCGACCACCAACACCGGCGCCCACCATCGCTGCCCTGTCCCTGCGCCACGAGGCGTGCCGGCCAGCGGCGCACGAGTGCACACGAGGGGGCTGGACTTCGCCTGTGAT | CD8A Extracellular domain (SEQ ID NO:27) |
| ATCTACATCTGGGCGCCCTTGGCCGGCACTTGTGGGGTCCTTCTCCTGTCACTGGTATCACC | CD8A transmembrane domain (SEQ ID NO:28) |
| CTTTACTGCAACCACAGGAACCGAAGACGTGTTTGCAAATGTCCCGGCCTGTGGTCAAATCGGGAGACAAGCCCAGCCTTTCGGGCGAGATACGTC | CD8A Intracellular domain (SEQ ID NO:29) |
| AGGGCTAAACGG | Furin cleavage site (SEQ ID NO:30) |
| GAATTCGGCTCCGGA | GSG Linker (SEQ ID NO:31) |
| GCCACTAACTTCTCCCTGTTGAAACAGGCTGGCGATGTTGAAGAAAACCCCGGTCCT | P2A (SEQ ID NO:32) |
| ATGGCCACCGGCTCTAGAACAAGCCTGCTGCTCGCCTTTGGCCTGCTCTGCCTCCCATGGCTCCAAGAAGGATCTGCT | HGH/SS/2 (SEQ ID NO:33) |

FIGURE 6 Cont.

[[TRB_VDJ Sequence, specific for the NeoTCR]]  Insertion site for neoTCR TRB_VDJ sequence CTGAAAAACGTGTCCCTCCAAAAGTGGCCGTGTTGAGCCTTCTGAGGCCGAGATCAGCC
ACACAGAAAGCCACACTCGTGTGTCTGGCTACGGCCTTCTACCCGGATCACGTGAACTG
TCTTGGGTCAACGGCAAAGAGGTGCACAGCGGTCAGCACAGATCCCCAGCTCTGA
AGAACAGCCCGCTCTGAACGACAGCCGCTACTGCTGTCTAGCAGACTGAGAGTGTCCGC
CACCTTCTGGCAGAAACCCAGAAACCACTTCAGATGCCAGGTCCAGTTCTACGGCTGAGCG
AGAACGATGAGTGGACCCAGGACAGAGCCAAGCTGTGACACAGATCGTGTCTGCCGAAG
CCTGGGGCAGAGCCGATTGTGGCTTTACCAGCGAGTCATACCAGCAGGGCGTGTCTGC
CACCATCCTGTATGAGATCCTGCTCGGCAAGGCCACACTGTACGCTGTGTGCTGTGTCTGCTCT
GGTGCTGATGGCTATGTCTCCCGGAGCCATCCCCGAGGCC  TCR-beta/constant (SEQ ID NO:35)

CGGGCCAAGCGG  Furin cleavage site (SEQ ID NO:36)

GGCAGCGGC  GSG linker (SEQ ID NO:37)

GCCACCAACTTCAGCCTGCTGAAGCAGGCCGGCGACGTGGAGGAGAACCCCGGCCCT  P2A (SEQ ID NO:38)

ATGGCCACAGGCAGCAGAACATCTCTGCTGCTCCTTCGGACTGCTGTCTGCCTTGGCT
GCAAGAGGGTTCCGCC  HGH/SS (SEQ ID NO:39)

[[TRA_VDJ Sequence, specific for the NeoTCR]]  Insertion site for neoTCR TRA_VDJ sequence ATATTCAGAACCCCGATCCTGCTGTGTATCAGTGCCGGCAGCAAGAGCAGGACAAGAGC  TCR-alpha/constant (SEQ ID NO:41)
GTGTGTTGTTC

FIGURE 6 Cont.

ACCGATTTTGATTCTCAAACAAATGTGTCACAAAGTAAGGATTCTGATGTGTATATCACAGAC    TRAC CDS/right HR arm
AAAACTGTGCTAGACACATGAGGTCTATGGACTTCAAGAGCAACAGTGCTGTGGCCTGGAGCA    (SEQ ID NO:42)
ACAAATCTGACTTTGCATGTGCAAACGCCTTCAACAACAGCATTATTCCAGAAGACACCTTCT
TCCCCAGCCCAGG TAAGGGCAGCTTTGGTGCCTTCGCAGGCTGTTTCCTTGCTTCAGGAATGGCCAGGTTCTGCC    Right HR arm (SEQ ID
CAGAGCTCTGGTCAATGATGTCTAAAACTCCTCTGATTGGTGGTCTCGGCCTTATCCATTGCC    NO:43)
ACCAAAACCCTCTTTTTACTAAGAAACAGTGAGCCTTGTTCTGGCAGTCCAGAGAATGACAC
GGGAAAAAAGCAGATGAAGAGAAGAAGGTTGCAGGAGAGGGCACGTGGCCCAGCCTCAGTCT
CTCCAACTGAGTTCCTGCCTGCCTTTGCTCAGACTGTTTGCCCCTTACTGCTCTTCTTAGG
CCTCATTCTAAGCCCCTTCTCCAAGTTGCCTCTTCCTCTCCCTGTCTGCCAAAAATCTTT
CCCAGCTCACTAAGTCAGTCACGCAGTCACTCATTAACCCACCAATCACTGATTGTGCCGG
CACATGAATGCACCAGGTGTTGAAGTGGAAGAATTAAAAAGTCAGATGAGGGGTGTGCCCA
GAGGAAGCACCATTCTAGTTGGGGGAGCCCATCTGTCAGCTGGGAAAAGTCAAATAACTT
CAGATTGGAATGTGTTTAACTCAGGGTTGAGAAAACAGCTACCTTCAGGACACAAAGTCAG
GGAAGGGCTCTCTGAAGAAATGCTACTTGAAGATACCAGCCCTACCAAGGGCAGGAGAG
GACCCTATAGAGGCCTGGGACAGGAGCTCAATGAGAAAGGAGAAGAGCAGGCAGGCATGA
GTTGAATGAAGGAGGCAGGGCCGGGTCACAGGGCCTTCTAGGCCATGAGAGGGTAGACAG

GCTAGC    (SEQ ID NO:44)

FIGURE 6 Cont.

pBR322_origin (SEQ ID NO:45)

CGCGTTGCTGGCGTTTTTCCATAGGCTCCGCCCCCCTGACGAGCATCACAAAAATCGACGCT
CAAGTCAGAGGTGGCGAAACCCGACAGGACTATAAAGATACCAGGCGTTTCCCCCTGGAAG
CTCCCTCGTGCGCTCTCCTGTTCCGACCCTGCCGCTTACCGGATACCTGTCCGCCTTTCTCCCT
TCGGGAAGCGTGGCGCTTTCTCATAGCTCACGCTGTAGGTATCTCAGTTCGGTGTAGGTCGTT
CGCTCCAAGCTGGGCTGTGTGCACGAACCCCCCGTTCAGCCCGACCGCTGCGCCTTATCCGG
TAACTATCGTCTTGAGTCCAACCCGGTAAGACACGACTTATCGCCACTGGCAGCAGCCACTG
GTAACAGGATTAGCAGAGCGAGGTATGTAGGCGGTGCTACAGAGTTCTTGAAGTGGTGGCC
TAACTACGGCTACACTAGAAGAACAGTATTTGGTATCTGCGCTCTGCTGAAGCCAGTTACCTT
CGGAAAAAGAGTTGGTAGCTCTTGATCCGGCAAACAAACCACCGCTGGTAGCGGTGGTTTT
TTTGTTTGCAAGCAGCAGATTACGCGCAGAAAAAAAGGATCTCAAGAAGATCCTTTGATCT

TTAGAAAAACTCATCGAGCATCAAATGAAACTGCAATTTATTCATATCAGGATTATCAATACCA
TATTTTGAAAAAGCCGTTTCTGTAATGAAGGAGAAAACTCACCGAGGCAGTTCCATAGGAT
GGCAAGATCCTGGTATCGGTCTGCGATTCCGACTCGTCCAACATCAATACAACCTATTAATTTC
CCCTCGTCAAAATAAGGTTATCAAGTGAGAAATCACCATGAGTGACGACTGAATCCGGTGA
GAATGGCAAAAGTTTATGCATTTCTTTCCAGACTTGTTCAACAGGCCAGCCATTACGCTCGTC
ATCAAATCACTCGCATCAACCAAACCGTTATTCATTCGTGATTGCGCCTGAGCCAGACGAAA
TACGCGATCGCTGTTAAAGGACAATATTTCACCTGAATCAGGATATTCTTCTAATACCTGGAATGCTG
ACTGCCAGGCATCAACAATATTTCACCTGAATCAGGATATTCTTCTAATACCTGGAATGCTG
TTTTTCCGGGGATCGCAGTGGTGAGTAACCATGCATCATCAGGAGTACGGATAAAATGCTTG
ATGGTCGGAAGAGGCATAAATTCGTCAGCCAGTTTAGTCTGACCATCTCATCGTAACATCA
ATGGTTTGGCAACGCTACCTTTGCCATGTTTCAGAAACAACTCTGGCGCATCGGGCTTCCATACAAG
CGATAGATTGTCGCACCTGATTGCCCGACATTATGCGGAGCCCATTATACCCATATAAATCAG
CATCCATGTTGGAATTTAATCGCGGCCTCGACGTTTCCCGTTGAATATGGCTCAT

Kanamycin resistance (KanR2) (SEQ ID NO:46)

Kanamycin promoter (SEQ ID NO:47)

AACACCCCTTGTATTACTGTTTATGTAAGCAGACAGTTTTATTGTTCATGATGATATATTTTTATC
TTGTGCAATGTAACATCAGAGATTTTGAGACAC

FIGURE 7

CD8 Product 2 Product Nucleic Acid Sequence

ACATTAAAAACACAAAATCCTACGAAATACTGAAGAATGAGTCTCAGCACTAAGGAAAAGC
CTCCAGCAGCTCCTGCTTCTGAGGGTGAAGGATAGACGCTGTGGCTCTGCATGACTCACTA
GCACTCTATCACGGCCATATTCTGGCAGGGTCAGTGGCTCCAACTAACATTTGTTTGGTACTT
TACAGTTTATTAAATAGATGTTTATATGGAGAAGCTCTCATTTCTTTCTCAGAAGAGCTGGCT
AGGAAGGTGGATGAGGCACCATATTCATTTGCAGGTGAAATTCCTGAGATGTAAGGAGCT
GCTGTGACTTGCTCAAGGCCTTATATCGAGTAAACGTAGTGCTGGGGCTTAGACGCAGGTG
TTCTGATTTATAGTTCAAAACCTCTATCAATGAGAGAGCAATCTCCTGGTAATGTGATAGATTT
CCCAACTTAATGCCAACATACCATAAACCTCTAATGCCCAGCCTAAGTTGGGGA
GACCACTCCAGATTCCAAGATGTACAGTTTGCTTTGCTGCGGCCTTTTCCCATGCCTGCCTTA
CTCTGCCAGAGTTATATGTGGGGTTTTGAAGAAGATCCTATTAAAAGAATAAAGCAGT
ATTATTAAGTAGCCCTGCATTTCAGTTTCCTTGGCAGGCCAGGCCTGGCGTGAACG
TTCACTGAAATCATGGCCTCTTGGCCAAGATTGATAGCTTGTGCCTGTCCCTGAGTCCAGTC
CATCACGAGCAGCTGGTTTCTAAGATGCTATTTCCCGTATAAAGCATGGACTCCAGCCTGCC
AGCCCCACAGAGCCCGCCCCTTGTCCATCTGGCATCTGGACTCCAGCCTGGGTTGGGGCA
AAGAGGGAAATGAGATCATGTCCTAACCCTGATCCTCTGTCCCACAG

Left HR Arm (SEQ ID NO:49)

ATATCCAGAACCCTGACCCTGCCGTGTACCAGCTGAGAGACTCTAAATCCAGTGACAAGTCTG
TCTGCCTATTC

TRAC CDS (SEQ ID NO:50)

GAATTCGGGCTCCGGA

GSG Linker 1 (SEQ ID NO:51)

GCCACTAACTTCAGCCTGTTGAAGCAGGCCGGCGACGTTGAGGAAAACCCCGGTCCT

P2A (SEQ ID NO:52)

FIGURE 7 Cont.

| Sequence | Label |
|---|---|
| ATGGCCTTACCAGTGACCGCCTTGCTCCTGCCGCTGGCCTTGCTGCTCCACGCCGCCAGGCCG | CD8A Signal peptide (SEQ ID NO:53) |
| AGCCAGTTCCGGGTGTCGCCGCTGGATCGGACCTGGAACCTGGGCGAGACAGTGGAGCTGAAGTGCCAGGTGCTGCTGTCCAACCCGACGTCGGGCTGCTCGTGGCTCTTCCAGCCGCGGCGCCGCCGCCAGTCCACCTTCCTCCTATACCTCTCCCAAAACAAGCCCAAGGCGGCCGAGGGGCTGGACACCCAGCGGTTCTCGGGCAAGAGGTTGGGGACACCTTCGTCCTCACCCTGAGCGACTTCCGCCGAGAGAACGAGGGCTACTATTTCTGTCGGGCCCTGAGCAACTCCATCATGTACTTCAGCCACTTCGTGCCGGTCTTCCTGCCAGCGAAGCCCACCACGACGCCAGCGCCGACCACCAACACGGGCCCACCATGCGTTCGCAGCCCCTGTCCCTGCGCCCTGAGAGGGCTGAGGGGTGCCGGGCCAGGCGGGGGGGCAGTGCACACGAGGGGCTGGACTTCGCCTGTGAT | CD8A Extracellular domain (SEQ ID NO:54) |
| ATCTACATCTGGGCGCCCCTTGCCGCCGGTCCTTCTCCTGTCACTGGTTATCACC | CD8A transmembrane domain (SEQ ID NO:55) |
| CTTTACTGCAACCACAGGAACCGAAGACGTGTTTGCAAATGTCCCGGCCTGTGGTCAAATCGGGAGACAAGCCCAGCCTTTCGGCGAGATACGTC | CD8A Intracellular domain (SEQ ID NO:56) |
| AGAGCAAAGCGG | Furin cleavage site (SEQ ID NO:57) |
| GGCTCCGGA | GSG Linker (SEQ ID NO:58) |
| GCTACCAATTTTAGCCTCCTGAAGCAGGCTGGCGATGTTGAGGAAAACCCTGGTCCC | P2A (SEQ ID NO:59) |
| ATGCGGGCCGGCGTGTCCTCTTGGCCGCCGCAGCTGACAGTTCTCCATGGCAACTCAGTC | CD8B Signal Peptide (SEQ ID NO:60) |

FIGURE 7 Cont.

CTCCAGCAGACCCCTGCATACATAAAGGTGCAAACCAACAAGATGGTGATGCTGTCCTGGA  CD8B Extracellular domain
GGCTAAAATCTCCCTCAGTAACATGCGCATCTACTGGCTGAGACAGCGCCAGGCACCGAGCA  (SEQ ID NO:61)
GTGACAGTCACCAGAGTTCCTGCGCCCTCTGGGATTCCGCAAAAGGGACTATCCACGGTGA
AGAGGTGGAACAGGAGAAGATAGCTGTGTTTCGGGATGCAAGCCGGTTCATTCTCAATCTC
ACAAGCGTGAAGCCGGAAGACAGTGACATTCTGTCATGATCGTCGGGAGCCCGAGC
TGACCTTCGGGAAGGGAACTCAGCTGAGTGTGGTTGATTTCCTTCCACCACTGCCCAGCC
ACCAAGAAGTCCACCCTCAAGAGAGAGAGTGTGCCGGTTACCCAGGCCAGAGACCCAGAAG
GGCCCACTTTGTAGCCCC ATCACCCTTGGCCTGCTGGTGGCGTCCTGGGTTCTGCTGGTTCCTGGAGTGGCCAT CD8B Transmembrane
C domain (SEQ ID NO:62)

CACCTGTGCTGCCGGCCGGAGGAGAGCCCGGCTTCGTTTCATGAAACAATTTTACAAA CD8B Intracellular domain
(SEQ ID NO:63)

AGGGCTAAACGG Furin cleavage site (SEQ ID NO:64)

GAATTCGGCTCCGGA GSG Linker (SEQ ID NO:65)

GCCACTAACTTCTCCCTGTTGAAACAGGCTGGCGATGTTGAAGAGAAACCCCGGTCCT P2A (SEQ ID NO:66)

ATGGCCACCGGCTCTAGAACAAGCCTGCTGCTCGCTTTTGGCCTGCTCTGCCTCCCATGGCTC HGH/SS/2 (SEQ ID NO:67)
CAAGAAGGATCTGCT

FIGURE 7 Cont.

[[TRB_VDJ Sequence, specific for the NeoTCR]] — Insertion site for neoTCR TRB_VDJ sequence CTGAAAAACGTGTTCCCTCCAAAAGTGGCCGTGTTCGAGCCTTCTGAGGCCGAGATCAGCC
ACACACAGAAAGCCACACTCGTGTGTCTGGCTGTTCTACCCGGATCACGTGGAACTG
TCTTGGTGGGTCAACGGCAAAGAGGTGCACAGCGGCGTCAGCACAGATCCCCAGCCTCTGA
AGAACAGCCCGCTCTGAACGACAGCGCTACTGCCTGTCTAGCAGACGATGAGAGTGTCCGC
CACCTTCTGGCAGAAACCCCAGAAACCACTTCAGATGCCAGGTCCAGTTCTACGGCCTGAGCG
AGAACGATGAGTGGGACCCAGGACAGAGACCAAGCTGTGACACAGATCGTGTCTGCGAAG
CCTGGGACAGAGCCGATTGTGGCTTTACCAGCAGCTCATACCAGCAGGCGTGTCTGC
CACCATCCTGTATGAGATCCTGCTCGGCAAGGCCACACTGTACGCTGTGTGTGGTCTGCTCT
GGTGCTGATGGCTATGGTCTCCCGGGAGCGCATCCCCGAGGCC
— TCR-beta/constant (SEQ ID NO:69)

CGGGCCAAGCGG — Furin cleavage site (SEQ ID NO:70)

GGCAGCGGC — GSG Linker (SEQ ID NO:71)

GCCACCAACTTCAGCCTGCTGAAGCAGGCCGGCGACGTGGAGGAGAACCCCGGCCCT — P2A (SEQ ID NO:72)

ATGGCCACAGGGCAGCAGAGAACATCTCTGCTGCTTCGGACTGCTGTGTCTGCCTTGGCT
GCAAGAGGGGTTCCGCC — HGH/SS/2 (SEQ ID NO:73)

[[TRA_VDJ Sequence, specific for the NeoTCR]] — Insertion site for neoTCR TRA_VDJ sequence ATATTCAGAACCCCGATCCTGCTGTGTATCAGCTGCGCGACAGCAAGAGCAGCGACAAGAGC
GTGTGTTTGTTC — TCR-alpha/constant (SEQ ID NO:75)

FIGURE 7 Cont.

ACCGATTTGATTCTCAAACAAATGTGTCACAAAGTAAGGATTCTGATGTGTATATCACAGAC    TRAC CDS/right HR arm
AAAACTGTGCTAGACATGAGGTCTATGGACTTCAAGAGCAACAGTGCTGTGGCCTGGAGCA    (SEQ ID NO:76)
ACAAATCTGACTTTGCATGTGCAAACGCCTTCAACAACAGCATTATTCCAGAAGACACCTTCT
TCCCCAGCCCAGG TAAGGGCAGCTTTGGTGCCTTCGCAGGCTGTTTCCTTGCTTCAGGAATGGCCAGGTTCTGCC    Right HR arm (SEQ ID
CAGAGCTCTGGTCAATGATGTCTAAAACTCCTCTGATTGGTGGTCTCGGCCTTATCCATTGCC    NO:77)
ACCAAAACCCTCTTTACTAAGAAACAGTGAGCCTTGTTCTGGCAGTCCAGAGAATGACAC
GGGAAAAAGCAGATGAAGAGAAGAAGGTGGCAGGAGAGGGCACGTGGCCCAGCCTCAGTCT
CTCCAACTGAGTTCCTGCCTGCTCTTGCCTGCCTCAGATGTGTTGCCCCTTACTGTCTTTCTAGG
CCTCATTCTAAGCCCTCCCAAGTTGCCTCTCCAAGTTGCCTCTTCCTTATTCTCCCTGTCTGCCAAAAATCTTT
CCCAGCTCACTAAGTCAGTCTCACGCAGTCAGTCACTCATTAACCCACCACTACTGATTGTGCCGG
CACATGAATGCACCAGGTGTTGAAGTGGAGGAATTAAAAAAGTCAGATGAGGGGTGTGCCCA
GAGGAAGCACCATTCTAGTGGGGAGCCCATCTGTCAGCTGGGAAAAGTCCAAATAACTT
CAGATTGGAATGTGTTTAACTCAGGGTTGAGAAAAACAGCTACCTTCAGGACAAAAGTCAG
GGAAGGGCTCTCTGAAGAAATGCTACTTGAAGATACCAGCCCTACCAAGGGCAGGGAGAG
GACCCTATAGAGGCCTGGGACAGGAGCTCAATGGAGAAAGGAGAAGAGCAGGCAGGCATGA
GTTGAATGAAGGAGGCAGGGCCGGGTCACAGGGCCTTCTAGCCATGAGAGGGTAGACAG

GCTAGC    (SEQ ID NO:78)

FIGURE 7 Cont.

CGCGTTGCTGGCGTTTTTCCATAGGCTCCGCCCCCCTGACGAGCATCACAAAAATCGACGCT
CAAGTCAGAGGTGGCGAAACCCGACAGGACTATAAAGATACCAGGCGTTTCCCCCTGGAAG
CTCCCTCGTGCGCTCTCCTGTTCCGACCCTGCCGCTTACCGGATACCTGTCCGCCTTTCTCCCT
TCGGGAAGCGTGGCGCTTTCTCATAGCTCACGCTGTAGGTATCTCAGTTCGGTGTAGGTCGTT
CGCTCCAAGCTGGGCTGTGTGCACGAACCCCCCGTTCAGCCCGACCGCTGCGCCTTATCCGG
TAACTATCGTCTTGAGTCCAACCCGGTAAGACACGACTTATCGCCACTGGCAGCAGCCACTG
GTAACAGGATTAGCAGAGCGAGGTATGTAGGCGGTGCTACAGAGTTCTTGAAGTGGTGGCC
TAACTACGGCTACACTAGAAGAACAGTATTTGGTATCTGCGCTCTGCTGAAGCCAGTTACCTT
CGGAAAAAGAGTTGGTAGCTCTTGATCCGGCAAACAAACCACCGCTGGTAGCGGTGGTTTT
TTTGTTTGCAAGCAGCAGATTACGCGCAGAAAAAAAGGATCTCAAGAAGATCCTTTGATCT pBR322_origin (SEQ ID NO:79)

TTAGAAAAACTCATGAGCATCAAATGAAACTGCAATTTATTCATATCAGGATTATCAATACCA
TATTTTTGAAAAAGCCGTTTCTGTAATGAAGGAGAAAACTCACCGAGGCAGTTCCATAGGAT
GGCAAGATCCTGGTATCGGTCTGCGATTCCGACTCGTCCAACATCAATACAACCTATTAATTTC
CCCTCGTCAAAAATAAGGTTATCAAGTGAGAAATCACCATGAGTGACGACTGAATCCGGTGA
GAATGGCAAAAGCTTATGCATTTCTTTCCAGACTTGTTCAACAGGCCAGCCATTACGCTCGTC
ATCAAAATCACTCGCATCAACCAAACCGTTATTCATTCGTGATTGCGCCTGAGCGAGACGAAA
TACGCGATCGCTGTTAAAGGACAATTACAAACAGGAATCGAATGCAACCGGCGCAGGAAC
ACTGCCAGCGCATCAACAATATTTTCACCTGAATCAGGATATTCTTCTAATACCTGGAATGCTG
TTTTTCCGGGGATCGCAGTGGTGAGTAACCATGCATCATCAGGAGTACGGATAAAATGCTTG
ATGGTCGGAAGAGGCATAAATTCCGTCAGCCAGTTTAGTCTGACCATCTCATCGTAACATCA
TGGCAACGCTACCTTTGCCATGTTTCAGAAACAACTCTGGCGCATCGGGCTTCCCATACAAG
CGATAGATTGTCGCACCTGATTGCCCGACATTATCGCGAGCCCATTTATACCCATATAAATCAG
CATCCATGTTGGAATTTAATCGCGGCCTCGACGTTTCCCGTTGAATATGGCTCAT

Kanamycin resistance (KanR2) (SEQ ID NO:80)

AACACCCCCTTGTATTACTGTTTATGTAAGCAGACAGTTTTATTGTTCATGATGATATATTTTTATC
TTGTGCAATGTAACATCAGAGATTTTGAGACAC

Kanamycin promoter (SEQ ID NO:81)

FIGURE 8

CD8 Product 3 Product Nucleic Acid Sequence

ACATTAAAAACACAAATCCTACGGAAATACTGAAGAATGAGTCTCAGCACTAAGGAAAAGC
CTCCAGCAGCTCCTGCTTTCTGAGGGTGAAGGATAGACGCTGTGGCTCTGCATGACTCACTA
GCACTCTATCACGGCCATATTCTGGCAGGGTCAGTGGCTCCAACTAACATTTGTTTGTACTT
TACAGTTTATTAAAATAGATGTTTATATGGAAGAAGCTCTCATTTCTTTCTCAGAAGAGCTGGCT
AGGAAGGTGGATGAGGCACCATATTCATTTGCAGGTGAAATTCCTGAGATGTAAGGAGCT
GCTGTGACTTGCTCAAGGCCTTATATCGAGTAAACGTAGTGCTGGGGCTTAGACGCAGGTG
TTCTGATTTATAGTTCAAAACCTCTATCAATGAGAGAGCAATCTCCTGGTAATGTGATAGATTT
CCCAACTTAATGCCAACATACCATAAACCTCCCATTCTGCTAATGCCAGCCTAAGTTGGGGA
GACCACTCCAGATTCCAAGATGTACAGTTTGCTTTGCTGGGCCTTTTCCCATGCCTGCCTTA
CTCTGCCAGAGTTATATGCTGGGGTTTCAGGTTTCCTGAGTGGCAGGCAGGCCTGGCCTGCCCTG
ATTATTAAGTAGCCCTGCATTTCAGTTTCCTTGGCCAAGATTGATAGCTTGTGCCTGTCCCTGAGTCCCAGTC
TTCACTGAAATCATGGCCTCTTGGCCAAGATTGATAGCTTGTGCCTGTCCCTGAGTCCCAGTC
CATCACGAGCAGCTGGTTTCTAAGATGTCTATTTCCCGTATAAAGCATGAGACCGTGACTTGCC
AGCCCCACAGAGCCCGCCCCTTGTCATCTGGACTCCAGCCTGGGTTGGGGCA
AAGAGGGAAATGAGATCATGTCCTAACCCTGATCCTCTTGTCCCACAG                          Left HR Arm (SEQ ID NO:83)

ATATCCAGAACCCTGACCCTGCCGTGTACCAGCTGAGAGACTCTAAATCCAGTGACAAGTCTG
TCTGCCTATTC                                                                TRAC CDS (SEQ ID NO:84)

GAATTCGGCTCCGGA                                                            GSG Linker 1 (SEQ ID NO:85)

GCCACTAACTTCAGCCTGTTGAAGCAGGCGGCGACGTTGAGGAAACCCCGGTCCT                    P2A (SEQ ID NO:86)

FIGURE 8 Cont.

ATGGCCTTACCAGTGACCGCCTTGCTCCTGCCGCTGGCTTGCTCCACGCCGCCAGGCCG — CD8A Signal peptide (SEQ ID NO:87)

AGCCAGTTCCGGGTGTCGCCGCTGGATCGGACCTGGAACCTGGGCGAGACAGTGGAGCTGAAGTGCCAGGTGCTGCTGTCCAACCCGACGTCGGGCTGTCGTGGCTCTTCCAGCGCCGCGGCGCGCCAGCCGCCAGTCCCACCTTCCTCTCCTATACCTTCCTCGGGCAAGTGGGGGACACCTTCGTCCTCACCCTGGGGCTGGACACCCAGCGGTTCTCCGGCAAGAGGTTGGGGGACACCTTCGTCCTCACCCTGAGCGACTTCCGCCGAGAGAACGAGGGCTACTATTTCTGTCGGGCCCTGAGCAACTCCATCATGTACTTCAGCCACTTCGTGCCGGTCTTCCTGCCAGCGAGGACCGCGATCAAGCCCACACACGAGCCGCCCCCGACCACCACAACACCGGCGCCCACCATCGCGCCCCCGCAGCCTCCTCTGCCTGCCGTCGAGGGGGTGCCGGCCAGCCAGCCACTGCGGCCAGGCTGGACTTCGCCTGTGAT — CD8A Extracellular domain (SEQ ID NO:88)

ATCTACATCTGGGCGCCCTTGGCCGGCACTTGTGGGGTCCTTCTCCTGTCACTGGTTATCACC — CD8A transmembrane domain (SEQ ID NO:89)

CACCTGTGCTGCCGGGAGAGAGCCCGGCTTCGTTTCATGAAACAATTTTACAAA — CD8B Intracellular domain (SEQ ID NO:90)

AGGGCTAAACGG — Furin cleavage site (SEQ ID NO:91)

GAATTCGGCTCCGGA — GSG Linker (SEQ ID NO:92)

GCCACTAACTTCTCCCTGTTGAAACAGGCTGGCGATGTTGAAGAAAACCCCGGTCCT — P2A (SEQ ID NO:93)

ATGGCCACCGGCTCTAGAACAAGCCTGCTGCTCGCTTTTGGCCTGCTGTGCCTCCCATGGCTCCAAGAAGGATCTGCT — HGH/SS/2 (SEQ ID NO:94)

FIGURE 8 Cont.

[[TRB_VDJ Sequence, specific for the NeoTCR]]  — Insertion site for neoTCR TRB_VDJ sequence CTGAAAAACGTGTTCCCTCCAAAAGTGGCCGTGTTCGAGCCTTCTGAGGCCGAGATCAGCC
ACACACAGAAAGCCACACTCGTGTGTCTGGCTACCGGCTTCTACCCGATCACGTGGAACTG
TCTTGGTGGGTCAACGGCAAAGAGGTGCACAGCGGCGTCAGCAGCGACATCCCCAGCCTGA
AAGAACAGCCCGCTCTGAACGACAGCCGCTACTGCCTGTCTAGCAGACTGAGAGTGTCCGC
CACCTTCTGGCAGAACCCCAGAAACCACTTCAGATGCCAGGTCCAGTTCTACGGCCTGAGCG
AGAACGATGAGTGGACCCAGGACAGAGCCAAGCCTGTGACACAGATCGTGTCTGCCGAAG
CCTGGGGCAGAGCCGATTGTGGCTTTACCAGCGAGTCATACCAGCAGGGCGTGCTGTCTG
CACCATCCTGTATGAGATCCTGCTCGGCAAGGCCACACTGTACGCTGTGCTGGTGTCTGCTCT
GGTGCTGATGGCTATGGTCTCCCGGGAGCGCATCCCCGAGGCC  — TCR-beta/constant (SEQ ID NO:96)

CGGGCCAAGCGG  — Furin cleavage site (SEQ ID NO:97)

GGCAGCGGC  — GSG Linker (SEQ ID NO:98)

GCCACCAACTTCAGCCTGCTGAAGCAGGCCGGCGACGTGGAGGAGAACCCCGGCCCT  — P2A (SEQ ID NO:99)

ATGGCCACAGGCAGCAGAGAACATCTCTGCTGCTGCTGGCCTTCGGACTGCTGTGTCTGCCTTGGCT
GCAAGAGGGGTTCCGCC  — HGH/SS/2 (SEQ ID NO:100)

[[TRA_VDJ Sequence, specific for the NeoTCR]]  — Insertion site for neoTCR TRA_VDJ sequence ATATTCAGAACCCCGATCCTGCTGTGTATCAGCTGCGCGACAGCAAGAGCAGCGACAAGAGC
GTGTGTTTGTTC  — TCR-alpha/constant (SEQ ID NO:102)

FIGURE 8 Cont.

ACCGATTTGATTCTCAAACAAATGTGTCACAAAGTAAGGATTCTGATGTGTATATCACAGAC  TRAC CDS/right HR arm (SEQ ID NO:103)
AAAACTGTGCTAGACACATGAGGTCTATGGACTTCAAGAGCAACAGTGCTGTGGCCTGGAGCA
ACAAATCTGACTTTGCATGTGCAAACGCCTTCAACAACAGCATTATTCCAGAAGACACCTTCT
TCCCCAGCCCAGG TAAGGGCAGCTTTGGTGCCTTCGCAGGCTGTTTCCTTGCTTCAGGAATGGCCAGGTTCTGCC  Right HR arm (SEQ ID NO:104)
CAGAGCTCTGGTGGTTCAATGATGTCTAAAACTCCTCTGATTGGTGGTCTCGGCCTTATCCATTGCC
ACCAAAACCCTCTTTTACTAAGAAACAGTGAGCCTTGTTCTGGCAGTCCAGAGAATGACAC
GGGAAAAAGCAGATGAAGAGAAGAAGGTTGGCAGGAGAGGGCACGTGGCCCAGCCTCAGTCT
CTCCAACTGAGTTCCTGCCTGCTTGCTCAGACTGTTTGCCCCTTACTGCTCTTTCTAGG
CCTCATTCTAAGCCCCTTCTCCAAGTTGCCTCTTCCAAGCCCTTCTCCAAGTTGCCAAAAATCTTT
CCCAGCTCACTAAGTCAGTCTCACGCAGTCACTCATTAACCCACCAATCACTGATTGTGCCGG
CACATGAATGCACCAGGTGTTGAAGTTGGAGAATTAAAAAGTCAGATGAGGGGTGTGCCCA
GAGGAAGCACCATTCTAGTTGGGGGAGCCCATCTGTCAGCTGGGAAAAGTCCAAATAACTT
CAGATTGGAATGTGTTTAACTCAGGGTTGAGAAAACAGCTACCTTCAGGACAAAAGTCAG
GGAAGGGCTCTCTGAAGAAATGCTACTTGAAGATACCAGCCCTACCAAGGGCAGGAGAG
GACCCTATAGAGGCCTGGGACAGGAGCTCAATGAGAAAGGAGAAGAGCAGCAGGCATGA
GTTGAATGAAGGAGGAGCAGGGCCGGGCACGGGTCACAGGGCCTTCTAGCCATGAGAGGGTAGACAG

GCTAGC  (SEQ ID NO:105)

FIGURE 8 Cont.

pBR322_origin (SEQ ID NO:106)

CGCGTTGCTGGCGTTTTTCCATAGGCTCCGCCCCCCTGACGAGCATCACAAAAATCGACGCT
CAAGTCAGAGGTGGCGAAACCCGACAGGACTATAAAGATACCAGGCGTTTCCCCCTGGAAG
CTCCCTCGTGCGCTCTCCTGTTCCGACCCTGCCGCTTACCGGATACCTGTCCGCCTTTCTCCCT
TCGGGAAGCGTGGCGCTTTCTCATAGCTCACGCTGTAGGTATCTCAGTTCGGTGTAGGTCGTT
CGCTCCAAGCTGGGCTGTGTGCACGAACCCCCCGTTCAGCCCGACCGCTGCGCCTTATCCGG
TAACTATCGTCTTGAGTCCAACCCGGTAAGACACGACTTATCGCCACTGGCAGCAGCCACTG
GTAACAGGATTAGCAGAGCGAGGTATGTAGGCGGTGCTACAGAGTTCTTGAAGTGGTGGCC
TAACTACGGCTACACTAGAAGAACAGTATTTGGTATCTGCGCTCTGCTGAAGCCAGTTACCTT
CGGAAAAAGAGTTGGTAGCTCTTGATCCGGCAAACAAACCACCGCTGGTAGCGGTGGTTTT
TTTGTTTGCAAGCAGCAGATTACGCGCAGAAAAAAAGGATCTCAAGAAGATCCTTTGATCT

Kanamycin resistance (KanR2) (SEQ ID NO:107)

TTAGAAAAACTCATCGAGCATCAAATGAAACTGCAATTTATTCATATCAGGATTATCAATACCA
TATTTTGAAAAAGCCGTTTCTGTAATGAAGGAGAAAACTCACCGAGGCAGTTCCATAGGAT
GGCAAGATCCTGGTATCGGTCTGCGATTCCGACTCGTCCAACATCAATACAACCTATTAATTC
CCCTCGTCAAAAATAAGGTTATCAAGTGAGAAATCACCATGAGTGACGACTGAATCCGGTGA
GAATGGCAAAAGTTTATGCATTTCTTTCCAGACTTGTTCAACAGGCCAGCCATTACGCTCGTC
ATCAAAATCACTCGCATCAACCAACCGTTATTCATTCGTGATTGCGCCTGAGCGAGACGAAA
TACGCGATCGCTGTTAAAAGGACAATTACAAACAGGAATCGAATGCAACCGGCGCAGGAAC
ACTGCCAGCGCATCAACAATATTTTCACCTGAATCAGGATATTCTTCTAATACCTGGAATGCTG
TTTTTCCGGGGATCGCAGTGGTGAGTAACCATGCATCATCAGGAGTACGGATAAAATGCTTG
ATGGTCGGAAGAGGCATAAATTCCGTCAGCCAGTTTAGTCTGACCATCTCATCGTAACATCA
TGGCAACGCTACCTTTGCCATGTTTCAGAAACAACTCTGGCGCATCGGGCTTCCCATACAAG
CGATAGATTGTCGCACCTGATTGCCCGACATTATCGCGAGCCCATTTATACCCATATAAATCAG
CATCCATGTTGGAATTTAATCGCGGCCTCGACGTTTCCGTTGAATATGGCTCAT

Kanamycin promoter (SEQ ID NO:108)

AACACCCCTTGTATTACTGTTTATGTAAGCAGACAGTTTTATTGTTCATGATGATATATTTTTATC
TTGTGCAATGTAACATCAGAGATTTTGAGACAC

FIGURE 9

CD8 Product 4 Product Nucleic Acid Sequence

ACATTAAAAACACAAAATCCTACGAAATACTGAAGAATGAGTCTCAGCACTAAGGAAAAGC
CTCCAGCAGCTCCTGCTTTCTGAGGGTGAAGGATAGACGCTGTGGCTCTGCATGACTCACTA
GCACTCTATCACGGCCATATTCTGGCAGGGTCAGTGGCTCCAACTAACATTTGTTTGGTACTT
TACAGTTTATTAAATAGATGTTTATATGGAGAAGCTCTCATTCTTTCTCAGAAGAGCCTGGCT
AGGAAGGTGGATGAGGCACCATATTCATTTTGCAGGTGAAATTCCTGAGATGTAAGGAGCT
GCTGTGACTTGCTCAAGGCCTTATATCGAGTAAACGTAGTGCTGGGGCTAGACGCAGGTG
TTCTGATTTATAGTTCAAAACCTCTATCAATGAGAGACAATCTCCTGGTAATGTGATAGATTT
CCCAACTTAATGCCAACATACCATAAACCTCCCATTCTGCTAATGCCCAGCCTAAGTTGGGGA
GACCACTCCAGATTCCAAGATGTACAGTTGCTTGCTGGGCCTTTTCCCATGCCTGCCTTTA
CTCTGCCAGAGAGTTATATTGCTGGGGTTTTGAAGAAGATCCTATTAAAAGAATAAGCAGT
ATTATTAAGTAGCCCTGCATTTCAGTTTCCTTGGCCAAGATTGATAGCTTGTGCCTGTCCCAGTC
TTCACTGAAATCATGGCCTCTGGCCAAGATTGATAGCTTGTGCCTGTCCCTGAGTCCAGTC
CATCAGAGCAGCTGGTTTCTAAGATGCTATTTCCCGTATAAAGCATGAGACCGTGACTTGCC
AGCCCCACAGAGCCCGCCCCTTGTCCATCACTGGACTCCAGCCTGGACTCTGGGTTGGGGCA
AAGAGGGAAATGAGATCATGTCCTAACCCTGATCCTCTTGTCCACAG

Left HR Arm (SEQ ID NO:110)

ATATCCAGAACCCTGACCCTGCCGTGTACCAGCTGAGAGACTCTAAATCCAGTGACAAGTCTG
TCTGCCTATTC

TRAC CDS (SEQ ID NO:111)

GAATTCGGGTCCGGA

GSG Linker 1 (SEQ ID NO:112)

GCCACTAACTTCAGCCTGTTGAAGCAGGCCGGCGACGTTGAGGAAAACCCCGGTCCT

P2A (SEQ ID NO:113)

FIGURE 9 Cont.

| Sequence | Label |
|---|---|
| ATGGCCTTACCAGTGACCGCCTTGCTCCTGCCGCTGGCCTTGCTGCTCCACGCCGCCAGGCCG | CD8A Signal peptide (SEQ ID NO:114) |
| AGCCAGTTCCGGGTGTCGCCGCTGGATCGGACCTGGAACCTGGGCGAGACAGTGGAGCTGAAGTGCCAGGTGCTGCTGTCCAACCCGACGTCGGGCTGCTCGTGGCTCTTCCAGCCGCGCGGCGCCGCCGCCAGTCCCACCTTCCTCCTATACCTCTCCAAACAAGCCAAGGGGGCCGAGGGGCTGGACACCCAGCGGTTCTCGGGCAAGAGGTTGGGGACACCTTCGTCTCTCACCCTGAGCGACTTCCGCCGAGAGAAGACGAGGGCTACTATTTCTGCTCGGCCCTGAGCAACTCCATCATGTACTTCAGCCACTTCGTGCCGGTCTTCCTGCCAGCGAAGCCCACCACGACGCCAGCGCCGCGACCACCAACCGGCGCCCACCATGCGTGCAGCCCCTGTCCCTGCGCCCAGAGGCGTGCCGGCCAGCGGGGGGGACGAGTGCACACGAGGGGGCTGGACTTCGCCTGTGAT | CD8A Extracellular domain (SEQ ID NO:115) |
| ATCTACATCTGGGCCCCTTGGCCATGGCCGGGACTTGTGGGGACTTGTCCTTCTCCTGTCACTGGTTATCACC | CD8A transmembrane domain (SEQ ID NO:116) |
| TGTGTCAGGTGCCGGCACCGAAGGCGCCAAGCAGAGCGGATGTCTCAGATCAAGAGACTCCTCAGTGAGAAGAGACCTGCCAGTGTCCTCACCGGTTTCAGAAGAGACATGTAGCCCCATT | CD4 Intracellular domain (SEQ ID NO:117) |
| AGGGCTAAACGG | Furin cleavage site (SEQ ID NO:118) |
| GAATTCGGCTCCGGA | GSG Linker (SEQ ID NO:119) |
| GCCACTAACTTCTCCCTGTTGAAACAGGCTGGCGATGTTGAAGAAAACCCGGTCCT | P2A (SEQ ID NO:120) |
| ATGGCCACCGGCTCTAGAACAAGCCTGCTGCTCGCCTTTGGCCTGCTCTGCCTCCCATGGCTCCAAGAAGGATCTGCT | HGH/SS/2 (SEQ ID NO:121) |

FIGURE 9 Cont.

[[TRB_VDJ Sequence, specific for the NeoTCR]]  — Insertion site for neoTCR TRB_VDJ sequence CTGAAAAACGTGTTCCCTCCAAAAGTGGCCGTGTTGAGCCTTCTGAGGCCGAGATCAGCC
ACACACAGAAAGCCACACTCGTGTGTCTGGCTACCCGGCTTCTACCCCGATCACGTGGAACTG
TCTTGGGTCAACGGCAAAGAGGTGCACAGCGGCGTCAGCACAGATCCCCAGCCTCTGA
AGAACAGCCCGCTCTGAACGACAGCGCTACTGCCTCTGTCTAGCAGACTGAGAGTGTCCGC
CACCTTCTGGCAGAACCCCAGAAACCACTTCAGATGCCAGGTCCAGTTCTACGGCCTGAGCG
AGAACGATGAGTGGACCCAGGACAGAGCCAAGCTGTGACACAGATCGTGTCTGCCGAAG
CCTGGGGCAGAGAGCCGATTGTGGCTTTACCAGGAGTCATACCAGCAGGGCGTGTCTGC
CACCATCCTGTATGAGATCCTGCTCGGCAAGGCCACACTGTACGCTGTGTGCTGTGTGTCT
GGTGCTGATGGCTATGGTCTCCCGGGAGGCCATCCCCGAGGCC — TCR-beta/constant (SEQ ID NO:123)

CGGGCCAAGCGG — Furin cleavage site (SEQ ID NO:124)

GGCAGCGGC — GSG Linker (SEQ ID NO:125)

GCCACCAACTTCAGCCTGCTGAAGCAGGCCGGCGACGTGGAGGAGAACCCCGGCCCT — P2A (SEQ ID NO:126)

ATGGCCACAGGCAGCAGAGAACATCTCTGCTGCTGCTGTGCCTTCGGACTGCTGTGTCTGCCTTGGCT
GCAAGAGGGTTCCGCC — HGH/SS/2 (SEQ ID NO:127)

[[TRA_VDJ Sequence, specific for the NeoTCR]]  — Insertion site for neoTCR TRA_VDJ sequence ATATTCAGAACCCCGATCCTGCTGTGTATCAGTGCGCGACAGCAAGAGCAGCGACAAGAGC
GTGTGTTTGTTC — TCR-alpha/constant (SEQ ID NO:129)

FIGURE 9 Cont.

TRAC CDS/right HR arm
(SEQ ID NO:130)

ACCGATTTTGATTCTCAAACAAATGTGTCACAAAGTAAGGATTCTGATGTGTATATCACAGAC
AAAACTGTGCTAGACACATGAGGTCTATGGACTTCAAGAGCAACAGTGCTGTGGCCTGGAGCA
ACAAATCTGACTTTGCATGTGCAAACGCCTTCAACAACAGCATTATTCCAGAAGACACCTTCT
TCCCCAGCCCAGG

Right HR arm (SEQ ID NO:131)

TAAGGGCAGCTTTGGTGCCTTCGCAGGCTGTTTCCTGCTTCAGGAATGGCCAGGTTCTGCC
CAGAGCTCTGGTCAATGTCTAAAACCTCCTCTGATTGGTGGTCTCGGCCTTATCCATTGCC
ACCAAAACCCTCTTTTACTAAGAAACAGTGAGCCTTGTTCTGGCAGTCCAGAGAATGACAC
GGGAAAAAGCAGATGAAGAGAAGGTTGGCAGGAGAGGGCACGTGGCCCAGCCTCAGTCT
CTCCAACTGAGTTCCTGCCTGCCTCCAAGTTGCCTCTCTATTTCTCCCTGTCTGCCAAAAATCTTT
CCCAGCTCACTAAGTCAGTCTCACGACAGTCTCCACGAGCAGTCACTCATTAACCACCACCACTACTGATTGTGCCGG
CACATGAATGCACCAGGTGTTGAAGTGGAGGAATTAAAAAGTCAGATGAGGGGTGTGCCCA
GAGGAAGCACCATTCTAGTGGGGGAGCCCATCTGTCAGCTGGGAAAAGTCCAAATAACTT
CAGATTGGAATGTGTTTAACTCAGGGTTGAGAAAACAGTCACCTTCAGGACAAAAGTCAG
GGAAGGGCTCTGAAGAAATGCTACTTGAAGATACCAGCCCTACCAAGGGCAGGGAGAG
GACCCTATAGAGGCCTGGGACAGGAGCTCAATGAGAAAGGAGAAGGAGCAGGCAGGCATGA
GTTGAATGAAGGAGGCAGGGCCGGGTCACAGGGCCTTCTAGCCATGAGAGGGTAGACAG

GCTAGC (SEQ ID NO:132)

FIGURE 9 Cont.

CGCGTTGCTGGCGTTTTCCATAGGCTCCGCCCCCTGACGAGCATCACAAAAATCGACGCT
CAAGTCAGAGGTGGCGAAACCCGACAGGACTATAAAGATACCAGGCGTTTCCCCCTGGAAG
CTCCCTCGTGCGCTCTCCTGTTCCGACCCTGCCGCTTACCGGATACCTGTCCGCCTTTCTCCCT
TCGGGAAGCGTGGCGCTTTCTCATAGCTCACGCTGTAGGTATCTCAGTTCGGTGTAGGTCGTT
CGCTCCAAGCTGGGCTGTGTGCACGAACCCCCCGTTCAGCCCGACCGCTGCGCCTTATCCGG
TAACTATCGTCTTGAGTCCAACCCGGTAAGACACGACTTATCGCCACTGGCAGCAGCCACTG
GTAACAGGATTAGCAGAGCGAGGTATGTAGGCGGTGCTACAGAGTTCTTGAAGTGGTGGCC
TAACTACGGCTACACTAGAAGAACAGTATTTGGTATCTGCGCTCTGCTGAAGCCAGTTACCTT
CGGAAAAAGAGTTGGTAGCTCTTGATCCGGCAAACAAACCACCGCTGGTAGCGGTGGTTTT
TTTGTTTGCAAGCAGCAGATTACGCGCAGAAAAAAAGGATCTCAAGAAGATCCTTTGATCT pBR322_origin (SEQ ID NO:133)

TTAGAAAAACTCATCGAGCATCAAATGAAACTGCAATTTATTCATATCAGGATTATCAATACCA
TATTTTGAAAAAGCCGTTTCTGTAATGAAGGAGAAAAACTCACCGAGGCAGTTCCATAGGAT
GGCAAGATCCTGGTATCGGTCTGCGATTCCGACTCGTCCAACATCAATACAACCTATTAATTTC
CCCTCGTCAAAAATAAGGTTATCAAGTGAGAAATCACCATGAGTGACGACTGAATCCGGTGA
GAATGGCAAAAGTTTATGCATTTCTTTCCAGACTTGTTCAACAGGCCAGCCATTACGCTCGTC
ATCAAAATCACTCGCATCAACCAAACCGTTATTCATTCGTGATTGCGCCTGAGCCAGACGAAA
TACGCGATCGCTGTTAAAAGGACAATATTTCACCTGAATCAGGATATTCTTCTAATACCTGGAATGCTG
ACTGCCAGCGCATCAACAATATTTTCACCTGTGAGTAACATGACATCATCAGGAGTACGGATAAAATGCTTG
TTTTTCCGGGGATCGCAGTGGTGAGTAACCATGCATCATCAGGAGTACGGATAAAATGCTTG
ATGGTCGGAAGAGGCATAAATTCGTGCAGCAGTTAGTCTGACCATCTCATCTGTAACATCA
TTGGCAACGCTACCTTTGCCATGTTTCAGAAACAACTCTGGCGCATCGGGCTTCCCATACAAG
CGATAGATTGTCGCACCTGATTGCCCGACATTATCGCGAGCCCATTTATACCCATATAAATCAG
CATCCATGTTGGAATTTAATCGCGGCCTCGACGTTTCCGGTTGAATATGGCTCAT

Kanamycin resistance (KanR2) (SEQ ID NO:134)

AACACCCCTTGTATTACTGTTTATGTAAGCAGACAGTTTTATTGTTCATGATGATATATTTTATC
TTGTGCAATGTAACATCAGAGATTTTGAGACAC

Kanamycin promoter (SEQ ID NO:135)

SEQUENCE LISTING

<160> NUMBER OF SEQ ID NOS: 148

<210> SEQ ID NO 1
<211> LENGTH: 926
<212> TYPE: DNA
<213> ORGANISM: Artificial Sequence
<220> FEATURE:
<223> OTHER INFORMATION: Description of Artificial Sequence: Synthetic
      Left Homology Arm_NeoTCR Product

<400> SEQUENCE: 1
acattaaaaa cacaaaatcc tacggaaata ctgaagaatg agtctcagca ctaaggaaaa      60

-continued

```
gcctccagca gctcctgctt tctgagggtg aaggatagac gctgtggctc tgcatgactc    120
actagcactc tatcacggcc atattctggc agggtcagtg gctccaacta acatttgttt    180
ggtactttac agtttattaa atagatgttt atatggagaa gctctcattt ctttctcaga    240
agagcctggc taggaaggtg gatgaggcac catattcatt ttgcaggtga aattcctgag    300
atgtaaggag ctgctgtgac ttgctcaagg ccttatatcg agtaaacggt agtgctgggg    360
cttagacgca ggtgttctga tttatagttc aaaacctcta tcaatgagag agcaatctcc    420
tggtaatgtg atagatttcc caacttaatg ccaacatacc ataaacctcc cattctgcta    480
atgcccagcc taagttgggg agaccactcc agattccaag atgtacagtt tgctttgctg    540 ggccttttc ccatgcctgc ctttactctg ccagagttat attgctgggg ttttgaagaa    600
gatcctatta aataaaagaa taagcagtat tattaagtag ccctgcattt caggtttcct    660
tgagtggcag gccaggcctg gccgtgaacg ttcactgaaa tcatggcctc ttggccaaga    720
ttgatagctt gtgcctgtcc ctgagtccca gtccatcacg agcagctggt ttctaagatg    780
ctatttcccg tataaagcat gagaccgtga cttgccagcc ccacagagcc ccgcccttgt    840
ccatcactgg catctggact ccagcctggg ttggggcaaa gagggaaatg agatcatgtc    900
ctaaccctga tcctcttgtc ccacag                                        926

<210> SEQ ID NO 2
<211> LENGTH: 74
<212> TYPE: DNA
<213> ORGANISM: Artificial Sequence
<220> FEATURE:
<223> OTHER INFORMATION: Description of Artificial Sequence: Synthetic
      TRAC CDS I_NeoTCR Product

<400> SEQUENCE: 2
atatccagaa ccctgaccct gccgtgtacc agctgagaga ctctaaatcc agtgacaagt    60
ctgtctgcct attc                                                      74

<210> SEQ ID NO 3
<211> LENGTH: 15
<212> TYPE: DNA
<213> ORGANISM: Artificial Sequence
<220> FEATURE:
<223> OTHER INFORMATION: Description of Artificial Sequence: Synthetic
      GSG Linker_NeoTCR Product

<400> SEQUENCE: 3
gaattcggct ccgga                                                     15

<210> SEQ ID NO 4
<211> LENGTH: 57
<212> TYPE: DNA
<213> ORGANISM: Artificial Sequence
<220> FEATURE:
<223> OTHER INFORMATION: Description of Artificial Sequence: Synthetic
      P2A 1_NeoTCR Product

<400> SEQUENCE: 4
gccactaact ctccctgtt gaaacaggct ggcgatgttg aagaaaaccc cggtcct        57

<210> SEQ ID NO 5
<211> LENGTH: 78
<212> TYPE: DNA
<213> ORGANISM: Artificial Sequence
<220> FEATURE:
<223> OTHER INFORMATION: Description of Artificial Sequence: Synthetic
```

HGH Signal Sequence and Furin sequence_NeoTCR Product

<400> SEQUENCE: 5
atggccaccg gctctagaac aagcctgctg ctcgcttttg gcctgctctg cctcccatgg    60
ctccaagaag gatctgct    78

<210> SEQ ID NO 6
<211> LENGTH: 345
<212> TYPE: DNA
<213> ORGANISM: Artificial Sequence
<220> FEATURE:
<223> OTHER INFORMATION: Description of Artificial Sequence: Synthetic
      Exemplary TRB_VDJ (TCR097)_NeoTCR Product

<400> SEQUENCE: 6
aatgctggtg tcactcagac cccaaaattc cgcatcctga agataggaca gagcatgaca    60
ctgcagtgta cccaggatat gaaccataac tacatgtact ggtatcgaca gacccaggc    120 atggggctga agctgattta ttattcagtt ggtgctggta tcactgataa aggagaagtc    180
ccgaatggct acaacgtctc cagatcaacc acagaggatt tcccgctcag gctggagttg    240
gctgctccct cccagacatc tgtgtacttc tgtgccagct ccctacaggt tccctacaat    300
gagcagttct cgggccagg gacacggctc accgtgctag aggac    345

<210> SEQ ID NO 7
<211> LENGTH: 534
<212> TYPE: DNA
<213> ORGANISM: Artificial Sequence
<220> FEATURE:
<223> OTHER INFORMATION: Description of Artificial Sequence: Synthetic
      TRBC Constant Region_NeoTCR Product

<400> SEQUENCE: 7
ctgaaaaacg tgttccctcc aaaagtggcc gtgttcgagc cttctgaggc cgagatcagc    60
cacacacaga aagccacact cgtgtgtctg gctaccggct ctacccccga tcacgtggaa    120
ctgtcttggt gggtcaacgg caaagaggtg cacagcggcg tcagcacaga tccccagcct    180
ctgaaagaac agcccgctct gaacgacagc cgctactgcc tgtctagcag actgagagtg    240
tccgccacct tctggcagaa ccccagaaac cacttcagat gccaggtcca gttctacggc    300
ctgagcgaga acgatgagtg gacccaggac agagccaagc ctgtgacaca gatcgtgtct    360
gccgaagcct ggggcagagc cgattgtggc tttaccagcg agtcatacca gcagggcgtg    420
ctgtctgcca ccatcctgta tgagatcctg ctcggcaagg ccacactgta cgctgtgctg    480
gtgtctgctc tggtgctgat ggctatggtc tcccgggagc gcatccccga ggcc    534

<210> SEQ ID NO 8
<211> LENGTH: 12
<212> TYPE: DNA
<213> ORGANISM: Artificial Sequence
<220> FEATURE:
<223> OTHER INFORMATION: Description of Artificial Sequence: Synthetic
      Furin cleavage site_NeoTCR Product

<400> SEQUENCE: 8
cgggccaagc gg    12

<210> SEQ ID NO 9
<211> LENGTH: 9
<212> TYPE: DNA
<213> ORGANISM: Artificial Sequence
<220> FEATURE:

<223> OTHER INFORMATION: Description of Artificial Sequence: Synthetic
      GSG Linker_NeoTCR Product

<400> SEQUENCE: 9 ggcagcggc                                                                9

<210> SEQ ID NO 10
<211> LENGTH: 57
<212> TYPE: DNA
<213> ORGANISM: Artificial Sequence
<220> FEATURE:
<223> OTHER INFORMATION: Description of Artificial Sequence: Synthetic
      P2A_NeoTCR Product

<400> SEQUENCE: 10
gccaccaact tcagcctgct gaagcaggcc ggcgacgtgg aggagaaccc cggccct        57

<210> SEQ ID NO 11
<211> LENGTH: 78
<212> TYPE: DNA
<213> ORGANISM: Artificial Sequence
<220> FEATURE:
<223> OTHER INFORMATION: Description of Artificial Sequence: Synthetic
      HGH SS_NeoTCR Product

<400> SEQUENCE: 11
atggccacag gcagcagaac atctctgctg ctggccttcg gactgctgtg tctgccttgg     60
ctgcaagagg gttccgcc                                                   78

<210> SEQ ID NO 12
<211> LENGTH: 337
<212> TYPE: DNA
<213> ORGANISM: Artificial Sequence
<220> FEATURE:
<223> OTHER INFORMATION: Description of Artificial Sequence: Synthetic
      Exemplary TRA-VDJ (TCR097)_NeoTCR Product

<400> SEQUENCE: 12
gctcagacag tcactcagtc tcaaccagag atgtctgtgc aggaggcaga gaccgtgacc     60
ctgagctgca catatgacac cagtgagagt gattattatt tattctggta caagcagcct    120
cccagcaggc agatgattct cgttattcgc aagaagctt ataagcaaca gaatgcaaca     180
gagaatcgtt tctctgtgaa cttccagaaa gcagccaaat ccttcagtct caagatctca    240
gactcacagc tgggggatgc cgcgatgtat ttctgtgctt ttgggaactt caacaaattt    300
tactttggat ctgggaccaa actcaatgta aaaccaa                             337

<210> SEQ ID NO 13
<211> LENGTH: 74
<212> TYPE: DNA
<213> ORGANISM: Artificial Sequence
<220> FEATURE:
<223> OTHER INFORMATION: Description of Artificial Sequence: Synthetic
      TCR-alpha/constant_NeoTCR Product

<400> SEQUENCE: 13
atattcagaa ccccgatcct gctgtgtatc agctgcgcga cagcaagagc agcgacaaga    60
gcgtgtgttt gttc                                                      74

<210> SEQ ID NO 14
<211> LENGTH: 200
<212> TYPE: DNA
<213> ORGANISM: Artificial Sequence
<220> FEATURE:

<223> OTHER INFORMATION: Description of Artificial Sequence: Synthetic
       TRAC CDS/Right HR arm_NeoTCR Product

<400> SEQUENCE: 14

```
accgattttg attctcaaac aaatgtgtca caaagtaagg attctgatgt gtatatcaca    60
gacaaaactg tgctagacat gaggtctatg gacttcaaga gcaacagtgc tgtggcctgg   120
agcaacaaat ctgactttgc atgtgcaaac gccttcaaca acagcattat tccagaagac   180
accttcttcc ccagcccagg                                                200
```

<210> SEQ ID NO 15
<211> LENGTH: 800
<212> TYPE: DNA
<213> ORGANISM: Artificial Sequence
<220> FEATURE:
<223> OTHER INFORMATION: Description of Artificial Sequence: Synthetic
       Right HR arm_NeoTCR Product

<400> SEQUENCE: 15

```
taagggcagc tttggtgcct tcgcaggctg tttccttgct tcaggaatgg ccaggttctg    60
cccagagctc tggtcaatga tgtctaaaac tcctctgatt ggtggtctcg gccttatcca   120
ttgccaccaa aaccctcttt ttactaagaa acagtgagcc ttgttctggc agtccagaga   180
atgacacggg aaaaagcag atgaagagaa ggtggcagga gagggcacgt ggcccagcct    240
cagtctctcc aactgagttc ctgcctgcct gcctttgctc agactgtttg ccccttactg   300
ctcttctagg cctcattcta agccccttct ccaagttgcc tctccttatt tctccctgtc   360
tgccaaaaaa tctttcccag ctcactaagt cagtctcacg cagtcactca ttaacccacc   420
aatcactgat tgtgccggca catgaatgca ccaggtgttg aagtggagga attaaaaagt   480
cagatgaggg gtgtgcccag aggaagcacc attctagttg ggggagccca tctgtcagct   540
gggaaaagtc caaataactt cagattggaa tgtgttttaa ctcaggggttg agaaaacagc   600 taccttcagg acaaaagtca gggaagggct ctctgaagaa atgctacttg aagataccag   660
ccctaccaag ggcagggaga ggaccctata gaggcctggg acaggagctc aatgagaaag   720
gagaagagca gcaggcatga gttgaatgaa ggaggcaggg ccgggtcaca gggccttcta   780
ggccatgaga gggtagacag                                                800
```

<210> SEQ ID NO 16
<211> LENGTH: 6
<212> TYPE: DNA
<213> ORGANISM: Artificial Sequence
<220> FEATURE:
<223> OTHER INFORMATION: Description of Artificial Sequence: Synthetic
       Artificial Sequence_NeoTCR Product

<400> SEQUENCE: 16

```
gctagc                                                                 6
```

<210> SEQ ID NO 17
<211> LENGTH: 620
<212> TYPE: DNA
<213> ORGANISM: Artificial Sequence
<220> FEATURE:
<223> OTHER INFORMATION: Description of Artificial Sequence: Synthetic
       pBR322_origin_NeoTCR Product

<400> SEQUENCE: 17

```
cgcgttgctg gcgttttttcc ataggctccg ccccccctgac gagcatcaca aaaatcgacg    60
ctcaagtcag aggtggcgaa acccgacagg actataaaga taccaggcgt ttccccctgg   120
```

```
aagctccctc gtgcgctctc ctgttccgac cctgccgctt accggatacc tgtccgcctt    180
tctcccttcg ggaagcgtgg cgctttctca tagctcacgc tgtaggtatc tcagttcggt    240
gtaggtcgtt cgctccaagc tgggctgtgt gcacgaaccc cccgttcagc ccgaccgctg    300
cgccttatcc ggtaactatc gtcttgagtc caacccggta agacacgact tatcgccact    360
ggcagcagcc actggtaaca ggattagcag agcgaggtat gtaggcggtg ctacagagtt    420
cttgaagtgg tggcctaact acggctacac tagaagaaca gtatttggta tctgcgctct    480
gctgaagcca gttaccttcg gaaaagagt tggtagctct tgatccggca acaaaccac    540 cgctggtagc ggtggttttt tgtttgcaa gcagcagatt acgcgcagaa aaaaggatc    600 tcaagaagat cctttgatct                                              620

<210> SEQ ID NO 18
<211> LENGTH: 810
<212> TYPE: DNA
<213> ORGANISM: Artificial Sequence
<220> FEATURE:
<223> OTHER INFORMATION: Description of Artificial Sequence: Synthetic
      Kanamycin resistance gene (KanR2) _NeoTCR Product

<400> SEQUENCE: 18
ttagaaaaac tcatcgagca tcaaatgaaa ctgcaattta ttcatatcag gattatcaat    60
accatatttt tgaaaagcc gtttctgtaa tgaaggagaa aactcaccga ggcagttcca    120
taggatggca agatcctggt atcggtctgc gattccgact cgtccaacat caatacaacc    180
tattaatttc ccctcgtcaa aaataaggtt atcaagtgag aaatcaccat gagtgacgac    240
tgaatccggt gagaatggca aaagtttatg catttctttc cagacttgtt caacaggcca    300
gccattacgc tcgtcatcaa aatcactcgc atcaaccaaa ccgttattca ttcgtgattg    360
cgcctgagcc agacgaaata cgcgatcgct gttaaaagga caattacaaa caggaatcga    420
atgcaaccgg cgcaggaaca ctgccagcgc atcaacaata ttttcacctg aatcaggata    480
ttcttctaat acctggaatg ctgtttttcc ggggatcgca gtggtgagta accatgcatc    540
atcaggagta cggataaaat gcttgatggt cggaagaggc ataaattccg tcagccagtt    600
tagtctgacc atctcatctg taacatcatt ggcaacgcta cctttgccat gtttcagaaa    660
caactctggc gcatcgggct tcccatacaa gcgatagatt gtcgcacctg attgcccgac    720
attatcgcga gcccatttat acccatataa atcagcatcc atgttggaat ttaatcgcgg    780
cctcgacgtt tcccgttgaa tatggctcat                                   810

<210> SEQ ID NO 19
<211> LENGTH: 99
<212> TYPE: DNA
<213> ORGANISM: Artificial Sequence
<220> FEATURE:
<223> OTHER INFORMATION: Description of Artificial Sequence: Synthetic
      Kanamycin promoter _NeoTCR Product

<400> SEQUENCE: 19
aacacccctt gtattactgt ttatgtaagc agacagtttt attgttcatg atgatatatt    60
tttatcttgt gcaatgtaac atcagagatt ttgagacac                          99

<210> SEQ ID NO 20
<211> LENGTH: 5137
<212> TYPE: DNA
<213> ORGANISM: Artificial Sequence
<220> FEATURE:
```

<223> OTHER INFORMATION: Description of Artificial Sequence: Synthetic
Complete NeoTCR Product construct with TCR97 insertion_NeoTCR
Product

<400> SEQUENCE: 20

| | | | | | |
|---|---|---|---|---|---|
| ggtaccacat | taaaaacaca | aaatcctacg | gaaatactga | agaatgagtc | tcagcactaa | 60 |
| ggaaaagcct | ccagcagctc | ctgctttctg | agggtgaagg | atagacgctg | tggctctgca | 120 |
| tgactcacta | gcactctatc | acggccatat | tctggcaggg | tcagtggctc | caactaacat | 180 |
| ttgtttggta | ctttacagtt | tattaaatag | atgtttatat | ggagaagctc | tcatttcttt | 240 |
| ctcagaagag | cctggctagg | aaggtggatg | aggcaccata | ttcattttgc | aggtgaaatt | 300 |
| cctgagatgt | aaggagctgc | tgtgacttgc | tcaaggcctt | atatcgagta | aacggtagtg | 360 |
| ctggggctta | gacgcaggtg | ttctgattta | tagttcaaaa | cctctatcaa | tgagagagca | 420 |
| atctcctggt | aatgtgatag | atttcccaac | ttaatgccaa | cataccataa | acctcccatt | 480 |
| ctgctaatgc | ccagcctaag | ttggggagac | cactccagat | tccaagatgt | acagtttgct | 540 |
| ttgctgggcc | tttttcccat | gcctgccttt | actctgccag | agttatattg | ctggggtttt | 600 |
| gaagaagatc | ctattaaata | aaagaataag | cagtattatt | aagtagccct | gcatttcagg | 660 |
| tttccttgag | tggcaggcca | ggcctggccg | tgaacgttca | ctgaaatcat | ggcctcttgg | 720 |
| ccaagattga | tagcttgtgc | ctgtccctga | gtcccagtcc | atcacgagca | gctggtttct | 780 |
| aagatgctat | ttcccgtata | aagcatgaga | ccgtgacttg | ccagcccac | agagcccgc | 840 |
| ccttgtccat | cactggcatc | tggactccag | cctgggttgg | ggcaaagagg | gaaatgagat | 900 |
| catgtcctaa | ccctgatcct | cttgtcccac | agatatccag | aaccctgacc | ctgccgtgta | 960 |
| ccagctgaga | gactctaaat | ccagtgacaa | gtctgtctgc | ctattcgaat | tcggctccgg | 1020 |
| agccactaac | ttctccctgt | tgaaacaggc | tggcgatgtt | gaagaaaacc | ccggtcctat | 1080 |
| ggccaccggc | tctagaacaa | gcctgctgct | cgcttttggc | ctgctctgcc | tcccatggct | 1140 |
| ccaagaagga | tctgctaatg | ctggtgtcac | tcagacccca | aaattccgca | tcctgaagat | 1200 |
| aggacagagc | atgacactgc | agtgtaccca | ggatatgaac | cataactaca | tgtactggta | 1260 |
| tcgacaagac | ccaggcatgg | ggctgaagct | gatttattat | tcagttggtg | ctggtatcac | 1320 |
| tgataaagga | gaagtcccga | atggctacaa | cgtctccaga | tcaaccacag | aggatttccc | 1380 |
| gctcaggctg | gagttggctg | ctccctccca | gacatctgtg | tacttctgtg | ccagctccct | 1440 |
| acaggttccc | tacaatgagc | agttcttcgg | gccagggaca | cggctcaccg | tgctagagga | 1500 |
| cctgaaaaac | gtgttccctc | caaaagtggc | cgtgttcgag | ccttctgagg | ccagatcag | 1560 |
| ccacacacag | aaagccacac | tcgtgtgtct | ggctaccggc | ttctaccccg | atcacgtgga | 1620 |
| actgtcttgg | tgggtcaacg | gcaaagaggt | gcacagcggc | gtcagcacag | atccccagcc | 1680 |
| tctgaaagaa | cagcccgctc | tgaacgacag | ccgctactgc | ctgtctagca | gactgagagt | 1740 |
| gtccgccacc | ttctggcaga | accccagaaa | ccacttcaga | tgccaggtcc | agttctacgg | 1800 |
| cctgagcgag | aacgatgagt | ggacccagga | cagagccaag | cctgtgacac | agatcgtgtc | 1860 |
| tgccgaagcc | tggggcagag | ccgattgtgg | ctttaccagc | gagtcatacc | agcagggcgt | 1920 |
| gctgtctgcc | accatcctgt | atgagatcct | gctcggcaag | gccacactgt | acgctgtgct | 1980 |
| ggtgtctgct | ctggtgctga | tggctatggt | ctcccgggag | cgcatccccg | aggcccgggc | 2040 |
| caagcggggc | agcggcgcca | ccaacttcag | cctgctgaag | caggccgcg | acgtggagga | 2100 |
| gaaccccggc | cctatggcca | caggcagcag | aacatctctg | ctgctggcct | tcggactgct | 2160 |
| gtgtctgcct | tggctgcaag | agggttccgc | cgctcagaca | gtcactcagt | ctcaaccaga | 2220 |

```
gatgtctgtg caggaggcag agaccgtgac cctgagctgc acatatgaca ccagtgagag   2280
tgattattat ttattctggt acaagcagcc tcccagcagg cagatgattc tcgttattcg   2340
ccaagaagct tataagcaac agaatgcaac agagaatcgt ttctctgtga acttccagaa   2400
agcagccaaa tccttcagtc tcaagatctc agactcacag ctgggggatg ccgcgatgta   2460
tttctgtgct tttgggaact tcaacaaatt ttactttgga tctgggacca aactcaatgt   2520
aaaaccaaat attcagaacc ccgatcctgc tgtgtatcag ctgcgcgaca gcaagagcag   2580
cgacaagagc gtgtgtttgt tcaccgattt tgattctcaa acaaatgtgt cacaaagtaa   2640
ggattctgat gtgtatatca cagacaaaac tgtgctagac atgaggtcta tggacttcaa   2700
gagcaacagt gctgtggcct ggagcaacaa atctgacttt gcatgtgcaa acgccttcaa   2760
caacagcatt attccagaag acaccttctt ccccagccca ggtaagggca gcttggtgc    2820 cttcgcaggc tgtttccttg cttcaggaat ggccaggttc tgcccagagc tctggtcaat   2880
gatgtctaaa actcctctga ttggtggtct cggccttatc cattgccacc aaaaccctct   2940
ttttactaag aaacagtgag ccttgttctg gcagtccaga gaatgacacg ggaaaaaagc   3000
agatgaagag aaggtggcag gagagggcac gtggcccagc ctcagtctct ccaactgagt   3060
tcctgcctgc ctgcctttgc tcagactgtt tgccccttac tgctcttcta ggcctcattc   3120 taagccccctt ctccaagttg cctctcctta tttctccctg tctgccaaaa aatctttccc   3180
agctcactaa gtcagtctca cgcagtcact cattaaccca ccaatcactg attgtgccgg   3240
cacatgaatg caccaggtgt tgaagtggag gaattaaaaa gtcagatgag gggtgtgccc   3300
agaggaagca ccattctagt tgggggagcc catctgtcag ctgggaaaag tccaaataac   3360
ttcagattgg aatgtgtttt aactcagggt tgagaaaaca gctaccttca ggacaaaagt   3420
cagggaaggg ctctctgaag aaatgctact tgaagatacc agccctacca agggcaggga   3480
gaggacccta tagaggcctg gacaggagc tcaatgagaa aggagaagag cagcaggcat    3540
gagttgaatg aaggaggcag ggccgggtca cagggccttc taggccatga gagggtagac   3600
aggctagccg cgttgctggc gttttttccat aggctccgcc ccctgacga gcatcacaaa   3660 aatcgacgct caagtcagag gtggcgaaac ccgacaggac tataaagata ccaggcgttt   3720 cccctggaa gctccctcgt gcgctctcct gttccgaccc tgccgcttac cggatacctg    3780
tccgcctttc tcccttcggg aagcgtggcg ctttctcata gctcacgctg taggtatctc   3840
agttcggtgt aggtcgttcg ctccaagctg ggctgtgtgc acgaaccccc cgttcagccc   3900
gaccgctgcg ccttatccgg taactatcgt cttgagtcca acccggtaag acacgactta   3960
tcgccactgg cagcagccac tggtaacagg attagcagag cgaggtatgt aggcggtgct   4020
acagagttct tgaagtggtg gcctaactac ggctacacta agaacagt atttggtatc    4080 tgcgctctgc tgaagccagt taccttcgga aaaagagttg gtagctcttg atccggcaaa   4140
caaaccaccg ctggtagcgg tggttttttt gtttgcaagc agcagattac gcgcagaaaa   4200
aaaggatctc aagaagatcc tttgatcttt agaaaaactc atcgagcatc aaatgaaact   4260
gcaatttatt catatcagga ttatcaatac catattttgt aaaaagccgt ttctgtaatg   4320
aaggagaaaa ctcaccgagg cagttccata ggatggcaag atcctggtat cggtctgcga   4380
ttccgactcg tccaacatca atacaaccta ttaatttccc ctcgtcaaaa ataaggttat   4440
caagtgagaa atcaccatga gtgacgactg aatccggtga agtggcaaa agtttatgca    4500 tttctttcca gacttgttca acaggccagc cattacgctc gtcatcaaaa tcactcgcat   4560
```

| | |
|---|---|
| caaccaaacc gttattcatt cgtgattgcg cctgagccag acgaaatacg cgatcgctgt | 4620 |
| taaaaggaca attacaaaca ggaatcgaat gcaaccggcg caggaacact gccagcgcat | 4680 |
| caacaatatt ttcacctgaa tcaggatatt cttctaatac ctggaatgct gttttccgg | 4740 |
| ggatcgcagt ggtgagtaac catgcatcat caggagtacg gataaaatgc ttgatggtcg | 4800 |
| gaagaggcat aaattccgtc agccagttta gtctgaccat ctcatctgta acatcattgg | 4860 |
| caacgctacc tttgccatgt ttcagaaaca actctggcgc atcgggcttc ccatacaagc | 4920 |
| gatagattgt cgcacctgat tgcccgacat tatcgcgagc ccatttatac ccatataaat | 4980 |
| cagcatccat gttggaattt aatcgcggcc tcgacgtttc ccgttgaata tggctcataa | 5040 |
| cacccccttgt attactgttt atgtaagcag acagttttat tgttcatgat gatatatttt | 5100 |
| tatcttgtgc aatgtaacat cagagatttt gagacac | 5137 |

<210> SEQ ID NO 21
<211> LENGTH: 5140
<212> TYPE: DNA
<213> ORGANISM: Artificial Sequence
<220> FEATURE:
<223> OTHER INFORMATION: Description of Artificial Sequence: Synthetic
      Complete NeoTCR Product construct with TCR89 insertion_NeoTCR
      Product

<400> SEQUENCE: 21

| | |
|---|---|
| ggtaccacat taaaaacaca aaatcctacg gaaatactga agaatgagtc tcagcactaa | 60 |
| ggaaaagcct ccagcagctc ctgctttctg agggtgaagg atagacgctg tggctctgca | 120 |
| tgactcacta gcactctatc acggccatat tctggcaggg tcagtggctc caactaacat | 180 |
| ttgtttggta ctttacagtt tattaaatag atgtttatat ggagaagctc tcatttcttt | 240 |
| ctcagaagag cctggctagg aaggtggatg aggcaccata ttcattttgc aggtgaaatt | 300 |
| cctgagatgt aaggagctgc tgtgacttgc tcaaggcctt atatcgagta acggtagtg | 360 |
| ctggggctta gacgcaggtg ttctgattta tagttcaaaa cctctatcaa tgagagagca | 420 |
| atctcctggt aatgtgatag atttcccaac ttaatgccaa cataccataa acctcccatt | 480 |
| ctgctaatgc ccagcctaag ttggggagac cactccagat tccaagatgt acagtttgct | 540 |
| ttgctgggcc tttttcccat gcctgccttt actctgccag agttatattg ctggggtttt | 600 |
| gaagaagatc ctattaaata aaagaataag cagtattatt aagtagccct gcatttcagg | 660 |
| tttccttgag tggcaggcca ggcctggccg tgaacgttca ctgaaatcat ggcctcttgg | 720 |
| ccaagattga tagcttgtgc ctgtccctga gtcccagtcc atcacgagca gctggtttct | 780 |
| aagatgctat ttcccgtata agcatgaga ccgtgacttg ccagccccac agagccccgc | 840 |
| ccttgtccat cactggcatc tggactccag cctgggttgg ggcaaagagg gaaatgagat | 900 |
| catgtcctaa ccctgatcct cttgtcccac agatatccag aaccctgacc ctgccgtgta | 960 |
| ccagctgaga gactctaaat ccagtgacaa gtctgtctgc ctattcgaat tcggctccgg | 1020 |
| agccactaac ttctcccctgt tgaaacaggc tggcgatgtt gaagaaaacc ccggtcctat | 1080 |
| ggccaccggc tctagaacaa gcctgctgct cgcttttggc ctgctctgcc tcccatggct | 1140 |
| ccaagaagga tctgctgatg ctggaatcac ccagagccca agatacaaga tcacagagac | 1200 |
| aggaaggcag gtgaccttga tgtgtcacca gacttggagc cacagctata tgttctggta | 1260 |
| tcgacaagac ctgggacatg ggctgaggct gatctattac tcagcagctg ctgatattac | 1320 |
| agataaagga gaagtctccg atggctatgt tgtctccaga tccaagacag agaatttccc | 1380 |
| cctcactctg gagtcagcta cccgctccca gacatctgtg tatttctgcg ccagcagtga | 1440 |

```
ggacagttac gagcagtact tcgggccggg caccaggctc acggtcacag aggacctgaa    1500
aaacgtgttc cctccaaaag tggccgtgtt cgagccttct gaggccgaga tcagccacac    1560
acagaaagcc acactcgtgt gtctggctac cggcttctac cccgatcacg tggaactgtc    1620
ttggtgggtc aacggcaaag aggtgcacag cggcgtcagc acagatcccc agcctctgaa    1680
agaacagccc gctctgaacg acagccgcta ctgcctgtct agcagactga gagtgtccgc    1740
caccttctgg cagaacccca gaaaccactt cagatgccag gtccagttct acggcctgag    1800
cgagaacgat gagtggaccc aggacagagc caagcctgtg acacagatcg tgtctgccga    1860
agcctggggc agagccgatt gtggctttac cagcgagtca taccagcagg gcgtgctgtc    1920
tgccaccatc ctgtatgaga tcctgctcgg caaggccaca ctgtacgctg tgctggtgtc    1980
tgctctggtg ctgatggcta tggtctcccg ggagcgcatc cccgaggccc gggccaagcg    2040
gggcagcggc gccaccaact tcagcctgct gaagcaggcc ggcgacgtgg aggagaaccc    2100
cggcccctat gccacaggca gcagaacatc tctgctgctg gccttcggac tgctgtgtct    2160
gccttggctg caagagggtt ccgccgccca gtcagtgacc cagcctgaca tccacatcac    2220
tgtctctgaa ggagcctcac tggagttgag atgtaactat tcctatgggg caacacctta    2280
tctcttctgg tatgtccagt cccccggcca aggcctccag ctgctcctga gtacttttc    2340 aggagacact ctggttcaag cattaaagg ctttgaggct gaatttaaga ggagtcaatc    2400
ttccttcaat ctgaggaaac cctctgtgca ttggagtgat gctgctgagt acttctgtgc    2460
tgtgggtgaa ttggacacag gctttcagaa acttgtattt ggaactggca cccgacttct    2520
ggtcagtcca aatattcaga accccgatcc tgctgtgtat cagctgcgcg acagcaagag    2580
cagcgacaag agcgtgtgtt tgttcaccga ttttgattct caaacaaatg tgtcacaaag    2640
taaggattct gatgtgtata tcacagacaa aactgtgcta gacatgaggt ctatggactt    2700
caagagcaac agtgctgtgg cctggagcaa caaatctgac tttgcatgtg caaacgcctt    2760
caacaacagc attattccag aagacacctt cttccccagc ccaggtaagg gcagctttgg    2820
tgccttcgca ggctgtttcc ttgcttcagg aatggccagg ttctgcccag agctctggtc    2880
aatgatgtct aaaactcctc tgattggtgg tctcggcctt atccattgcc accaaaaccc    2940 tcttttact aagaaacagt gagccttgtt ctggcagtcc agagaatgac acgggaaaaa    3000
agcagatgaa gagaaggtgg caggagaggg cacgtggccc agcctcagtc tctccaactg    3060
agttcctgcc tgcctgcctt tgctcagact gtttgcccct tactgctctt ctaggcctca    3120
ttctaagccc cttctccaag ttgcctctcc ttatttctcc ctgtctgcca aaaatctttt    3180
cccagctcac taagtcagtc tcacgcagtc actcattaac ccaccaatca ctgattgtgc    3240
cggcacatga atgcaccagg tgttgaagtg gaggaattaa aaagtcagat gaggggtgtg    3300
cccagaggaa gcaccattct agttggggga gcccatctgt cagctgggaa aagtccaaat    3360
aacttcagat tggaatgtgt tttaactcag ggttgagaaa acagctacct tcaggacaaa    3420
agtcagggaa gggctctctg aagaaatgct acttgaagat accagcccta ccaagggcag    3480
ggagaggacc ctatagaggc ctgggacagg agctcaatga gaaggagaa gagcagcagg    3540 catgagttga atgaaggagg cagggccggg tcacagggcc ttctaggcca tgagagggta    3600
gacaggctag ccgcgttgct ggcgtttttc cataggctcc gccccctga cgagcatcac    3660 aaaaatcgac gctcaagtca gaggtggcga aacccgacag gactataaag ataccaggcg    3720
tttccccctg gaagctccct cgtgcgctct cctgttccga ccctgccgct taccggatac    3780
```

```
ctgtccgcct ttctcccttc gggaagcgtg gcgctttctc atagctcacg ctgtaggtat    3840
ctcagttcgg tgtaggtcgt tcgctccaag ctgggctgtg tgcacgaacc ccccgttcag    3900
cccgaccgct gcgccttatc cggtaactat cgtcttgagt ccaacccggt aagacacgac    3960
ttatcgccac tggcagcagc cactggtaac aggattagca gagcgaggta tgtaggcggt    4020
gctacagagt tcttgaagtg gtggcctaac tacggctaca ctagaagaac agtatttggt    4080
atctgcgctc tgctgaagcc agttaccttc ggaaaaagag ttggtagctc ttgatccggc    4140
aaacaaacca ccgctggtag cggtggtttt tttgtttgca agcagcagat tacgcgcaga    4200
aaaaaaggat ctcaagaaga tcctttgatc tttagaaaaa ctcatcgagc atcaaatgaa    4260
actgcaattt attcatatca ggattatcaa taccatattt tgaaaaagc cgtttctgta    4320 atgaaggaga aaactcaccg aggcagttcc ataggatggc aagatcctgg tatcggtctg    4380
cgattccgac tcgtccaaca tcaatacaac ctattaattt ccctcgtca aaataaggt     4440 tatcaagtga gaaatcacca tgagtgacga ctgaatccgg tgagaatggc aaaagtttat    4500
gcatttcttt ccagacttgt tcaacaggcc agccattacg ctcgtcatca aaatcactcg    4560
catcaaccaa accgttattc attcgtgatt gcgcctgagc cagacgaaat acgcgatcgc    4620
tgttaaaagg acaattacaa acaggaatcg aatgcaaccg gcgcaggaac actgccagcg    4680
catcaacaat attttcacct gaatcaggat attcttctaa tacctggaat gctgttttc     4740 cggggatcgc agtggtgagt aaccatgcat catcaggagt acggataaaa tgcttgatgg    4800
tcggaagagg cataaattcc gtcagccagt ttagtctgac catctcatct gtaacatcat    4860
tggcaacgct acctttgcca tgtttcagaa acaactctgg cgcatcgggc ttcccataca    4920
agcgatagat tgtcgcacct gattgcccga cattatcgcg agcccattta tacccatata    4980
aatcagcatc catgttggaa tttaatcgcg gcctcgacgt ttcccgttga atatggctca    5040
taacacccct tgtattactg tttatgtaag cagacagttt tattgttcat gatgatatat    5100
ttttatcttg tgcaatgtaa catcagagat tttgagacac                           5140

<210> SEQ ID NO 22
<211> LENGTH: 926
<212> TYPE: DNA
<213> ORGANISM: Artificial Sequence
<220> FEATURE:
<223> OTHER INFORMATION: Description of Artificial Sequence: Synthetic
      Left HR arm_CD8 Product 1

<400> SEQUENCE: 22
acattaaaaa cacaaaatcc tacgaaaata ctgaagaatg agtctcagca ctaaggaaaa      60
gcctccagca gctcctgctt tctgagggtg aaggatagac gctgtggctc tgcatgactc     120
actagcactc tatcacggcc atattctggc agggtcagtg gctccaacta acatttgttt     180
ggtactttac agtttattaa atagatgttt atatggagaa gctctcattt ctttctcaga     240
agagcctggc taggaaggtg gatgaggcac catattcatt ttgcaggtga aattcctgag     300
atgtaaggag ctgctgtgac ttgctcaagg ccttatatcg agtaaacggt agtgctgggg     360
cttagacgca ggtgttctga tttatagttc aaaacctcta tcaatgagag agcaatctcc     420
tggtaatgtg atagatttcc caacttaatg ccaacatacc ataaacctcc cattctgcta     480
atgcccagcc taagttgggg agaccactcc agattccaag atgtacagtt tgctttgctg     540 ggccttttc ccatgcctgc ctttactctg ccagagttat attgctgggg ttttgaagaa      600
gatcctatta aataaaagaa taagcagtat tattaagtag ccctgcattt caggtttcct     660
```

```
tgagtggcag gccaggcctg gccgtgaacg ttcactgaaa tcatggcctc ttggccaaga    720
ttgatagctt gtgcctgtcc ctgagtccca gtccatcacg agcagctggt ttctaagatg    780
ctatttcccg tataaagcat gagaccgtga cttgccagcc ccacagagcc ccgcccttgt    840
ccatcactgg catctggact ccagcctggg ttggggcaaa gagggaaatg agatcatgtc    900
ctaaccctga tcctcttgtc ccacag                                          926

<210> SEQ ID NO 23
<211> LENGTH: 74
<212> TYPE: DNA
<213> ORGANISM: Artificial Sequence
<220> FEATURE:
<223> OTHER INFORMATION: Description of Artificial Sequence: Synthetic
      TRAC CDS_CD8 Product 1

<400> SEQUENCE: 23
atatccagaa ccctgaccct gccgtgtacc agctgagaga ctctaaatcc agtgacaagt    60
ctgtctgcct attc                                                       74

<210> SEQ ID NO 24
<211> LENGTH: 15
<212> TYPE: DNA
<213> ORGANISM: Artificial Sequence
<220> FEATURE:
<223> OTHER INFORMATION: Description of Artificial Sequence: Synthetic
      GSG Linker_CD8 Product 1

<400> SEQUENCE: 24
gaattcggct ccgga                                                      15

<210> SEQ ID NO 25
<211> LENGTH: 57
<212> TYPE: DNA
<213> ORGANISM: Artificial Sequence
<220> FEATURE:
<223> OTHER INFORMATION: Description of Artificial Sequence: Synthetic
      P2A_CD8 Product 1

<400> SEQUENCE: 25
gccactaact tcagcctgtt gaagcaggcc ggcgacgttg aggaaaaccc cggtcct       57

<210> SEQ ID NO 26
<211> LENGTH: 63
<212> TYPE: DNA
<213> ORGANISM: Artificial Sequence
<220> FEATURE:
<223> OTHER INFORMATION: Description of Artificial Sequence: Synthetic
      CD8A Signal peptide_CD8 Product 1

<400> SEQUENCE: 26
atggccttac cagtgaccgc cttgctcctg ccgctggcct tgctgctcca cgccgccagg    60
ccg                                                                   63

<210> SEQ ID NO 27
<211> LENGTH: 483
<212> TYPE: DNA
<213> ORGANISM: Artificial Sequence
<220> FEATURE:
<223> OTHER INFORMATION: Description of Artificial Sequence: Synthetic
      CD8A Extracellular domain_CD8 Product 1

<400> SEQUENCE: 27
agccagttcc gggtgtcgcc gctggatcgg acctggaacc tgggcgagac agtggagctg    60
```

-continued

```
aagtgccagg tgctgctgtc caacccgacg tcgggctgct cgtggctctt ccagccgcgc    120
ggcgccgccg ccagtcccac cttcctccta tacctctccc aaaacaagcc caaggcggcc    180
gaggggctgg acacccagcg gttctcgggc aagaggttgg gggacacctt cgtcctcacc    240
ctgagcgact ccgccgaga gaacgagggc tactatttct gctcggccct gagcaactcc    300
atcatgtact tcagccactt cgtgccggtc ttcctgccag cgaagcccac cacgacgcca    360
gcgccgcgac caccaacacc ggcgcccacc atcgcgtcgc agcccctgtc cctgcgccca    420
gaggcgtgcc ggccagcggc ggggggcgca gtgcacacga gggggctgga cttcgcctgt    480
gat                                                                 483
```

<210> SEQ ID NO 28
<211> LENGTH: 63
<212> TYPE: DNA
<213> ORGANISM: Artificial Sequence
<220> FEATURE:
<223> OTHER INFORMATION: Description of Artificial Sequence: Synthetic
      CD8A transmembrane domain_CD8 Product 1

<400> SEQUENCE: 28

```
atctacatct gggcgccctt ggccgggact tgtggggtcc ttctcctgtc actggttatc    60
acc                                                                  63
```

<210> SEQ ID NO 29
<211> LENGTH: 96
<212> TYPE: DNA
<213> ORGANISM: Artificial Sequence
<220> FEATURE:
<223> OTHER INFORMATION: Description of Artificial Sequence: Synthetic
      CD8A Intracellular domain_CD8 Product 1

<400> SEQUENCE: 29

```
ctttactgca accacaggaa ccgaagacgt gtttgcaaat gtccccggcc tgtggtcaaa    60
tcgggagaca agcccagcct ttcggcgaga tacgtc                              96
```

<210> SEQ ID NO 30
<211> LENGTH: 12
<212> TYPE: DNA
<213> ORGANISM: Artificial Sequence
<220> FEATURE:
<223> OTHER INFORMATION: Description of Artificial Sequence: Synthetic
      Furin cleavage site_CD8 Product 1

<400> SEQUENCE: 30

```
agggctaaac gg                                                        12
```

<210> SEQ ID NO 31
<211> LENGTH: 15
<212> TYPE: DNA
<213> ORGANISM: Artificial Sequence
<220> FEATURE:
<223> OTHER INFORMATION: Description of Artificial Sequence: Synthetic
      GSG Linker_CD8 Product 1

<400> SEQUENCE: 31

```
gaattcggct ccgga                                                     15
```

<210> SEQ ID NO 32
<211> LENGTH: 57
<212> TYPE: DNA
<213> ORGANISM: Artificial Sequence
<220> FEATURE:
<223> OTHER INFORMATION: Description of Artificial Sequence: Synthetic P2A_CD8 Product 1

<400> SEQUENCE: 32
gccactaact tctccctgtt gaaacaggct ggcgatgttg aagaaaaccc cggtcct      57

<210> SEQ ID NO 33
<211> LENGTH: 78
<212> TYPE: DNA
<213> ORGANISM: Artificial Sequence
<220> FEATURE:
<223> OTHER INFORMATION: Description of Artificial Sequence: Synthetic
      HGH/SS/2_CD8 Product 1

<400> SEQUENCE: 33
atggccaccg gctctagaac aagcctgctg ctcgcttttg cctgctctg cctcccatgg    60 ctccaagaag gatctgct                                                 78

<210> SEQ ID NO 34
<211> LENGTH: 345
<212> TYPE: DNA
<213> ORGANISM: Artificial Sequence
<220> FEATURE:
<223> OTHER INFORMATION: Description of Artificial Sequence: Synthetic
      Exemplary TRB_VDJ (TCR097) _CD8 Product 1

<400> SEQUENCE: 34
aatgctggtg tcactcagac cccaaaattc cgcatcctga agataggaca gagcatgaca    60
ctgcagtgta cccaggatat gaaccataac tacatgtact ggtatcgaca gacccaggc   120 atggggctga agctgattta ttattcagtt ggtgctggta tcactgataa aggagaagtc   180
ccgaatggct acaacgtctc cagatcaacc acagaggatt tcccgctcag gctggagttg   240
gctgctccct cccagacatc tgtgtacttc tgtgccagct ccctacaggt tccctacaat   300
gagcagttct tcgggccagg gacacggctc accgtgctag aggac                   345

<210> SEQ ID NO 35
<211> LENGTH: 534
<212> TYPE: DNA
<213> ORGANISM: Artificial Sequence
<220> FEATURE:
<223> OTHER INFORMATION: Description of Artificial Sequence: Synthetic
      TCR-beta/constant_CD8 Product 1

<400> SEQUENCE: 35
ctgaaaaacg tgttccctcc aaaagtggcc gtgttcgagc cttctgaggc cgagatcagc    60
cacacacaga aagccacact cgtgtgtctg gctaccggct tctacccga tcacgtggaa    120 ctgtcttggt gggtcaacgg caaagaggtg cacagcggcg tcagcacaga tccccagcct   180
ctgaaagaac agcccgctct gaacgacagc cgctactgcc tgtctagcag actgagagtg   240
tccgccacct tctggcagaa ccccagaaac cacttcagat gccaggtcca gttctacggc   300
ctgagcgaga cgatgagtg gacccaggac agagccaagc tgtgacaca gatcgtgtct   360 gccgaagcct ggggcagagc cgattgtggc tttaccagcg agtcatacca gcagggcgtg   420
ctgtctgcca ccatcctgta tgagatcctg ctcggcaagg ccacactgta cgctgtgctg   480
gtgtctgctc tggtgctgat ggctatggtc tcccgggagc gcatccccga ggcc         534

<210> SEQ ID NO 36
<211> LENGTH: 12
<212> TYPE: DNA
<213> ORGANISM: Artificial Sequence
<220> FEATURE:

<223> OTHER INFORMATION: Description of Artificial Sequence: Synthetic
      Furin cleavage site_CD8 Product 1

<400> SEQUENCE: 36
cgggccaagc gg                                                              12

<210> SEQ ID NO 37
<211> LENGTH: 9
<212> TYPE: DNA
<213> ORGANISM: Artificial Sequence
<220> FEATURE:
<223> OTHER INFORMATION: Description of Artificial Sequence: Synthetic
      GSG linker_CD8 Product 1

<400> SEQUENCE: 37 ggcagcggc                                                                   9

<210> SEQ ID NO 38
<211> LENGTH: 57
<212> TYPE: DNA
<213> ORGANISM: Artificial Sequence
<220> FEATURE:
<223> OTHER INFORMATION: Description of Artificial Sequence: Synthetic
      P2A_CD8 Product 1

<400> SEQUENCE: 38
gccaccaact tcagcctgct gaagcaggcc ggcgacgtgg aggagaaccc cggccct            57

<210> SEQ ID NO 39
<211> LENGTH: 78
<212> TYPE: DNA
<213> ORGANISM: Artificial Sequence
<220> FEATURE:
<223> OTHER INFORMATION: Description of Artificial Sequence: Synthetic
      HGH/SS_CD8 Product 1

<400> SEQUENCE: 39
atggccacag gcagcagaac atctctgctg ctggccttcg gactgctgtg tctgccttgg          60
ctgcaagagg gttccgcc                                                        78

<210> SEQ ID NO 40
<211> LENGTH: 337
<212> TYPE: DNA
<213> ORGANISM: Artificial Sequence
<220> FEATURE:
<223> OTHER INFORMATION: Description of Artificial Sequence: Synthetic
      Exemplary TRA-VDJ (TCR097) _CD8 Product 1

<400> SEQUENCE: 40
gctcagacag tcactcagtc tcaaccagag atgtctgtgc aggaggcaga gaccgtgacc          60
ctgagctgca catatgacac cagtgagagt gattattatt tattctgtgta caagcagcct        120 cccagcaggc agatgattct cgttattcgc caagaagctt ataagcaaca gaatgcaaca        180
gagaatcgtt tctctgtgaa cttccagaaa gcagccaaat ccttcagtct caagatctca        240
gactcacagc tgggggatgc cgcgatgtat ttctgtgctt ttgggaactt caacaaattt        300
tactttggat ctgggaccaa actcaatgta aaaccaa                                  337

<210> SEQ ID NO 41
<211> LENGTH: 74
<212> TYPE: DNA
<213> ORGANISM: Artificial Sequence
<220> FEATURE:
<223> OTHER INFORMATION: Description of Artificial Sequence: Synthetic
      TCR-alpha/constant_CD8 Product 1

<400> SEQUENCE: 41
atattcagaa ccccgatcct gctgtgtatc agctgcgcga cagcaagagc agcgacaaga    60
gcgtgtgttt gttc    74

<210> SEQ ID NO 42
<211> LENGTH: 200
<212> TYPE: DNA
<213> ORGANISM: Artificial Sequence
<220> FEATURE:
<223> OTHER INFORMATION: Description of Artificial Sequence: Synthetic
      TRAC CDS/right HR arm_CD8 Product 1

<400> SEQUENCE: 42
accgattttg attctcaaac aaatgtgtca caaagtaagg attctgatgt gtatatcaca    60
gacaaaactg tgctagacat gaggtctatg gacttcaaga gcaacagtgc tgtggcctgg    120
agcaacaaat ctgactttgc atgtgcaaac gccttcaaca acagcattat tccagaagac    180
accttcttcc ccagcccagg    200

<210> SEQ ID NO 43
<211> LENGTH: 800
<212> TYPE: DNA
<213> ORGANISM: Artificial Sequence
<220> FEATURE:
<223> OTHER INFORMATION: Description of Artificial Sequence: Synthetic
      Right HR arm_CD8 Product 1

<400> SEQUENCE: 43
taagggcagc tttggtgcct tcgcaggctg tttccttgct tcaggaatgg ccaggttctg    60
cccagagctc tggtcaatga tgtctaaaac tcctctgatt ggtggtctcg gccttatcca    120
ttgccaccaa aaccctcttt ttactaagaa acagtgagcc ttgttctggc agtccagaga    180
atgacacggg aaaaaagcag atgaagagaa ggtggcagga gagggcacgt ggcccagcct    240
cagtctctcc aactgagttc ctgcctgcct gcctttgctc agactgtttg ccccttactg    300
ctcttctagg cctcattcta agccccttct ccaagttgcc tctccttatt tctccctgtc    360
tgccaaaaaa tctttcccag ctcactaagt cagtctcacg cagtcactca ttaacccacc    420
aatcactgat tgtgccggca catgaatgca ccaggtgttg aagtggagga attaaaaagt    480
cagatgaggg gtgtgcccag aggaagcacc attctagttg ggggagccca tctgtcagct    540
gggaaaagtc caaataactt cagattggaa tgtgttttaa ctcagggttg agaaaacagc    600
taccttcagg acaaaagtca gggaagggct ctctgaagaa atgctacttg aagataccag    660
ccctaccaag ggcagggaga ggaccctata gaggcctggg acaggagctc aatgagaaag    720
gagaagagca gcaggcatga gttgaatgaa ggaggcaggg ccgggtcaca gggccttcta    780
ggccatgaga gggtagacag    800

<210> SEQ ID NO 44
<211> LENGTH: 6
<212> TYPE: DNA
<213> ORGANISM: Artificial Sequence
<220> FEATURE:
<223> OTHER INFORMATION: Description of Artificial Sequence: Synthetic
      Artificial Sequence_CD8 Product 1

<400> SEQUENCE: 44 gctagc    6

<210> SEQ ID NO 45
<211> LENGTH: 620
<212> TYPE: DNA
<213> ORGANISM: Artificial Sequence
<220> FEATURE:
<223> OTHER INFORMATION: Description of Artificial Sequence: Synthetic
      pBR322_origin_CD8 Product 1

<400> SEQUENCE: 45

| | | | | | | |
|---|---|---|---|---|---|---|
| cgcgttgctg | gcgttttcc | ataggctccg | ccccctgac | gagcatcaca | aaaatcgacg | 60 |
| ctcaagtcag | aggtggcgaa | acccgacagg | actataaaga | taccaggcgt | ttccccctgg | 120 |
| aagctccctc | gtgcgctctc | ctgttccgac | cctgccgctt | accggatacc | tgtccgcctt | 180 |
| tctcccttcg | ggaagcgtgg | cgctttctca | tagctcacgc | tgtaggtatc | tcagttcggt | 240 |
| gtaggtcgtt | cgctccaagc | tgggctgtgt | gcacgaaccc | cccgttcagc | ccgaccgctg | 300 |
| cgccttatcc | ggtaactatc | gtcttgagtc | aacccggta | agacacgact | tatcgccact | 360 |
| ggcagcagcc | actggtaaca | ggattagcag | agcgaggtat | gtaggcggtg | ctacagagtt | 420 |
| cttgaagtgg | tggcctaact | acggctacac | tagaagaaca | gtatttggta | tctgcgctct | 480 |
| gctgaagcca | gttaccttcg | gaaaaagagt | tggtagctct | tgatccggca | aacaaaccac | 540 |
| cgctggtagc | ggtggttttt | ttgtttgcaa | gcagcagatt | acgcgcagaa | aaaaggatc | 600 |
| tcaagaagat | cctttgatct | | | | | 620 |

<210> SEQ ID NO 46
<211> LENGTH: 810
<212> TYPE: DNA
<213> ORGANISM: Artificial Sequence
<220> FEATURE:
<223> OTHER INFORMATION: Description of Artificial Sequence: Synthetic
      Kanamycin resistance (KanR2) _CD8 Product 1

<400> SEQUENCE: 46

| | | | | | | |
|---|---|---|---|---|---|---|
| ttagaaaaac | tcatcgagca | tcaaatgaaa | ctgcaattta | ttcatatcag | gattatcaat | 60 |
| accatatttt | tgaaaaagcc | gtttctgtaa | tgaaggagaa | aactcaccga | ggcagttcca | 120 |
| taggatggca | agatcctggt | atcggtctgc | gattccgact | cgtccaacat | caatacaacc | 180 |
| tattaattc | ccctcgtcaa | aataaggtt | atcaagtgag | aaatcaccat | gagtgacgac | 240 |
| tgaatccggt | gagaatggca | aaagtttatg | catttctttc | cagacttgtt | caacaggcca | 300 |
| gccattacgc | tcgtcatcaa | aatcactcgc | atcaaccaaa | ccgttattca | ttcgtgattg | 360 |
| cgcctgagcc | agacgaaata | cgcgatcgct | gttaaaagga | caattacaaa | caggaatcga | 420 |
| atgcaaccgg | cgcaggaaca | ctgccagcgc | atcaacaata | ttttcacctg | aatcaggata | 480 |
| ttcttctaat | acctggaatg | ctgttttttcc | ggggatcgca | gtggtgagta | accatgcatc | 540 |
| atcaggagta | cggataaaat | gcttgatggt | cggaagaggc | ataaattccg | tcagccagtt | 600 |
| tagtctgacc | atctcatctg | taacatcatt | ggcaacgcta | cctttgccat | gtttcagaaa | 660 |
| caactctggc | gcatcgggct | tcccatacaa | gcgatagatt | gtcgcacctg | attgcccgac | 720 |
| attatcgcga | gcccatttat | acccatataa | atcagcatcc | atgttggaat | ttaatcgcgg | 780 |
| cctcgacgtt | tcccgttgaa | tatggctcat | | | | 810 |

<210> SEQ ID NO 47
<211> LENGTH: 99
<212> TYPE: DNA
<213> ORGANISM: Artificial Sequence
<220> FEATURE:
<223> OTHER INFORMATION: Description of Artificial Sequence: Synthetic
      Kanamycin promoter_CD8 Product 1

<400> SEQUENCE: 47

```
aacacccctt gtattactgt ttatgtaagc agacagtttt attgttcatg atgatatatt    60
tttatcttgt gcaatgtaac atcagagatt ttgagacac                          99
```

<210> SEQ ID NO 48
<211> LENGTH: 5926
<212> TYPE: DNA
<213> ORGANISM: Artificial Sequence
<220> FEATURE:
<223> OTHER INFORMATION: Description of Artificial Sequence: Synthetic
   Complete CD8 Product 1 construct with TCR97 insertion_CD8 Product
   1

<400> SEQUENCE: 48

```
ggtaccacat taaaaacaca aaatcctacg gaaatactga agaatgagtc tcagcactaa     60
ggaaaagcct ccagcagctc ctgctttctg agggtgaagg atagacgctg tggctctgca   120
tgactcacta gcactctatc acggccatat tctggcaggg tcagtggctc caactaacat   180
ttgtttggta ctttacagtt tattaaatag atgtttatat ggagaagctc tcatttcttt   240
ctcagaagag cctggctagg aaggtggatg aggcaccata ttcattttgc aggtgaaatt   300
cctgagatgt aaggagctgc tgtgacttgc tcaaggcctt atatcgagta aacggtagtg   360
ctggggctta gacgcaggtg ttctgattta tagttcaaaa cctctatcaa tgagagagca   420
atctcctggt aatgtgatag atttcccaac ttaatgccaa cataccataa acctcccatt   480
ctgctaatgc ccagcctaag ttggggagac cactccagat tccaagatgt acagtttgct   540
ttgctgggcc ttttttccat gcctgccttt actctgccag agttatattg ctggggtttt   600
gaagaagatc ctattaaata aaagaataag cagtattatt aagtagccct gcatttcagg   660
tttccttgag tggcaggcca ggcctggccg tgaacgttca ctgaaatcat ggcctcttgg   720
ccaagattga tagcttgtgc ctgtccctga gtcccagtcc atcacgagca gctggtttct   780
aagatgctat ttcccgtata aagcatgaga ccgtgacttg ccagccccac agagcccgc    840
ccttgtccat cactggcatc tggactccag cctgggttgg ggcaaagagg gaaatgagat   900
catgtcctaa ccctgatcct cttgtcccac agatatccag aaccctgacc ctgccgtgta   960
ccagctgaga gactctaaat ccagtgacaa gtctgtctgc ctattcgaat tcggctccgg   1020
agccactaac ttcagcctgt tgaagcaggc cggcgacgtt gaggaaaacc ccggtcctat   1080
ggccttacca gtgaccgcct tgctcctgcc gctggccttg ctgctccacg ccgccaggcc   1140
gagccagttc cgggtgtcgc cgctggatcg gacctggaac ctgggcgaga cagtggagct   1200
gaagtgccag gtgctgctgt ccaacccgac gtcgggctgc tcgtggctct ccagccgcg   1260
cggcgccgcc gccagtccca ccttcctcct atacctctcc caaaacaagc caaggcggc   1320
cgaggggctg gacacccagc ggttctcggg caagaggttg ggggacacct tcgtcctcac   1380
cctgagcgac ttccgccgag agaacgaggg ctactatttc tgctcggccc tgagcaactc   1440
catcatgtac ttcagccact cgtgccggt cttcctgcca gcgaagccca ccacgacgcc   1500
agcgccgcga ccaccaacac cggcgcccac catcgcgtcg cagcccctgt ccctgcgccc   1560
agaggcgtgc cggccagcgg cggggggcgc agtgcacacg agggggctgg acttcgcctg   1620
tgatatctac atctgggcgc ccttggccgg gacttgtggg gtccttctcc tgtcactggt   1680
tatcacccnt tactgcaacc acaggaaccg aagacgtgtt tgcaaatgtc cccggcctgt   1740
ggtcaaatcg ggagacaagc ccagcctttc ggcgagatac gtcagggcta aacgggaatt   1800
```

```
cggctccgga gccactaact tctccctgtt gaaacaggct ggcgatgttg aagaaaaccc      1860
cggtcctatg gccaccggct ctagaacaag cctgctgctc gcttttggcc tgctctgcct      1920
cccatggctc caagaaggat ctgctaatgc tggtgtcact cagaccccaa aattccgcat      1980
cctgaagata ggacagagca tgacactgca gtgtacccag gatatgaacc ataactacat      2040
gtactggtat cgacaagacc caggcatggg gctgaagctg atttattatt cagttggtgc      2100
tggtatcact gataaaggag aagtcccgaa tggctacaac gtctccagat caaccacaga      2160
ggatttcccg ctcaggctgg agttggctgc tccctcccag acatctgtgt acttctgtgc      2220
cagctcccta caggttccct acaatgagca gttcttcggg ccagggacac ggctcaccgt      2280
gctagaggac ctgaaaaacg tgttccctcc aaaagtggcc gtgttcgagc cttctgaggc      2340
cgagatcagc cacacacaga aagccacact cgtgtgtctg gctaccggct ctaccccga      2400 tcacgtggaa ctgtcttggt gggtcaacgg caaagaggtg cacagcggcg tcagcacaga      2460
tccccagcct ctgaaagaac agcccgctct gaacgacagc cgctactgcc tgtctagcag      2520
actgagagtg tccgccacct tctggcagaa ccccagaaac cacttcagat gccaggtcca      2580
gttctacggc ctgagcgaga cgatgagtg gacccaggac agagccaagc ctgtgacaca      2640
gatcgtgtct gccgaagcct ggggcagagc cgattgtggc tttaccagcg agtcatacca      2700
gcagggcgtg ctgtctgcca ccatcctgta tgagatcctg ctcggcaagg ccacactgta      2760
cgctgtgctg gtgtctgctc tggtgctgat ggctatggtc tcccgggagc gcatccccga      2820
ggcccgggcc aagcggggca gcggcgccac caacttcagc ctgctgaagc aggccggcga      2880
cgtggaggag aaccccggcc ctatggccac aggcagcaga acatctctgc tgctggcctt      2940
cggactgctg tgtctgcctt ggctgcaaga gggttccgcc gctcagacag tcactcagtc      3000
tcaaccagag atgtctgtgc aggaggcaga gaccgtgacc ctgagctgca catatgacac      3060
cagtgagagt gattattatt tattctggta caagcagcct cccagcaggc agatgattct      3120
cgttattcgc caagaagctt ataagcaaca gaatgcaaca gagaatcgtt tctctgtgaa      3180
cttccagaaa gcagccaaat ccttcagtct caagatctca gactcacagc tgggggatgc      3240
cgcgatgtat ttctgtgctt ttgggaactt caacaaattt acttttggat ctgggaccaa      3300
actcaatgta aaaccaaata ttcagaaccc cgatcctgct gtgtatcagc tgcgcgacag      3360
caagagcagc gacaagagcg tgtgtttgtt caccgatttt gattctcaaa caatgtgtc      3420 acaaagtaag gattctgatg tgtatatcac agacaaaact gtgctagaca tgaggtctat      3480
ggacttcaag agcaacagtg ctgtggcctg gagcaacaaa tctgactttg catgtgcaaa      3540
cgccttcaac aacagcatta ttccagaaga caccttcttc cccagcccag gtaagggcag      3600
ctttggtgcc ttcgcaggct gtttccttgc ttcaggaatg ccaggttct gcccagagct      3660 ctggtcaatg atgtctaaaa ctcctctgat tggtggtctc ggccttatcc attgccacca      3720
aaaccctctt tttactaaga aacagtgagc cttgttctgg cagtccagag aatgacacgg      3780
gaaaaaagca gatgaagaga aggtggcagg agagggcacg tggcccagcc tcagtctctc      3840
caactgagtt cctgcctgcc tgcctttgct cagactgttt gccccttact gctcttctag      3900
gcctcattct aagcccttc tccaagttgc ctctccttat ttctccctgt ctgccaaaaa      3960
atctttccca gctcactaag tcagtctcac gcagtcactc attaacccac caatcactga      4020
ttgtgccggc acatgaatgc accaggtgtt gaagtggagg aattaaaaag tcagatgagg      4080
ggtgtgccca gaggaagcac cattctagtt ggggagccc atctgtcagc tgggaaaagt      4140
ccaaataact tcagattgga atgtgtttta actcagggtt gagaaaacag ctaccttcag      4200
```

```
gacaaaagtc agggaagggc tctctgaaga aatgctactt gaagatacca gccctaccaa    4260
gggcagggag aggaccctat agaggcctgg gacaggagct caatgagaaa ggagaagagc    4320
agcaggcatg agttgaatga aggaggcagg gccgggtcac agggccttct aggccatgag    4380
agggtagaca ggctagccgc gttgctggcg ttttccata ggctccgccc ccctgacgag     4440
catcacaaaa atcgacgctc aagtcagagg tggcgaaacc cgacaggact ataaagatac    4500
caggcgtttc cccctggaag ctccctcgtg cgctctcctg ttccgaccct gccgcttacc    4560
ggatacctgt ccgcctttct cccttcggga agcgtggcgc tttctcatag ctcacgctgt    4620
aggtatctca gttcggtgta ggtcgttcgc tccaagctgg gctgtgtgca cgaaccccc     4680 gttcagcccg accgctgcgc cttatccggt aactatcgtc ttgagtccaa cccggtaaga    4740
cacgacttat cgccactggc agcagccact ggtaacagga ttagcagagc gaggtatgta    4800
ggcggtgcta cagagttctt gaagtggtgg cctaactacg gctacactag aagaacagta    4860
tttggtatct gcgctctgct gaagccagtt accttcggaa aaagagttgg tagctcttga    4920
tccggcaaac aaaccaccgc tggtagcggt ggtttttttg tttgcaagca gcagattacg    4980
cgcagaaaaa aaggatctca agaagatcct ttgatcttta gaaaaactca tcgagcatca    5040
aatgaaactg caatttattc atatcaggat tatcaatacc atattttga aaaagccgtt    5100 tctgtaatga aggagaaaac tcaccgaggc agttccatag gatggcaaga tcctggtatc    5160
ggtctgcgat tccgactcgt ccaacatcaa tacaacctat aatttcccc tcgtcaaaaa    5220 taaggttatc aagtgagaaa tcaccatgag tgacgactga atccggtgag aatggcaaaa    5280
gtttatgcat ttctttccag acttgttcaa caggccagcc attacgctcg tcatcaaaat    5340
cactcgcatc aaccaaaccg ttattcattc gtgattgcgc ctgagccaga cgaaatacgc    5400
gatcgctgtt aaaaggacaa ttacaaacag gaatcgaatg caaccggcgc aggaacactg    5460
ccagcgcatc aacaatattt tcacctgaat caggatattc ttctaatacc tggaatgctg    5520 ttttccggg gatcgcagtg gtgagtaacc atgcatcatc aggagtacgg ataaaatgct    5580
tgatggtcgg aagaggcata aattccgtca gccagtttag tctgaccatc tcatctgtaa    5640
catcattggc aacgctacct ttgccatgtt tcagaaacaa ctctggcgca tcgggcttcc    5700
catacaagcg atagattgtc gcacctgatt gcccgacatt atcgcgagcc catttatacc    5760
catataaatc agcatccatg ttggaattta atcgcggcct cgacgtttcc cgttgaatat    5820
ggctcataac accccttgta ttactgttta tgtaagcaga cagttttatt gttcatgatg    5880
atatattttt atcttgtgca atgtaacatc agagattttg agacac                  5926
```

<210> SEQ ID NO 49
<211> LENGTH: 926
<212> TYPE: DNA
<213> ORGANISM: Artificial Sequence
<220> FEATURE:
<223> OTHER INFORMATION: Description of Artificial Sequence: Synthetic
      Left HR Arm_CD8 Product 2

<400> SEQUENCE: 49

```
acattaaaaa cacaaaatcc tacggaaata ctgaagaatg agtctcagca ctaaggaaaa      60
gcctccagca gctcctgctt tctgagggtg aaggatagac gctgtggctc tgcatgactc     120
actagcactc tatcacggcc atattctggc agggtcagtg gctccaacta acatttgttt     180
ggtactttac agtttattaa atagatgttt atatggagaa gctctcattt ctttctcaga     240
agagcctggc taggaaggtg gatgaggcac catattcatt ttgcaggtga aattcctgag     300
```

```
atgtaaggag ctgctgtgac ttgctcaagg ccttatatcg agtaaacggt agtgctgggg    360
cttagacgca ggtgttctga tttatagttc aaaacctcta tcaatgagag agcaatctcc    420
tggtaatgtg atagatttcc caacttaatg ccaacatacc ataaacctcc cattctgcta    480
atgcccagcc taagttgggg agaccactcc agattccaag atgtacagtt tgctttgctg    540 ggccttttc ccatgcctgc ctttactctg ccagagttat attgctgggg ttttgaagaa    600
gatcctatta aataaaagaa taagcagtat tattaagtag ccctgcattt caggtttcct    660
tgagtggcag gccaggcctg gccgtgaacg ttcactgaaa tcatggcctc ttggccaaga    720
ttgatagctt gtgcctgtcc ctgagtccca gtccatcacg agcagctggt ttctaagatg    780
ctatttcccg tataaagcat gagaccgtga cttgccagcc ccacagagcc ccgcccttgt    840
ccatcactgg catctggact ccagcctggg ttggggcaaa gagggaaatg agatcatgtc    900
ctaaccctga tcctcttgtc ccacag                                        926

<210> SEQ ID NO 50
<211> LENGTH: 74
<212> TYPE: DNA
<213> ORGANISM: Artificial Sequence
<220> FEATURE:
<223> OTHER INFORMATION: Description of Artificial Sequence: Synthetic
      TRAC CDS_CD8 Product 2

<400> SEQUENCE: 50
atatccagaa ccctgaccct gccgtgtacc agctgagaga ctctaaatcc agtgacaagt    60
ctgtctgcct attc                                                      74

<210> SEQ ID NO 51
<211> LENGTH: 15
<212> TYPE: DNA
<213> ORGANISM: Artificial Sequence
<220> FEATURE:
<223> OTHER INFORMATION: Description of Artificial Sequence: Synthetic
      GSG Linker_CD8 Product 2

<400> SEQUENCE: 51
gaattcggct ccgga                                                     15

<210> SEQ ID NO 52
<211> LENGTH: 57
<212> TYPE: DNA
<213> ORGANISM: Artificial Sequence
<220> FEATURE:
<223> OTHER INFORMATION: Description of Artificial Sequence: Synthetic
      P2A_CD8 Product 2

<400> SEQUENCE: 52
gccactaact tcagcctgtt gaagcaggcc ggcgacgttg aggaaaaccc cggtcct       57

<210> SEQ ID NO 53
<211> LENGTH: 63
<212> TYPE: DNA
<213> ORGANISM: Artificial Sequence
<220> FEATURE:
<223> OTHER INFORMATION: Description of Artificial Sequence: Synthetic
      CD8A Signal Peptide_CD8 Product 2

<400> SEQUENCE: 53
atggccttac cagtgaccgc cttgctcctg ccgctggcct tgctgctcca cgccgccagg    60
ccg                                                                  63
```

<210> SEQ ID NO 54
<211> LENGTH: 483
<212> TYPE: DNA
<213> ORGANISM: Artificial Sequence
<220> FEATURE:
<223> OTHER INFORMATION: Description of Artificial Sequence: Synthetic
      CD8A Extracellular domain_CD8 Product 2

<400> SEQUENCE: 54
agccagttcc gggtgtcgcc gctggatcgg acctggaacc tgggcgagac agtggagctg      60
aagtgccagg tgctgctgtc aacccgacg tcgggctgct cgtggctctt ccagccgcgc     120
ggcgccgccg ccagtcccac cttcctccta tacctctccc aaaacaagcc caaggcggcc     180
gaggggctgg acacccagcg gttctcgggc aagaggttgg gggacacctt cgtcctcacc     240
ctgagcgact ccgccgaga gaacgagggc tactatttct gctcggccct gagcaactcc     300
atcatgtact tcagccactt cgtgccggtc ttcctgccag cgaagcccac cacgacgcca     360
gcgccgcgac caccaacacc ggcgcccacc atcgcgtcgc agcccctgtc cctgcgccca     420
gaggcgtgcc ggccagcggc ggggggcgca gtgcacacga gggggctgga cttcgcctgt     480
gat                                                                  483

<210> SEQ ID NO 55
<211> LENGTH: 63
<212> TYPE: DNA
<213> ORGANISM: Artificial Sequence
<220> FEATURE:
<223> OTHER INFORMATION: Description of Artificial Sequence: Synthetic
      CD8A Transmembrane domain_CD8 Product 2

<400> SEQUENCE: 55
atctacatct gggcgcccctt ggccgggact tgtggggtcc ttctcctgtc actggttatc      60
acc                                                                   63

<210> SEQ ID NO 56
<211> LENGTH: 96
<212> TYPE: DNA
<213> ORGANISM: Artificial Sequence
<220> FEATURE:
<223> OTHER INFORMATION: Description of Artificial Sequence: Synthetic
      CD8A intracellular domain_CD8 Product 2

<400> SEQUENCE: 56
ctttactgca accacaggaa ccgaagacgt gtttgcaaat gtccccggcc tgtggtcaaa      60
tcgggagaca agcccagcct ttcggcgaga tacgtc                                96

<210> SEQ ID NO 57
<211> LENGTH: 12
<212> TYPE: DNA
<213> ORGANISM: Artificial Sequence
<220> FEATURE:
<223> OTHER INFORMATION: Description of Artificial Sequence: Synthetic
      Furin cleavage site_CD8 Product 2

<400> SEQUENCE: 57
agagcaaagc gg                                                          12

<210> SEQ ID NO 58
<211> LENGTH: 9
<212> TYPE: DNA
<213> ORGANISM: Artificial Sequence
<220> FEATURE:
<223> OTHER INFORMATION: Description of Artificial Sequence: Synthetic GSG Linker_CD8 Product 2

<400> SEQUENCE: 58 ggctccgga                                                                9

<210> SEQ ID NO 59
<211> LENGTH: 57
<212> TYPE: DNA
<213> ORGANISM: Artificial Sequence
<220> FEATURE:
<223> OTHER INFORMATION: Description of Artificial Sequence: Synthetic
      P2A_CD8 Product 2

<400> SEQUENCE: 59
gctaccaatt ttagcctcct gaagcaggct ggcgatgttg aggaaaaccc tggtccc        57

<210> SEQ ID NO 60
<211> LENGTH: 63
<212> TYPE: DNA
<213> ORGANISM: Artificial Sequence
<220> FEATURE:
<223> OTHER INFORMATION: Description of Artificial Sequence: Synthetic
      CD8B Signal Peptide_CD8 Product 2

<400> SEQUENCE: 60
atgcggccgc ggctgtggct cctcttggcc gcgcagctga cagttctcca tggcaactca    60
gtc                                                                  63

<210> SEQ ID NO 61
<211> LENGTH: 447
<212> TYPE: DNA
<213> ORGANISM: Artificial Sequence
<220> FEATURE:
<223> OTHER INFORMATION: Description of Artificial Sequence: Synthetic
      CD8B Extracellular domain_CD8 Product 2

<400> SEQUENCE: 61
ctccagcaga cccctgcata cataaaggtg caaaccaaca agatggtgat gctgtcctgc    60
gaggctaaaa tctcccctcag taacatgcgc atctactggc tgagacacgc ccaggcaccg  120
agcagtgaca gtcaccacga gttcctggcc ctctgggatt ccgcaaaagg gactatccac   180
ggtgaagagg tggaacagga gaagatagct gtgtttcggg atgcaagccg gttcattctc   240
aatctcacaa gcgtgaagcc ggaagacagt ggcatctact ctgcatgat cgtcgggagc    300 cccgagctga ccttcgggaa gggaactcag ctgagtgtgg ttgatttcct tcccaccact   360
gcccagccca ccaagaagtc cacccctcaag aagagagtgt gccggttacc caggccagag  420
acccagaagg gcccactttg tagcccc                                        447

<210> SEQ ID NO 62
<211> LENGTH: 63
<212> TYPE: DNA
<213> ORGANISM: Artificial Sequence
<220> FEATURE:
<223> OTHER INFORMATION: Description of Artificial Sequence: Synthetic
      CD8B Transmembrane domain_CD8 Product 2

<400> SEQUENCE: 62
atcacccttg gcctgctggt ggctggcgtc ctggttctgc tggtttccct gggagtggcc    60
atc                                                                  63

<210> SEQ ID NO 63
<211> LENGTH: 57

```
<212> TYPE: DNA
<213> ORGANISM: Artificial Sequence
<220> FEATURE:
<223> OTHER INFORMATION: Description of Artificial Sequence: Synthetic
      CD8B Intracellular domain_CD8 Product 2

<400> SEQUENCE: 63
cacctgtgct gccggcggag gagagcccgg cttcgtttca tgaaacaatt ttacaaa          57

<210> SEQ ID NO 64
<211> LENGTH: 12
<212> TYPE: DNA
<213> ORGANISM: Artificial Sequence
<220> FEATURE:
<223> OTHER INFORMATION: Description of Artificial Sequence: Synthetic
      Furin cleavage site_CD8 Product 2

<400> SEQUENCE: 64
agggctaaac gg                                                           12

<210> SEQ ID NO 65
<211> LENGTH: 15
<212> TYPE: DNA
<213> ORGANISM: Artificial Sequence
<220> FEATURE:
<223> OTHER INFORMATION: Description of Artificial Sequence: Synthetic
      GSG Linker_CD8 Product 2

<400> SEQUENCE: 65
gaattcggct ccgga                                                        15

<210> SEQ ID NO 66
<211> LENGTH: 57
<212> TYPE: DNA
<213> ORGANISM: Artificial Sequence
<220> FEATURE:
<223> OTHER INFORMATION: Description of Artificial Sequence: Synthetic
      P2A_CD8 Product 2

<400> SEQUENCE: 66
gccactaact tctccctgtt gaaacaggct ggcgatgttg aagaaaaccc cggtcct          57

<210> SEQ ID NO 67
<211> LENGTH: 78
<212> TYPE: DNA
<213> ORGANISM: Artificial Sequence
<220> FEATURE:
<223> OTHER INFORMATION: Description of Artificial Sequence: Synthetic
      HGH/SS/2_CD8 Product 2

<400> SEQUENCE: 67
atggccaccg gctctagaac aagcctgctg ctcgcttttg cctgctctg cctcccatgg        60 ctccaagaag gatctgct                                                     78

<210> SEQ ID NO 68
<211> LENGTH: 345
<212> TYPE: DNA
<213> ORGANISM: Artificial Sequence
<220> FEATURE:
<223> OTHER INFORMATION: Description of Artificial Sequence: Synthetic
      Exemplary TRB_VDJ (TCR097) _CD8 Product 2

<400> SEQUENCE: 68
aatgctggtg tcactcagac cccaaaattc cgcatcctga agataggaca gagcatgaca       60
ctgcagtgta cccaggatat gaaccataac tacatgtact ggtatcgaca agacccaggc     120
```

```
atggggctga agctgattta ttattcagtt ggtgctggta tcactgataa aggagaagtc    180
ccgaatggct acaacgtctc cagatcaacc acagaggatt tcccgctcag gctggagttg    240
gctgctccct cccagacatc tgtgtacttc tgtgccagct ccctacaggt tccctacaat    300
gagcagttct cgggccagg gacacggctc accgtgctag aggac                    345
```

<210> SEQ ID NO 69
<211> LENGTH: 534
<212> TYPE: DNA
<213> ORGANISM: Artificial Sequence
<220> FEATURE:
<223> OTHER INFORMATION: Description of Artificial Sequence: Synthetic
      TCR-beta/constant_CD8 Product 2

<400> SEQUENCE: 69

```
ctgaaaaacg tgttccctcc aaaagtggcc gtgttcgagc cttctgaggc cgagatcagc     60
cacacacaga aagccacact cgtgtgtctg gctaccggct ctaccccga tcacgtggaa    120 ctgtcttggt gggtcaacgg caaagaggtg cacagcggcg tcagcacaga tccccagcct    180
ctgaaagaac agcccgctct gaacgacagc cgctactgcc tgtctagcag actgagagtg    240
tccgccacct tctggcagaa ccccagaaac cacttcagat gccaggtcca gttctacggc    300
ctgagcgaga acgatgagtg gacccaggac agagccaagc ctgtgacaca gatcgtgtct    360
gccgaagcct ggggcagagc cgattgtggc tttaccagcg agtcatacca gcagggcgtg    420
ctgtctgcca ccatcctgta tgagatcctg ctcggcaagg ccacactgta cgctgtgctg    480
gtgtctgctc tggtgctgat ggctatggtc tcccgggagc gcatccccga ggcc         534
```

<210> SEQ ID NO 70
<211> LENGTH: 12
<212> TYPE: DNA
<213> ORGANISM: Artificial Sequence
<220> FEATURE:
<223> OTHER INFORMATION: Description of Artificial Sequence: Synthetic
      Furin cleavage site_CD8 Product 2

<400> SEQUENCE: 70

```
cgggccaagc gg                                                         12
```

<210> SEQ ID NO 71
<211> LENGTH: 9
<212> TYPE: DNA
<213> ORGANISM: Artificial Sequence
<220> FEATURE:
<223> OTHER INFORMATION: Description of Artificial Sequence: Synthetic
      GSG linker_CD8 Product 2

<400> SEQUENCE: 71

```
ggcagcggc                                                              9
```

<210> SEQ ID NO 72
<211> LENGTH: 57
<212> TYPE: DNA
<213> ORGANISM: Artificial Sequence
<220> FEATURE:
<223> OTHER INFORMATION: Description of Artificial Sequence: Synthetic
      P2A_CD8 Product 2

<400> SEQUENCE: 72

```
gccaccaact tcagcctgct gaagcaggcc ggcgacgtgg aggagaaccc cggccct        57
```

<210> SEQ ID NO 73
<211> LENGTH: 78

<212> TYPE: DNA
<213> ORGANISM: Artificial Sequence
<220> FEATURE:
<223> OTHER INFORMATION: Description of Artificial Sequence: Synthetic
      HGH/SS_CD8 Product 2

<400> SEQUENCE: 73
atggccacag gcagcagaac atctctgctg ctggccttcg actgctgtg tctgccttgg    60 ctgcaagagg gttccgcc                                                 78

<210> SEQ ID NO 74
<211> LENGTH: 337
<212> TYPE: DNA
<213> ORGANISM: Artificial Sequence
<220> FEATURE:
<223> OTHER INFORMATION: Description of Artificial Sequence: Synthetic
      Exemplary TRA-VDJ (TCR097) _CD8 Product 2

<400> SEQUENCE: 74
gctcagacag tcactcagtc tcaaccagag atgtctgtgc aggaggcaga gaccgtgacc    60
ctgagctgca catatgacac cagtgagagt gattattatt tattctggta caagcagcct   120
cccagcaggc agatgattct cgttattcgc caagaagctt ataagcaaca gaatgcaaca   180
gagaatcgtt tctctgtgaa cttccagaaa gcagccaaat ccttcagtct caagatctca   240
gactcacagc tgggggatgc cgcgatgtat ttctgtgctt ttgggaactt caacaaattt   300
tactttggat ctgggaccaa actcaatgta aaaccaa                            337

<210> SEQ ID NO 75
<211> LENGTH: 74
<212> TYPE: DNA
<213> ORGANISM: Artificial Sequence
<220> FEATURE:
<223> OTHER INFORMATION: Description of Artificial Sequence: Synthetic
      TCR-alpha/constant_CD8 Product 2

<400> SEQUENCE: 75
atattcagaa ccccgatcct gctgtgtatc agctgcgcga cagcaagagc agcgacaaga    60
gcgtgtgttt gttc                                                     74

<210> SEQ ID NO 76
<211> LENGTH: 200
<212> TYPE: DNA
<213> ORGANISM: Artificial Sequence
<220> FEATURE:
<223> OTHER INFORMATION: Description of Artificial Sequence: Synthetic
      TRAC CDS/right HR arm_CD8 Product 2

<400> SEQUENCE: 76
accgattttg attctcaaac aaatgtgtca caaagtaagg attctgatgt gtatatcaca    60
gacaaaactg tgctagacat gaggtctatg gacttcaaga gcaacagtgc tgtggcctgg   120
agcaacaaat ctgactttgc atgtgcaaac gccttcaaca acagcattat tccagaagac   180
accttcttcc ccagcccagg                                               200

<210> SEQ ID NO 77
<211> LENGTH: 800
<212> TYPE: DNA
<213> ORGANISM: Artificial Sequence
<220> FEATURE:
<223> OTHER INFORMATION: Description of Artificial Sequence: Synthetic
      Right HR arm_CD8 Product 2

<400> SEQUENCE: 77

```
taagggcagc tttggtgcct tcgcaggctg tttccttgct tcaggaatgg ccaggttctg      60
cccagagctc tggtcaatga tgtctaaaac tcctctgatt ggtggtctcg gccttatcca     120
ttgccaccaa aaccctcttt ttactaagaa acagtgagcc ttgttctggc agtccagaga     180
atgacacggg aaaaaagcag atgaagaaa ggtggcagga gagggcacgt ggcccagcct      240
cagtctctcc aactgagttc ctgcctgcct gcctttgctc agactgtttg cccttactg      300 ctcttctagg cctcattcta agccccttct ccaagttgcc tctccttatt tctccctgtc     360
tgccaaaaaa tctttcccag ctcactaagt cagtctcacg cagtcactca ttaacccacc     420
aatcactgat tgtgccggca catgaatgca ccaggtgttg aagtggagga attaaaaagt     480
cagatgaggg gtgtgcccag aggaagcacc attctagttg ggggagccca tctgtcagct     540
gggaaaagtc caaataactt cagattggaa tgtgttttaa ctcagggttg agaaaacagc     600
taccttcagg acaaaagtca gggaagggct ctctgaagaa atgctacttg aagataccag     660
ccctaccaag gcagggaga ggaccctata gaggcctggg acaggagctc aatgagaaag      720
gagaagagca gcaggcatga gttgaatgaa ggaggcaggg ccgggtcaca gggccttcta     780
ggccatgaga gggtagacag                                                 800

<210> SEQ ID NO 78
<211> LENGTH: 6
<212> TYPE: DNA
<213> ORGANISM: Artificial Sequence
<220> FEATURE:
<223> OTHER INFORMATION: Description of Artificial Sequence: Synthetic
      Artificial Sequence_CD8 Product 2

<400> SEQUENCE: 78 gctagc                                                                  6

<210> SEQ ID NO 79
<211> LENGTH: 620
<212> TYPE: DNA
<213> ORGANISM: Artificial Sequence
<220> FEATURE:
<223> OTHER INFORMATION: Description of Artificial Sequence: Synthetic
      pBR322_origin_CD8 Product 2

<400> SEQUENCE: 79
cgcgttgctg gcgtttttcc ataggctccg ccccccTGAC gagcatcaca aaaatcgacg      60
ctcaagtcag aggtggcgaa acccgacagg actataaaga taccaggcgt ttccccctgg     120
aagctccctc gtgcgctctc ctgttccgac cctgccgctt accggatacc tgtccgcctt     180
tctcccttcg ggaagcgtgg cgctttctca gctcacgc tgtaggtatc tcagttcggt       240
gtaggtcgtt cgctccaagc tgggctgtgt gcacgaaccc ccgttcagc ccgaccgctg      300 cgccttatcc ggtaactatc gtcttgagtc caacccggta agacacgact tatcgccact     360
ggcagcagcc actggtaaca ggattagcag agcgaggtat gtaggcggtg ctacagagtt     420
cttgaagtgg tggcctaact acggctacac tagaagaaca gtatttggta tctgcgctct     480
gctgaagcca gttaccttcg gaaaaagagt tggtagctct tgatccggca acaaaccac      540 cgctggtagc ggtggttttt ttgtttgcaa gcagcagatt acgcgcagaa aaaaaggatc     600
tcaagaagat cctttgatct                                                 620

<210> SEQ ID NO 80
<211> LENGTH: 810
<212> TYPE: DNA
```

<213> ORGANISM: Artificial Sequence
<220> FEATURE:
<223> OTHER INFORMATION: Description of Artificial Sequence: Synthetic
      Kanamycin resistance (KanR2) _CD8 Product 2

<400> SEQUENCE: 80

```
ttagaaaaac tcatcgagca tcaaatgaaa ctgcaattta ttcatatcag gattatcaat    60
accatatttt tgaaaaagcc gtttctgtaa tgaaggagaa aactcaccga ggcagttcca   120
taggatggca agatcctggt atcggtctgc gattccgact cgtccaacat caatacaacc   180
tattaatttc ccctcgtcaa aaataaggtt atcaagtgag aaatcaccat gagtgacgac   240
tgaatccggt gagaatggca aaagtttatg catttctttc cagacttgtt caacaggcca   300
gccattacgc tcgtcatcaa aatcactcgc atcaaccaaa ccgttattca ttcgtgattg   360
cgcctgagcc agacgaaata cgcgatcgct gttaaaagga caattacaaa caggaatcga   420
atgcaaccgg cgcaggaaca ctgccagcgc atcaacaata ttttcacctg aatcaggata   480
ttcttctaat acctggaatg ctgtttttcc ggggatcgca gtggtgagta accatgcatc   540
atcaggagta cggataaaat gcttgatggt cggaagaggc ataaattccg tcagccagtt   600
tagtctgacc atctcatctg taacatcatt ggcaacgcta cctttgccat gtttcagaaa   660
caactctggc gcatcgggct tcccatacaa gcgatagatt gtcgcacctg attgcccgac   720
attatcgcga gcccatttat acccatataa atcagcatcc atgttggaat ttaatcgcgg   780
cctcgacgtt tcccgttgaa tatggctcat                                    810
```

<210> SEQ ID NO 81
<211> LENGTH: 99
<212> TYPE: DNA
<213> ORGANISM: Artificial Sequence
<220> FEATURE:
<223> OTHER INFORMATION: Description of Artificial Sequence: Synthetic
      Kanamycin promoter_CD8 Product 2

<400> SEQUENCE: 81

```
aacaccccctt gtattactgt ttatgtaagc agacagtttt attgttcatg atgatatatt    60
tttatcttgt gcaatgtaac atcagagatt ttgagacac                            99
```

<210> SEQ ID NO 82
<211> LENGTH: 6634
<212> TYPE: DNA
<213> ORGANISM: Artificial Sequence
<220> FEATURE:
<223> OTHER INFORMATION: Description of Artificial Sequence: Synthetic
      Complete CD8 Product 2 construct with TCR97 insertion_CD8 Product
      2

<400> SEQUENCE: 82

```
ggtaccacat taaaaacaca aaatcctacg gaaatactga agaatgagtc tcagcactaa    60
ggaaaagcct ccagcagctc ctgctttctg agggtgaagg atagacgctg tggctctgca   120
tgactcacta gcactctatc acggccatat tctggcaggg tcagtggctc caactaacat   180
ttgtttggta ctttacagtt tattaaatag atgtttatat ggagaagctc tcatttcttt   240
ctcagaagag cctggctagg aaggtggatg aggcaccata ttcattttgc aggtgaaatt   300
cctgagatgt aaggagctgc tgtgacttgc tcaaggcctt atatcgagta aacggtagtg   360
ctggggctta gacgcaggtg ttctgattta tagttcaaaa cctctatcaa tgagagagca   420
atctcctggt aatgtgatag atttcccaac ttaatgccaa cataccataa acctcccatt   480
ctgctaatgc ccagcctaag ttggggagac cactccagat tccaagatgt acagtttgct   540
```

```
ttgctgggcc ttttcccat gcctgccttt actctgccag agttatattg ctggggtttt      600
gaagaagatc ctattaaata aagaataag cagtattatt aagtagccct gcatttcagg      660
tttccttgag tggcaggcca ggcctggccg tgaacgttca ctgaaatcat ggcctcttgg     720
ccaagattga tagcttgtgc ctgtccctga gtcccagtcc atcacgagca gctggtttct    780
aagatgctat ttcccgtata aagcatgaga ccgtgacttg ccagcccac agagccccgc     840 ccttgtccat cactggcatc tggactccag cctgggttgg ggcaaagagg gaatgagat     900 catgtcctaa ccctgatcct cttgtcccac agatatccag aaccctgacc ctgccgtgta   960
ccagctgaga gactctaaat ccagtgacaa gtctgtctgc ctattcgaat tcggctccgg  1020
agccactaac ttcagcctgt tgaagcaggc cggcgacgtt gaggaaaacc ccggtcctat  1080
ggccttacca gtgaccgcct tgctcctgcc gctggccttg ctgctccacg ccgccaggcc  1140
gagccagttc cgggtgtcgc cgctggatcg gacctggaac ctgggcgaga cagtggagct  1200
gaagtgccag gtgctgctgt ccaacccgac gtcgggctgc tcgtggctct tccagccgcg  1260
cggcgccgcc gccagtccca ccttcctcct atacctctcc caaaacaagc caaggcggc   1320 cgaggggctg gacacccagc ggttctcggg caagaggttg ggggacacct tcgtcctcac  1380
cctgagcgac ttccgccgag agaacgaggg ctactatttc tgctcggccc tgagcaactc  1440
catcatgtac ttcagccact tcgtgccggt cttcctgcca gcgaagccca ccacgacgcc  1500
agcgccgcga ccaccaacac cggcgcccac catcgcgtcg cagcccctgt ccctgcgccc  1560
agaggcgtgc cggccagcgg cggggggcgc agtgcacacg aggggggctgg acttcgcctg  1620 tgatatctac atctgggcgc ccttggccgg gacttgtggg gtccttctcc tgtcactggt  1680
tatcaccctt tactgcaacc acaggaaccg aagacgtgtt tgcaaatgtc cccggcctgt  1740
ggtcaaatcg ggagacaagc ccagccttc ggcgagatac gtcagagcaa agcggggctc   1800
cggagctacc aattttagcc tcctgaagca ggctggcgat gttgaggaaa ccctggtcc   1860 catgcggccg cggctgtggc tcctcttggc cgcgcagctg acagttctcc atggcaactc  1920
agtcctccag cagaccctg catacataaa ggtgcaaacc aacaagatgg tgatgctgtc   1980
ctgcgaggct aaaatctccc tcagtaacat gcgcatctac tggctgagac agcgccaggc  2040
accgagcagt gacagtcacc acgagttcct ggccctctgg gattccgcaa aagggactat  2100
ccacggtgaa gaggtggaac aggagaagat agctgtgttt cggggatgcaa gccggttcat  2160 tctcaatctc acaagcgtga agccggaaga cagtggcatc tacttctgca tgatcgtcgg  2220
gagccccgag ctgaccttcg ggaagggaac tcagctgagt gtggttgatt tccttcccac  2280
cactgcccag cccaccaaga agtccaccct caagaagaga gtgtgccggt acccaggcc   2340 agagacccag aagggcccac tttgtagccc catcacccctt ggcctgctgg tggctggcgt  2400
cctggttctg ctggtttccc tgggagtggc catccacctg tgctgccggc ggaggagagc  2460
ccggcttcgt ttcatgaaac aattttacaa aagggctaaa cgggaattcg ctccggagc   2520 cactaacttc tccctgttga acaggctggg cgatgttgaa gaaaaccccg gtcctatggc  2580
caccggctct agaacaagcc tgctgctcgc ttttggcctg ctctgcctcc catggctcca  2640
agaaggatct gctaatgctg gtgtcactca gaccccaaaa ttccgcatcc tgaagatagg  2700
acagagcatg acactgcagt gtacccagga tatgaaccat aactacatgt actggtatcg  2760
acaagaccca ggcatgggc tgaagctgat ttattattca gttggtgctg gtatcactga   2820
taaaggagaa gtcccgaatg gctacaacgt ctccagatca accacagagg atttccccgct  2880
```

```
caggctggag ttggctgctc cctcccagac atctgtgtac ttctgtgcca gctccctaca    2940
ggttccctac aatgagcagt tcttcgggcc agggacacgg ctcaccgtgc tagaggacct    3000
gaaaaacgtg ttccctccaa aagtggccgt gttcgagcct tctgaggccg agatcagcca    3060
cacacagaaa gccacactcg tgtgtctggc taccggcttc taccccgatc acgtggaact    3120
gtcttggtgg gtcaacggca aagaggtgca cagcggcgtc agcacagatc cccagcctct    3180
gaaagaacag cccgctctga cgacagccg ctactgcctg tctagcagac tgagagtgtc    3240
cgccaccttc tggcagaacc ccagaaacca cttcagatgc caggtccagt tctacggcct    3300
gagcgagaac gatgagtgga cccaggacag agccaagcct gtgacacaga tcgtgtctgc    3360
cgaagcctgg ggcagagccg attgtggctt taccagcgag tcataccagc agggcgtgct    3420
gtctgccacc atcctgtatg agatcctgct cggcaaggcc acactgtacg ctgtgctggt    3480
gtctgctctg gtgctgatgg ctatggtctc ccggagcgc atccccgagg cccgggccaa    3540
gcggggcagc ggcgccacca acttcagcct gctgaagcag gccggcgacg tggaggagaa    3600
ccccggccct atggccacag gcagcagaac atctctgctg ctggccttcg gactgctgtg    3660
tctgccttgg ctgcaagagg gttccgccgc tcagacagtc actcagtctc aaccagagat    3720
gtctgtgcag gaggcagaga ccgtgaccct gagctgcaca tatgacacca gtgagagtga    3780
ttattattta ttctggtaca gcagcctcc cagcaggcag atgattctcg ttattcgcca    3840
agaagcttat aagcaacaga atgcaacaga gaatcgtttc tctgtgaact tccagaaagc    3900
agccaaatcc ttcagtctca agatctcaga ctcacagctg ggggatgccg cgatgtattt    3960
ctgtgctttt gggaacttca acaaatttta ctttggatct gggaccaaac tcaatgtaaa    4020
accaaatatt cagaaccccg atcctgctgt gtatcagctg cgcgacagca agagcagcga    4080
caagagcgtg tgtttgttca ccgattttga ttctcaaaca aatgtgtcac aaagtaagga    4140
ttctgatgtg tatatcacag acaaaactgt gctagacatg aggtctatgg acttcaagag    4200
caacagtgct gtggcctgga gcaacaaatc tgactttgca tgtgcaaacg ccttcaacaa    4260
cagcattatt ccagaagaca ccttcttccc cagcccaggt aagggcagct tggtgccttt    4320
cgcaggctgt ttccttgctt caggaatggc caggttctgc ccagagctct ggtcaatgat    4380
gtctaaaact cctctgattg gtggtctcgg ccttatccat gccaccaaa ccctcttttt    4440
tactaagaaa cagtgagcct tgttctggca gtccagagaa tgacgggga aaaagcaga    4500
tgaagagaag gtggcaggag agggcacgtg gcccagcctc agtctctcca actgagttcc    4560
tgcctgcctg cctttgctca gactgtttgc cccttactgc tcttctaggc ctcattctaa    4620
gccccttctc caagttgcct ctccttattt ctccctgtct gccaaaaaat ctttcccagc    4680
tcactaagtc agtctcacgc agtcactcat taacccacca atcactgatt gtgccggcac    4740
atgaatgcac caggtgttga agtggaggaa ttaaaaagtc agatgagggg tgtgcccaga    4800
ggaagcacca ttctagttgg gggagcccat ctgtcagctg gaaaagtcc aaataacttc    4860
agattggaat gtgttttaac tcagggttga gaaacagct accttcagga caaaagtcag    4920
ggaagggctc tctgaagaaa tgctacttga agataccagc cctaccaagg gcagggagag    4980
gaccctatag aggcctggga caggagctca atgagaaagg agaagagcag caggcatgag    5040
ttgaatgaag gaggcagggc cgggtcacag ggccttctag gccatgagag ggtagacagg    5100
ctagccgcgt tgctggcgtt tttccatagg ctccgccccc ctgacgagca tcacaaaaat    5160
cgacgctcaa gtcagaggtg gcgaaacccg acaggactat aaagatacca ggcgtttccc    5220
cctggaagct ccctcgtgcg ctctcctgtt ccgaccctgc cgcttaccgg atacctgtcc    5280
```

-continued

```
gcctttctcc cttcgggaag cgtggcgctt tctcatagct cacgctgtag gtatctcagt    5340
tcggtgtagg tcgttcgctc caagctgggc tgtgtgcacg aaccccccgt tcagcccgac    5400
cgctgcgcct tatccggtaa ctatcgtctt gagtccaacc cggtaagaca cgacttatcg    5460
ccactggcag cagccactgg taacaggatt agcagagcga ggtatgtagg cggtgctaca    5520
gagttcttga agtggtggcc taactacggc tacactagaa gaacagtatt tggtatctgc    5580
gctctgctga agccagttac cttcggaaaa agagttggta gctcttgatc cggcaaacaa    5640
accaccgctg gtagcggtgg ttttttttgtt tgcaagcagc agattacgcg cagaaaaaaa    5700
ggatctcaag aagatccttt gatctttaga aaaactcatc gagcatcaaa tgaaactgca    5760
atttattcat atcaggatta tcaataccat attttttgaaa aagccgtttc tgtaatgaag    5820
gagaaaactc accgaggcag ttccatagga tggcaagatc ctggtatcgg tctgcgattc    5880
cgactcgtcc aacatcaata caacctatta atttcccctc gtcaaaaata aggttatcaa    5940
gtgagaaatc accatgagtg acgactgaat ccggtgagaa tggcaaaagt ttatgcattt    6000
ctttccagac ttgttcaaca ggccagccat tacgctcgtc atcaaaatca ctcgcatcaa    6060
ccaaaccgtt attcattcgt gattgcgcct gagccagacg aaatacgcga tcgctgttaa    6120
aaggacaatt acaaacagga atcgaatgca accggcgcag gaacactgcc agcgcatcaa    6180
caatattttc acctgaatca ggatattctt ctaatacctg gaatgctgtt tttccgggga    6240
tcgcagtggt gagtaaccat gcatcatcag gagtacggat aaaatgcttg atggtcggaa    6300
gaggcataaa ttccgtcagc cagtttagtc tgaccatctc atctgtaaca tcattggcaa    6360 cgctacctttt gccatgtttc agaaacaact ctggcgcatc gggcttccca tacaagcgat    6420
agattgtcgc acctgattgc ccgacattat cgcgagccca tttataccca tataaatcag    6480
catccatgtt ggaatttaat cgcggcctcg acgtttcccg ttgaatatgg ctcataacac    6540
cccttgtatt actgtttatg taagcagaca gttttattgt tcatgatgat atatttttat    6600
cttgtgcaat gtaacatcag agattttgag acac                                6634
```

<210> SEQ ID NO 83
<211> LENGTH: 926
<212> TYPE: DNA
<213> ORGANISM: Artificial Sequence
<220> FEATURE:
<223> OTHER INFORMATION: Description of Artificial Sequence: Synthetic
      Left HR Arm_CD8 Product 3

<400> SEQUENCE: 83

```
acattaaaaa cacaaaatcc tacggaaata ctgaagaatg agtctcagca ctaaggaaaa      60
gcctccagca gctcctgctt tctgagggtg aaggatagac gctgtggctc tgcatgactc     120
actagcactc tatcacggcc atattctggc agggtcagtg gctccaacta acatttgttt     180
ggtactttac agtttattaa atagatgttt atatggagaa gctctcattt ctttctcaga     240
agagcctggc taggaaggtg gatgaggcac catattcatt ttgcaggtga aattcctgag     300
atgtaaggag ctgctgtgac ttgctcaagg ccttatatcg agtaaacggt agtgctgggg     360
cttagacgca ggtgttctga tttatagttc aaaacctcta tcaatgagag agcaatctcc     420
tggtaatgtg atagatttcc caacttaatg ccaacatacc ataaacctcc cattctgcta     480
atgcccagcc taagttgggg agaccactcc agattccaag atgtacagtt tgctttgctg     540
ggcctttttc ccatgcctgc ctttactctg ccagagttat attgctgggg ttttgaagaa     600
gatcctatta aataaaagaa taagcagtat tattaagtag ccctgcattt caggtttcct     660
```

```
tgagtggcag gccaggcctg gccgtgaacg ttcactgaaa tcatggcctc ttggccaaga    720
ttgatagctt gtgcctgtcc ctgagtccca gtccatcacg agcagctggt ttctaagatg    780
ctatttcccg tataaagcat gagaccgtga cttgccagcc ccacagagcc ccgcccttgt    840
ccatcactgg catctggact ccagcctggg ttggggcaaa gagggaaatg agatcatgtc    900
ctaaccctga tcctcttgtc ccacag                                         926

<210> SEQ ID NO 84
<211> LENGTH: 74
<212> TYPE: DNA
<213> ORGANISM: Artificial Sequence
<220> FEATURE:
<223> OTHER INFORMATION: Description of Artificial Sequence: Synthetic
      TRAC (part of homology arm) _CD8 Product 3

<400> SEQUENCE: 84
atatccagaa ccctgaccct gccgtgtacc agctgagaga ctctaaatcc agtgacaagt    60
ctgtctgcct attc                                                      74

<210> SEQ ID NO 85
<211> LENGTH: 15
<212> TYPE: DNA
<213> ORGANISM: Artificial Sequence
<220> FEATURE:
<223> OTHER INFORMATION: Description of Artificial Sequence: Synthetic
      GSG Linker_CD8 Product 3

<400> SEQUENCE: 85
gaattcggct ccgga                                                     15

<210> SEQ ID NO 86
<211> LENGTH: 57
<212> TYPE: DNA
<213> ORGANISM: Artificial Sequence
<220> FEATURE:
<223> OTHER INFORMATION: Description of Artificial Sequence: Synthetic
      P2A_CD8 Product 3

<400> SEQUENCE: 86
gccactaact tcagcctgtt gaagcaggcc ggcgacgttg aggaaaaccc cggtcct       57

<210> SEQ ID NO 87
<211> LENGTH: 63
<212> TYPE: DNA
<213> ORGANISM: Artificial Sequence
<220> FEATURE:
<223> OTHER INFORMATION: Description of Artificial Sequence: Synthetic
      CD8A Signal Peptide_CD8 Product 3

<400> SEQUENCE: 87
atggccttac cagtgaccgc cttgctcctg ccgctggcct tgctgctcca cgccgccagg    60
ccg                                                                  63

<210> SEQ ID NO 88
<211> LENGTH: 483
<212> TYPE: DNA
<213> ORGANISM: Artificial Sequence
<220> FEATURE:
<223> OTHER INFORMATION: Description of Artificial Sequence: Synthetic
      CD8A Extracellular domain_CD8 Product 3

<400> SEQUENCE: 88
agccagttcc gggtgtcgcc gctggatcgg acctggaacc tgggcgagac agtggagctg    60
```

```
aagtgccagg tgctgctgtc caacccgacg tcgggctgct cgtggctctt ccagccgcgc    120
ggcgccgccg ccagtcccac cttcctccta tacctctccc aaaacaagcc caaggcggcc    180
gaggggctgg acacccagcg gttctcgggc aagaggttgg gggacacctt cgtcctcacc    240
ctgagcgact tccgccgaga gaacgagggc tactatttct gctcggccct gagcaactcc    300
atcatgtact tcagccactt cgtgccggtc ttcctgccag cgaagcccac cacgacgcca    360
gcgccgcgac caccaacacc ggcgcccacc atcgcgtcgc agcccctgtc cctgcgccca    420
gaggcgtgcc ggccagcggc ggggggcgca gtgcacacga gggggctgga cttcgcctgt    480
gat                                                                   483

<210> SEQ ID NO 89
<211> LENGTH: 63
<212> TYPE: DNA
<213> ORGANISM: Artificial Sequence
<220> FEATURE:
<223> OTHER INFORMATION: Description of Artificial Sequence: Synthetic
      CD8A Transmembrane domain_CD8 Product 3

<400> SEQUENCE: 89
atctacatct gggcgccctt ggccgggact tgtggggtcc ttctcctgtc actggttatc     60
acc                                                                    63

<210> SEQ ID NO 90
<211> LENGTH: 57
<212> TYPE: DNA
<213> ORGANISM: Artificial Sequence
<220> FEATURE:
<223> OTHER INFORMATION: Description of Artificial Sequence: Synthetic
      CD8B intracellular domain_CD8 Product 3

<400> SEQUENCE: 90
cacctgtgct gccggcggag gagagcccgg cttcgtttca tgaaacaatt ttacaaa        57

<210> SEQ ID NO 91
<211> LENGTH: 12
<212> TYPE: DNA
<213> ORGANISM: Artificial Sequence
<220> FEATURE:
<223> OTHER INFORMATION: Description of Artificial Sequence: Synthetic
      Furin cleavage site_CD8 Product 3

<400> SEQUENCE: 91
agggctaaac gg                                                          12

<210> SEQ ID NO 92
<211> LENGTH: 15
<212> TYPE: DNA
<213> ORGANISM: Artificial Sequence
<220> FEATURE:
<223> OTHER INFORMATION: Description of Artificial Sequence: Synthetic
      GSG Linker_CD8 Product 3

<400> SEQUENCE: 92
gaattcggct ccgga                                                       15

<210> SEQ ID NO 93
<211> LENGTH: 57
<212> TYPE: DNA
<213> ORGANISM: Artificial Sequence
<220> FEATURE:
<223> OTHER INFORMATION: Description of Artificial Sequence: Synthetic
      P2A_CD8 Product 3
```

<400> SEQUENCE: 93
gccactaact tctccctgtt gaaacaggct ggcgatgttg aagaaaaccc cggtcct      57

<210> SEQ ID NO 94
<211> LENGTH: 78
<212> TYPE: DNA
<213> ORGANISM: Artificial Sequence
<220> FEATURE:
<223> OTHER INFORMATION: Description of Artificial Sequence: Synthetic
      HGH/SS/2_CD8 Product 3

<400> SEQUENCE: 94
atggccaccg gctctagaac aagcctgctg ctcgcttttg gcctgctctg cctcccatgg      60
ctccaagaag gatctgct                                                   78

<210> SEQ ID NO 95
<211> LENGTH: 345
<212> TYPE: DNA
<213> ORGANISM: Artificial Sequence
<220> FEATURE:
<223> OTHER INFORMATION: Description of Artificial Sequence: Synthetic
      TRB_VDJ (TCR097)_CD8 Product 3

<400> SEQUENCE: 95
aatgctggtg tcactcagac cccaaaattc cgcatcctga agataggaca gagcatgaca      60
ctgcagtgta cccaggatat gaaccataac tacatgtact ggtatcgaca gacccaggc     120 atggggctga agctgattta ttattcagtt ggtgctggta tcactgataa aggagaagtc    180
ccgaatggct acaacgtctc cagatcaacc acagaggatt tcccgctcag gctggagttg    240
gctgctccct cccagacatc tgtgtacttc tgtgccagct ccctacaggt tccctacaat    300
gagcagttct tcgggccagg gacacggctc accgtgctag aggac                    345

<210> SEQ ID NO 96
<211> LENGTH: 534
<212> TYPE: DNA
<213> ORGANISM: Artificial Sequence
<220> FEATURE:
<223> OTHER INFORMATION: Description of Artificial Sequence: Synthetic
      TCR-beta/constant_CD8 Product 3

<400> SEQUENCE: 96
ctgaaaaacg tgttccctcc aaaagtggcc gtgttcgagc cttctgaggc cgagatcagc      60
cacacacaga aagccacact cgtgtgtctg ctaccggct tctacccga tcacgtggaa       120 ctgtcttggt gggtcaacgg caaagaggtg cacagcggcg tcagcacaga tccccagcct    180
ctgaaagaac agcccgctct gaacgacagc cgctactgcc tgtctagcag actgagagtg    240
tccgccacct tctggcagaa ccccagaaac cacttcagat gccaggtcca gttctacggc    300
ctgagcgaga cgatgagtg gacccaggac agagccaagc ctgtgacaca gatcgtgtct    360
gccgaagcct ggggcagagc cgattgtggc tttaccagcg agtcatacca gcagggcgtg    420
ctgtctgcca ccatcctgta tgagatcctg ctcggcaagg ccacactgta cgctgtgctg    480
gtgtctgctc tggtgctgat ggctatggtc tcccgggagc gcatccccga ggcc          534

<210> SEQ ID NO 97
<211> LENGTH: 12
<212> TYPE: DNA
<213> ORGANISM: Artificial Sequence
<220> FEATURE:
<223> OTHER INFORMATION: Description of Artificial Sequence: Synthetic Furin cleavage site_CD8 Product 3

<400> SEQUENCE: 97
cgggccaagc gg                                                               12

<210> SEQ ID NO 98
<211> LENGTH: 9
<212> TYPE: DNA
<213> ORGANISM: Artificial Sequence
<220> FEATURE:
<223> OTHER INFORMATION: Description of Artificial Sequence: Synthetic
      GSG linker_CD8 Product 3

<400> SEQUENCE: 98 ggcagcggc                                                                    9

<210> SEQ ID NO 99
<211> LENGTH: 57
<212> TYPE: DNA
<213> ORGANISM: Artificial Sequence
<220> FEATURE:
<223> OTHER INFORMATION: Description of Artificial Sequence: Synthetic
      P2A_CD8 Product 3

<400> SEQUENCE: 99
gccaccaact tcagcctgct gaagcaggcc ggcgacgtgg aggagaaccc cggccct       57

<210> SEQ ID NO 100
<211> LENGTH: 78
<212> TYPE: DNA
<213> ORGANISM: Artificial Sequence
<220> FEATURE:
<223> OTHER INFORMATION: Description of Artificial Sequence: Synthetic
      HGH/SS_CD8 Product 3

<400> SEQUENCE: 100
atggccacag gcagcagaac atctctgctg ctggccttcg gactgctgtg tctgccttgg   60
ctgcaagagg gttccgcc                                                 78

<210> SEQ ID NO 101
<211> LENGTH: 337
<212> TYPE: DNA
<213> ORGANISM: Artificial Sequence
<220> FEATURE:
<223> OTHER INFORMATION: Description of Artificial Sequence: Synthetic
      Exemplary TRA-VDJ (TCR097) _CD8 Product 3

<400> SEQUENCE: 101
gctcagacag tcactcagtc tcaaccagag atgtctgtgc aggaggcaga gaccgtgacc   60
ctgagctgca catatgacac cagtgagagt gattattatt tattctggta caagcagcct  120
cccagcaggc agatgattct cgttattcgc caagaagctt ataagcaaca gaatgcaaca  180
gagaatcgtt tctctgtgaa cttccagaaa gcagccaaat ccttcagtct caagatctca  240
gactcacagc tgggggatgc cgcgatgtat ttctgtgctt tgggaacttt caacaaattt  300
tactttggat ctgggaccaa actcaatgta aaaccaa                            337

<210> SEQ ID NO 102
<211> LENGTH: 74
<212> TYPE: DNA
<213> ORGANISM: Artificial Sequence
<220> FEATURE:
<223> OTHER INFORMATION: Description of Artificial Sequence: Synthetic
      TCR-alpha/constant_CD8 Product 3

<400> SEQUENCE: 102

```
atattcagaa ccccgatcct gctgtgtatc agctgcgcga cagcaagagc agcgacaaga    60
gcgtgtgttt gttc                                                      74
```

<210> SEQ ID NO 103
<211> LENGTH: 200
<212> TYPE: DNA
<213> ORGANISM: Artificial Sequence
<220> FEATURE:
<223> OTHER INFORMATION: Description of Artificial Sequence: Synthetic
      TRAC CDS/right HR arm_CD8 Product 3

<400> SEQUENCE: 103

```
accgattttg attctcaaac aaatgtgtca caaagtaagg attctgatgt gtatatcaca    60
gacaaaactg tgctagacat gaggtctatg gacttcaaga gcaacagtgc tgtggcctgg   120
agcaacaaat ctgactttgc atgtgcaaac gccttcaaca acagcattat tccagaagac   180
accttcttcc ccagcccagg                                               200
```

<210> SEQ ID NO 104
<211> LENGTH: 800
<212> TYPE: DNA
<213> ORGANISM: Artificial Sequence
<220> FEATURE:
<223> OTHER INFORMATION: Description of Artificial Sequence: Synthetic
      Right HR arm_CD8 Product 3

<400> SEQUENCE: 104

```
taagggcagc tttggtgcct tcgcaggctg tttccttgct tcaggaatgg ccaggttctg    60
cccagagctc tggtcaatga tgtctaaaac tcctctgatt ggtggtctcg gccttatcca   120
ttgccaccaa aaccctcttt ttactaagaa acagtgagcc ttgttctggc agtccagaga   180
atgacacggg aaaaaagcag atgaagagaa ggtggcagga gagggcacgt ggcccagcct   240
cagtctctcc aactgagttc ctgcctgcct gcctttgctc agactgtttg ccccttactg   300
ctcttctagg cctcattcta agccccttct ccaagttgcc tctccttatt tctccctgtc   360
tgccaaaaaa tctttcccag ctcactaagt cagtctcacg cagtcactca ttaacccacc   420
aatcactgat tgtgccggca catgaatgca ccaggtgttg aagtggagga attaaaaagt   480
cagatgaggg gtgtgcccag aggaagcacc attctagttg ggggagccca tctgtcagct   540
gggaaaagtc caaataactt cagattggaa tgtgttttaa ctcagggttg agaaaacagc   600
taccttcagg acaaaagtca gggaagggct ctctgaagaa atgctacttg aagataccag   660
ccctaccaag ggcagggaga ggaccctata gaggcctggg acaggagctc aatgagaaag   720
gagaagagca gcaggcatga gttgaatgaa ggaggcaggg ccgggtcaca gggccttcta   780
ggccatgaga gggtagacag                                               800
```

<210> SEQ ID NO 105
<211> LENGTH: 6
<212> TYPE: DNA
<213> ORGANISM: Artificial Sequence
<220> FEATURE:
<223> OTHER INFORMATION: Description of Artificial Sequence: Synthetic
      Artificial Sequence_CD8 Product 3

<400> SEQUENCE: 105

```
gctagc                                                               6
```

<210> SEQ ID NO 106

<211> LENGTH: 620
<212> TYPE: DNA
<213> ORGANISM: Artificial Sequence
<220> FEATURE:
<223> OTHER INFORMATION: Description of Artificial Sequence: Synthetic
pBR322_origin_CD8 Product 3

<400> SEQUENCE: 106

```
cgcgttgctg gcgttttcc ataggctccg ccccctgac gagcatcaca aaatcgacg      60
ctcaagtcag aggtggcgaa acccgacagg actataaaga taccaggcgt ttccccctgg  120
aagctccctc gtgcgctctc ctgttccgac cctgccgctt accggatacc tgtccgcctt  180
tctcccttcg ggaagcgtgg cgctttctca tagctcacgc tgtaggtatc tcagttcggt  240
gtaggtcgtt cgctccaagc tgggctgtgt gcacgaaccc cccgttcagc ccgaccgctg  300
cgccttatcc ggtaactatc gtcttgagtc aacccggta agacacgact tatcgccact  360
ggcagcagcc actggtaaca ggattagcag agcgaggtat gtaggcggtg ctacagagtt  420
cttgaagtgg tggcctaact acggctacac tagaagaaca gtatttggta tctgcgctct  480
gctgaagcca gttaccttcg gaaaaagagt tggtagctct tgatccggca acaaaccac   540
cgctggtagc ggtggttttt ttgtttgcaa gcagcagatt acgcgcagaa aaaaggatc   600
tcaagaagat cctttgatct                                              620
```

<210> SEQ ID NO 107
<211> LENGTH: 810
<212> TYPE: DNA
<213> ORGANISM: Artificial Sequence
<220> FEATURE:
<223> OTHER INFORMATION: Description of Artificial Sequence: Synthetic
Kanamycin resistance (KanR2)_CD8 Product 3

<400> SEQUENCE: 107

```
ttagaaaaac tcatcgagca tcaaatgaaa ctgcaattta ttcatatcag gattatcaat   60
accatatttt tgaaaaagcc gtttctgtaa tgaaggagaa aactcaccga ggcagttcca  120
taggatggca agatcctggt atcggtctgc gattccgact cgtccaacat caatacaacc  180
tattaatttc ccctcgtcaa aaataaggtt atcaagtgag aaatcaccat gagtgacgac  240
tgaatccggt gagaatggca aaagtttatg catttctttc cagacttgtt caacaggcca  300
gccattacgc tcgtcatcaa aatcactcgc atcaaccaaa ccgttattca ttcgtgattg  360
cgcctgagcc agacgaaata cgcgatcgct gttaaaagga cattacaaa caggaatcga  420
atgcaaccgg cgcaggaaca ctgccagcgc atcaacaata ttttcacctg aatcaggata  480
ttcttctaat acctggaatg ctgttttcc ggggatcgca gtggtgagta accatgcatc  540
atcaggagta cggataaaat gcttgatggt cggaagaggc ataaattccg tcagccagtt  600
tagtctgacc atctcatctg taacatcatt ggcaacgcta cctttgccat gtttcagaaa  660
caactctggc gcatcgggct tcccatacaa gcgatagatt gtcgcacctg attcccgac   720
attatcgcga gcccatttat acccatataa atcagcatcc atgttggaat ttaatcgcgg  780
cctcgacgtt tcccgttgaa tatggctcat                                   810
```

<210> SEQ ID NO 108
<211> LENGTH: 99
<212> TYPE: DNA
<213> ORGANISM: Artificial Sequence
<220> FEATURE:
<223> OTHER INFORMATION: Description of Artificial Sequence: Synthetic
Kanamycin promoter_CD8 Product 3

<400> SEQUENCE: 108

```
aacacccctt gtattactgt ttatgtaagc agacagtttt attgttcatg atgatatatt      60
tttatcttgt gcaatgtaac atcagagatt ttgagacac                             99
```

<210> SEQ ID NO 109
<211> LENGTH: 5887
<212> TYPE: DNA
<213> ORGANISM: Artificial Sequence
<220> FEATURE:
<223> OTHER INFORMATION: Description of Artificial Sequence: Synthetic
      Complete CD8 Product 3 construct with TCR97 insertion_CD8 Product
      3

<400> SEQUENCE: 109

```
ggtaccacat taaaaacaca aaatcctacg gaaatactga agaatgagtc tcagcactaa      60
ggaaaagcct ccagcagctc ctgctttctg agggtgaagg atagacgctg tggctctgca     120
tgactcacta gcactctatc acggccatat tctggcaggg tcagtggctc caactaacat     180
ttgtttggta ctttacagtt tattaaatag atgtttatat ggagaagctc tcatttcttt     240
ctcagaagag cctggctagg aaggtggatg aggcaccata ttcattttgc aggtgaaatt     300
cctgagatgt aaggagctgc tgtgacttgc tcaaggcctt atatcgagta aacggtagtg     360
ctggggctta gacgcaggtg ttctgattta tagttcaaaa cctctatcaa tgagagagca     420
atctcctggt aatgtgatag atttcccaac ttaatgccaa cataccataa acctcccatt     480
ctgctaatgc ccagcctaag ttggggagac cactccagat tccaagatgt acagtttgct     540
ttgctgggcc ttttttccat gcctgccttt actctgccag agttatattg ctggggtttt     600
gaagaagatc ctattaaata aaagaataag cagtattatt aagtagccct gcatttcagg     660
tttccttgag tggcaggcca ggcctggccg tgaacgttca ctgaaatcat ggcctcttgg     720
ccaagattga tagcttgtgc ctgtccctga gtcccagtcc atcacgagca gctggttt ct    780 aagatgctat ttcccgtata aagcatgaga ccgtgacttg ccagccccac agagcccgc     840 ccttgtccat cactggcatc tggactccag cctgggttgg ggcaaagagg gaaatgagat     900
catgtcctaa ccctgatcct cttgtcccac agatatccag aaccctgacc ctgccgtgta     960
ccagctgaga gactctaaat ccagtgacaa gtctgtctgc ctattcgaat tcggctccgg    1020
agccactaac ttcagcctgt tgaagcaggc cggcgacgtt gaggaaaaac ccggtcctat    1080
ggccttacca gtgaccgcct tgctcctgcc gctggccttg ctgctccacg ccgccaggcc    1140
gagccagttc cgggtgtcgc cgctggatcg gacctggaac ctgggcgaga cagtggagct    1200
gaagtgccag gtgctgctgt ccaacccgac gtcgggctgc tcgtggctct ccagccgcg    1260 cggcgccgcc gccagtccca ccttcctcct atacctctcc caaaacaagc caaggcggc    1320 cgaggggctg gacacccagc ggttctcggg caagaggttg ggggacacct tcgtcctcac    1380
cctgagcgac ttccgccgag agaacgaggg ctactatttc tgctcggccc tgagcaactc    1440
catcatgtac ttcagccact tcgtgccggt cttcctgcca gcgaagccca ccacgacgcc    1500
agcgccgcga ccaccaacac cggcgcccac catcgcgtcg cagcccctgt ccctgcgccc    1560
agaggcgtgc cggccagcgg cggggggcgc agtgcacacg aggggggctgg acttcgcctg    1620 tgatatctac atctgggcgc ccttggccgg gacttgtggg gtccttctcc tgtcactggt    1680
tatcacccac ctgtgctgcc ggcggaggag agccggctt cgtttcatga acaattttta    1740
caaaggggct aaacgggaat cggctccgg agccactaac ttctcccctgt tgaaacaggc    1800 tggcgatgtt gaagaaaacc ccggtcctat ggccaccggc tctagaacaa gcctgctgct    1860
```

```
cgcttttggc ctgctctgcc tcccatggct ccaagaagga tctgctaatg ctggtgtcac    1920
tcagacccca aaattccgca tcctgaagat aggacagaga atgacactgc agtgtaccca    1980
ggatatgaac cataactaca tgtactggta tcgacaagac ccaggcatgg ggctgaagct    2040
gatttattat tcagttggtg ctggtatcac tgataaagga gaagtcccga atggctacaa    2100
cgtctccaga tcaaccacag aggatttccc gctcaggctg agttggctg ctccctccca    2160 gacatctgtg tacttctgtg ccagctccct acaggttccc tacaatgagc agttcttcgg    2220
gccagggaca cggctcaccg tgctagagga cctgaaaaac gtgttccctc caaaagtggc    2280
cgtgttcgag ccttctgagg ccgagatcag ccacacacag aaagccacac tcgtgtgtct    2340
ggctaccggc ttctaccccg atcacgtgga actgtcttgg tgggtcaacg gcaaagaggt    2400
gcacagcggg gtcagcacag atccccagcc tctgaaagaa cagcccgctc tgaacgacag    2460
ccgctactgc ctgtctagca gactgagagt gtccgccacc ttctggcaga accccagaaa    2520
ccacttcaga tgccaggtcc agttctacgg cctgagcgag aacgatgagt ggacccagga    2580
cagagccaag cctgtgacac agatcgtgtc tgccgaagcc tggggcagag ccgattgtgg    2640
ctttaccagc gagtcatacc agcagggcgt gctgtctgcc accatcctgt atgagatcct    2700
gctcggcaag gccacactgt acgctgtgct ggtgtctgct ctggtgctga tggctatggt    2760
ctcccgggag cgcatccccg aggcccgggc caagcgggc agcggcgcca ccaacttcag    2820
cctgctgaag caggccggcg acgtggagga aaccccggc cctatggcca caggcagcag    2880
aacatctctg ctgctggcct tcggactgct gtgtctgcct tggctgcaag agggttccgc    2940
cgctcagaca gtcactcagt ctcaaccaga gatgtctgtg caggaggcag agaccgtgac    3000
cctgagctgc acatatgaca ccagtgagag tgattattat ttattctggt acaagcagcc    3060
tcccagcagg cagatgattc tcgttattcg ccaagaagct tataagcaac agaatgcaac    3120
agagaatcgt ttctctgtga acttccagaa agcagccaaa tccttcagtc tcaagatctc    3180
agactcacag ctgggggatg ccgcgatgta tttctgtgct tttgggaact tcaacaaatt    3240
ttactttgga tctgggacca aactcaatgt aaaaccaaat attcagaacc ccgatcctgc    3300
tgtgtatcag ctgcgcgaca gcaagagcag cgacaagagc gtgtgtttgt tcaccgattt    3360
tgattctcaa acaaatgtgt cacaaagtaa ggattctgat gtgtatatca cagacaaaac    3420
tgtgctagac atgaggtcta tggacttcaa gagcaacagt gctgtggcct ggagcaacaa    3480
atctgacttt gcatgtgcaa acgccttcaa caacagcatt attccagaag acaccttctt    3540
ccccagccca ggtaagggca gctttggtgc cttcgcagc tgtttccttg cttcaggaat    3600
ggccaggttc tgcccagagc tctggtcaat gatgtctaaa actcctctga ttggtggtct    3660
cggccttatc cattgccacc aaaaccctct ttttactaag aaacagtgag ccttgttctg    3720
gcagtccaga gaatgacacg ggaaaaaagc agatgaagag aaggtggcag gagagggcac    3780
gtggcccagc ctcagtctct ccaactgagt tcctgcctgc ctgcctttgc tcagactgtt    3840
tgccccttac tgctcttcta ggcctcattc taagccccctt ctccaagttg cctctcctta    3900
tttctccctg tctgccaaaa aatctttccc agctcactaa gtcagtctca cgcagtcact    3960
cattaaccca ccaatcactg attgtgccgg cacatgaatg caccaggtgt tgaagtggag    4020
gaattaaaaa gtcagatgag gggtgtgccc agaggaagca ccattctagt tggggagcc    4080 catctgtcag ctgggaaaag tccaaataac ttcagattgg aatgtgtttt aactcagggt    4140
tgagaaaaca gctaccttca ggacaaaagt cagggaaggg ctctctgaag aaatgctact    4200
```

```
tgaagatacc agccctacca agggcaggga gaggaccctg tagaggcctg ggacaggagc    4260
tcaatgagaa aggagaagag cagcaggcat gagttgaatg aaggaggcag ggccgggtca    4320
cagggccttc taggccatga gagggtagac aggctagccg cgttgctggc gttttttccat   4380 aggctccgcc ccctgacga gcatcacaaa atcgacgct caagtcagag gtggcgaaac     4440
ccgacaggac tataaagata ccaggcgttt cccctggaa gctccctcgt gcgctctcct    4500
gttccgaccc tgccgcttac cggatacctg tccgcctttc tcccttcggg aagcgtggcg   4560
cttcctcata gctcacgctg taggtatctc agttcggtgt aggtcgttcg ctccaagctg   4620
ggctgtgtgc acgaaccccc cgttcagccc gaccgctgcg ccttatccgg taactatcgt   4680
cttgagtcca acccggtaag acacgactta tcgccactgg cagcagccac tggtaacagg   4740
attagcagag cgaggtatgt aggcggtgct acagagttct tgaagtggtg cctaactac    4800 ggctacacta gaagaacagt atttggtatc tgcgctctgc tgaagccagt taccttcgga   4860
aaaagagttg gtagctcttg atccggcaaa caaaccaccg ctggtagcgg tggtttttt   4920 gtttgcaagc agcagattac gcgcagaaaa aaggatctc aagaagatcc tttgatcttt   4980
agaaaaactc atcgagcatc aaatgaaact gcaatttatt catatcagga ttatcaatac   5040
catatttttg aaaagccgt ttctgtaatg aaggagaaaa ctcaccgagg cagttccata    5100
ggatggcaag atcctggtat cggtctgcga ttccgactcg tccaacatca atacaaccta   5160
ttaatttccc ctcgtcaaaa ataaggttat caagtgagaa atcaccatga gtgacgactg   5220
aatccggtga atggcaaa agtttatgca tttctttcca gacttgttca acaggccagc     5280
cattacgctc gtcatcaaaa tcactcgcat caaccaaacc gttattcatt cgtgattgcg   5340
cctgagccag acgaaatacg cgatcgctgt taaaaggaca attacaaaca ggaatcgaat   5400
gcaaccggcg caggaacact gccagcgcat caacaatatt ttcacctgaa tcaggatatt   5460
cttctaatac ctggaatgct gttttccgg ggatcgcagt ggtgagtaac catgcatcat    5520
caggagtacg gataaaatgc ttgatggtcg gaagaggcat aaattccgtc agccagttta   5580
gtctgaccat ctcatctgta acatcattgg caacgctacc tttgccatgt ttcagaaaca   5640
actctggcgc atcgggcttc ccatacaagc gatagattgt cgcacctgat tgcccgacat   5700
tatcgcgagc ccatttatac ccatataaat cagcatccat gttggaattt aatcgcggcc   5760
tcgacgtttc ccgttgaata tggctcataa caccccttgt attactgttt atgtaagcag   5820
acagttttat tgttcatgat gatatatttt tatcttgtgc aatgtaacat cagagatttt   5880
gagacac                                                             5887
```

<210> SEQ ID NO 110
<211> LENGTH: 926
<212> TYPE: DNA
<213> ORGANISM: Artificial Sequence
<220> FEATURE:
<223> OTHER INFORMATION: Description of Artificial Sequence: Synthetic
      Left HR Arm_CD8 Product 4

<400> SEQUENCE: 110

```
acattaaaaa cacaaaatcc tacgaaaata ctgaagaatg agtctcagca ctaaggaaaa     60
gcctccagca gctcctgctt tctgagggtg aaggatagac gctgtggctc tgcatgactc    120
actagcactc tatcacggcc atattctggc agggtcagtg gctccaacta acatttgttt   180
ggtactttac agtttattaa atagatgttt atatggagaa gctctcattt ctttctcaga   240
agagcctggc taggaaggtg gatgaggcac catattcatt ttgcaggtga aattcctgag   300
```

```
atgtaaggag ctgctgtgac ttgctcaagg cctatatcg agtaaacggt agtgctgggg      360
cttagacgca ggtgttctga tttatagttc aaaacctcta tcaatgagag agcaatctcc      420
tggtaatgtg atagatttcc caacttaatg ccaacatacc ataaacctcc cattctgcta      480
atgcccagcc taagttgggg agaccactcc agattccaag atgtacagtt tgctttgctg      540
ggcctttttc ccatgcctgc ctttactctg ccagagttat attgctgggg ttttgaagaa      600
gatcctatta aataaaagaa taagcagtat tattaagtag ccctgcattt caggtttcct      660
tgagtggcag gccaggcctg gccgtgaacg ttcactgaaa tcatggcctc ttggccaaga      720
ttgatagctt gtgcctgtcc ctgagtccca gtccatcacg agcagctggt ttctaagatg      780
ctatttcccg tataaagcat gagaccgtga cttgccagcc ccacagagcc ccgcccttgt      840
ccatcactgg catctggact ccagcctggg ttggggcaaa gagggaaatg agatcatgtc      900
ctaaccctga tcctcttgtc ccacag                                          926
```

<210> SEQ ID NO 111
<211> LENGTH: 74
<212> TYPE: DNA
<213> ORGANISM: Artificial Sequence
<220> FEATURE:
<223> OTHER INFORMATION: Description of Artificial Sequence: Synthetic
      TRAC CDS_CD8 Product 4

<400> SEQUENCE: 111

```
atatccagaa ccctgaccct gccgtgtacc agctgagaga ctctaaatcc agtgacaagt      60
ctgtctgcct attc                                                       74
```

<210> SEQ ID NO 112
<211> LENGTH: 15
<212> TYPE: DNA
<213> ORGANISM: Artificial Sequence
<220> FEATURE:
<223> OTHER INFORMATION: Description of Artificial Sequence: Synthetic
      GSG Linker_CD8 Product 4

<400> SEQUENCE: 112

```
gaattcggct ccgga                                                      15
```

<210> SEQ ID NO 113
<211> LENGTH: 57
<212> TYPE: DNA
<213> ORGANISM: Artificial Sequence
<220> FEATURE:
<223> OTHER INFORMATION: Description of Artificial Sequence: Synthetic
      P2A_CD8 Product 4

<400> SEQUENCE: 113

```
gccactaact tcagcctgtt gaagcaggcc ggcgacgttg aggaaaaccc cggtcct         57
```

<210> SEQ ID NO 114
<211> LENGTH: 63
<212> TYPE: DNA
<213> ORGANISM: Artificial Sequence
<220> FEATURE:
<223> OTHER INFORMATION: Description of Artificial Sequence: Synthetic
      CD8A Signal peptide_CD8 Product 4

<400> SEQUENCE: 114

```
atggccttac cagtgaccgc cttgctcctg ccgctggcct tgctgctcca cgccgccagg      60
ccg                                                                   63
```

```
<210> SEQ ID NO 115
<211> LENGTH: 483
<212> TYPE: DNA
<213> ORGANISM: Artificial Sequence
<220> FEATURE:
<223> OTHER INFORMATION: Description of Artificial Sequence: Synthetic
      CD8A Extracellular Domain_CD8 Product 4

<400> SEQUENCE: 115
agccagttcc gggtgtcgcc gctggatcgg acctggaacc tgggcgagac agtggagctg        60
aagtgccagg tgctgctgtc aacccgacg tcgggctgct cgtggctctt ccagccgcgc       120
ggcgccgccg ccagtcccac cttcctccta tacctctccc aaaacaagcc caaggcggcc      180
gaggggctgg acacccagcg gttctcgggc aagaggttgg gggacacctt cgtcctcacc      240
ctgagcgact ccgccgaga gaacgagggc tactatttct gctcggccct gagcaactcc       300
atcatgtact tcagccactt cgtgccggtc ttcctgccag cgaagcccac cacgacgcca      360
gcgccgcgac caccaacacc ggcgcccacc atcgcgtcgc agcccctgtc cctgcgccca      420
gaggcgtgcc ggccagcggc gggggcgca gtgcacacga ggggctgga cttcgcctgt        480 gat                                                                    483

<210> SEQ ID NO 116
<211> LENGTH: 63
<212> TYPE: DNA
<213> ORGANISM: Artificial Sequence
<220> FEATURE:
<223> OTHER INFORMATION: Description of Artificial Sequence: Synthetic
      CD8A transmembrane domain_CD8 Product 4

<400> SEQUENCE: 116
atctacatct gggcgcctt ggccgggact tgtggggtcc ttctcctgtc actggttatc         60
acc                                                                     63

<210> SEQ ID NO 117
<211> LENGTH: 120
<212> TYPE: DNA
<213> ORGANISM: Artificial Sequence
<220> FEATURE:
<223> OTHER INFORMATION: Description of Artificial Sequence: Synthetic
      CD4 intracellular domain_CD8 Product 4

<400> SEQUENCE: 117
tgtgtcaggt gccggcaccg aaggcgccaa gcagagcgga tgtctcagat caagagactc        60
ctcagtgaga agaagacctg ccagtgtcct caccggtttc agaagacatg tagccccatt      120

<210> SEQ ID NO 118
<211> LENGTH: 12
<212> TYPE: DNA
<213> ORGANISM: Artificial Sequence
<220> FEATURE:
<223> OTHER INFORMATION: Description of Artificial Sequence: Synthetic
      Furin Cleavage site_CD8 Product 4

<400> SEQUENCE: 118
agggctaaac gg                                                           12

<210> SEQ ID NO 119
<211> LENGTH: 15
<212> TYPE: DNA
<213> ORGANISM: Artificial Sequence
<220> FEATURE:
<223> OTHER INFORMATION: Description of Artificial Sequence: Synthetic
      GSG Linker_CD8 Product 4
```

<400> SEQUENCE: 119
gaattcggct ccgga                                                          15

<210> SEQ ID NO 120
<211> LENGTH: 57
<212> TYPE: DNA
<213> ORGANISM: Artificial Sequence
<220> FEATURE:
<223> OTHER INFORMATION: Description of Artificial Sequence: Synthetic
      P2A_CD8 Product 4

<400> SEQUENCE: 120
gccactaact tctccctgtt gaaacaggct ggcgatgttg aagaaaaccc cggtcct           57

<210> SEQ ID NO 121
<211> LENGTH: 78
<212> TYPE: DNA
<213> ORGANISM: Artificial Sequence
<220> FEATURE:
<223> OTHER INFORMATION: Description of Artificial Sequence: Synthetic
      HGH/SS/2_CD8 Product 4

<400> SEQUENCE: 121
atggccaccg gctctagaac aagcctgctg ctcgcttttg gcctgctctg cctcccatgg        60
ctccaagaag gatctgct                                                      78

<210> SEQ ID NO 122
<211> LENGTH: 345
<212> TYPE: DNA
<213> ORGANISM: Artificial Sequence
<220> FEATURE:
<223> OTHER INFORMATION: Description of Artificial Sequence: Synthetic
      TRB_VDJ (TCR097) _CD8 Product 4

<400> SEQUENCE: 122
aatgctggtg tcactcagac cccaaaattc cgcatcctga agataggaca gagcatgaca        60
ctgcagtgta cccaggatat gaaccataac tacatgtact ggtatcgaca gacccaggc       120 atggggctga agctgattta ttattcagtt ggtgctggta tcactgataa aggagaagtc      180
ccgaatggct acaacgtctc cagatcaacc acagaggatt tcccgctcag gctggagttg      240
gctgctccct cccagacatc tgtgtacttc tgtgccagct ccctacaggt tccctacaat      300
gagcagttct cgggccagg gacacggctc accgtgctag aggac                       345

<210> SEQ ID NO 123
<211> LENGTH: 534
<212> TYPE: DNA
<213> ORGANISM: Artificial Sequence
<220> FEATURE:
<223> OTHER INFORMATION: Description of Artificial Sequence: Synthetic
      TCR-beta/constant_CD8 Product 4

<400> SEQUENCE: 123
ctgaaaaacg tgttccctcc aaaagtggcc gtgttcgagc cttctgaggc cgagatcagc       60
cacacacaga agccacacact cgtgtgtctg ctaccggct tctaccccga tcacgtggaa      120
ctgtcttggt gggtcaacgg caagaggtg cacagcggcg tcagcacaga tccccagcct      180
ctgaaagaac agcccgctct gaacgacagc cgctactgcc tgtctagcag actgagagtg      240
tccgccacct tctggcagaa ccccagaaac cacttcagat gccaggtcca gttctacggc      300
ctgagcgaga acgatgagtg gacccaggac agagccaagc ctgtgacaca gatcgtgtct      360

```
gccgaagcct ggggcagagc cgattgtggc tttaccagcg agtcatacca gcagggcgtg     420
ctgtctgcca ccatcctgta tgagatcctg ctcggcaagg ccacactgta cgctgtgctg     480
gtgtctgctc tggtgctgat ggctatggtc tcccgggagc gcatccccga ggcc           534
```

```
<210> SEQ ID NO 124
<211> LENGTH: 12
<212> TYPE: DNA
<213> ORGANISM: Artificial Sequence
<220> FEATURE:
<223> OTHER INFORMATION: Description of Artificial Sequence: Synthetic
      Furin cleavage site_CD8 Product 4

<400> SEQUENCE: 124
cgggccaagc gg                                                         12
```

```
<210> SEQ ID NO 125
<211> LENGTH: 9
<212> TYPE: DNA
<213> ORGANISM: Artificial Sequence
<220> FEATURE:
<223> OTHER INFORMATION: Description of Artificial Sequence: Synthetic
      GSG linker_CD8 Product 4

<400> SEQUENCE: 125 ggcagcggc                                                              9
```

```
<210> SEQ ID NO 126
<211> LENGTH: 57
<212> TYPE: DNA
<213> ORGANISM: Artificial Sequence
<220> FEATURE:
<223> OTHER INFORMATION: Description of Artificial Sequence: Synthetic
      P2A_CD8 Product 4

<400> SEQUENCE: 126
gccaccaact tcagcctgct gaagcaggcc ggcgacgtgg aggagaaccc cggccct        57
```

```
<210> SEQ ID NO 127
<211> LENGTH: 78
<212> TYPE: DNA
<213> ORGANISM: Artificial Sequence
<220> FEATURE:
<223> OTHER INFORMATION: Description of Artificial Sequence: Synthetic
      HGH/SS_CD8 Product 4

<400> SEQUENCE: 127
atggccacag gcagcagaac atctctgctg ctggccttcg gactgctgtg tctgccttgg     60
ctgcaagagg gttccgcc                                                    78
```

```
<210> SEQ ID NO 128
<211> LENGTH: 337
<212> TYPE: DNA
<213> ORGANISM: Artificial Sequence
<220> FEATURE:
<223> OTHER INFORMATION: Description of Artificial Sequence: Synthetic
      Exemplary TRA-VDJ (TCR097) _CD8 Product 4

<400> SEQUENCE: 128
gctcagacag tcactcagtc tcaaccagag atgtctgtgc aggaggcaga gaccgtgacc     60
ctgagctgca catatgacac cagtgagagt gattattatt tattctggta caagcagcct    120
cccagcaggc agatgattct cgttattcgc caagaagctt ataagcaaca gaatgcaaca    180
gagaatcgtt tctctgtgaa cttccagaaa gcagccaaat ccttcagtct caagatctca    240
```
gactcacagc tggggatgc cgcgatgtat ttctgtgctt ttgggaactt caacaaattt    300
tactttggat ctgggaccaa actcaatgta aaaccaa    337

<210> SEQ ID NO 129
<211> LENGTH: 74
<212> TYPE: DNA
<213> ORGANISM: Artificial Sequence
<220> FEATURE:
<223> OTHER INFORMATION: Description of Artificial Sequence: Synthetic
      TCR-alpha/constant_CD8 Product 4

<400> SEQUENCE: 129
atattcagaa ccccgatcct gctgtgtatc agctgcgcga cagcaagagc agcgacaaga    60
gcgtgtgttt gttc    74

<210> SEQ ID NO 130
<211> LENGTH: 200
<212> TYPE: DNA
<213> ORGANISM: Artificial Sequence
<220> FEATURE:
<223> OTHER INFORMATION: Description of Artificial Sequence: Synthetic
      TRAC CDS/right HR arm_CD8 Product 4

<400> SEQUENCE: 130
accgattttg attctcaaac aaatgtgtca caaagtaagg attctgatgt gtatatcaca    60
gacaaaactg tgctagacat gaggtctatg gacttcaaga gcaacagtgc tgtggcctgg    120
agcaacaaat ctgactttgc atgtgcaaac gccttcaaca acagcattat tccagaagac    180
accttcttcc ccagcccagg    200

<210> SEQ ID NO 131
<211> LENGTH: 800
<212> TYPE: DNA
<213> ORGANISM: Artificial Sequence
<220> FEATURE:
<223> OTHER INFORMATION: Description of Artificial Sequence: Synthetic
      Right HR arm_CD8 Product 4

<400> SEQUENCE: 131
taagggcagc tttggtgcct tcgcaggctg tttccttgct tcaggaatgg ccaggttctg    60
cccagagctc tggtcaatga tgtctaaaac tcctctgatt ggtggtctcg gccttatcca    120
ttgccaccaa aaccctcttt ttactaagaa acagtgagcc ttgttctggc agtccagaga    180
atgacacggg aaaaaagcag atgaagagaa ggtggcagga gagggcacgt ggcccagcct    240
cagtctctcc aactgagttc ctgcctgcct gcctttgctc agactgtttg ccccttactg    300
ctcttctagg cctcattcta agccccttct ccaagttgcc tctccttatt tctccctgtc    360
tgccaaaaaa tctttcccag ctcactaagt cagtctcacg cagtcactca ttaacccacc    420
aatcactgat tgtgccggca catgaatgca ccaggtgttg aagtggagga attaaaaagt    480
cagatgaggg gtgtgcccag aggaagcacc attctagttg ggggagccca tctgtcagct    540
gggaaaagtc caaataactt cagattggaa tgtgttttaa ctcagggttg agaaaacagc    600
taccttcagg acaaaagtca gggaagggct ctctgaagaa atgctacttg aagataccag    660
ccctaccaag ggcagggaga ggaccctata gaggcctggg acaggagctc aatgagaaag    720
gagaagagca gcaggcatga gttgaatgaa ggaggcaggg ccgggtcaca gggccttcta    780
ggccatgaga gggtagacag    800

<210> SEQ ID NO 132

```
<211> LENGTH: 6
<212> TYPE: DNA
<213> ORGANISM: Artificial Sequence
<220> FEATURE:
<223> OTHER INFORMATION: Description of Artificial Sequence: Synthetic
      Artificial Sequence_CD8 Product 4

<400> SEQUENCE: 132 gctagc                                                                    6

<210> SEQ ID NO 133
<211> LENGTH: 620
<212> TYPE: DNA
<213> ORGANISM: Artificial Sequence
<220> FEATURE:
<223> OTHER INFORMATION: Description of Artificial Sequence: Synthetic
      pBR322_origin_CD8 Product 4

<400> SEQUENCE: 133
cgcgttgctg gcgttttttcc ataggctccg cccccctgac gagcatcaca aaaatcgacg          60
ctcaagtcag aggtggcgaa acccgacagg actataaaga taccaggcgt ttccccctgg         120
aagctccctc gtgcgctctc ctgttccgac cctgccgctt accggatacc tgtccgcctt         180
tctcccttcg ggaagcgtgg cgctttctca tagctcacgc tgtaggtatc tcagttcggt         240
gtaggtcgtt cgctccaagc tgggctgtgt gcacgaaccc cccgttcagc ccgaccgctg         300
cgccttatcc ggtaactatc gtcttgagtc aacccggta agacacgact tatcgccact          360
ggcagcagcc actggtaaca ggattagcag agcgaggtat gtaggcggtg ctacagagtt         420
cttgaagtgg tggcctaact acggctacac tagaagaaca gtatttggta tctgcgctct         480
gctgaagcca gttaccttcg gaaaaagagt tggtagctct tgatccggca acaaaccac          540 cgctggtagc ggtggttttt tgtttgcaa gcagcagatt acgcgcagaa aaaaggatc           600 tcaagaagat cctttgatct                                                    620

<210> SEQ ID NO 134
<211> LENGTH: 810
<212> TYPE: DNA
<213> ORGANISM: Artificial Sequence
<220> FEATURE:
<223> OTHER INFORMATION: Description of Artificial Sequence: Synthetic
      Kanamycin resistance (KanR2) _CD8 Product 4

<400> SEQUENCE: 134
ttagaaaaac tcatcgagca tcaaatgaaa ctgcaattta ttcatatcag gattatcaat          60
accatatttt tgaaaaagcc gtttctgtaa tgaaggagaa aactcaccga ggcagttcca         120
taggatggca agatcctggt atcggtctgc gattccgact cgtccaacat caatacaacc         180
tattaatttc ccctcgtcaa aaataaggtt atcaagtgag aaatcaccat gagtgacgac         240
tgaatccggt gagaatggca aaagtttatg catttctttc cagacttgtt caacaggcca         300
gccattacgc tcgtcatcaa aatcactcgc atcaaccaaa ccgttattca ttcgtgattg         360
cgcctgagcc agacgaaata cgcgatcgct gttaaaagga caattacaaa caggaatcga         420
atgcaaccgg cgcaggaaca ctgccagcgc atcaacaata ttttcacctg aatcaggata         480
ttcttctaat acctggaatg ctgttttccc gggatcgca gtggtgagta accatgcatc          540
atcaggagta cggataaaat gcttgatggt cggaagaggc ataaattccg tcagccagtt         600
tagtctgacc atctcatctg taacatcatt ggcaacgcta cctttgccat gtttcagaaa         660
caactctggc gcatcgggct tcccatacaa gcgatagatt gtcgcacctg attgcccgac         720
```

```
attatcgcga gcccatttat acccatataa atcagcatcc atgttggaat ttaatcgcgg    780
cctcgacgtt tcccgttgaa tatggctcat                                    810
```

<210> SEQ ID NO 135
<211> LENGTH: 99
<212> TYPE: DNA
<213> ORGANISM: Artificial Sequence
<220> FEATURE:
<223> OTHER INFORMATION: Description of Artificial Sequence: Synthetic
      CD8 Product 4 Kanamycin promoter

<400> SEQUENCE: 135

```
aacacccctt gtattactgt ttatgtaagc agacagtttt attgttcatg atgatatatt    60
tttatcttgt gcaatgtaac atcagagatt ttgagacac                           99
```

<210> SEQ ID NO 136
<211> LENGTH: 5950
<212> TYPE: DNA
<213> ORGANISM: Artificial Sequence
<220> FEATURE:
<223> OTHER INFORMATION: Description of Artificial Sequence: Synthetic
      Complete CD8 Product 4 construct with TCR97 insertion_CD8 Product
      4

<400> SEQUENCE: 136

```
ggtaccacat taaaaacaca aaatcctacg gaaatactga agaatgagtc tcagcactaa    60
ggaaaagcct ccagcagctc ctgctttctg agggtgaagg atagacgctg tggctctgca   120
tgactcacta gcactctatc acggccatat tctggcaggg tcagtggctc caactaacat   180
ttgtttggta ctttacagtt tattaaatag atgtttatat ggagaagctc tcatttcttt   240
ctcagaagag cctggctagg aaggtggatg aggcaccata ttcattttgc aggtgaaatt   300
cctgagatgt aaggagctgc tgtgacttgc tcaaggcctt atatcgagta aacggtagtg   360
ctggggctta gacgcaggtg ttctgattta tagttcaaaa cctctatcaa tgagagagca   420
atctcctggt aatgtgatag atttcccaac ttaatgccaa cataccataa acctcccatt   480
ctgctaatgc ccagcctaag ttggggagac cactccagat tccaagatgt acagtttgct   540
ttgctgggcc ttttttccat gcctgccttt actctgccag agttatattg ctggggtttt   600
gaagaagatc ctattaaata aaagaataag cagtattatt aagtagccct gcatttcagg   660
tttccttgag tggcaggcca ggcctggccg tgaacgttca ctgaaatcat ggcctcttgg   720
ccaagattga tagcttgtgc ctgtccctga gtcccagtcc atcacgagca gctggttttct  780 aagatgctat ttcccgtata aagcatgaga ccgtgacttg ccagcccac agagccccgc    840 ccttgtccat cactggcatc tggactccag cctgggttgg ggcaaagagg gaaatgagat   900
catgtcctaa ccctgatcct cttgtcccac agatatccag aaccctgacc ctgccgtgta   960
ccagctgaga gactctaaat ccagtgacaa gtctgtctgc ctattcgaat tcggctccgg  1020
agccactaac ttcagcctgt tgaagcaggc cggcgacgtt gaggaaaacc ccggtcctat  1080
ggccttacca gtgaccgcct tgctcctgcc gctggccttg ctgctccacg ccgccaggcc  1140
gagccagttc cgggtgtcgc cgctggatcg gacctggaac ctgggcgaga cagtggagct  1200
gaagtgccag gtgctgctgt ccaacccgac gtcgggctgc tcgtggctct tccagccgcg  1260
cggcgccgcc gccagtccca ccttcctcct atacctctcc caaaacaagc caaggcggc   1320 cgagggctg acacccagc ggttctcggg caagagggttg ggacacct tcgtcctcac     1380 cctgagcgac ttccgccgag agaacgaggg ctactatttc tgctcggccc tgagcaactc  1440
```

```
catcatgtac ttcagccact tcgtgccggt cttcctgcca gcgaagccca ccacgacgcc    1500
agcgccgcga ccaccaacac cggcgcccac catcgcgtcg cagcccctgt ccctgcgccc    1560
agaggcgtgc cggccagcgg cgggggggcgc agtgcacacg agggggctgg acttcgcctg   1620
tgatatctac atctgggcgc ccttggccgg gacttgtggg gtccttctcc tgtcactggt    1680
tatcacctgt gtcaggtgcc ggcaccgaag gcgccaagca gagcggatgt ctcagatcaa    1740
gagactcctc agtgagaaga agacctgcca gtgtcctcac cggtttcaga agacatgtag    1800
ccccattagg gctaaacggg aattcggctc cggagccact aacttctccc tgttgaaaca    1860
ggctggcgat gttgaagaaa accccggtcc tatggccacc ggctctagaa caagcctgct    1920
gctcgctttt ggcctgctct gcctcccatg gctccaagaa ggatctgcta atgctggtgt    1980
cactcagacc ccaaaattcc gcatcctgaa gataggacag agcatgacac tgcagtgtac    2040
ccaggatatg aaccataact acatgtactg gtatcgacaa gacccaggca tggggctgaa    2100
gctgatttat tattcagttg gtgctggtat cactgataaa ggagaagtcc cgaatggcta    2160
caacgtctcc agatcaacca cagaggattt cccgctcagg ctggagttgg ctgctccctc    2220
ccagacatct gtgtacttct gtgccagctc cctacaggtt ccctacaatg agcagttctt    2280
cgggccaggg acacggctca ccgtgctaga ggacctgaaa aacgtgttcc ctccaaaagt    2340
ggccgtgttc gagccttctg aggccgagat cagccacaca cagaaagcca cactcgtgtg    2400
tctggctacc ggcttctacc ccgatcacgt ggaactgtct tggtgggtca acggcaaaga    2460
ggtgcacagc ggcgtcagca cagatcccca gcctctgaaa gaacagcccg ctctgaacga    2520
cagccgctac tgcctgtcta gcagactgag agtgtccgcc accttctggc agaaccccag    2580
aaaccacttc agatgccagg tccagttcta cggcctgagc gagaacgatg agtggaccca    2640
ggacagagcc aagcctgtga cacagatcgt gtctgccgaa gctgggggca gagccgattg    2700
tggctttacc agcgagtcat accagcaggg cgtgctgtct gccaccatcc tgtatgagat    2760
cctgctcggc aaggccacac tgtacgctgt gctggtgtct gctctggtgc tgatggctat    2820
ggtctcccgg gagcgcatcc ccgaggcccg ggccaagcgg ggcagcggcg ccaccaactt    2880
cagcctgctg aagcaggccg cgacgtggga ggagaacccc ggccctatgg ccacaggcag    2940
cagaacatct ctgctgctgg ccttcggact gctgtgtctg ccttggctgc aagagggttc    3000
cgccgctcag acagtcactc agtctcaacc agagatgtct gtgcaggagg cagagaccgt    3060
gaccctgagc tgcacatatg acaccagtga gagtgattat tatttattct ggtacaagca    3120
gcctcccagc aggcagatga ttctcgttat tcgccaagaa gcttataagc aacagaatgc    3180
aacagagaat cgtttctctg tgaacttcca gaaagcagcc aaatccttca gtctcaagat    3240
ctcagactca cagctggggg atgccgcgat gtatttctgt gcttttggga acttcaacaa    3300
attttacttt ggatctggga ccaaactcaa tgtaaaacca atattcaga accccgatcc    3360 tgctgtgtat cagctgcgcg acagcaagag cagcgacaag agcgtgtgtt tgttcaccga    3420
ttttgattct caaacaaatg tgtcacaaag taaggattct gatgtgtata tcacagacaa    3480
aactgtgcta gacatgaggt ctatggactt caagagcaac agtgctgtgg cctggagcaa    3540
caaatctgac tttgcatgtg caaacgcctt caacaacagc attattccag aagacacctt    3600
cttccccagc ccaggtaagg gcagctttgg tgccttcgca ggctgttttcc ttgcttcagg    3660 aatggccagg ttctgcccag agctctggtc aatgatgtct aaaactcctc tgattggtgg    3720
tctcggcctt atccattgcc accaaaaccc tcttttact aagaaacagt gagccttgtt    3780
ctggcagtcc agagaatgac acgggaaaaa agcagatgaa gagaaggtgg caggagaggg    3840
```

```
cacgtggccc agcctcagtc tctccaactg agttcctgcc tgcctgcctt tgctcagact    3900
gtttgcccct tactgctctt ctaggcctca ttctaagccc cttctccaag ttgcctctcc    3960
ttatttctcc ctgtctgcca aaaaatcttt cccagctcac taagtcagtc tcacgcagtc    4020
actcattaac ccaccaatca ctgattgtgc cggcacatga atgcaccagg tgttgaagtg    4080
gaggaattaa aaagtcagat gaggggtgtg cccagaggaa gcaccattct agttggggga    4140
gcccatctgt cagctgggaa aagtccaaat aacttcagat tggaatgtgt tttaactcag    4200
ggttgagaaa acagctacct tcaggacaaa agtcagggaa gggctctctg aagaaatgct    4260
acttgaagat accagcccta ccaagggcag ggagaggacc ctatagaggc ctgggacagg    4320
agctcaatga gaaaggagaa gagcagcagg catgagttga atgaaggagg cagggccggg    4380
tcacagggcc ttctaggcca tgagagggta gacaggctag ccgcgttgct ggcgtttttc    4440
cataggctcc gccccctga cgagcatcac aaaaatcgac gctcaagtca gaggtggcga    4500
aacccgacag gactataaag ataccaggcg tttccccctg gaagctccct cgtgcgctct    4560
cctgttccga ccctgccgct taccggatac ctgtccgcct ttctcccttc gggaagcgtg    4620
gcgctttctc atagctcacg ctgtaggtat ctcagttcgg tgtaggtcgt tcgctccaag    4680
ctgggctgtg tgcacgaacc ccccgttcag cccgaccgct gcgccttatc cggtaactat    4740
cgtcttgagt ccaacccggt aagacacgac ttatcgccac tggcagcagc cactggtaac    4800
aggattagca gagcgaggta tgtaggcggt gctacagagt tcttgaagtg gtggcctaac    4860
tacggctaca ctagaagaac agtatttggt atctgcgctc tgctgaagcc agttaccttc    4920 ggaaaagag ttggtagctc ttgatccggc aaacaaacca ccgctggtag cggtggtttt    4980
tttgtttgca agcagcagat tacgcgcaga aaaaaaggat ctcaagaaga tcctttgatc    5040
tttagaaaaa ctcatcgagc atcaaatgaa actgcaattt attcatatca ggattatcaa    5100
taccatattt tgaaaaagc cgtttctgta atgaaggaga aaactcaccg aggcagttcc    5160
ataggatggc aagatcctgg tatcggtctg cgattccgac tcgtccaaca tcaatacaac    5220
ctattaattt cccctcgtca aaaataaggt tatcaagtga aaatcacca tgagtgacga    5280 ctgaatccgg tgagaatggc aaaagtttat gcatttcttt ccagacttgt tcaacaggcc    5340
agccattacg ctcgtcatca aaatcactcg catcaaccaa accgttattc attcgtgatt    5400
gcgcctgagc cagacgaaat acgcgatcgc tgttaaaagg acaattacaa acaggaatcg    5460
aatgcaaccg gcgcaggaac actgccagcg catcaacaat attttcacct gaatcaggat    5520
attcttctaa tacctggaat gctgtttttc cggggatcgc agtggtgagt aaccatgcat    5580
catcaggagt acggataaaa tgcttgatgg tcggaagagg cataaattcc gtcagccagt    5640
ttagtctgac catctcatct gtaacatcat tggcaacgct acctttgcca tgtttcagaa    5700
acaactctgg cgcatcgggc ttcccataca agcgatagat tgtcgcacct gattgcccga    5760
cattatcgcg agcccattta tacccatata aatcagcatc catgttggaa tttaatcgcg    5820
gcctcgacgt ttcccgttga atatggctca taacacccct tgtattactg tttatgtaag    5880
cagacagttt tattgttcat gatgatatat ttttatcttg tgcaatgtaa catcagagat    5940
tttgagacac                                                          5950
```

<210> SEQ ID NO 137
<211> LENGTH: 3
<212> TYPE: PRT
<213> ORGANISM: Artificial Sequence
<220> FEATURE:

```
<223> OTHER INFORMATION: Description of Artificial Sequence: Synthetic
      GSG Linker_CD8 Products 1, 2, 3, 4

<400> SEQUENCE: 137

Gly Ser Gly
1

<210> SEQ ID NO 138
<211> LENGTH: 19
<212> TYPE: PRT
<213> ORGANISM: Artificial Sequence
<220> FEATURE:
<223> OTHER INFORMATION: Description of Artificial Sequence: Synthetic
      P2A_CD8 Products 1, 2, 3, 4

<400> SEQUENCE: 138

Ala Thr Asn Phe Ser Leu Leu Lys Gln Ala Gly Asp Val Glu Glu Asn
1               5                   10                  15

Pro Gly Pro

<210> SEQ ID NO 139
<211> LENGTH: 21
<212> TYPE: PRT
<213> ORGANISM: Artificial Sequence
<220> FEATURE:
<223> OTHER INFORMATION: Description of Artificial Sequence: Synthetic
      CD8alpha Signal Peptide_CD8 Products 1, 2, 3, 4

<400> SEQUENCE: 139

Met Ala Leu Pro Val Thr Ala Leu Leu Leu Pro Leu Ala Leu Leu Leu
1               5                   10                  15

His Ala Ala Arg Pro
            20

<210> SEQ ID NO 140
<211> LENGTH: 161
<212> TYPE: PRT
<213> ORGANISM: Artificial Sequence
<220> FEATURE:
<223> OTHER INFORMATION: Description of Artificial Sequence: Synthetic
      CD8alpha Extracellular Domain_CD8 Products 1, 2, 3, 4

<400> SEQUENCE: 140

Ser Gln Phe Arg Val Ser Pro Leu Asp Arg Thr Trp Asn Leu Gly Glu
1               5                   10                  15

Thr Val Glu Leu Lys Cys Gln Val Leu Leu Ser Asn Pro Thr Ser Gly
                20                  25                  30

Cys Ser Trp Leu Phe Gln Pro Arg Gly Ala Ala Ala Ser Pro Thr Phe
            35                  40                  45

Leu Leu Tyr Leu Ser Gln Asn Lys Pro Lys Ala Ala Glu Gly Leu Asp
        50                  55                  60

Thr Gln Arg Phe Ser Gly Lys Arg Leu Gly Asp Thr Phe Val Leu Thr
65                  70                  75                  80

Leu Ser Asp Phe Arg Arg Glu Asn Glu Gly Tyr Tyr Phe Cys Ser Ala
                85                  90                  95

Leu Ser Asn Ser Ile Met Tyr Phe Ser His Phe Val Pro Val Phe Leu
            100                 105                 110

Pro Ala Lys Pro Thr Thr Thr Pro Ala Pro Arg Pro Pro Thr Pro Ala
        115                 120                 125

Pro Thr Ile Ala Ser Gln Pro Leu Ser Leu Arg Pro Glu Ala Cys Arg
    130                 135                 140
```

Pro Ala Ala Gly Gly Ala Val His Thr Arg Gly Leu Asp Phe Ala Cys
145                 150                 155                 160

Asp

<210> SEQ ID NO 141
<211> LENGTH: 21
<212> TYPE: PRT
<213> ORGANISM: Artificial Sequence
<220> FEATURE:
<223> OTHER INFORMATION: Description of Artificial Sequence: Synthetic
      CD8alpha Transmembrane Domain_CD8 Products 1, 2, 3, 4

<400> SEQUENCE: 141

Ile Tyr Ile Trp Ala Pro Leu Ala Gly Thr Cys Gly Val Leu Leu Leu
1               5                   10                  15

Ser Leu Val Ile Thr
            20

<210> SEQ ID NO 142
<211> LENGTH: 32
<212> TYPE: PRT
<213> ORGANISM: Artificial Sequence
<220> FEATURE:
<223> OTHER INFORMATION: Description of Artificial Sequence: Synthetic
      CD8alpha Intracellular Domain_CD8 Product 1 and 2

<400> SEQUENCE: 142

Leu Tyr Cys Asn His Arg Asn Arg Arg Arg Val Cys Lys Cys Pro Arg
1               5                   10                  15

Pro Val Val Lys Ser Gly Asp Lys Pro Ser Leu Ser Ala Arg Tyr Val
            20                  25                  30

<210> SEQ ID NO 143
<211> LENGTH: 4
<212> TYPE: PRT
<213> ORGANISM: Artificial Sequence
<220> FEATURE:
<223> OTHER INFORMATION: Description of Artificial Sequence: Synthetic
      Furin Cleavage Site_CD8 Products 1, 2, 3, 4

<400> SEQUENCE: 143

Arg Ala Lys Arg
1

<210> SEQ ID NO 144
<211> LENGTH: 21
<212> TYPE: PRT
<213> ORGANISM: Artificial Sequence
<220> FEATURE:
<223> OTHER INFORMATION: Description of Artificial Sequence: Synthetic
      CD8beta Signal Peptide _CD8 Product 2

<400> SEQUENCE: 144

Met Arg Pro Arg Leu Trp Leu Leu Leu Ala Ala Gln Leu Thr Val Leu
1               5                   10                  15

His Gly Asn Ser Val
            20

<210> SEQ ID NO 145
<211> LENGTH: 149
<212> TYPE: PRT
<213> ORGANISM: Artificial Sequence
<220> FEATURE:
<223> OTHER INFORMATION: Description of Artificial Sequence: Synthetic
      CD8beta Extracellular Domain _CD8 Product 2

-continued

```
<400> SEQUENCE: 145

Leu Gln Gln Thr Pro Ala Tyr Ile Lys Val Gln Thr Asn Lys Met Val
1               5                   10                  15

Met Leu Ser Cys Glu Ala Lys Ile Ser Leu Ser Asn Met Arg Ile Tyr
            20                  25                  30

Trp Leu Arg Gln Arg Gln Ala Pro Ser Ser Asp Ser His Glu Phe
        35                  40                  45

Leu Ala Leu Trp Asp Ser Ala Lys Gly Thr Ile His Gly Glu Val
    50                  55                  60

Glu Gln Glu Lys Ile Ala Val Phe Arg Asp Ala Ser Arg Phe Ile Leu
65                  70                  75                  80

Asn Leu Thr Ser Val Lys Pro Glu Asp Ser Gly Ile Tyr Phe Cys Met
                85                  90                  95

Ile Val Gly Ser Pro Glu Leu Thr Phe Gly Lys Gly Thr Gln Leu Ser
            100                 105                 110

Val Val Asp Phe Leu Pro Thr Thr Ala Gln Pro Thr Lys Lys Ser Thr
        115                 120                 125

Leu Lys Lys Arg Val Cys Arg Leu Pro Arg Pro Glu Thr Gln Lys Gly
    130                 135                 140

Pro Leu Cys Ser Pro
145

<210> SEQ ID NO 146
<211> LENGTH: 21
<212> TYPE: PRT
<213> ORGANISM: Artificial Sequence
<220> FEATURE:
<223> OTHER INFORMATION: Description of Artificial Sequence: Synthetic
      CD8beta Transmembrane Domain_CD8 Product 2

<400> SEQUENCE: 146

Ile Thr Leu Gly Leu Leu Val Ala Gly Val Leu Val Leu Leu Val Ser
1               5                   10                  15

Leu Gly Val Ala Ile
            20

<210> SEQ ID NO 147
<211> LENGTH: 19
<212> TYPE: PRT
<213> ORGANISM: Artificial Sequence
<220> FEATURE:
<223> OTHER INFORMATION: Description of Artificial Sequence: Synthetic
      CD8beta Intracellular Domain_CD8 Products 2 and 3

<400> SEQUENCE: 147

His Leu Cys Cys Arg Arg Arg Arg Ala Arg Leu Arg Phe Met Lys Gln
1               5                   10                  15

Phe Tyr Lys

<210> SEQ ID NO 148
<211> LENGTH: 40
<212> TYPE: PRT
<213> ORGANISM: Artificial Sequence
<220> FEATURE:
<223> OTHER INFORMATION: Description of Artificial Sequence: Synthetic
      CD4 Intracellular Domain_CD8 Product 4

<400> SEQUENCE: 148

Cys Val Arg Cys Arg His Arg Arg Arg Gln Ala Glu Arg Met Ser Gln
1               5                   10                  15
```

-continued

```
Ile Lys Arg Leu Leu Ser Glu Lys Lys Thr Cys Gln Cys Pro His Arg
             20                  25                  30

Phe Gln Lys Thr Cys Ser Pro Ile
             35              40
```

COMPOSITIONS AND METHODS FOR THE TREATMENT OF CANCER USING A CD8 ENGINEERED T CELL THERAPY

CROSS-REFERENCE TO RELATED APPLICATIONS

This application is a Divisional of U.S. patent application Ser. No. 17/100,223, filed on Nov. 20, 2020, which a Continuation of International Patent Application No. PCT/US20/30818, filed on Apr. 30, 2020, which claims priority to U.S. Provisional Application No. 62/841,748, filed on May 1, 2019, and U.S. Provisional Application No. 62/841,753, filed on May 1, 2019, the content of each of which is incorporated in its entirety, and to each of which priority is claimed.

SEQUENCE LISTINGS

The instant application contains a Sequence Listing which has been submitted electronically in ASCII format and is hereby incorporated by reference in its entirety. Said ASCII copy, created on Mar. 10, 2022, is named 087520_0252_SL.txt and is 121,398 bytes in size.

BACKGROUND OF THE INVENTION

Activation of T cells requires signaling through the T cell receptor (TCR) and its coreceptor molecules. CD4 and CD8 are membrane proteins that are expressed on T helper cells and cytotoxic T lymphocytes that serve as coreceptors that augment TCR signaling by stabilizing the interactions between the peptide-major histocompatibility (pMHC) ligands and the TCR (Li Q J, et al. (2004) CD4 enhances T cell sensitivity to antigen by coordinating Lck accumulation at the immunological synapse. Nat Immunol 5:791-799; Holler P D, Kranz D M (2003) Quantitative analysis of the contribution of TCR/pepMHC affinity and CD8 to T cell activation. Immunity 18:255-264). Specifically, the CD4 and CD8 coreceptors are essential for the initiation of signaling because they facilitate the recruitment of a kinase to the TCR-pMHC complex. Furthermore, research has shown that while the CD4 and CD8 coreceptors both augment T cell sensitivity to its ligands, only CD8 plays a role in the stabilization of TCR-pMHC interactions.

Furthermore, while naturally occurring MHC-I TCRs are presumed to require concurrent CD8 co-receptor help to stabilize peptide-MHC binding, higher affinity TCRs drive CD8-independent target binding and T cell activation. CD4 T cells, when engineered with high affinity NeoTCRs, are thus able to recognize peptide-MHC-I targets and trigger effector T cell functions. However, lower affinity TCRs are dependent on CD8 co-receptors to trigger T cell activation.

Accordingly, a NeoTCR cell therapy that is engineered to have CD8 co-receptor expression could stabilize the TCR-pMHC interactions and increase the efficacy of NeoTCR cell therapies that comprise low affinity TCRs that are dependent on such CD8 co-receptors.

SUMMARY OF THE INVENTION

In certain embodiments, the presently disclosed subject matter provides a cell, comprising an exogenous T cell receptor (TCR), and an exogenous CD8. In certain embodiments, the exogenous CD8 comprises at least one monomer. In certain embodiments, the at least one monomer of the exogenous CD8 comprises an extracellular domain, a transmembrane domain, an intracellular domain, fragments thereof, or combinations thereof. In certain embodiments, the extracellular domain comprises a CD8α extracellular domain or a CD8β extracellular domain. In certain embodiments, the transmembrane a CD8α transmembrane domain or a CD8β transmembrane domain. In certain embodiments, the intracellular domain comprises a CD8α intracellular domain or a CD8β intracellular domain. In certain embodiments, the intracellular domain comprises a CD4 intracellular domain.

In certain embodiments, the at least one monomer comprises a CD8α extracellular domain, a CD8α transmembrane domain, and a CD8α intracellular domain. In certain embodiments, the at least one monomer comprises a CD8β extracellular domain, a CD8β transmembrane domain, and a CD8β intracellular domain. In certain embodiments, the at least one monomer comprises a CD8α extracellular domain, a CD8α transmembrane domain, and a CD8β intracellular domain. In certain embodiments, the at least one monomer comprises a CD8α extracellular domain, a CD8α transmembrane domain, and a CD4 intracellular domain. In certain embodiments, the at least one monomer comprises a signal peptide. In certain embodiments, the signal peptide is a CD8 signal peptide.

In certain embodiments, the extracellular domain comprises the amino acid sequence set forth in SEQ ID NO: 140, or SEQ ID NO: 145. In certain embodiments, the transmembrane domain comprises the amino acid sequence set forth in SEQ ID NO: 141, or SEQ ID NO: 146. In certain embodiments, the intracellular domain comprises the amino acid sequence set forth in SEQ ID NO: 142, SEQ ID NO: 147, or SEQ ID NO: 148. In certain embodiments, the signal peptide comprises the amino acid sequence set forth in SEQ ID NO: 139, or SEQ ID NO: 144.

In certain embodiments, the exogenous CD8 comprises a 2A sequence. In certain embodiments, the exogenous CD8 comprises a linker. In certain embodiments, the linker comprises the amino acid sequence set forth in SEQ ID NO: 137. In certain embodiments, the exogenous CD8 comprises a protease cleavage site. In certain embodiments, the protease cleavage site is a Furin cleavage site.

In certain embodiments, the exogenous TCR is a patient derived TCR. In certain embodiments, the exogenous TCR comprises a signal sequence, a first and second 2A sequence, and a TCR polypeptide sequence. In certain embodiments, the exogenous TCR recognizes a cancer antigen. In certain embodiments, the cancer antigen is a neoantigen. In certain embodiments, the cancer antigen is a patient specific antigen.

In certain embodiments, the cell is a primary cell. In certain embodiments, the cell is a patient-derived cell. In certain embodiments, the cell is a lymphocyte. In certain embodiments, the cell is a T cell. In certain embodiments, the cell if a young T cell. In certain embodiments, the cell is CD45RA+, CD62L−, CD28+, CD95−, CCR7+, and CD27+. In certain embodiments, the cell is CD45RA+, CD62L+, CD28+, CD95+, CD27+, CCR7+. In certain embodiments, the cell is CD45RO+, CD62L+, CD28+, CD95+, CCR7+, CD27+, CD127+.

In certain embodiments, the cell further comprises a gene modification to enhance cell persistence and/or enhances memory cell differentiation. In certain embodiments, killing activity of the cell is increased between about 10% to about 500% as compared to killing activity of a cell that does not have the exogenous CD8. In certain embodiments, proliferation of the cell upon binding of the TCR to the antigen is increased between about 10% to about 500% as compared to proliferation of a cell that does not have the exogenous CD8. In certain embodiments, secretion of pro-inflammatory cytokine upon binding of the TCR to the antigen by the cell is increased between about 10% to about 500% as compared to secretion by a cell that does not have the exogenous CD8. In certain embodiments, LCK affinity of the cell is increased between about 10% to about 500% as compared to LCK affinity of a cell that does not have the exogenous CD8. In certain embodiments, persistence of the cell is increased between about 10% to about 500% as compared to persistence of a cell that does not have the exogenous CD8. In certain embodiments, tumor infiltration ability of the cell is increased between about 10% to about 500% as compared to tumor infiltration ability of a cell that does not have the exogenous CD8.

In certain embodiments, wherein the exogenous TCR is a CD8-dependent TCR. In certain embodiments, the exogenous TCR is a CD8-independent TCR. In certain embodiments, the exogenous CD8 is encoded by a CD8 Construct 1, a CD8 Construct 2, a CD8 Construct 3, or a CD8 Construct 4. In certain embodiments, the exogenous CD8 comprises: a CD8α extracellular domain, a CD8α transmembrane domain, and a CD8α intracellular domain; a CD8α extracellular domain, a CD8α transmembrane domain, a CD8α intracellular domain, a CD8β extracellular domain, a CD8β transmembrane domain, and a CD8β intracellular domain; a CD8α extracellular domain, a CD8α transmembrane domain, and a CD8β intracellular domain; or a CD8α extracellular domain, a CD8α transmembrane domain, and a CD4 intracellular domain. In certain embodiments, the exogenous CD8 comprises: a CD8α signal peptide (SEQ ID NO:139), a CD8α extracellular domain (SEQ ID NO:140), a CD8α transmembrane domain (SEQ ID NO:141), and a CD8α intracellular domain (SEQ ID NO: 142); a CD8α signal peptide (SEQ ID NO:139), a CD8α extracellular domain (SEQ ID NO:140), a CD8α transmembrane domain (SEQ ID NO:141), a CD8α intracellular domain (SEQ ID NO: 142), a CD8β signal peptide (SEQ ID NO:144), a CD8β extracellular domain (SEQ ID NO:145), a CD8β transmembrane domain (SEQ ID NO:146), and a CD8β intracellular domain (SEQ ID NO: 147); a CD8α signal peptide (SEQ ID NO:139), a CD8α extracellular domain (SEQ ID NO:140), a CD8α transmembrane domain (SEQ ID NO:141), and a CD8β intracellular domain (SEQ ID NO: 147); or a CD8α signal peptide (SEQ ID NO:139), a CD8α extracellular domain (SEQ ID NO:140), a CD8α transmembrane domain (SEQ ID NO:141), and a CD4 intracellular domain (SEQ ID NO: 148).

In certain embodiments, the presently disclosed subject matter provides a method of modifying a cell, the method comprising introducing into the cell a homologous recombination (HR) template nucleic acid sequence, wherein the HR template comprises first and second homology arms homologous to first and second target nucleic acid sequences, a TCR gene sequence positioned between the first and second homology arms, a CD8 gene sequence positioned between the first and the second homology arms, and recombining the HR template nucleic acid into an endogenous locus of the cell. In certain embodiments, the HR template comprises a first 2A-coding sequence positioned upstream of the CD8 gene sequence, a second 2A-coding sequence positioned downstream of the CD8 gene sequence and upstream of the TCR gene sequence, and a third 2A-coding sequence positioned downstream of the TCR gene sequence; wherein the first, second, and third 2A-coding sequences code for the same amino acid sequence and are codon-diverged relative to each other. In certain embodiments, the HR template comprises a sequence coding for the amino acid sequence Gly Ser Gly positioned immediately upstream of the first, second, and/or third 2A-coding sequences. In certain embodiments, the HR template further comprises a sequence coding for a Furin cleavage site positioned upstream of the first, second, and/or third 2A-coding sequences. In certain embodiments, the HR template further comprises a sequence encoding a signal sequence positioned immediately upstream of the TCR gene sequence and/or the CD8 gene sequence.

In certain embodiments, the HR template comprises a second TCR sequence positioned between the third 2A-coding sequence and the second homology arm. In certain embodiments, the HR template comprises a sequence encoding a first signal sequence positioned immediately upstream the first TCR gene sequence, and a sequence encoding a second signal sequence positioned immediately upstream of the second TCR gene sequence. In certain embodiments, the HR template comprises a second CD8 gene sequence positioned between the first CD8 gene sequence and the second 2A-coding sequence. In certain embodiments, a 2A coding sequence is positioned between the first and second CD8 gene sequence. In certain embodiments, a sequence coding for the amino acid sequence Gly Ser Gly is positioned between the first and second CD8 gene sequences. In certain embodiments, a sequence coding for a Furin cleavage site is positioned between the first and second CD8 gene sequences.

In certain embodiments, the CD8 gene sequence comprises a sequence encoding an extracellular domain, a sequence encoding an intracellular domain, a sequence encoding an intracellular domain, fragments thereof, or combinations thereof. In certain embodiments, the sequence encoding an extracellular domain comprises a sequence encoding a CD8α extracellular domain or a CD8β extracellular domain. In certain embodiments, the sequence encoding a transmembrane domain comprises a sequence encoding a CD8α transmembrane domain or a CD8β transmembrane domain. In certain embodiments, the sequence encoding an intracellular domain comprises a sequence encoding a CD8α intracellular domain or a CD8β intracellular domain. In certain embodiments, the sequence encoding an intracellular domain comprises a sequence encoding a CD4 intracellular domain.

In certain embodiments, the CD8 gene sequence comprises a sequence encoding a CD8α extracellular domain, a CD8α transmembrane domain, and a CD8α intracellular domain. In certain embodiments, the CD8 gene sequence comprises a sequence encoding a CD8β extracellular domain, a CD8β transmembrane domain, and a CD8β intracellular domain. In certain embodiments, the CD8 gene sequence comprises a sequence encoding a CD8α extracellular domain, a CD8α transmembrane domain, and a CD8β intracellular domain. In certain embodiments, the CD8 gene sequence comprises a sequence encoding a CD8α extracellular domain, a CD8α transmembrane domain, and a CD4 intracellular domain.

In certain embodiments, the HR template comprises a sequence encoding a first signal sequence positioned immediately upstream the first CD8 gene sequence, and a sequence encoding a second signal sequence positioned immediately upstream of the second CD8 gene sequence. In certain embodiments, the signal sequence is a CD8 signal sequence, a human growth hormone signal sequence, fragments thereof, or combinations thereof. In certain embodiments, the first and second homology arms of the HR template are each from about 300 bases to about 2,000 bases in length. In certain embodiments, the first and second homology arms of the HR template are each from about 600 bases to about 2,000 bases in length.

In certain embodiments, the exogenous TCR is a patient derived TCR. In certain embodiments, the exogenous TCR comprises a signal sequence, a first and second 2A sequence, and a TCR polypeptide sequence. In certain embodiments, the exogenous TCR recognizes a cancer antigen. In certain embodiments, the cancer antigen is a neoantigen. In certain embodiments, the cancer antigen is a patient specific antigen. In certain embodiments, the HR template is non-viral. In certain embodiments, the HR template is a circular DNA. In certain embodiments, the HR template is a linear DNA. In certain embodiments, the introducing occurs via electroporation.

In certain embodiments, the recombining comprises cleavage of the endogenous locus by a nuclease, and recombination of the HR template nucleic acid sequence into the endogenous locus by homology directed repair. In certain embodiments, the nuclease is a Clustered Regularly Interspaced Short Palindromic Repeats (CRISPR) family nuclease, or derivative thereof. In certain embodiments, the nuclease further comprises a gRNA.

In certain embodiments, the method further comprises culturing the cell. In certain embodiments, the culturing is conducted in the presence of at least one cytokine. In certain embodiments, the culturing is conducted in the presence of IL2, IL7, IL15, or any combination thereof. In certain embodiments, the culturing is conducted in the presence of IL7 and IL15. In certain embodiments, the method comprises a gene modification to enhance cell persistence and/or enhances memory cell differentiation.

In certain embodiments, the cell is a primary cell. In certain embodiments, the cell is a patient-derived cell. In certain embodiments, the cell is a lymphocyte. In certain embodiments, the cell is a T cell. In certain embodiments, the cell is a young T cell. In certain embodiments, the cell is CD45RA+, CD62L−, CD28+, CD95−, CCR7+, and CD27+. In certain embodiments, the cell is CD45RA+, CD62L+, CD28+, CD95+, CD27+, CCR7+. In certain embodiments, the cell is CD45RO+, CD62L+, CD28+, CD95+, CCR7+, CD27+, CD127+.

In certain embodiments, killing activity of the cell is increased between about 10% to about 500% as compared to killing activity of a cell that does not have the CD8 gene sequence. In certain embodiments, proliferation of the cell upon binding of the TCR to the antigen is increased between about 10% to about 500% as compared to proliferation of a cell that does not have the CD8 gene sequence. In certain embodiments, secretion of pro-inflammatory cytokine upon binding of the TCR to the antigen by the cell is increased between about 10% to about 500% as compared to secretion by a cell that does not have the CD8 gene sequence. In certain embodiments, LCK affinity of the cell is increased between about 10% to about 500% as compared to LCK affinity of a cell that does not have the CD8 gene sequence. In certain embodiments, wherein persistence of the cell is increased between about 10% to about 500% as compared to persistence of a cell that does not have the CD8 gene sequence. In certain embodiments, tumor infiltration ability of the cell is increased between about 10% to about 500% as compared to tumor infiltration ability of a cell that does not have the CD8 gene sequence.

In certain embodiments, the TCR gene encodes a CD8-dependent TCR. In certain embodiments, the TCR gene encodes a CD8-independent TCR. In certain embodiments, the CD8 gene sequence is encoded by a CD8 Construct 1, a CD8 Construct 2, a CD8 Construct 3, or a CD8 Construct 4. In certain embodiments, wherein the CD8 gene sequence comprises: a CD8α extracellular domain, a CD8α transmembrane domain, and a CD8α intracellular domain; a CD8α extracellular domain, a CD8α transmembrane domain, a CD8α intracellular domain, a CD8β extracellular domain, a CD8β transmembrane domain, and a CD8β intracellular domain; a CD8α extracellular domain, a CD8α transmembrane domain, and a CD8β intracellular domain; or a CD8α extracellular domain, CD8α transmembrane domain, CD4 intracellular domain. In certain embodiments, the CD8 gene sequence comprises: a CD8α signal peptide (SEQ ID NO:139), a CD8α extracellular domain (SEQ ID NO:140), a CD8α transmembrane domain (SEQ ID NO:141), and a CD8α intracellular domain (SEQ ID NO: 142); a CD8α signal peptide (SEQ ID NO:139), a CD8α extracellular domain (SEQ ID NO:140), a CD8α transmembrane domain (SEQ ID NO:141), a CD8α intracellular domain (SEQ ID NO: 142), a CD8β signal peptide (SEQ ID NO:144), a CD8β extracellular domain (SEQ ID NO:145), a CD8β transmembrane domain (SEQ ID NO:146), and a CD8β intracellular domain (SEQ ID NO: 147); a CD8α signal peptide (SEQ ID NO:139), a CD8α extracellular domain (SEQ ID NO:140), a CD8α transmembrane domain (SEQ ID NO:141), and a CD8β intracellular domain (SEQ ID NO: 147); or a CD8α signal peptide (SEQ ID NO:139), a CD8α extracellular domain (SEQ ID NO:140), a CD8α transmembrane domain (SEQ ID NO:141), and a CD4 intracellular domain (SEQ ID NO: 148).

In certain embodiments, the presently disclosed subject matter provides a cell modified by any of the methods disclosed herein.

In certain embodiments, the presently disclosed subject matter provides a composition comprising an effective amount of a cell disclosed herein. In certain embodiments, the composition is a pharmaceutical composition that further comprises a pharmaceutically acceptable excipient. In certain embodiments, the composition is administered to a patient in need thereof for the treatment of cancer. In certain embodiments, the composition comprises a cryopreservation agent. In certain embodiments, the composition comprises serum albumin. In certain embodiments, the composition comprises Plasma-Lyte A, HSA, and CryoStor CS10.

In certain embodiments, the presently disclosed subject matter provides a method of treating cancer in a subject in need thereof, the method comprising administering a therapeutically effective amount of a cell or a composition disclosed herein.

In certain embodiments, prior to administering the therapeutically effective amount of cells disclosed herein, a non-myeloablative lymphodepletion regimen is administered to the subject. In certain embodiments, the cancer is a solid tumor. In certain embodiments, the cancer is a liquid tumor. In certain embodiments, the solid tumor is selected from the group consisting of melanoma, thoracic cancer, lung cancer, ovarian cancer, breast cancer, pancreatic cancer, head and neck cancer, prostate cancer, gynecological cancer, central nervous system cancer, cutaneous cancer, HPV+ cancer, esophageal cancer, thyroid cancer, gastric cancer, hepatocellular cancer, cholangiocarcinomas, renal cell cancers, testicular cancer, sarcomas, and colorectal cancer. In certain embodiments, the liquid tumor is selected from the group consisting of follicular lymphoma, leukemia, and multiple myeloma.

In certain embodiments, the presently disclosed subject matter provides a kit comprising a cell disclosed herein, reagents for performing a method disclosed herein, or a composition disclosed herein. In certain embodiments, the kit further comprises written instructions for treating a cancer.

In certain embodiments, the presently disclosed subject matter provides a cell, comprising: an exogenous T cell receptor (TCR); and an exogenous CD8, comprising: a CD8α extracellular domain, a CD8α transmembrane domain, a CD8α intracellular domain; a CD8α extracellular domain, a CD8α transmembrane domain, a CD8α intracellular domain, a CD8β extracellular domain, a CD8β transmembrane domain, and a CD8β intracellular domain; a CD8α extracellular domain, a CD8α transmembrane domain, and a CD8β intracellular domain; or a CD8α extracellular domain, a CD8α transmembrane domain, and a CD4 intracellular domain.

In certain embodiments, the presently disclosed subject matter provides a cell, comprising: an exogenous T cell receptor (TCR); and an exogenous CD8, comprising: a CD8α signal peptide (SEQ ID NO:139), a CD8α extracellular domain (SEQ ID NO:140), a CD8α transmembrane domain (SEQ ID NO:141), and a CD8α intracellular domain (SEQ ID NO: 142); a CD8α signal peptide (SEQ ID NO:139), a CD8α extracellular domain (SEQ ID NO:140), a CD8α transmembrane domain (SEQ ID NO:141), a CD8α intracellular domain (SEQ ID NO: 142), a CD8β signal peptide (SEQ ID NO:144), a CD8β extracellular domain (SEQ ID NO:145), a CD8β transmembrane domain (SEQ ID NO:146), and a CD8β intracellular domain (SEQ ID NO: 147); a CD8α signal peptide (SEQ ID NO:139), a CD8α extracellular domain (SEQ ID NO:140), a CD8α transmembrane domain (SEQ ID NO:141), and a CD8β intracellular domain (SEQ ID NO: 147); or a CD8α signal peptide (SEQ ID NO:139), a CD8α extracellular domain (SEQ ID NO:140), a CD8α transmembrane domain (SEQ ID NO:141), and a CD4 intracellular domain (SEQ ID NO: 148).

In certain embodiments, the presently disclosed subject matter provides a method of modifying a cell, the method comprising: introducing into the cell a homologous recombination (HR) template nucleic acid sequence, wherein the HR template comprises: first and second homology arms homologous to first and second target nucleic acid sequences; a TCR gene sequence positioned between the first and second homology arms; a CD8 gene sequence positioned between the first and the second homology arms; and recombining the HR template nucleic acid into an endogenous locus of the cell, wherein the CD8 gene sequence comprises: a CD8α extracellular domain, a CD8α transmembrane domain, and a CD8α intracellular domain; a CD8α extracellular domain, a CD8α transmembrane domain, a CD8α intracellular domain, a CD8β extracellular domain, a CD8β transmembrane domain, and a CD8β intracellular domain; a CD8α extracellular domain, a CD8α transmembrane domain, a CD8β intracellular domain; or a CD8α extracellular domain, a CD8α transmembrane domain, and a CD4 intracellular domain.

In certain embodiments, the presently disclosed subject matter provides a method of modifying a cell, the method comprising: introducing into the cell a homologous recombination (HR) template nucleic acid sequence, wherein the HR template comprises: first and second homology arms homologous to first and second target nucleic acid sequences; a TCR gene sequence positioned between the first and second homology arms; a CD8 gene sequence positioned between the first and the second homology arms; and recombining the HR template nucleic acid into an endogenous locus of the cell, wherein the CD8 gene sequence comprises: a CD8α signal peptide (SEQ ID NO:139), a CD8α extracellular domain (SEQ ID NO:140), a CD8α transmembrane domain (SEQ ID NO:141), and a CD8α intracellular domain (SEQ ID NO: 142); a CD8α signal peptide (SEQ ID NO:139), a CD8α extracellular domain (SEQ ID NO:140), a CD8α transmembrane domain (SEQ ID NO:141), a CD8α intracellular domain (SEQ ID NO: 142), a CD8β signal peptide (SEQ ID NO:144), a CD8β extracellular domain (SEQ ID NO:145), a CD8β transmembrane domain (SEQ ID NO:146), and a CD8β intracellular domain (SEQ ID NO: 147); a CD8α signal peptide (SEQ ID NO:139), a CD8α extracellular domain (SEQ ID NO:140), a CD8α transmembrane domain (SEQ ID NO:141), and a CD8β intracellular domain (SEQ ID NO: 147); or a CD8α signal peptide (SEQ ID NO:139), a CD8α extracellular domain (SEQ ID NO:140), a CD8α transmembrane domain (SEQ ID NO:141), and a CD4 intracellular domain (SEQ ID NO: 148).

In certain embodiments, the presently disclosed subject matter provides a composition comprising a cell, wherein the cell comprises an exogenous T cell receptor (TCR) and an exogenous CD8, wherein the exogenous CD8 comprises: a CD8α extracellular domain, a CD8α transmembrane domain, and a CD8α intracellular domain; a CD8α extracellular domain, a CD8α transmembrane domain, a CD8α intracellular domain, a CD8β extracellular domain, a CD8β transmembrane domain, and a CD8β intracellular domain; a CD8α extracellular domain, a CD8α transmembrane domain, and a CD8β intracellular domain; or a CD8α extracellular domain, a CD8α transmembrane domain, and a CD4 intracellular domain.

In certain embodiments, the presently disclosed subject matter provides a composition comprising a cell, wherein the cell comprises an exogenous T cell receptor (TCR) and an exogenous CD8, wherein the exogenous CD8 comprises: a CD8α signal peptide (SEQ ID NO:139), a CD8α extracellular domain (SEQ ID NO:140), a CD8α transmembrane domain (SEQ ID NO:141), and a CD8α intracellular domain (SEQ ID NO: 142); a CD8α signal peptide (SEQ ID NO:139), a CD8α extracellular domain (SEQ ID NO:140), a CD8α transmembrane domain (SEQ ID NO:141), a CD8α intracellular domain (SEQ ID NO: 142), a CD8β signal peptide (SEQ ID NO:144), a CD8β extracellular domain (SEQ ID NO:145), a CD8β transmembrane domain (SEQ ID NO:146), and a CD8β intracellular domain (SEQ ID NO: 147); a CD8α signal peptide (SEQ ID NO:139), a CD8α extracellular domain (SEQ ID NO:140), a CD8α transmembrane domain (SEQ ID NO:141), and a CD8β intracellular domain (SEQ ID NO: 147); or a CD8α signal peptide (SEQ ID NO:139), a CD8α extracellular domain (SEQ ID NO:140), a CD8α transmembrane domain (SEQ ID NO:141), and a CD4 intracellular domain (SEQ ID NO: 148).

In certain embodiments, the presently disclosed subject matter provides a method of treating cancer in a subject in need thereof, the method comprising administering a therapeutically effective amount of a cell, wherein the cell comprises an exogenous T cell receptor (TCR) and an exogenous CD8, wherein the exogenous CD8 comprises: a CD8α extracellular domain, a CD8α transmembrane domain, and a CD8α intracellular domain; a CD8α extracellular domain, a CD8α transmembrane domain, a CD8α intracellular domain, a CD8β extracellular domain, a CD8β transmembrane domain, and a CD8β intracellular domain; a CD8α extracellular domain, a CD8α transmembrane domain, and a CD8β intracellular domain; or a CD8α extracellular domain, a CD8α transmembrane domain, and a CD4 intracellular domain.

In certain embodiments, the presently disclosed subject matter provides a method of treating cancer in a subject in need thereof, the method comprising administering a therapeutically effective amount of a cell, wherein the cell comprises an exogenous T cell receptor (TCR) and an exogenous CD8, wherein the exogenous CD8 comprises: a CD8α signal peptide (SEQ ID NO:139), a CD8α extracellular domain (SEQ ID NO:140), a CD8α transmembrane domain (SEQ ID NO:141), and a CD8α intracellular domain (SEQ ID NO: 142); a CD8α signal peptide (SEQ ID NO:139), a CD8α extracellular domain (SEQ ID NO:140), a CD8α transmembrane domain (SEQ ID NO:141), a CD8α intracellular domain (SEQ ID NO: 142), a CD8β signal peptide (SEQ ID NO:144), a CD8β extracellular domain (SEQ ID NO:145), a CD8β transmembrane domain (SEQ ID NO:146), and a CD8β intracellular domain (SEQ ID NO: 147); a CD8α signal peptide (SEQ ID NO:139), a CD8α extracellular domain (SEQ ID NO:140), a CD8α transmembrane domain (SEQ ID NO:141), and a CD8β intracellular domain (SEQ ID NO: 147); or a CD8α signal peptide (SEQ ID NO:139), a CD8α extracellular domain (SEQ ID NO:140), a CD8α transmembrane domain (SEQ ID NO:141), and a CD4 intracellular domain (SEQ ID NO: 148).

BRIEF DESCRIPTION OF THE DRAWINGS

FIGS. 1A-1C show an example of a NeoE TCR cassette and gene editing methods that can be used to make NeoTCR Products. FIG. 1A shows a schematic representing the general targeting strategy used for integrating neoantigen-specific TCR constructs (neoTCRs) into the TCRα locus. FIGS. 1B and 1C show a neoantigen-specific TCR construct design used for integrating a NeoTCR into the TCRα locus wherein the cassette is shown with signal sequences ("SS"), protease cleavage sites ("P"), and 2A peptides ("2A"). FIG. 1B shows a target TCRα locus (endogenous TRAC, top panel) and its CRISPR Cas9 target site (horizontal stripes, cleavage site designated by the arrow), and the circular plasmid HR template (bottom panel) with the polynucleotide encoding the neoTCR, which is located between left and right homology arms ("LHA" and "RHA" respectively) prior to integration. FIG. 1C shows the integrated neoTCR in the TCRα locus (top panel), the transcribed and spliced neoTCR mRNA (middle panel), and translation and processing of the expressed neoTCR (bottom panel).

FIGS. 2A-2D show the circular plasmids used to encode CD8 constructs 1, 2, 3, and 4. FIG. 2A shows CD8 Construct 1 used to produce the CD8 Product 1. FIG. 2B shows CD8 Construct 2 used to produce the CD8 Product 2. FIG. 2C shows CD8 Construct 3 used to produce the CD8 Product 3. FIG. 2D shows CD8 Construct 4 used to produce the CD8 Product 4. As shown in FIGS. 2A-2D, SS stands for a signal sequence. As described in FIGS. 6, 7, 8, and 9, the SS may be HGH; however other signal sequences may be used as needed for appropriate trafficking. As shown in FIGS. 2A-2D, P stands for a protease cleavage site. As described in FIGS. 6, 7, 8, and 9, the P may be Furin; however other protease cleavage sites may be used as appropriate to provide the cleavage action described herein. As shown in FIGS. 2A-2D, 2A stands for the 2A peptide. As described in FIGS. 6, 7, 8, and 9, the 2A may be the P2A peptide; however, other 2A peptides may be used.

FIG. 3. As shown in FIGS. 3A-3D, SS stands for a signal sequence. As described in FIGS. 6, 7, 8, and 9, the SS may be HGH; however other signal sequences may be used as needed for appropriate trafficking. As shown in FIGS. 3A-3D, P stands for a protease cleavage site. As described in FIGS. 6, 7, 8, and 9, the P may be Furin; however other protease cleavage sites may be used as appropriate to provide the cleavage action described herein. As shown in FIGS. 3A-3D, 2A stands for the 2A peptide. As described in FIGS. 6, 7, 8, and 9, the 2A may be the P2A peptide; however, other 2A peptides may be used.

FIG. 4A shows translated products of CD8 Product 1 and CD8 Product 2. FIG. 4B shows the translated products of CD8 Product 3 and CD8 Product 4.

FIG. 5. FIG. 5 provides an exemplary DNA sequence of the NeoTCR construct described in FIGS. 1A-1C. Conservative substitutions of nucleic acids can be used throughout to result in the same translated product. Furthermore, where amino acids can be substituted without a change in function, substitutions of the nucleic acids provided in FIG. 5 can also be used to achieve the substituted amino acids conferring a substantially similar or identical function of the translated proteins.

FIG. 6. FIG. 6 provides an exemplary DNA sequence of the CD8 Construct 1 (and translated CD8 Product 1) described in FIGS. 2A, 3A, and 4A. Conservative substitutions of nucleic acids can be used throughout to result in the same translated product. Furthermore, where amino acids can be substituted without a change in function, substitutions of the nucleic acids provided in FIG. 6 can also be used to achieve the substituted amino acids conferring a substantially similar or identical function of the translated proteins.

FIG. 7. FIG. 7 provides an exemplary DNA sequence of the CD8 Construct 2 (and translated CD8 Product 2) described in FIGS. 2B, 3B, and 4A. Conservative substitutions of nucleic acids can be used throughout to result in the same translated product. Furthermore, where amino acids can be substituted without a change in function, substitutions of the nucleic acids provided in FIG. 7 can also be used to achieve the substituted amino acids conferring a substantially similar or identical function of the translated proteins.

FIG. 8. FIG. 8 provides an exemplary DNA sequence of the CD8 Construct 3 (and translated CD8 Product 3) described in FIGS. 2C, 3C, and 4B. Conservative substitutions of nucleic acids can be used throughout to result in the same translated product. Furthermore, where amino acids can be substituted without a change in function, substitutions of the nucleic acids provided in FIG. 8 can also be used to achieve the substituted amino acids conferring a substantially similar or identical function of the translated proteins.

FIG. 9. FIG. 9 provides an exemplary DNA sequence of the CD8 Construct 4 (and translated CD8 Product 4) described in FIGS. 2D, 3D, and 4B. Conservative substitutions of nucleic acids can be used throughout to result in the same translated product. Furthermore, where amino acids can be substituted without a change in function, substitutions of the nucleic acids provided in FIG. 9 can also be used to achieve the substituted amino acids conferring a substantially similar or identical function of the translated proteins.

FIG. 10 presents a visual depiction of CD8 Products 1, 2, 3, and 4 along with the predicted LCK activity of each of CD8 Products 1, 2, 3, and 4.

FIG. 11A provides an exemplary expression construct of CD8 Product 1. FIG. 11B provides an exemplary expression construct of CD8 Product 2. FIG. 11C provides an exemplary expression construct of CD8 Product 3. FIG. 11D provides an exemplary expression construct of CD8 Product 4.

FIG. 12 diagrams the design of an Incucyte experiment to show the killing ability of the CD8 Products.

FIGS. 13A and 13B show the increased tumor killing ability of CD8 Product 4 compared to a NeoTCR Product with the same NeoTCR as the CD8 Product 4 in a population of CD4 T cells. Specifically, both the CD8 Product 4 and the NeoTCR Product express TCR097. However, the CD8 Product 4 also expresses CD8 Construct 4 which comprises the extracellular domain of CD8α and the intracellular domain of CD4. The effector: target cell ratio (E:T Ration) was 1:1 (FIG. 13A) or 2:1 (FIG. 13B) and each were normalized for gene editing per cell line. The SW620 COX6C R20Q heterozygous tumor cells used in this experiment was a cell line that expresses the cognate antigen for TCR097 (a CD8 dependent TCR). This shows that the low affinity binding of TCR097 can be saved by co-expressing the extracellular domain of CD8α and the intracellular domain of CD4.

FIG. 14 shows the increased tumor killing ability of CD8 Product 4 compared to a NeoTCR Product with the same NeoTCR as the CD8 Product 4 in a population of CD4 T cells. Specifically, both the CD8 Product 4 and the NeoTCR Product express TCR097. However, the CD8 Product 4 also expresses CD8 Construct 4 which comprises the extracellular domain of CD8α and the intracellular domain of CD4. The effector:target cell ratio (E:T Ration) was 1:1, 1:2, or 1:4 and each were normalized for gene editing per cell line. The SW620 COX6C R20Q homozygous tumor cells used in this experiment was a cell line that expresses the cognate antigen for TCR097. An increased killing can be seen in this experiment compared to that shown in FIGS. 13A and 13B because the cell line is homozygous for the cognate antigen expression; thus, even though TCR97 is a low affinity TCR, the increased amount of cognate antigen overcame the low affinity limitations.

FIGS. 15A and 15B provide exemplary control experiments showing that there is an increased tumor killing ability of CD8 Product 4 compared to a NeoTCR Product with the same NeoTCR as the CD8 Product 4 in a population of CD4 T cells (top graphs in FIGS. 15A and 15B) or CD8 T cells (bottom graphs in FIGS. 15A and 15B) and that CD8 Product 4 is more effective at tumor killing than simply expressing the NeoTCR construct and CD8 Product 4 in CD8 T cells. FIG. 15A shows an E:T ration of 2:1 and FIG. 15B shows an E:T ratio of 1:1.

FIG. 16 shows the surface expression of CD8 Construct 4. Peak #1 is a NeoTCR Product in CD4+/CD8− T cells (expressing TCR089). Peak #2 is a CD8 Product 4 in CD8+/CD4+ T cells. Peak #3 is a NeoTCR Product in CD8+/CD4− T cells. As shown CD8 Construct 4 exhibited proper and comparable surface expression as the NeoTCR Products. Similar results were achieved with the other CD8 Constructs (data not shown).

FIGS. 17A and 17B shows that CD8α expression boosts CD4 T cell sensitivity while maintaining specificity. FIG. 17A shows that the expression of CD8 Constructs 1-4 increases the sensitivity of the T cells and does not change the specificity of the CD8 Product to the NeoTCR. As shown, co-expression of the CD8 Constructs decreases the EC50 which shows the increased sensitivity to the NeoTCR. FIG. 17B shows that the CD8 Products 1-4 are specific for the cognate antigen to NeoTCR 097 because there is only INFγ production by the CD8 Cells of the CD8 Products 1-4 in the presence of cognate antigen (i.e., no INFγ production by the CD8 Cells of the CD8 Products 1-4 in the presence of mismatched antigen). The same experiment as shown in FIGS. 17A and 17B were performed with CD107a instead of INFγ and the same increased sensitivity with maintained specificity to the NeoTCR was shown (data not shown) to confirm the results with INFγ.

FIG. 18 shows that CD8α expression boosts CD4 T cell sensitivity among CD8− independent NeoTCRs. The figure shows data from the CD8-independent NeoTCR089. This shows that even when a NeoTCR is CD8-independent, there is an increase in sensitivity of CD8 Product 4. This was a surprising result to find that sensitivity can be increased even for CD8-independent TCRs. Similar results were achieved with CD8 Products 1-3 (data not shown). Thus, CD8-dependent (e.g., NeoTCR097) and CD8-independent (e.g., NeoTCR089) exhibit increased sensitivity compared to NeoTCR Products expressing the same NeoTCRs.

DETAILED DESCRIPTION

Definitions

Figure 1A:
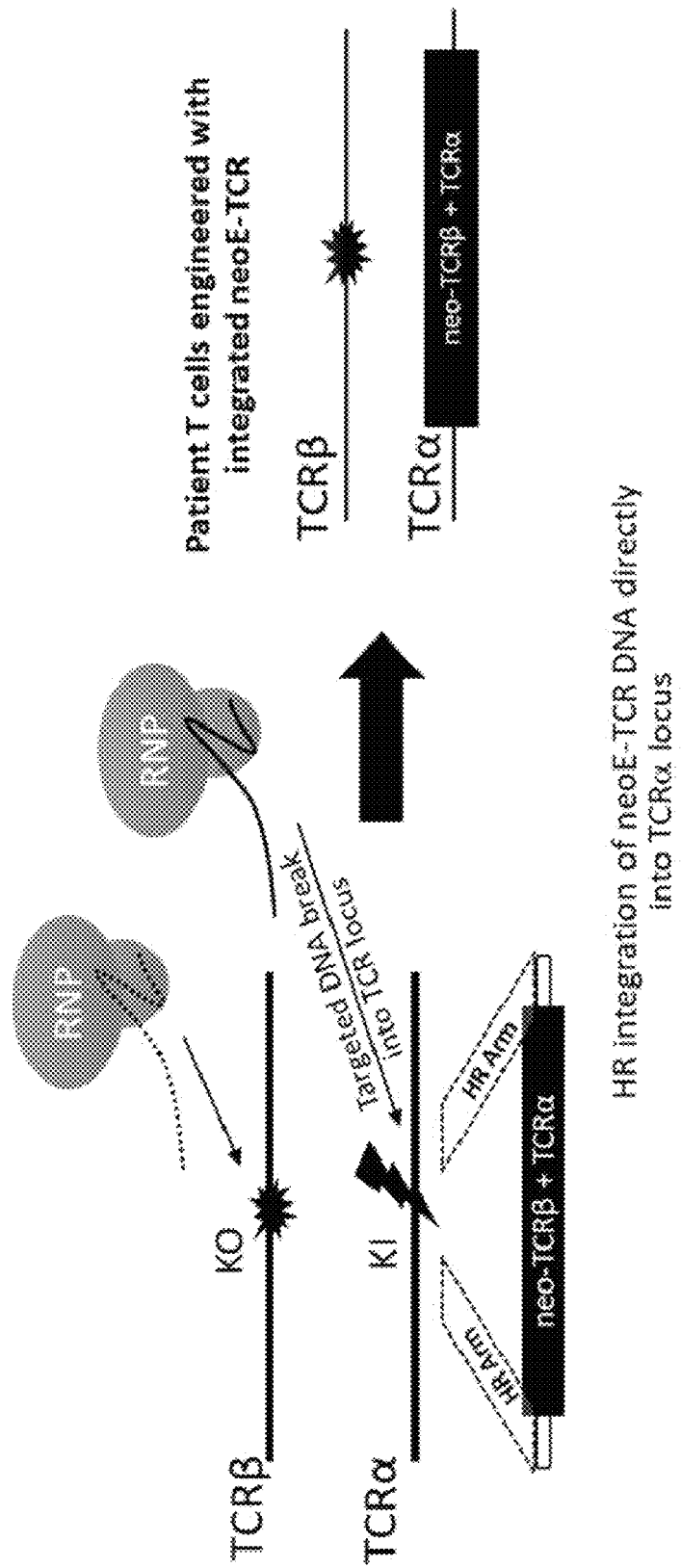
FIGS. 1A-1C.

Unless defined otherwise, all technical and scientific terms used herein have the meaning commonly understood by a person skilled in the art. The following references provide one of skill with a general definition of many of the terms used in the presently disclosed subject matter: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

It is understood that aspects and embodiments of the invention described herein include "comprising," "consisting," and "consisting essentially of" aspects and embodiments. The terms "comprises" and "comprising" are intended to have the broad meaning ascribed to them in U.S. Patent Law and can mean "includes", "including" and the like.

As used herein, the term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, e.g., up to 10%, up to 5%, or up to 1% of a given value. Alternatively, particularly with respect to biological systems or processes, the term can mean within an order of magnitude, e.g., within 5-fold or within 2-fold, of a value.

The term "antibody" as used herein is used in the broadest sense and encompasses various antibody structures, including but not limited to monoclonal antibodies, polyclonal antibodies, multispecific antibodies (e.g., bispecific and trispecific antibodies), and antibody fragments (e.g., bis-Fabs) so long as they exhibit the desired antigen-binding activity. "Antibody Fragment" as used herein refers to a molecule other than an intact antibody that comprises a portion of an intact antibody that binds the antigen to which the intact antibody binds. Examples of antibody fragments include but are not limited to bis-Fabs; Fv; Fab; Fab, Fab'-SH; F(ab')$_2$;

diabodies; linear antibodies; single-chain antibody molecules (e.g., scFv); and multispecific antibodies formed from antibody fragments.

The terms "Cancer" and "Tumor" are used interchangeably herein. As used herein, the terms "Cancer" or "Tumor" refer to all neoplastic cell growth and proliferation, whether malignant or benign, and all pre-cancerous and cancerous cells and tissues. The terms are further used to refer to or describe the physiological condition in mammals that is typically characterized by unregulated cell growth/proliferation. Cancer can affect a variety of cell types, tissues, or organs, including but not limited to an organ selected from the group consisting of bladder, bone, brain, breast, cartilage, glia, esophagus, fallopian tube, gallbladder, heart, intestines, kidney, liver, lung, lymph node, nervous tissue, ovaries, pancreas, prostate, skeletal muscle, skin, spinal cord, spleen, stomach, testes, thymus, thyroid, trachea, urogenital tract, ureter, urethra, uterus, and vagina, or a tissue or cell type thereof. Cancer includes cancers, such as sarcomas, carcinomas, or plasmacytomas (malignant tumor of the plasma cells). Examples of cancer include, but are not limited to, those described herein. The terms "Cancer" or "Tumor" and "Proliferative Disorder" are not mutually exclusive as used herein.

"CD8" is a cell surface glycoprotein found on most cytotoxic T lymphocytes that mediates efficient cell-cell interactions within the immune system. The CD8 antigen acts as a coreceptor with the T-cell receptor on the T lymphocyte to recognize antigens displayed by an antigen presenting cell in the context of class I MHC molecules.

"CD8 Cells" as used herein means one or more cells precision engineered to express one or more NeoTCRs and a CD8 Construct.

"CD8 Construct" as used herein means any one of a CD8 Construct 1, a CD8 Construct 2, a CD8 Construct 3, or a CD8 Construct 4.

"CD8 Product" as used herein means a product comprising CD8 Cells.

"CD8 Construct 1" and "CD8 Product 1" refer to a construct that comprises a NeoTCR and CD8α (CD8α extracellular domain, CD8α transmembrane domain, and CD8α intracellular domain) and the resulting product that comprises an expressed NeoTCR and CD8α. Non-limiting examples of a CD8 Product 1 is provided in FIGS. 2A, 3A, and 6. A non-limiting example of a CD8 Product 1 is provided in FIG. 4A.

"CD8 Construct 2" and "CD8 Product 2" refer to a construct that comprises a NeoTCR, CD8α (CD8α extracellular domain, CD8α transmembrane domain, and CD8α intracellular domain), and CD8β (CD8β extracellular domain, CD8β transmembrane domain, and CD8β intracellular domain) and the resulting product that comprises an expressed NeoTCR, CD8α, and CD8β. Non-limiting examples of a CD8 Product 2 is provided in FIGS. 2B, 3B, and 7. A non-limiting example of a CD8 Product 1 is provided in FIG. 4A.

"CD8 Construct 3" and "CD8 Product 3" refer to a construct that comprises a NeoTCR, CD8α extracellular domain, CD8α transmembrane domain, and CD8β intracellular domain and the resulting product that comprises an expressed NeoTCR, CD8α extracellular domain, CD8α transmembrane domain, and CD8β intracellular domain. Non-limiting examples of a CD8 Product 3 is provided in FIGS. 2C, 3C, and 8. A non-limiting example of a CD8 Product 1 is provided in FIG. 4B.

"CD8 Construct 4" and "CD8 Product 4" refer to a construct that comprises a NeoTCR, CD8α extracellular domain, CD8α transmembrane domain, and CD4 intracellular domain) and the resulting product that comprises an expressed NeoTCR, CD8α extracellular domain, CD8α transmembrane domain, and CD4 intracellular domain. Non-limiting examples of a CD8 Product 4 is provided in FIGS. 2D, 3D, and 9. A non-limiting example of a CD8 Product 1 is provided in FIG. 4B.

A "conservative substitution" or a "conservative amino acid," refers to the substitution of an amino acid with a chemically or functionally similar amino acid. Conservative substitution tables providing similar amino acids are well known in the art.

In certain embodiments, acidic amino acids D and E are conservative substitutions for one another; basic amino acids K, R, and H are conservative substitutions for one another; hydrophilic uncharged amino acids S, T, N. and Q are conservative substitutions for one another; aliphatic uncharged amino acids G, A, V, L, and I are conservative substitutions for one another; non-polar uncharged amino acids C, M, and P are conservative substitutions for one another; aromatic amino acids F, Y, and W are conservative substitutions for one another; A, S, and T are conservative substitutions for one another; D and E are conservative substitutions for one another; N and Q are conservative substitutions for one another; R and K are conservative substitutions for one another; I, L, and M are conservative substitutions for one another; F, Y, and W are conservative substitutions for one another; A and G are conservative substitutions for one another; D and E are conservative substitutions for one another; N and Q are conservative substitutions for one another; R, K and H are conservative substitutions for one another; I, L, M, and V are conservative substitutions for one another; F, Y and W are conservative substitutions for one another; S and T are conservative substitutions for one another; and C and M are conservative substitutions for one another.

Additional conservative substitutions may be found, for example, in Creighton, *Proteins: Structures and Molecular Properties* 2nd ed. (1993) W. H. Freeman & Co., New York, NY.

"Treat," "Treatment," and "treating" are used interchangeably and as used herein mean obtaining beneficial or desired results including clinical results. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, the NeoTCR Product of the invention is used to delay development of a proliferative disorder (e.g., cancer) or to slow the progression of such disease.

"Dextramer" as used herein means a multimerized neoepitope-HLA complex that specifically binds to its cognate NeoTCR.

As used herein, the terms "neoantigen", "neoepitope" or "neoE" refer to a newly formed antigenic determinant that arises, e.g., from a somatic mutation(s) and is recognized as "non-self." A mutation giving rise to a "neoantigen", "neoepitope" or "neoE" can include a frameshift or non-frameshift indel, missense or nonsense substitution, splice site alteration (e.g., alternatively spliced transcripts), genomic rearrangement or gene fusion, any genomic or expression alterations, or any post-translational modifications.

"NeoTCR", "NeoE TCR" and "exogenous TCR" as used herein mean a neoepitope-specific T cell receptor that is introduced into a T cell, e.g., by gene editing methods. As used herein, the term "TCR gene sequence" refers to a NeoTCR gene sequence.

"NeoTCR cells" as used herein means one or more cells precision engineered to express one or more NeoTCRs. In certain embodiments, the cells are T cells. In certain embodiments, the T cells are CD8+ and/or CD4+ T cells. In certain embodiments, the CD8+ and/or CD4+ T cells are autologous cells from the patient for whom a NeoTCR Product will be administered. The terms "NeoTCR cells" and "NeoTCR-P1 T cells" and "NeoTCR-P1 cells" are used interchangeably herein.

"NeoTCR Product" as used herein means a pharmaceutical formulation comprising one or more NeoTCR cells. NeoTCR Product consists of autologous precision genome-engineered CD8+ and CD4+ T cells. Using a targeted DNA-mediated non-viral precision genome engineering approach, expression of the endogenous TCR is eliminated and replaced by a patient-specific NeoTCR isolated from peripheral CD8+ T cells targeting the tumor-exclusive neoepitope. In certain embodiments, the resulting engineered CD8+ or CD4+ T cells express NeoTCRs on their surface of native sequence, native expression levels, and native TCR function. The sequences of the NeoTCR external binding domain and cytoplasmic signaling domains are unmodified from the TCR isolated from native CD8+ T cells. Regulation of the NeoTCR gene expression is driven by the native endogenous TCR promoter positioned upstream of where the NeoTCR gene cassette is integrated into the genome. Through this approach, native levels of NeoTCR expression are observed in unstimulated and antigen-activated T cell states.

The NeoTCR Product manufactured for each patient represents a defined dose of autologous CD8+ and/or CD4+ T cells that are precision genome engineered to express a single neoE-specific TCR cloned from neoE-specific CD8+ T cells individually isolated from the peripheral blood of that same patient.

"NeoTCR Viral Product" as used herein has the same definition of NeoTCR Product except that the genome engineering is performed using viral mediated methods.

"Pharmaceutical Formulation" refers to a preparation which is in such form as to permit the biological activity of an active ingredient contained therein to be effective, and which contains no additional components which are unacceptably toxic to a subject to which the formulation would be administered. For clarity, DMSO at quantities used in a NeoTCR Product is not considered unacceptably toxic.

A "subject," "patient," or an "individual" for purposes of treatment refers to any animal classified as a mammal, including humans, domestic and farm animals, and zoo, sports, or pet animals, such as dogs, horses, cats, cows, etc. Preferably, the mammal is human.

"TCR" as used herein means T cell receptor.

The term "tumor antigen" as used herein refers to an antigen (e.g., a polypeptide) that is uniquely or differentially expressed on a tumor cell compared to a normal or non-neoplastic cell. In certain embodiments, a tumor antigen includes any polypeptide expressed by a tumor that is capable of activating or inducing an immune response via an antigen-recognizing receptor or capable of suppressing an immune response via receptor-ligand binding.

"2A" and "2A peptide" are used interchangeably herein and mean a class of 18-22 amino acid long, viral, self-cleaving peptides that are able to mediate cleavage of peptides during translation in eukaryotic cells.

Four well-known members of the 2A peptide class are T2A, P2A, E2A, and F2A. The T2A peptide was first identified in the Thosea asigna virus 2A. The P2A peptide was first identified in the porcine teschovirus-1 2A. The E2A peptide was first identified in the equine rhinitis A virus. The F2A peptide was first identified in the foot-and-mouth disease virus.

The self-cleaving mechanism of the 2A peptides is a result of ribosome skipping the formation of a glycyl-prolyl peptide bond at the C-terminus of the 2A. Specifically, the 2A peptides have a C-terminal conserved sequence that is necessary for the creation of steric hindrance and ribosome skipping. The ribosome skipping can result in one of three options: 1) successful skipping and recommencement of translation resulting in two cleaved proteins (the upstream of the 2A protein which is attached to the complete 2A peptide except for the C-terminal proline and the downstream of the 2A protein which is attached to one proline at the N-terminal; 2) successful skipping but ribosome fall-off that results in discontinued translation and only the protein upstream of the 2A; or 3) unsuccessful skipping and continued translation (i.e., a fusion protein).

The term "endogenous" as used herein refers to a nucleic acid molecule or polypeptide that is normally expressed in a cell or tissue.

The term "exogenous" as used herein refers to a nucleic acid molecule or polypeptide that is not endogenously present in a cell. The term "exogenous" would therefore encompass any recombinant nucleic acid molecule or polypeptide expressed in a cell, such as foreign, heterologous, and over-expressed nucleic acid molecules and polypeptides. By "exogenous" nucleic acid is meant a nucleic acid not present in a native wild-type cell; for example, an exogenous nucleic acid may vary from an endogenous counterpart by sequence, by position/location, or both. For clarity, an exogenous nucleic acid may have the same or different sequence relative to its native endogenous counterpart; it may be introduced by genetic engineering into the cell itself or a progenitor thereof, and may optionally be linked to alternative control sequences, such as a non-native promoter or secretory sequence.

"Young" or "Younger" or "Young T cell" as it relates to T cells means memory stem cells ($T_{MSC}$) and central memory cells ($T_{CM}$). These cells have T cell proliferation upon specific activation and are competent for multiple cell divisions. They also have the ability to engraft after re-infusion, to rapidly differentiate into effector T cells upon exposure to their cognate antigen and target and kill tumor cells, as well as to persist for ongoing cancer surveillance and control.

NeoTCR Products

Figure 1B:
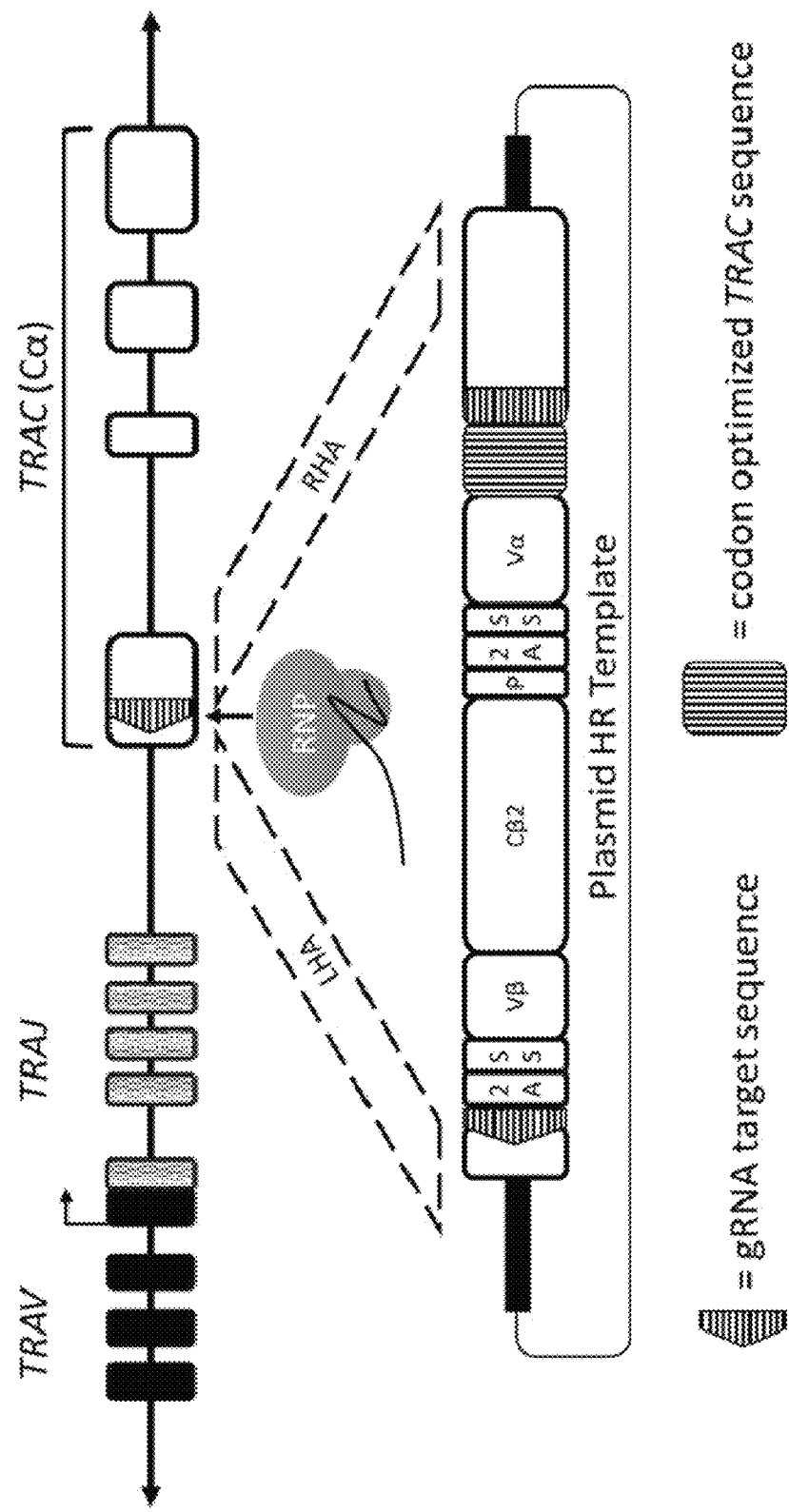
Figure 1C:
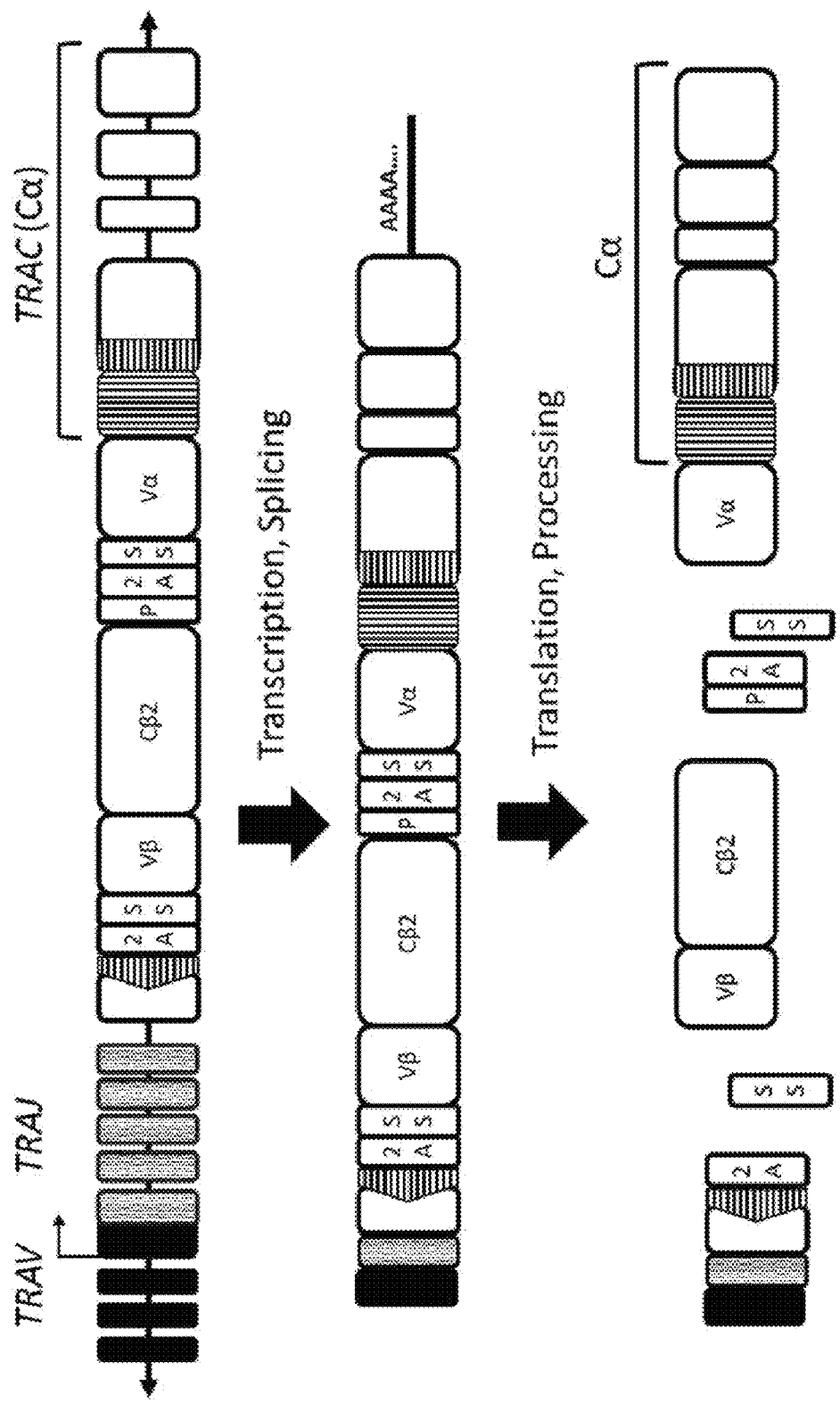

In some embodiments, using the gene editing technology and neoTCR isolation technology described in PCT/US2020/17887 and PCT/US2019/025415, which are incorporated herein in their entireties, NeoTCRs are cloned in autologous CD8+ and CD4+ T cells from the same patient with cancer by precision genome engineered (using a DNA-mediated (non-viral) method as described in FIGS. 1A-1C) to express the neoTCR. In other words, the NeoTCRs that are tumor specific are identified in cancer patients, such NeoTCRs are then cloned, and then the cloned NeoTCRs are inserted into the cancer patient's T cells. NeoTCR expressing T cells are then expanded in a manner that preserves a "young" T cell phenotypes, resulting in a NeoTCR-P1 product (i.e., a NeoTCR Product) in which the majority of the T cells exhibit T memory stem cell and T central memory phenotypes.

These 'young' or 'younger' or less-differentiated T cell phenotypes are described to confer improved engraftment potential and prolonged persistence post-infusion. Thus, the administration of NeoTCR Product, consisting significantly of 'young' T cell phenotypes, has the potential to benefit patients with cancer, through improved engraftment potential, prolonged persistence post-infusion, and rapid differentiation into effector T cells to eradicate tumor cells throughout the body.

Ex vivo mechanism-of-action studies were also performed with NeoTCR Product manufactured with T cells from patients with cancer. Comparable gene editing efficiencies and functional activities, as measured by antigen-specificity of T cell killing activity, proliferation, and cytokine production, were observed demonstrating that the manufacturing process described herein is successful in generating products with T cells from patients with cancer as starting material.

In certain embodiments, the NeoTCR Product manufacturing process involves electroporation of dual ribonucleoprotein species of CRISPR-Cas9 nucleases bound to guide RNA sequences, with each species targeting the genomic TCRα and the genomic TCRβ loci. The specificity of targeting Cas9 nucleases to each genomic locus has been previously described in the literature as being highly specific. Comprehensive testing of the NeoTCR Product was performed in vitro and in silico analyses to survey possible off-target genomic cleavage sites, using COSMID and GUIDE-seq, respectively. Multiple NeoTCR Product or comparable cell products from healthy donors were assessed for cleavage of the candidate off-target sites by deep sequencing, supporting the published evidence that the selected nucleases are highly specific.

Further aspects of the precision genome engineering process have been assessed for safety. No evidence of genomic instability following precision genome engineering was found in assessing multiple NeoTCR Products by targeted locus amplification (TLA) or standard FISH cytogenetics. No off-target integration anywhere into the genome of the NeoTCR sequence was detected. No evidence of residual Cas9 was found in the cell product.

The comprehensive assessment of the NeoTCR Product and precision genome engineering process indicates that the NeoTCR Product will be well tolerated following infusion back to the patient.

The genome engineering approach described herein enables highly efficient generation of bespoke NeoTCR T cells (i.e., NeoTCR Products) for personalized adoptive cell therapy for patients with solid and liquid tumors. Furthermore, the engineering method is not restricted to the use in T cells and has also been applied successfully to other primary cell types, including natural killer and hematopoietic stem cells.

CD8 Products

Coexpression of MHC class I—restricted neoTCRs and ectopic CD8 receptors in precision genome engineered CD4 T cells significantly potentiates antigen-specific effector functions.

Neoepitopes from tumor-exclusive mutations represent compelling targets for personalized neoE-specific autologous TCR-T cell therapies for patients with solid tumors. The imPACT Isolation Technology as described in PCT/US2020/17887, which is incorporated by reference in its entirety, is an ultra-sensitive and high-throughput process for capturing neoE-specific CD8 T cells from the blood of patients with solid cancers. Leveraging this technology, neoepitope-specific MHC class I-restricted TCRs ("MHC-I neoTCRs") were cloned from individually captured CD8 T cells. Using DNA-mediated (non-viral) gene editing as described in Example 1, fresh CD8 and CD4 T cells from the same patient with cancer were engineered to express the WIC-I neoTCR (concomitant with elimination of the endogenous TCR).

While naturally occurring MHC-I TCRs were presumed to require concurrent CD8 co-receptor help to stabilize peptide-WIC binding, higher affinity TCRs were able to drive CD8– independent target binding and T cell activation. CD4 T cells, when engineered with high affinity neoTCRs, were thus able to recognize peptide-MHC-I targets and trigger effector T cell functions. However, lower affinity TCRs were dependent on CD8 co-receptors to trigger T cell activation. By precision genome engineering CD8 co-receptor genes together with the neoTCR into CD4 T cells, WIC-I neoTCRs were made competent to trigger antigen-specific effector T cell function.

CD8 stabilizes TCR-pMHC interactions and synergizes with TCRs for avidity. CD8 also serves to enhance avidity from low affinity TCRs, while the intracellular domain of CD8α is critical for enhanced T cell activation. Expression of CD8 may enhance CD4 T cell responses, which may not respond to physiological concentrations of pMHC. Disruption of CD8 binding to MHC can convert catch-bond TCR-pMHC into slip-bonds, highlighting the importance of CD8-WIC interactions even for TCRs that bind pMHC independent of CD8.

CD8α has a lower affinity to LCK than CD8β, suggesting that either co-expression of both CD8α and CD8β or generation of a chimeric CD8α-CD8β molecule which contains the extracellular CD8α and intracellular domain of CD8β can improve effectiveness. The CD8 Constructs described herein are:

1. CD8α homodimer (CD8 Construct 1)
2. CD8α-P2A-CD8β (CD8 Construct 2)
3. CD8α with CD8β intracellular domain (CD8 Construct 3)
4. CD8α homodimer with CD4 intracellular domain (CD8 Construct 4)

In some embodiments, the NeoTCR Products described above include an additional modification to include the expression of CD8 Construct 1, CD8 Construct 2, CD8 Construct 3, or CD8 Construct 4 (each a CD8 Product). Specifically, using the gene editing technology and neoTCR isolation technology described in PCT/US2020/17887 and PCT/US2019/025415, which are incorporated herein in their entireties, NeoTCRs are cloned in autologous CD8+ and CD4+ T cells from the same patient with cancer by precision genome engineered (using a DNA-mediated (non-viral) method as described in FIGS. 1A-1C) to express the neoTCR.

Each of the CD8 Constructs, when expressed, result in CD8 Products. Table 1 provides a description of each construct and product.

TABLE 1

CD8 Products and CD8 Constructs

Figure 2A:
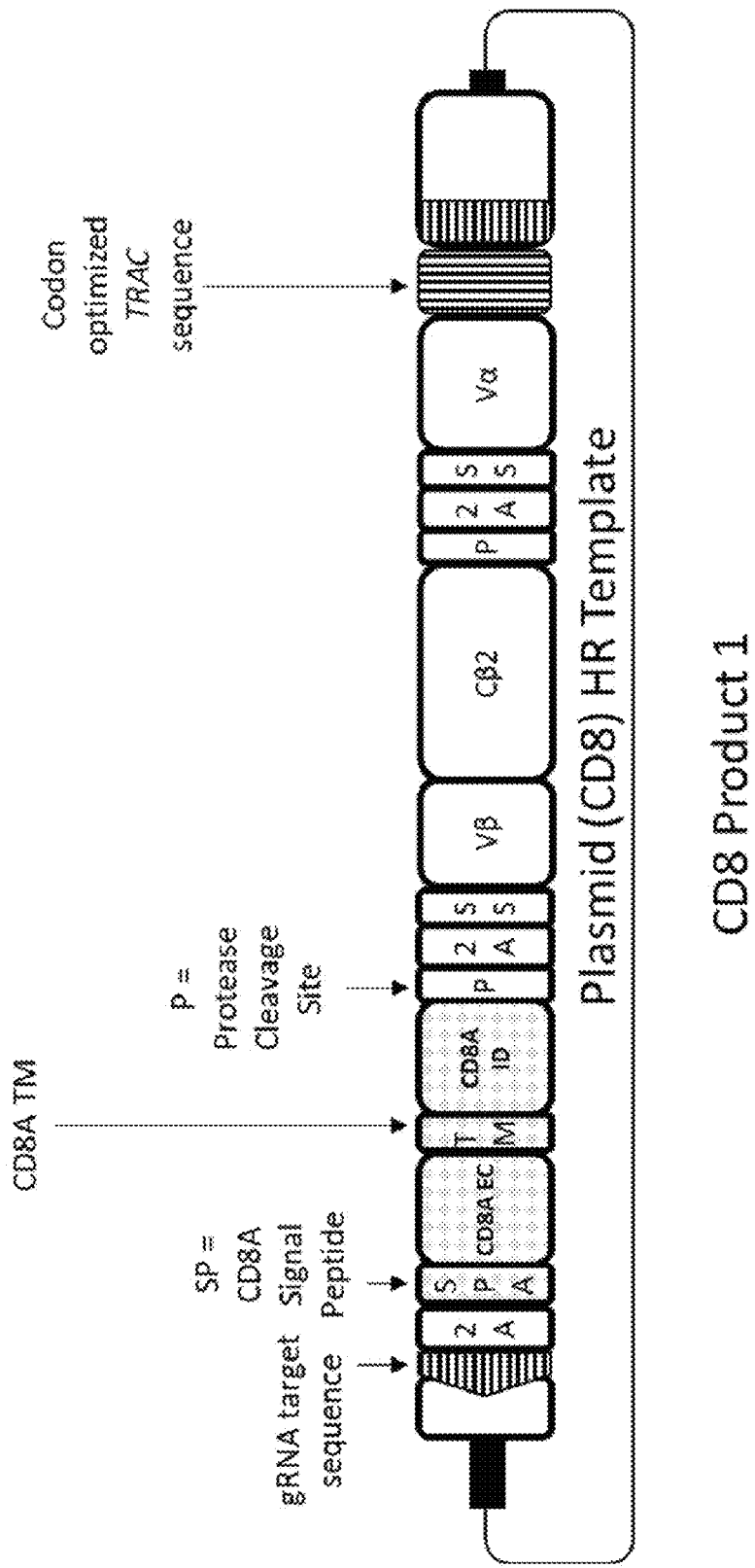
FIGS. 2A-2D.
Figure 2B:
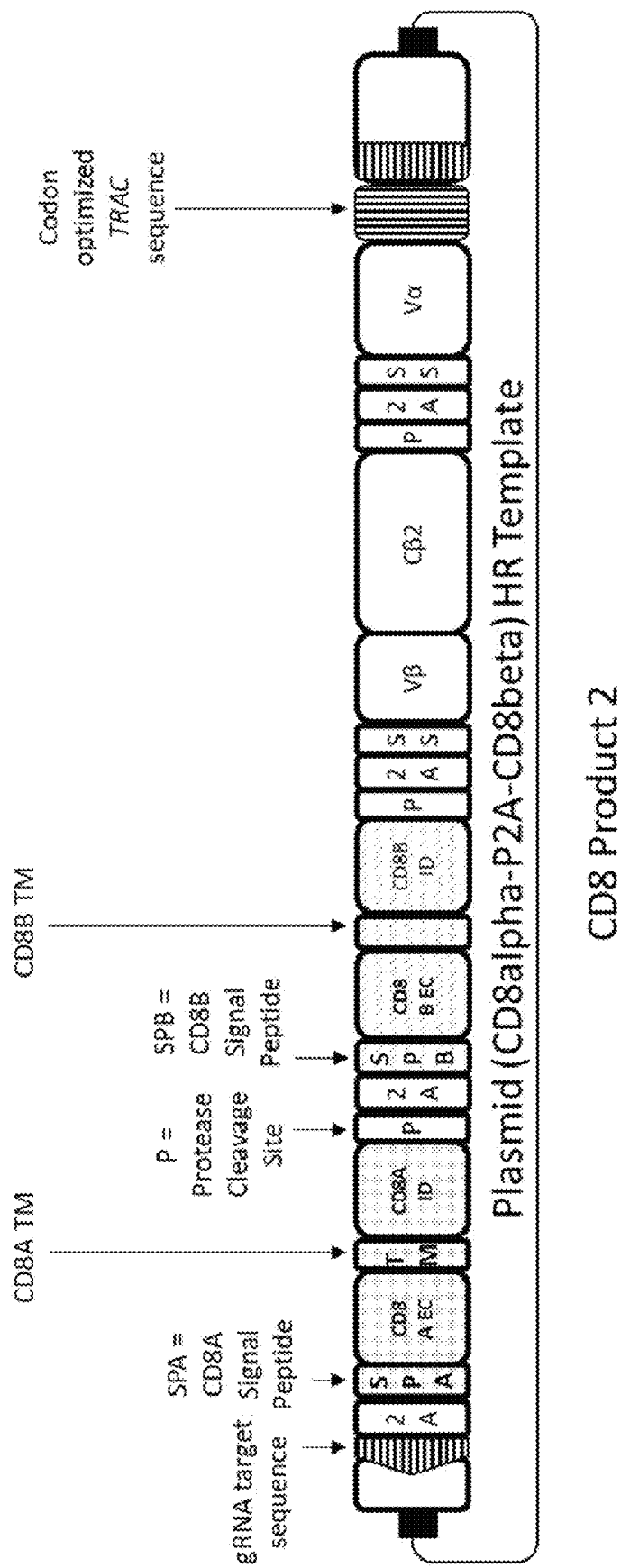
Figure 2C:
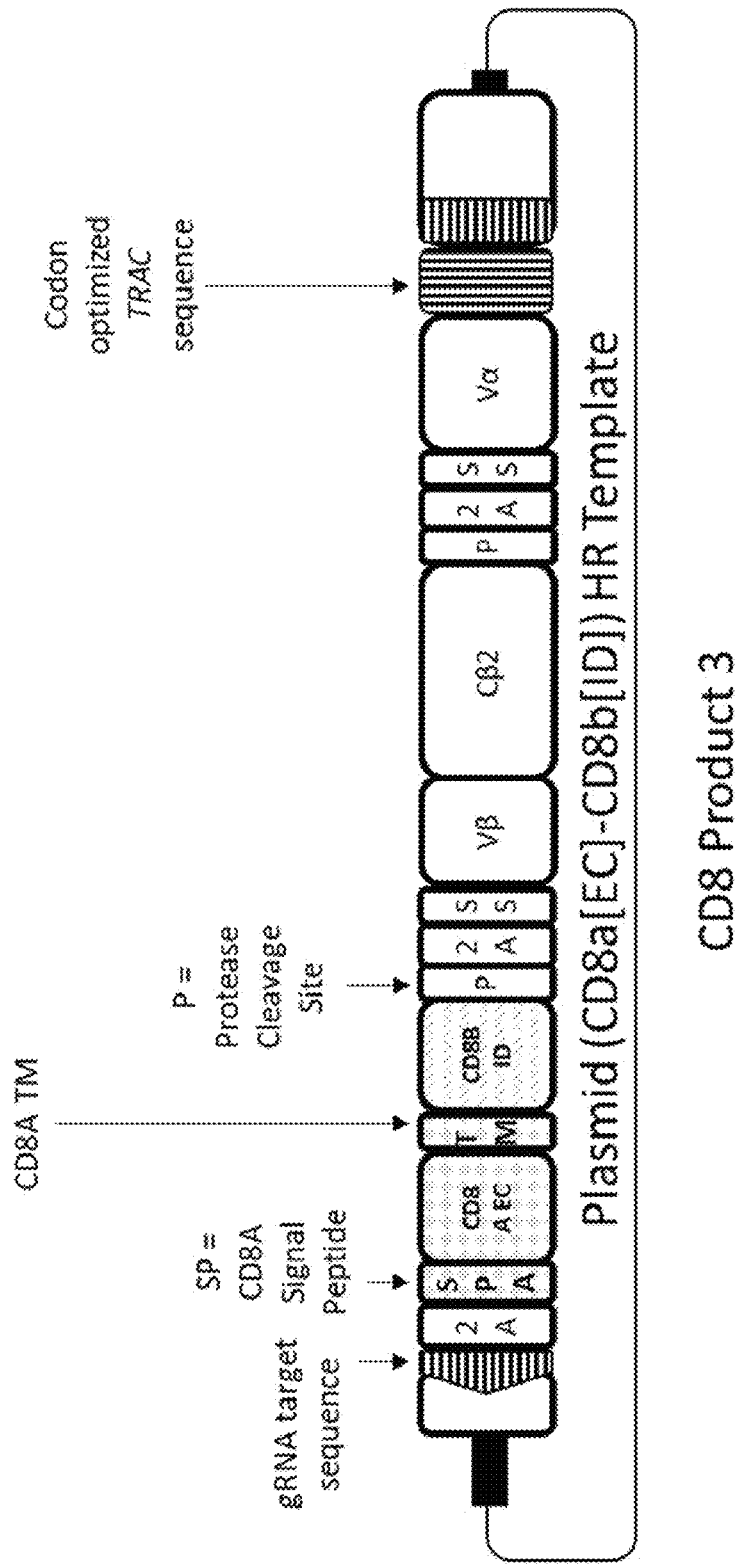
Figure 2D:
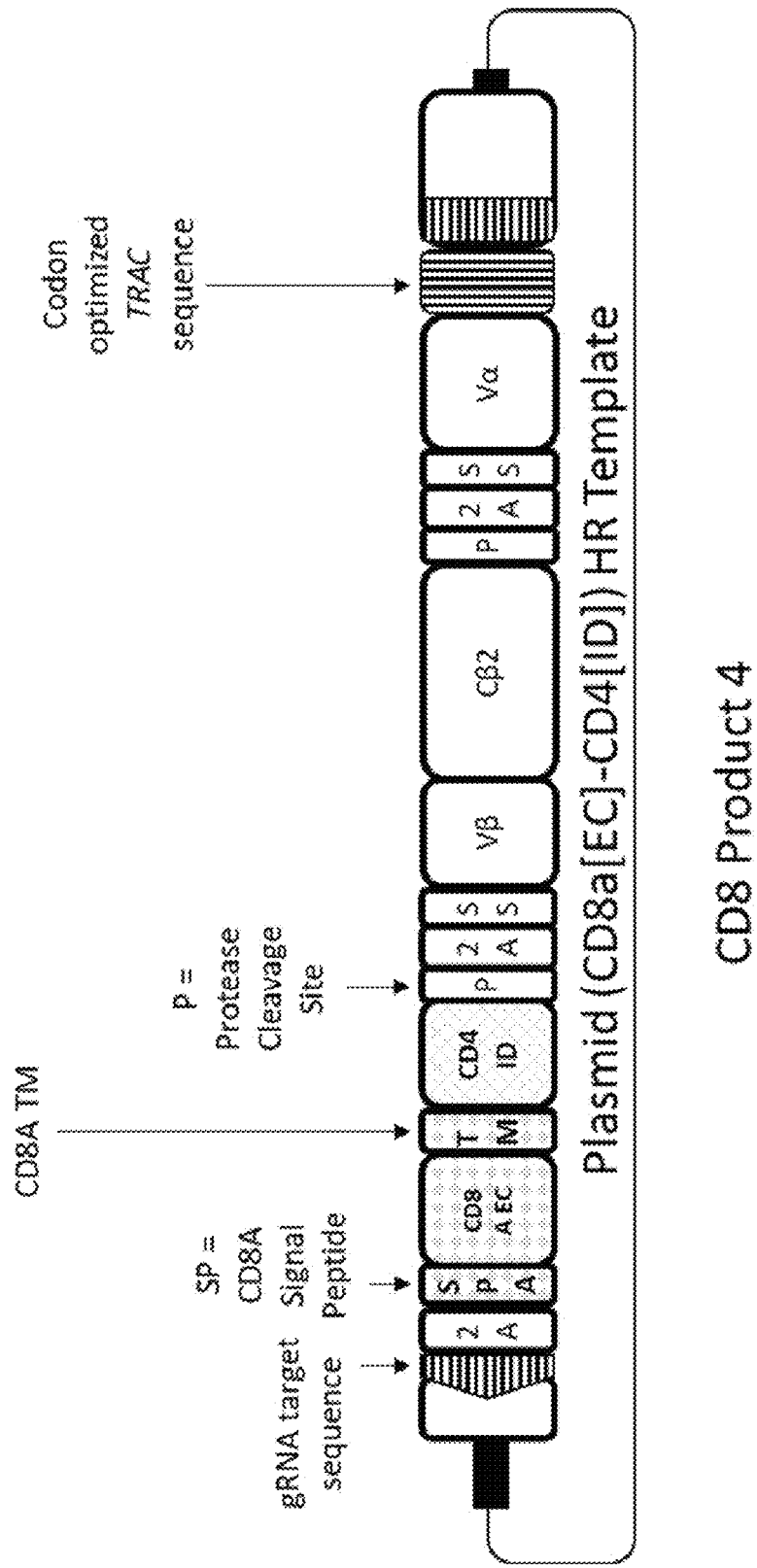
Figure 3A:
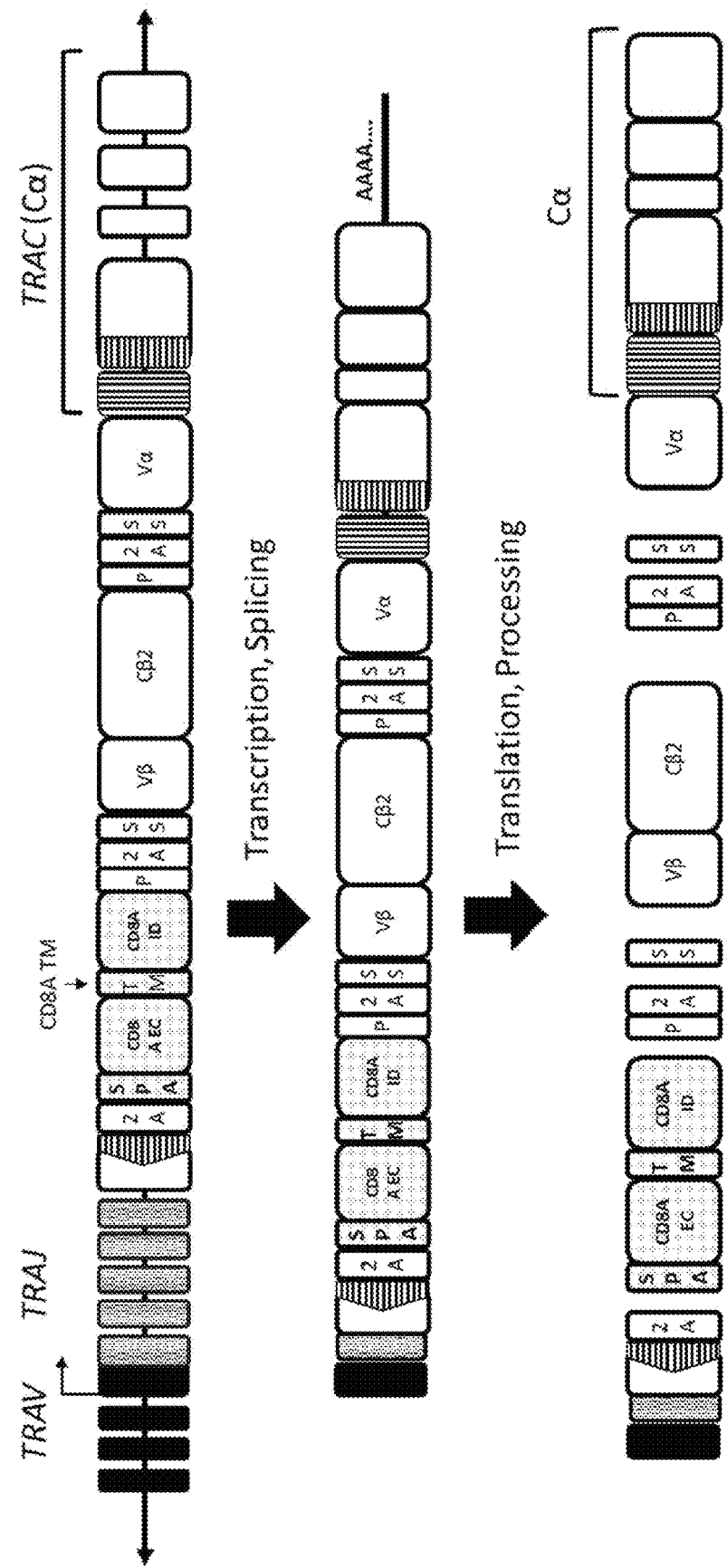
FIGS. 3A-3D show the transcription/splicing and translation processing of each of CD8 Constructs 1, 2, 3, and 4 to yield CD8 Products 1, 2, 3, and 4.
Figure 3B:
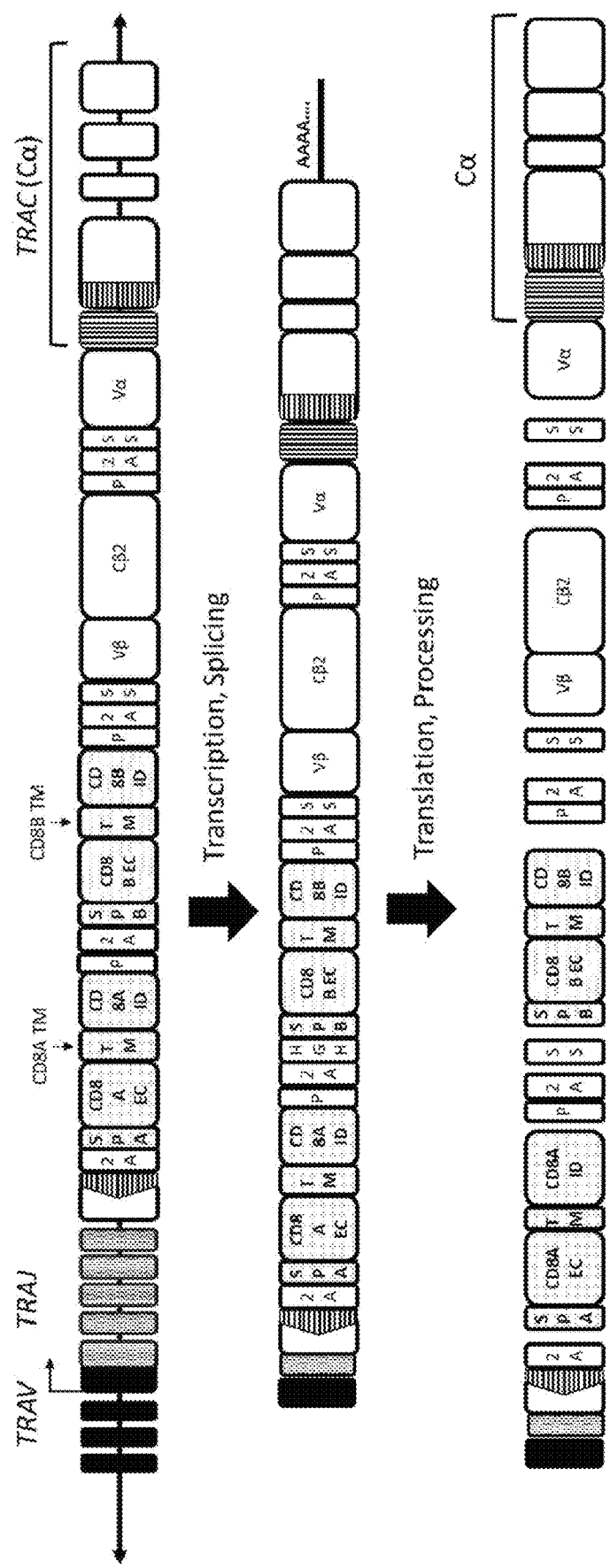
Figure 3C:
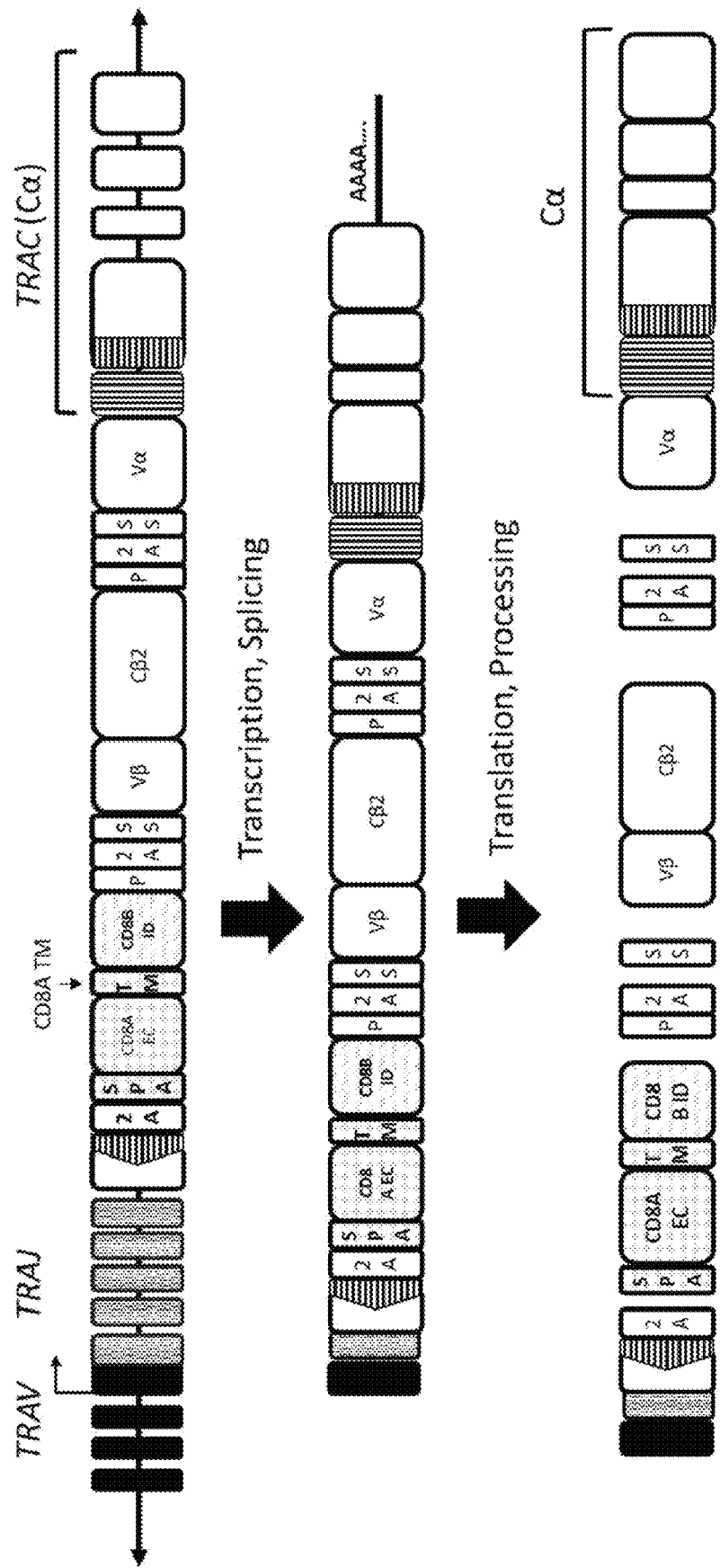
Figure 3D:
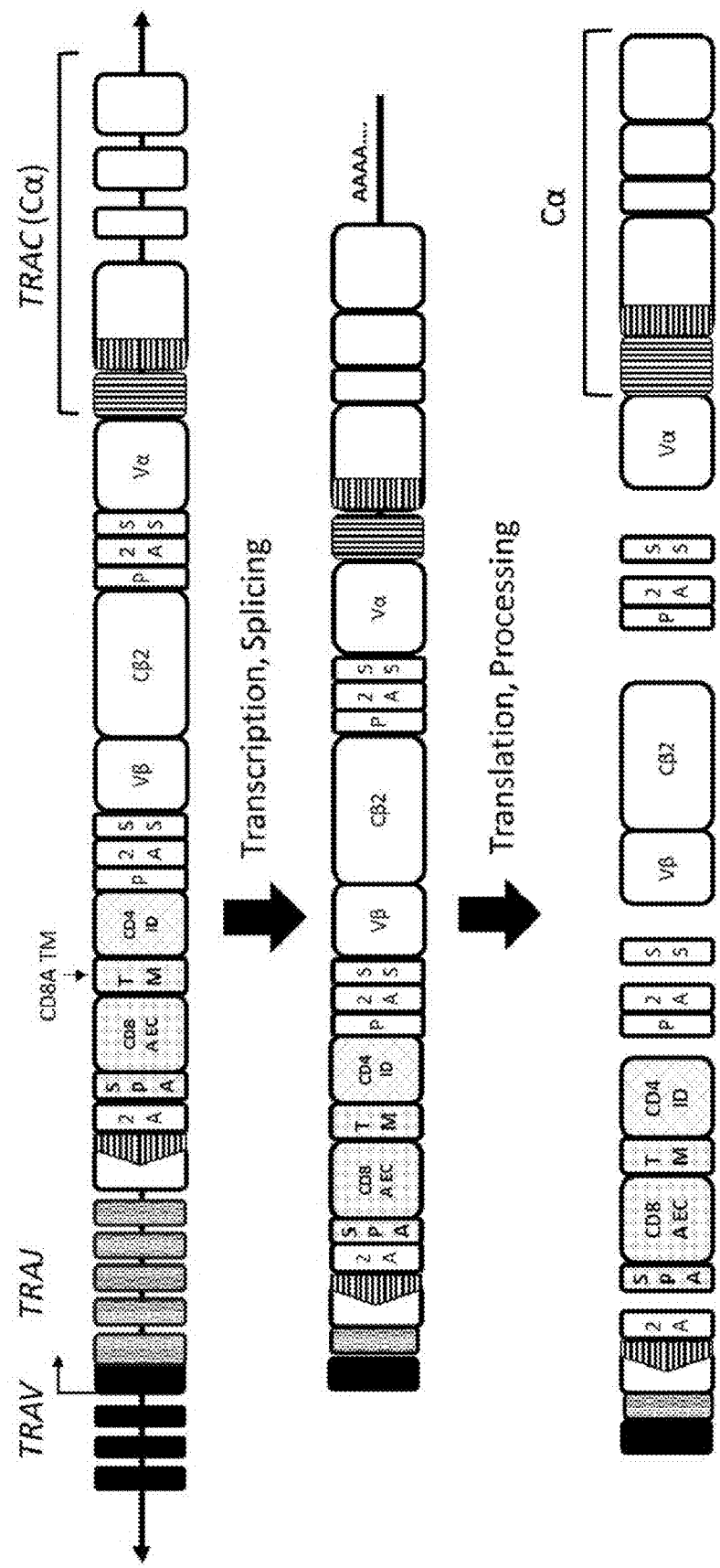
Figure 4A:
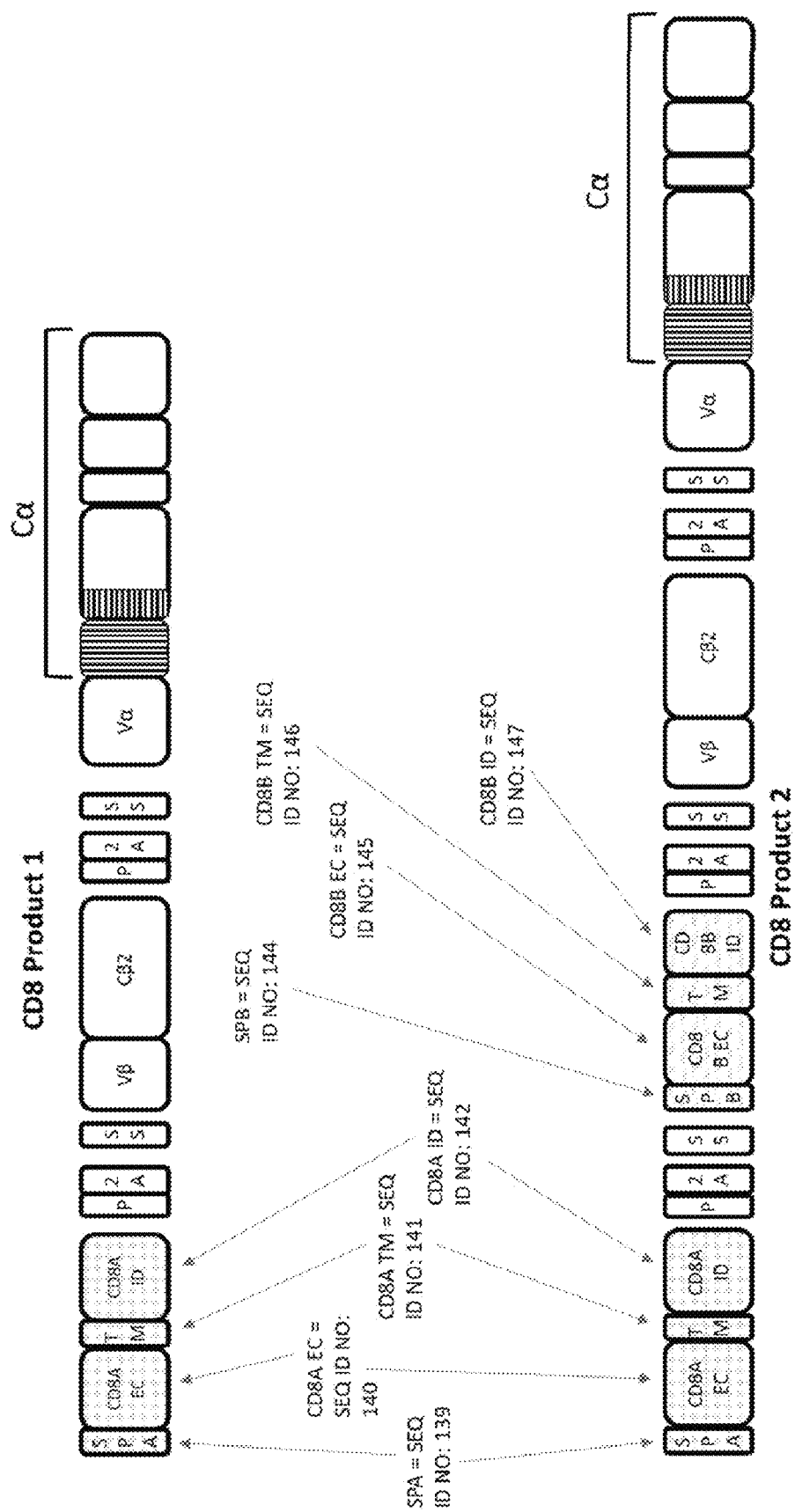
FIGS. 4A and 4B.
Figure 4B:
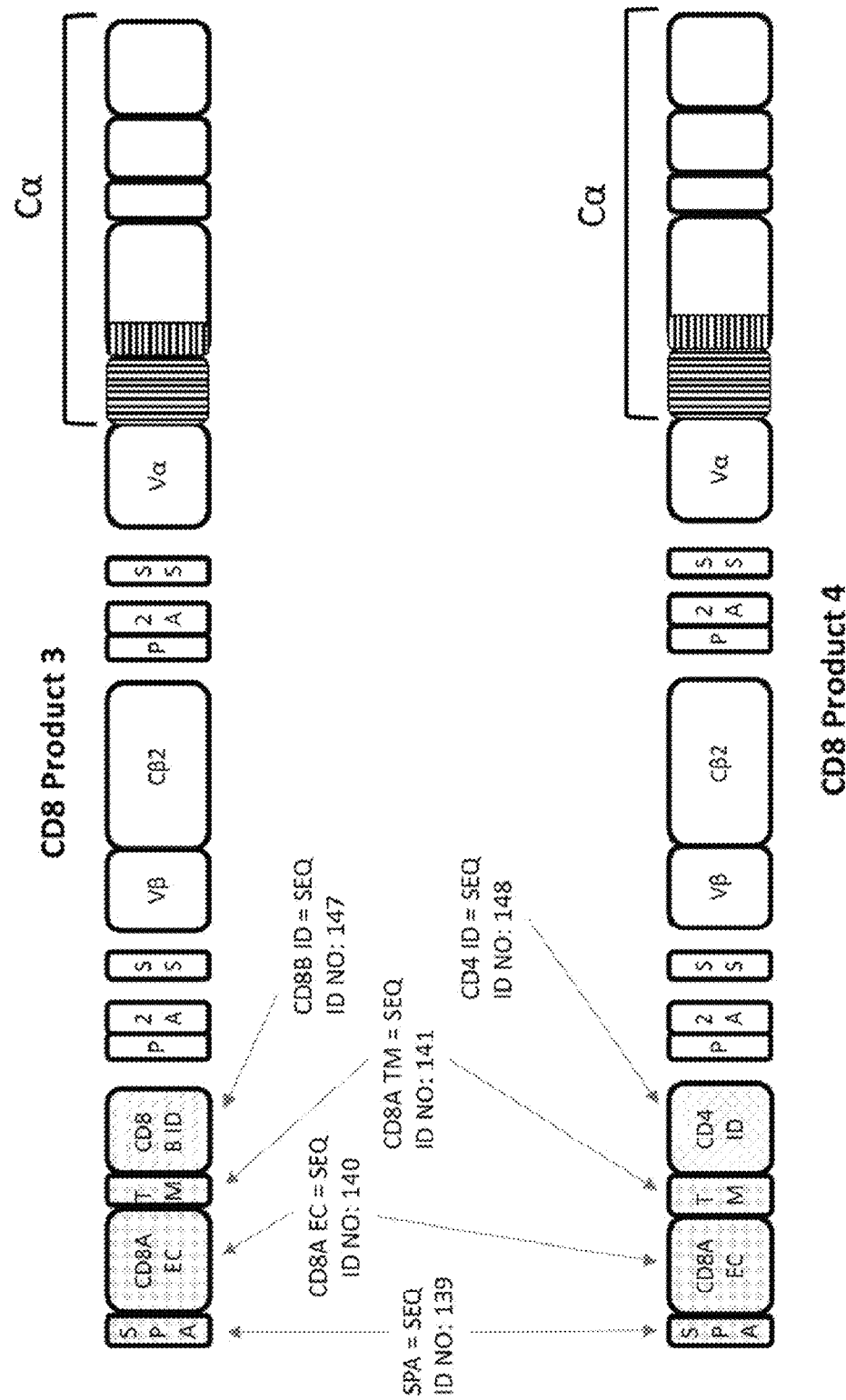

| CD8 Construct | CD8 Product | Expression components | Exemplary constructs | Exemplary products |
|---|---|---|---|---|
| CD8 Construct 1 | CD8 Product 1 | NeoTCR, CD8α extracellular domain, CD8α transmembrane domain, CD8α intracellular domain | FIG. 2A, FIG. 6 | FIG. 3A, FIG. 4A |
| CD8 Construct 2 | CD8 Product 1 | NeoTCR, CD8α extracellular domain, CD8α transmembrane domain, CD8α intracellular domain, CD8β extracellular domain, CD8β transmembrane domain, CD8β intracellular domain | FIG. 2B, FIG. 7 | FIG. 3B, FIG. 4A |
| CD8 Construct 3 | CD8 Product 1 | NeoTCR, CD8α extracellular domain, CD8α transmembrane domain, CD8β intracellular domain | FIG. 2C, FIG. 8 | FIG. 3C, FIG. 4B |
| CD8 Construct 4 | CD8 Product 1 | NeoTCR, CD8α extracellular domain, CD8α transmembrane domain, CD4 intracellular domain | FIG. 2D, FIG. 9 | FIG. 3D, FIG. 4B |

In certain embodiments, the CD8 Product 1 comprises a NeoTCR and a CD8 homodimer. In certain embodiments, the CD8 Product 1 comprises the expression of a NeoTCR, a CD8α extracellular domain, a CD8α transmembrane domain, and a CD8α intracellular domain. In certain embodiments, the CD8 Product 1 further includes the expression of a CD8α signal peptide. In certain embodiments, the CD8 Product 1 comprises the translated elements presented in FIG. 3A. In a non-limiting exemplary embodiment, the CD8 Product 1 comprises a NeoTCR, a CD8α signal peptide (SEQ ID NO:139), a CD8α extracellular domain (SEQ ID NO:140), a CD8α transmembrane domain (SEQ ID NO:141), and a CD8α intracellular domain (SEQ ID NO: 142). In certain embodiments, sequence modifications of the CD8α signal peptide, CD8α extracellular domain, CD8α transmembrane domain, and CD8α intracellular domain can be made that conserve or substantially conserve function of each element. In certain embodiments, such sequence modifications are conservative substitutions of amino acids.

In a non-limiting embodiment, the CD8 Product 1 is manufactured from a CD8 Construct 1 provided in FIG. 6. In certain embodiments, the sequence of CD8 Construct 1 provided in FIG. 6 can be modified in any number of ways so long as the translation of the CD8α signal peptide, CD8α extracellular domain, CD8α transmembrane domain, and CD8α intracellular domain leave each element with conserved function. In certain embodiments, the order of each element of the CD8 Construct 1 in FIG. 6 remains the same but the sequences of each individual element can be changed so long as the amino acids that the nucleic acid encodes remain the same or only comprise conservative substitutions. In certain embodiments, the order of each element of the CD8 Construct 1 in FIG. 6 remains the same but the sequences of each individual element can be changed so long as the function of the encoded proteins remains substantially unchanged.

In certain embodiments, the CD8 Product 2 comprises a NeoTCR, a CD8α, and aCD8β. In certain embodiments, the CD8α and CD8β are separated by a protease cleavage site and a 2A peptide in the CD8 Product 2 construct for expression. In certain embodiments, the CD8 Product 2 comprises the expression of a NeoTCR, a CD8α extracellular domain, a CD8α transmembrane domain, a CD8α intracellular domain, a CD8β extracellular domain, a CD8β transmembrane domain, and a CD8β intracellular domain. In certain embodiments, the CD8 Product 2 further comprises the expression of a CD8α signal peptide. In certain embodiments, the CD8 Product further comprises the expression of a CD8β signal peptide. In certain embodiments, the CD8 Product further comprises the expression of a CD8α signal peptide and a CD8β signal peptide. In certain embodiments, the CD8 Product 2 comprises the translated elements presented in FIG. 3B. In a non-limiting exemplary embodiment, the CD8 Product 2 comprises a NeoTCR, a CD8α signal peptide (SEQ ID NO:139), a CD8α extracellular domain (SEQ ID NO:140), a CD8α transmembrane domain (SEQ ID NO:141), a CD8α intracellular domain (SEQ ID NO: 142), a CD8β signal peptide (SEQ ID NO:144), a CD8β extracellular domain (SEQ ID NO:145), a CD8β transmembrane domain (SEQ ID NO:146), and a CD8β intracellular domain (SEQ ID NO: 147). In certain embodiments, sequence modifications of the CD8α signal peptide, CD8α extracellular domain, CD8α transmembrane domain, CD8α intracellular domain, CD8β extracellular domain, CD8β transmembrane domain, and CD8β intracellular domain can be made that conserve or substantially conserve function of each element. In certain embodiments, such sequence modifications are conservative substitutions of amino acids.

In a non-limiting embodiment, the CD8 Product 2 is manufactured from a CD8 Construct 2 provided in FIG. 7. In certain embodiments, the sequence of CD8 Construct 2 provided in FIG. 7 can be modified in any number of ways so long as the translation of the CD8α signal peptide, CD8α extracellular domain, CD8α transmembrane domain, CD8α intracellular domain, CD8β extracellular domain, CD8β transmembrane domain, and CD8β intracellular domain leave each element with conserved function. In certain embodiments, the order of each element of the CD8 Construct 2 in FIG. 7 remains the same but the sequences of each individual element can be changed so long as the amino acids that the nucleic acid encodes remain the same or only comprise conservative substitutions. In certain embodiments, the order of each element of the CD8 Construct 2 in FIG. 7 remains the same but the sequences of each individual element can be changed so long as the function of the encoded proteins remains substantially unchanged.

In certain embodiments, the CD8 Product 3 comprises a NeoTCR and a CD8α with CD8β intracellular domain. In certain embodiments, the CD8 Product 3 comprises the expression of a NeoTCR, a CD8α extracellular domain, a CD8α transmembrane domain, and a CD8β intracellular domain. In certain embodiments, the CD8 Product 3 further includes the expression of a CD8α signal peptide. In certain embodiments, the CD8 Product 3 comprises the translated elements presented in FIG. 3C. In a non-limiting exemplary embodiment, the CD8 Product 3 comprises a NeoTCR, a CD8α signal peptide (SEQ ID NO:139), a CD8α extracellular domain (SEQ ID NO:140), a CD8α transmembrane domain (SEQ ID NO:141), and a CD8β intracellular domain (SEQ ID NO: 147). In certain embodiments, sequence modifications of the CD8α signal peptide, CD8α extracellular domain, CD8α transmembrane domain, and CD8β intracellular domain can be made that conserve or substantially conserve function of each element. In certain embodiments, such sequence modifications are conservative substitutions of amino acids.

In a non-limiting embodiment, the CD8 Product 3 is manufactured from a CD8 Construct 3 provided in FIG. 8. In certain embodiments, the sequence of CD8 Construct 3 provided in FIG. 8 can be modified in any number of ways so long as the translation of the CD8α signal peptide, CD8α extracellular domain, CD8α transmembrane domain, and CD8β intracellular domain leave each element with conserved function. In certain embodiments, the order of each element of the CD8 Construct 3 in FIG. 8 remains the same but the sequences of each individual element can be changed so long as the amino acids that the nucleic acid encodes remain the same or only comprise conservative substitutions. In certain embodiments, the order of each element of the CD8 Construct 3 in FIG. 8 remains the same but the sequences of each individual element can be changed so long as the function of the encoded proteins remains substantially unchanged.

In certain embodiments, the CD8 Product 4 comprises a NeoTCR and a CD8α homodimer with a CD4 intracellular domain. In certain embodiments, the CD8 Product 4 comprises the expression of a NeoTCR, a CD8α extracellular domain, aCD8α transmembrane domain, and a CD4 intracellular domain. In certain embodiments, the CD8 Product 4 further includes the expression of a CD8α signal peptide. In certain embodiments, the CD8 Product 4 comprises the translated elements presented in FIG. 3D. In a non-limiting exemplary embodiment, the CD8 Product 4 comprises a NeoTCR, a CD8α signal peptide (SEQ ID NO:139), a CD8α extracellular domain (SEQ ID NO:140), a CD8α transmembrane domain (SEQ ID NO:141), and a CD4 intracellular domain (SEQ ID NO: 148). In certain embodiments, sequence modifications of the CD8α signal peptide, CD8α extracellular domain, CD8α transmembrane domain, and CD4 intracellular domain can be made that conserve or substantially conserve function of each element. In certain embodiments, such sequence modifications are conservative substitutions of amino acids.

In a non-limiting embodiment, the CD8 Product 4 is manufactured from a CD8 Construct 4 provided in FIG. 9. In certain embodiments, the sequence of CD8 Construct 4 provided in FIG. 9 can be modified in any number of ways so long as the translation of the CD8α signal peptide, CD8α extracellular domain, CD8α transmembrane domain, and CD4 intracellular domain leave each element with conserved function. In certain embodiments, the order of each element of the CD8 Construct 4 in FIG. 9 remains the same but the sequences of each individual element can be changed so long as the amino acids that the nucleic acid encodes remain the same or only comprise conservative substitutions. In certain embodiments, the order of each element of the CD8 Construct 4 in FIG. 9 remains the same but the sequences of each individual element can be changed so long as the function of the encoded proteins remains substantially unchanged.

In certain embodiments, the CD8 Products comprise a TET2 knockout or TET2 knockdown. In certain embodiments, the cells of the CD8 Product are further engineered to knockout the TET2 gene using non-viral methods. In certain embodiments, the cells of the CD8 Product are further engineered to knockout the TET2 gene using viral methods. In certain embodiments, the cells of the CD8 Product are further engineered to increase T cell persistence by knocking out, knocked down, or modifying the function of a gene associated with T cell persistence using non-viral methods. In certain embodiments, the cells of the CD8 Product are further engineered to increase T cell persistence by knocking out, knocking down, or modifying the function of a gene associated with T cell persistence using viral methods.

In some embodiments, the CD8 Products comprise cells that were engineered to express a NeoTCR and a CD8 Construct using viral methods (i.e., CD8 Viral Product). In certain embodiments, the cells of the CD8 Viral Product are further engineered to knockout the TET2 gene using non-viral methods. In certain embodiments, the cells of the CD8 Viral Product are further engineered to knockout the TET2 gene using viral methods. In certain embodiments, the cells of the CD8 Viral Product are further engineered to increase T cell persistence by knocking out, knocking down, or modifying the function of a gene associated with T cell persistence using non-viral methods. In certain embodiments, the cells of the CD8 Viral Product are further engineered to increase T cell persistence by knocking out, knocking down, or modifying the function of a gene associated with T cell persistence using viral methods.

In certain embodiments, the T cell persistence gene that is knocked out, knocked down, or with a modified function is a gene that confers downregulation of T cell activity. In certain embodiments, the gene that is knocked out, knocked down, or modified is a gene that downregulates T cell memory function. In certain embodiments, the gene that is knocked out, knocked down, or modified is a gene that decreases T-cell function, proliferation, and/or survival.

In certain embodiments, additional modifications to the CD8 Products and CD8 Cells thereof include modifications to increase tumor microenvironment resilience, increase T cell activity, increase tumor microenvironment homing/retention, increase T cell persistence, and increase ectopic effector functions of T cells. In certain embodiments, the tumor microenvironment resilience includes but is not limited to converting/counteracting negative environmental signals. In certain embodiments, TCR-mediated signal enhancements include but are not limited to increasing T cell activity. In certain embodiments, the tumor microenvironment homing/retention includes but is not limited to enhancing tumor infiltration. In certain embodiments, the functional T cell persistence includes but is not limited to metabolic and transcriptional regulation. In certain embodiments, the ectopic effector functions include but is not limited to TCR-induced antibody, cytokine, or peptide secretion.

In certain embodiments, functional T cell persistence can be accomplished by genetic engineering as described herein, by co-administration of a pharmaceutical agent that improves the functional T cell persistence of a modified T cells (modified to incorporate at least a neoTCR as described herein), and by manufacturing and culture conditions of the modified T cells (modified to incorporate at least a neoTCR as described herein).

In certain embodiments, the TCR-induced antibodies used to improve ectopic effector functions are any one of the antibodies or functional fragments thereof described herein. In certain embodiments, the TCR-induced cytokines used to improve ectopic effector functions are naturally occurring cytokines, modified cytokines, fusion proteins of the cytokines, or any combination thereof In certain embodiments, the TCR-induced cytokines are not cytokines but rather other co-factors or expression elements that induce endogenous cytokine production.

In certain embodiments, additional modifications to the CD8 Products and CD8 Cells thereof include modifications to knock in one or more additional genes and/or functional proteins. In certain embodiments, the genes and/or functional proteins knocked in include but are not limited c-Myb, dominant negative FAS, FAS truncations, FBXW7, CTP1A, OPA1, GLUT1, CA-STAT5A, dominant negative TGFβR, DNMT3a, dominant negative PD-1R, dominant negative PD-1 or PD-L1, or PD-L2, dominant negative SHIP-1 protein, integrins, chemokine receptors, cytokines, and interleukins. In certain embodiments, the dominant negative form of a gene is an antibody or functional fragment thereof that is an antagonist of the gene. For example, a dominant negative PD-1 can be an anti-PD-1 antibody or functional fragment thereof. In certain embodiments, any of the knock in genes and/or functional proteins is a functional fragment (including but not limited to truncations) of the gene and/or protein.

In certain embodiments, additional modifications to the CD8 Products and CD8 Cells thereof include modifications to knock out or knock down of one or more additional genes and/or functional proteins. In certain embodiments, the genes and/or functional proteins knocked out or knocked down include but are not limited to TET2, IFNGR1, RICTOR, NR4A1, DNMT3A, SUV39H1, PPP2RD, adenosine 2A receptor, PP2A3, and PP2A4.

In certain embodiments, instead of knocking in a gene for the expression of a functional protein, a different gene can be modulated through genetic engineering described herein that upregulates the expression of the gene that would otherwise be knocked in.

In certain embodiments, instead of knocking out or knocking out a gene, a different gene can be modulated through genetic engineering described herein that down-regulates the expression of the gene that would otherwise be knocked out.

The CD8 Product manufacturing process involves electroporation of dual ribonucleoprotein species of CRISPR-Cas9 nucleases bound to guide RNA sequences, with each species targeting the genomic TCRα and the genomic TCRβ loci. The specificity of targeting Cas9 nucleases to each genomic locus has been previously described in the literature as being highly specific. Comprehensive testing of the CD8 Product was performed in vitro and in silico analyses to survey possible off-target genomic cleavage sites, using COSMID and GUIDE-seq, respectively. Multiple CD8 Product or comparable cell products from healthy donors were assessed for cleavage of the candidate off-target sites by deep sequencing, supporting the published evidence that the selected nucleases are highly specific.

In certain embodiments, the CD8 Products described herein can be T cells, NK cells, NKT cells, macrophages, hematopoietic stem cells (HSCs), cells derived from HSCs, or dendritic/antigen-presenting cells.

In certain embodiments, CD8 Cells are expanded in a manner that preserves a "young" T cell phenotypes, resulting in a CD8 Product in which the majority of the T cells exhibit T memory stem cell and T central memory phenotypes These 'young' or 'younger' or less-differentiated T cell phenotypes are described to confer improved engraftment potential and prolonged persistence post-infusion. Thus, the administration of CD8 Product, consisting significantly of 'young' T cell phenotypes, has the potential to benefit patients with cancer, through improved engraftment potential, prolonged persistence post-infusion, and rapid differentiation into effector T cells to eradicate tumor cells throughout the body.

In certain embodiments, the CD8 Cells of the CD8 Products predominantly comprise memory stem cells (Tmsc) and/or central memory cells (Tcm). In certain embodiments, at least 25% of the CD8 Cells of the CD8 Products comprise memory stem cells (Tmsc) and/or central memory cells (Tcm). In certain embodiments, at least 30% of the CD8 Cells of the CD8 Products comprise memory stem cells (Tmsc) and/or central memory cells (Tcm). In certain embodiments, at least 35% of the CD8 Cells of the CD8 Products comprise memory stem cells (Tmsc) and/or central memory cells (Tcm). In certain embodiments, at least 40% of the CD8 Cells of the CD8 Products comprise memory stem cells (Tmsc) and/or central memory cells (Tcm). In certain embodiments, at least 45% of the CD8 Cells of the CD8 Products comprise memory stem cells (Tmsc) and/or central memory cells (Tcm). In certain embodiments, at least 50% of the CD8 Cells of the CD8 Products comprise memory stem cells (Tmsc) and/or central memory cells (Tcm). In certain embodiments, at least 55% of the CD8 Cells of the CD8 Products comprise memory stem cells (Tmsc) and/or central memory cells (Tcm). In certain embodiments, at least 60% of the CD8 Cells of the CD8 Products comprise memory stem cells (Tmsc) and/or central memory cells (Tcm). In certain embodiments, at least 65% of the CD8 Cells of the CD8 Products comprise memory stem cells (Tmsc) and/or central memory cells (Tcm). In certain embodiments, at least 70% of the CD8 Cells of the CD8 Products comprise memory stem cells (Tmsc) and/or central memory cells (Tcm). In certain embodiments, at least 75% of the CD8 Cells of the CD8 Products comprise memory stem cells (Tmsc) and/or central memory cells (Tcm). In certain embodiments, greater than 75% of the CD8 Cells of the CD8 Products comprise memory stem cells (Tmsc) and/or central memory cells (Tcm). Tmsc are characterized as cells that are CD45RA+ CD62L+, CD28+CD95+, and CCR7+CD27+. Tcm are characterized as cells that are CD45RO+CD62L+, CD28+ CD95+, and CCR7+CD27+CD127+. Both Tmsc and Tcm are characterized as having weak effector T cell function, robust proliferation, robust engraftment, and long telomeres.

In certain embodiments, the CD8 cells disclosed herein show improved properties (e.g., killing activity, cell proliferation, secretion of cytokines, LCK affinity, persistence, tumor infiltration ability) about 10%, about 20%, about 30%, about 40%, about 50%, about 60%, about 70%, about 80%, about 100%, about 150%, about 200%, about 250%, about 300%, about 350%, about 400%, about 450%, or about 500% as compared to the cells that do not have a CD8 construct.

Methods of Producing CD8 Products with a Young Phenotype

In certain embodiments, the present disclosure relates, in part, on the production of engineered "young" T cells. In certain embodiments, the present disclosure comprises methods for producing antigen-specific cells, e.g., T cells, ex vivo, comprising activating, engineering, and expanding antigen-specific cells originally obtained from a subject or isolated from such sample.

In certain embodiments, the methods for activating cells comprise the steps of activating the TCR/CD3 complex. For example, without limitation, the T cells can be incubated and/or cultured with CD3 agonists, CD28 agonists, or a combination thereof.

In certain embodiments, engineered activated antigen-specific cells, e.g., engineered activated T cells, can be expanded by culturing the engineered activated antigen-specific cells, e.g., T cells, with cytokines, chemokine, soluble peptides, or combination thereof. In certain embodiments, the engineered activated antigen-specific cells, e.g., engineered activated T cells, can be cultured with one or more cytokines. In certain embodiments, the cytokines can be IL2, IL7, IL15, or combinations thereof. For example, engineered activated antigen-specific cells, e.g., engineered activated T cells, can be cultured with IL7 and IL15. In certain embodiments, the cytokine used in connection with the engineered activated antigen-specific cell, e.g., engineered activated T cell, culture can be present at a concentration from about 1 pg/ml to about 1 g/ml, from about 1 ng/ml to about 1 g/ml, from about 1 µg/ml to about 1 g/ml, or from about 1 mg/ml to about 1 g/ml, and any values in between.

Pharmaceutical Formulations.

Pharmaceutical formulations of the CD8 Product are prepared by combining the CD8 Cells in a solution that can preserve the 'young' phenotype of the cells in a cryopreserved state. Table 1 provides an example of one such pharmaceutical formulation. Alternatively, pharmaceutical formulations of the CD8 Product can be prepared by combining the CD8 Cells in a solution that can preserve the 'young' phenotype of the cells without the need to freeze or cryopreserve the product (i.e., the CD8 Product is maintained in an aqueous solution or as a non-frozen/cryopreserved cell pellet).

Additional pharmaceutically acceptable carriers, buffers, stabilizers, and/or preservatives can also be added to the cryopreservation solution or the aqueous storage solution (if the CD8 Product is not cryopreserved). Any cryopreservation agent and/or media can be used to cryopreserve the CD8 Product, including but not limited to CryoStor, CryoStor CS5, CELLBANKER, and custom cryopreservation media that optionally include DMSO.

Gene-Editing Methods

In certain embodiments, the present disclosure involves, in part, methods of engineering human cells, e.g., engineered T cells or engineered human stem cells. In certain embodiments, the present disclosure involves, in part, methods of engineering human cells, e.g., NK cells, NKT cells, macrophages, hematopoietic stem cells (HSCs), cells derived from HSCs, or dendritic/antigen-presenting cells. In certain embodiments, such engineering involves genome editing. For example, but not by way of limitation, such genome editing can be accomplished with nucleases targeting one or more endogenous loci, e.g., TCR alpha (TCRα) locus and TCR beta (TCRβ) locus. In certain embodiments, the nucleases can generate single-stranded DNA nicks or double-stranded DNA breaks in an endogenous target sequence. In certain embodiments, the nuclease can target coding or non-coding portions of the genome, e.g., exons, introns. In certain embodiments, the nucleases contemplated herein comprise homing endonuclease, meganuclease, megaTAL nuclease, transcription activator-like effector nuclease (TALEN), zinc-finger nuclease (ZFN), and clustered regularly interspaced short palindromic repeats (CRISPR)/Cas nuclease. In certain embodiments, the nucleases can themselves be engineered, e.g., via the introduction of amino acid substitutions and/or deletions, to increase the efficiency of the cutting activity.

In certain embodiments, a CRISPR/Cas nuclease system is used to engineer human cells. In certain embodiments, the CRISPR/Cas nuclease system comprises a Cas nuclease and one or more RNAs that recruit the Cas nuclease to the endogenous target sequence, e.g., single guide RNA. In certain embodiments, the Cas nuclease and the RNA are introduced in the cell separately, e.g. using different vectors or compositions, or together, e.g., in a polycistronic construct or a single protein-RNA complex. In certain embodiments, the Cas nuclease is Cas9 or Cas12a. In certain embodiments, the Cas9 polypeptide is obtained from a bacterial species including, without limitation, *Streptococcus pyogenes* or *Neisseria menengitidis*. Additional examples of CRISPR/Cas systems are known in the art. See Adli, Mazhar. "The CRISPR tool kit for genome editing and beyond." Nature communications vol. 9, 1 1911 (2018), herein incorporated by reference for all that it teaches.

In certain embodiments, genome editing occurs at one or more genome loci that regulate immunological responses. In certain embodiments, the loci include, without limitation, TCR alpha (TCRα) locus, TCR beta (TCRβ) locus, TCR gamma (TCRγ), and TCR delta (TCRδ). In certain embodiments, the loci for inserting a CD8 Construct is anywhere in the genome. In certain embodiments, the loci for inserting a CD8 Construct is the TRAC locus. In certain embodiments, the loci for inserting a CD8 Construct is one of the two TRBC loci. In certain embodiments, the locus for inserting a CD8 Construct is a locus other than the TRAC locus or TRAB loci. In certain embodiments, the loci for inserting a CD8 Construct is inserted into a gene locus wherein such gene is knocked out. By way of a non-limiting example, if the desired phenotype of a CD8 Product is the expression of a NeoTCR, the expression of a CD8 Construct, and the knockout of the TET2 gene or the AAVS1 gene, the CD8 Construct can be inserted at the TET2 locus or AAVS1 locus. In certain embodiments, the insertion of the CD8 Construct is in tandem with the NeoTCR insertion. In certain embodiments, the insertion of the CD8 Construct is a separate locus than the NeoTCR insertion.

In certain embodiments, genome editing is performed by using non-viral delivery systems. For example, a nucleic acid molecule can be introduced into a cell by administering the nucleic acid in the presence of lipofection (Feigner et al., Proc. Natl. Acad. Sci. U.S.A. 84:7413, 1987; Ono et al., Neuroscience Letters 17:259, 1990; Brigham et al., Am. J. Med. Sci. 298:278, 1989; Staubinger et al., Methods in Enzymology 101:512, 1983), asialoorosomucoid-polylysine conjugation (Wu et al., Journal of Biological Chemistry 263:14621, 1988; Wu et al., Journal of Biological Chemistry 264:16985, 1989), or by micro-injection under surgical conditions (Wolff et al., Science 247:1465, 1990). Other non-viral means for gene transfer include transfection in vitro using calcium phosphate, DEAE dextran, electroporation, and protoplast fusion. Liposomes can also be potentially beneficial for delivery of DNA into a cell. Transplantation of normal genes into the affected tissues of a subject can also be accomplished by transferring a normal nucleic acid into a cultivatable cell type ex vivo (e.g., an autologous or heterologous primary cell or progeny thereof), after which the cell (or its descendants) are injected into a targeted tissue or are injected systemically.

In certain embodiments, genome editing is performed by using viral delivery systems. In certain embodiments, the viral methods include targeted integration (including but not limited to AAV) and random integration (including but not limited to lentiviral approaches). In certain embodiments, the viral delivery would be accomplished without integration of the nuclease. In such embodiments, the viral delivery system can be Lentiflash or another similar delivery system.

Homology Recombination Templates

In certain embodiments, the present disclosure provides genome editing of a cell by introducing and recombining a homologous recombination (HR) template nucleic acid sequence into an endogenous locus of a cell. In certain embodiments, the HR template nucleic acid sequence is linear. In certain embodiments, the HR template nucleic acid sequence is circular. In certain embodiments, the circular HR template can be a plasmid, minicircle, or nanoplasmid. In certain embodiments, the HR template nucleic acid sequence comprises a first and a second homology arms. In certain embodiments, the homology arms can be of about 300 bases to about 2,000 bases. For example, each homology arm can be 1,000 bases. In certain embodiments, the homology arms can be homologous to a first and second endogenous sequences of the cell. In certain embodiments, the endogenous locus is a TCR locus. For example, the first and second endogenous sequences are within a TCR alpha locus or a TCR beta locus. In certain embodiments, the HR template comprises a TCR gene sequences. In non-limiting embodiments, the TCR gene sequence is a patient specific TCR gene sequence. In non-limiting embodiments, the TCR gene sequence is tumor-specific. In non-limiting embodiments, the TCR gene sequence can be identified and obtained using the methods described in PCT/US2020/017887, the content of which is herein incorporated by reference. In certain embodiments, the HR template comprises a TCR alpha gene sequence and a TCR beta gene sequence.

In certain embodiments, the HR template is a polycistronic polynucleotide. In certain embodiments, the HR template comprises sequences encoding for flexible polypeptide sequences (e.g., Gly-Ser-Gly sequence). In certain embodiments, the HR template comprises sequences encoding an internal ribosome entry site (IRES). In certain embodiments, the HR template comprises a 2A peptide (e.g., P2A, T2A, E2A, and F2A). Additional information on the HR template nucleic acids and methods of modifying a cell thereof can be found in International Patent Application no. PCT/US2018/058230, the content of which is herein incorporated by reference.

Methods of Treatment

The presently disclosed subject matter provides methods for inducing and/or increasing an immune response in a subject in need thereof. The CD8 Products can be used for treating and/or preventing a cancer in a subject. The CD8 Products can be used for prolonging the survival of a subject suffering from a cancer. The CD8 Products can also be used for treating and/or preventing a cancer in a subject. The CD8 Products can also be used for reducing tumor burden in a subject. Such methods comprise administering the CD8 Products in an amount effective or a composition (e.g., a pharmaceutical composition) comprising thereof to achieve the desired effect, be it palliation of an existing condition or prevention of recurrence. For treatment, the amount administered is an amount effective in producing the desired effect. An effective amount can be provided in one or a series of administrations. An effective amount can be provided in a bolus or by continuous perfusion.

In certain embodiments, the CD8 Products can be used for treating viral or bacterial diseases. In certain embodiments, the CD8 Products can be used for treating autoimmune diseases.

In certain embodiments, an effective amount of the CD8 Products are delivered through IV administration. In certain embodiments, the CD8 Products are delivered through IV administration in a single administration. In certain embodiments, the CD8 Products are delivered through IV administration in multiple administrations. In certain embodiments, the CD8 Products are delivered through IV administration in two or more administrations. In certain embodiments, the CD8 Products are delivered through IV administration in two administrations. In certain embodiments, the CD8 Products are delivered through IV administration in three administrations.

The presently disclosed subject matter provides methods for treating and/or preventing cancer in a subject. In certain embodiments, the method comprises administering an effective amount of CD8 Products to a subject having cancer.

Non-limiting examples of cancer include blood cancers (e.g. leukemias, lymphomas, and myelomas), ovarian cancer, breast cancer, bladder cancer, brain cancer, colon cancer, intestinal cancer, liver cancer, lung cancer, pancreatic cancer, prostate cancer, skin cancer, stomach cancer, glioblastoma, throat cancer, melanoma, neuroblastoma, adenocarcinoma, glioma, soft tissue sarcoma, and various carcinomas (including prostate and small cell lung cancer). Suitable carcinomas further include any known in the field of oncology, including, but not limited to, astrocytoma, fibrosarcoma, myxosarcoma, liposarcoma, oligodendroglioma, ependymoma, medulloblastoma, primitive neural ectodermal tumor (PNET), chondrosarcoma, osteogenic sarcoma, pancreatic ductal adenocarcinoma, small and large cell lung adenocarcinomas, chordoma, angiosarcoma, endotheliosarcoma, squamous cell carcinoma, bronchoalveolarcarcinoma, epithelial adenocarcinoma, and liver metastases thereof, lymphangiosarcoma, lymphangioendotheliosarcoma, hepatoma, cholangiocarcinoma, synovioma, mesothelioma, Ewing's tumor, rhabdomyosarcoma, colon carcinoma, basal cell carcinoma, sweat gland carcinoma, papillary carcinoma, sebaceous gland carcinoma, papillary adenocarcinoma, cystadenocarcinoma, medullary carcinoma, bronchogenic carcinoma, renal cell carcinoma, bile duct carcinoma, choriocarcinoma, seminoma, embryonal carcinoma, Wilms' tumor, testicular tumor, medulloblastoma, craniopharyngioma, ependymoma, pinealoma, hemangioblastoma, acoustic neuroma, oligodendroglioma, meningioma, neuroblastoma, retinoblastoma, leukemia, multiple myeloma, Waldenstrom's macroglobulinemia, and heavy chain disease, breast tumors such as ductal and lobular adenocarcinoma, squamous and adenocarcinomas of the uterine cervix, uterine and ovarian epithelial carcinomas, prostatic adenocarcinomas, transitional squamous cell carcinoma of the bladder, B and T cell lymphomas (nodular and diffuse) plasmacytoma, acute and chronic leukemias, malignant melanoma, soft tissue sarcomas and leiomyosarcomas. In certain embodiments, the neoplasia is selected from the group consisting of blood cancers (e.g. leukemias, lymphomas, and myelomas), ovarian cancer, prostate cancer, breast cancer, bladder cancer, brain cancer, colon cancer, intestinal cancer, liver cancer, lung cancer, pancreatic cancer, prostate cancer, skin cancer, stomach cancer, glioblastoma, and throat cancer. In certain embodiments, the presently disclosed young T cells and compositions comprising thereof can be used for treating and/or preventing blood cancers (e.g., leukemias, lymphomas, and myelomas) or ovarian cancer, which are not amenable to conventional therapeutic interventions.

In certain embodiments, the neoplasia is a solid cancer or a solid tumor. In certain embodiments, the solid tumor or solid cancer is selected from the group consisting of glioblastoma, prostate adenocarcinoma, kidney papillary cell carcinoma, sarcoma, ovarian cancer, pancreatic adenocarcinoma, rectum adenocarcinoma, colon adenocarcinoma, esophageal carcinoma, uterine corpus endometrioid carcinoma, breast cancer, skin cutaneous melanoma, lung adenocarcinoma, stomach adenocarcinoma, cervical and endocervical cancer, kidney clear cell carcinoma, testicular germ cell tumors, and aggressive B-cell lymphomas.

The subjects can have an advanced form of disease, in which case the treatment objective can include mitigation or reversal of disease progression, and/or amelioration of side effects. The subjects can have a history of the condition, for which they have already been treated, in which case the therapeutic objective will typically include a decrease or delay in the risk of recurrence.

Suitable human subjects for therapy typically comprise two treatment groups that can be distinguished by clinical criteria. Subjects with "advanced disease" or "high tumor burden" are those who bear a clinically measurable tumor. A clinically measurable tumor is one that can be detected on the basis of tumor mass (e.g., by palpation, CAT scan, sonogram, mammogram or X-ray; positive biochemical or histopathologic markers on their own are insufficient to identify this population). A pharmaceutical composition is administered to these subjects to elicit an anti-tumor response, with the objective of palliating their condition. Ideally, reduction in tumor mass occurs as a result, but any clinical improvement constitutes a benefit. Clinical improvement includes decreased risk or rate of progression or reduction in pathological consequences of the tumor.

Articles of Manufacture

The CD8 Products can be used in combination with articles of manufacture. Such articles of manufacture can be useful for the prevention or treatment of proliferative disorders (e.g., cancer). Examples of articles of manufacture include but are not limited to containers (e.g., infusion bags, bottles, storage containers, flasks, vials, syringes, tubes, and IV solution bags) and a label or package insert on or associated with the container. The containers may be made of any material that is acceptable for the storage and preservation of the CD8 Cells within the CD8 Products. In certain embodiments, the container may be an intravenous solution bag or a vial having a stopper pierceable by a hypodermic injection needle. For example, the container may be a CryoMACS freezing bag. The label or package insert indicates that the CD8 Products are used for treating the condition of choice and the patient of origin. The patient is identified on the container of the CD8 Product because the CD8 Products is made from autologous cells and engineered as a patient-specific and individualized treatment.

The article of manufacture may comprise: 1) a first container with a CD8 Product contained therein.

The article of manufacture may comprise: 1) a first container with a CD8 Product contained therein; and 2) a second container with the same CD8 Product as the first container contained therein. Optionally, additional containers with the same CD8 Product as the first and second containers may be prepared and made. Optionally, additional containers containing a composition comprising a different cytotoxic or otherwise therapeutic agent may also be combined with the containers described above.

The article of manufacture may comprise: 1) a first container with a CD8 Product contained therein; and 2) a second container with a composition contained therein, wherein the composition comprises a further cytotoxic or otherwise therapeutic agent.

The article of manufacture may comprise: 1) a first container with two CD8 Products contained therein; and 2) a second container with a composition contained therein, wherein the composition comprises a further cytotoxic or otherwise therapeutic agent.

The article of manufacture may comprise: 1) a first container with a CD8 Product contained therein; 2) a second container with a second CD8 Product contained therein; and 3) optionally a third container with a composition contained therein, wherein the composition comprises a further cytotoxic or otherwise therapeutic agent. In certain embodiments, the first and second CD8 Products are different CD8 Products. In certain embodiments, the first and second CD8 Products are the same CD8 Products.

The article of manufacture may comprise: 1) a first container with three CD8 Products contained therein; and 2) optionally a second container with a composition contained therein, wherein the composition comprises a further cytotoxic or otherwise therapeutic agent.

The article of manufacture may comprise: 1) a first container with a CD8 Product contained therein; 2) a second container with a second CD8 Product contained therein; 3) a third container with a third CD8 Product contained therein; and 4) optionally a fourth container with a composition contained therein, wherein the composition comprises a further cytotoxic or otherwise therapeutic agent. In certain embodiments, the first, second, and third CD8 Products are different CD8 Products. In certain embodiments, the first, second, and third CD8 Products are the same CD8 Products. In certain embodiments, two of the first, second, and third CD8 Products are the same CD8 Products.

The article of manufacture may comprise: 1) a first container with four CD8 Products contained therein; and 2) optionally a second container with a composition contained therein, wherein the composition comprises a further cytotoxic or otherwise therapeutic agent.

The article of manufacture may comprise: 1) a first container with a CD8 Product contained therein; 2) a second container with a second CD8 Product contained therein; 3) a third container with a third CD8 Product contained therein; 4) a fourth container with a fourth CD8 Product contained therein; and 5) optionally a fifth container with a composition contained therein, wherein the composition comprises a further cytotoxic or otherwise therapeutic agent. In certain embodiments, the first, second, third, and fourth CD8 Products are different CD8 Products. In certain embodiments, the first, second, third, and fourth CD8 Products are the same NeoTCR Products. In certain embodiments, two of the first, second, third, and fourth CD8 Products are the same NeoTCR Products. In certain embodiments, three of the first, second, third, and fourth CD8 Products are the same CD8 Products.

The article of manufacture may comprise: 1) a first container with five or more CD8 Products contained therein; and 2) optionally a second container with a composition contained therein, wherein the composition comprises a further cytotoxic or otherwise therapeutic agent.

The article of manufacture may comprise: 1) a first container with a CD8 Product contained therein; 2) a second container with a second CD8 Product contained therein; 3) a third container with a third CD8 Product contained therein; 4) a fourth container with a fourth CD8 Product contained therein; 5) a fifth container with a fifth CD8 Product contained therein; 6) optionally a sixth or more additional containers with a sixth or more CD8 Product contained therein; and 7) optionally an additional container with a composition contained therein, wherein the composition comprises a further cytotoxic or otherwise therapeutic agent. In certain embodiments, all of the containers of CD8 Products are different CD8 Products. In certain embodiments, all of the containers of CD8 Products are the same CD8 Products. In certain embodiments, there can be any combination of same or different CD8 Products in the five or more containers based on the availability of detectable CD8s in a patient's tumor sample(s), the need and/or desire to have multiple CD8 Products for the patient, and the availability of any one CD8 Product that may require or benefit from one or more container.

The article of manufacture may comprise: 1) a first container with a CD8 Product contained therein; 2) a second container with a second CD8 Product contained therein; and 3) a third container with a third CD8 Product contained therein.

The article of manufacture may comprise: 1) a first container with a CD8 Product contained therein; 2) a second container with a second CD8 Product contained therein; 3) a third container with a third CD8 Product contained therein; and 4) optionally a fourth container with a fourth CD8 Product contained therein.

The article of manufacture may comprise: 1) a first container with a CD8 Product contained therein; 2) a second container with a second CD8 Product contained therein; 3) a third container with a third CD8 Product contained therein; 4) a fourth container with a fourth CD8 Product contained therein; and 5) optionally a fifth container with a fourth CD8 Product contained therein.

The article of manufacture may comprise a container with one CD8 Product contained therein. The article of manufacture may comprise a container with two CD8 Products contained therein. The article of manufacture may comprise a container with three CD8 Products contained therein. The article of manufacture may comprise a container with four CD8 Products contained therein. The article of manufacture may comprise a container with five CD8 Products contained therein.

The article of manufacture may comprise 1) a first container with one CD8 Product contained therein, and 2) a second container with two CD8 Products contained therein. The article of manufacture may comprise 1) a first container with two CD8 Products contained therein, and 2) a second container with one CD8 Product contained therein. In the examples above, a third and/or fourth container comprising one or more additional CD8 Products may be included in the article of manufacture. Additionally, a fifth container comprising one or more additional CD8 Products may be included in the article of manufacture.

Furthermore, any container of CD8 Product described herein can be split into two, three, or four separate containers for multiple time points of administration and/or based on the appropriate dose for the patient.

In certain embodiments, the CD8 Products are provided in a kit. The kit can, by means of non-limiting examples, contain package insert(s), labels, instructions for using the CD8 Product(s), syringes, disposal instructions, administration instructions, tubing, needles, and anything else a clinician would need in order to properly administer the CD8 Product(s).

Therapeutic Compositions and Methods of Manufacturing

As described herein, plasmid DNA-mediated precision genome engineering process for Good Manufacturing Practice (GMP) manufacturing of CD8 Products was developed. Targeted integration of the patient-specific neoTCR was accomplished by electroporating CRISPR endonuclease ribonucleoproteins (RNPs) together with the personalized neoTCR gene cassette, encoded by the plasmid DNA. In addition to the neoTCR, the CD8 Constructs were inserted by incorporating them into the neoTCR vector and then electroporating with CRISPR endonuclease ribonucleoproteins (RNPs) as described above.

The CD8 Products can be formulated into a drug product using the clinical manufacturing process. Under this process, the CD8 Products are cryopreserved in CryoMACS Freezing Bags. One or more bags may be shipped to the site for each patient depending on patient needs. The product is composed of apheresis-derived, patient-autologous, CD8 and CD4 T cells that have been precision genome engineered to express one or more autologous neoTCRs targeting a neoepitope complexed to one of the endogenous HLA receptors presented exclusively on the surface of that patient's tumor cells.

The final product will contain 5% dimethyl sulfoxide (DMSO), human serum albumin, and Plasma-Lyte. The final cell product will contain the list of components provided in Table 2. Composition of the CD8 Product

| Component | Specification/Grade |
| --- | --- |
| Total nucleated NeoTCR cells | cGMP manufactured |
| Plasma-Lyte A | USP |
| Human Serum Albumin in 0.02-0.08M sodium caprylate and sodium tryptophanate | USP |
| CryoStor CS10 | cGMP manufactured with USP grade materials |

Compositions and Vectors

The presently disclosed subject matter provides compositions comprising cells (e.g., immunoresponsive cells) disclosed herein.

In certain embodiments, the presently disclosed subject matter provides nucleic acid compositions comprising a polynucleotide encoding the NeoTCR disclosed herein. In certain embodiments, the nucleic acid compositions disclosed herein comprise a polynucleotide encoding a CD8 Construct disclosed herein. Also provided are cells comprising such nucleic acid compositions.

In certain embodiments, the nucleic acid composition further comprises a promoter that is operably linked to the NeoTCR disclosed herein. In certain embodiments, the nucleic acid composition further comprises a promoter that is operably linked to the CD8 Construct disclosed herein.

In certain embodiments, the promoter is endogenous or exogenous. In certain embodiments, the exogenous promoter is selected from the group consisting of an elongation factor (EF)-1 promoter, a CMV promoter, a SV40 promoter, a PGK promoter, a long terminal repeat (LTR) promoter and a metallothionein promoter. In certain embodiments, the promoter is an inducible promoter. In certain embodiments, the inducible promoter is selected from the group consisting of a NFAT transcriptional response element (TRE) promoter, a CD69 promoter, a CD25 promoter, an IL-2 promoter, an IL-12 promoter, a p40 promoter, and a Bcl-xL promoter.

The compositions and nucleic acid compositions can be administered to subjects or and/delivered into cells by art-known methods or as described herein. Genetic modification of a cell (e.g., a T cell) can be accomplished by transducing a substantially homogeneous cell composition with a recombinant DNA construct. In certain embodiments, a retroviral vector (either a gamma-retroviral vector or a lentiviral vector) is employed for the introduction of the DNA construct into the cell. Non-viral vectors may be used as well.

Possible methods of transduction also include direct co-culture of the cells with producer cells, e.g., by the method of Bregni, et al. (1992) *Blood* 80:1418-1422, or culturing with viral supernatant alone or concentrated vector stocks with or without appropriate growth factors and polycations, e.g., by the method of Xu, et al. (1994) *Exp. Hemat.* 22:223-230; and Hughes, et al. (1992) *J. Clin. Invest.* 89:1817.

Other transducing viral vectors can be used to modify a cell. In certain embodiments, the chosen vector exhibits high efficiency of infection and stable integration and expression (see, e.g., Cayouette et al., Human Gene Therapy 8:423-430, 1997; Kido et al., Current Eye Research 15:833-844, 1996; Bloomer et al., Journal of Virology 71:6641-6649, 1997; Naldini et al., Science 272:263-267, 1996; and Miyoshi et al., Proc. Natl. Acad. Sci. U.S.A. 94:10319, 1997). Other viral vectors that can be used include, for example, adenoviral, lentiviral, and adena-associated viral vectors, vaccinia virus, a bovine papilloma virus, or a herpes virus, such as Epstein-Barr Virus (also see, for example, the vectors of Miller, Human Gene Therapy 15-14, 1990; Friedman, Science 244:1275-1281, 1989; Eglitis et al., BioTechniques 6:608-614, 1988; Tolstoshev et al., Current Opinion in Biotechnology 1:55-61, 1990; Sharp, The Lancet 337:1277-1278, 1991; Cornetta et al., Nucleic Acid Research and Molecular Biology 36:311-322, 1987; Anderson, Science 226:401-409, 1984; Moen, Blood Cells 17:407-416, 1991; Miller et al., Biotechnology 7:980-990, 1989; LeGal La Salle et al., Science 259:988-990, 1993; and Johnson, Chest 107:77S-83S, 1995). Retroviral vectors are particularly well developed and have been used in clinical settings (Rosenberg et al., N. Engl. J. Med 323:370, 1990; Anderson et al., U.S. Pat. No. 5,399,346).

Non-viral approaches can also be employed for genetic modification of a cell. For example, a nucleic acid molecule can be introduced into a cell by administering the nucleic acid in the presence of lipofection (Feigner et al., Proc. Natl. Acad. Sci. U.S.A. 84:7413, 1987; Ono et al., Neuroscience Letters 17:259, 1990; Brigham et al., Am. J. Med. Sci. 298:278, 1989; Staubinger et al., Methods in Enzymology 101:512, 1983), asialoorosomucoid-polylysine conjugation (Wu et al., Journal of Biological Chemistry 263:14621, 1988; Wu et al., Journal of Biological Chemistry 264:16985, 1989), or by micro-injection under surgical conditions (Wolff et al., Science 247:1465, 1990). Other non-viral means for gene transfer include transfection in vitro using calcium phosphate, DEAE dextran, electroporation, and protoplast fusion. Liposomes can also be potentially beneficial for delivery of DNA into a cell. Transplantation of normal genes into the affected tissues of a subject can also be accomplished by transferring a normal nucleic acid into a cultivatable cell type ex vivo (e.g., an autologous or heterologous primary cell or progeny thereof), after which the cell (or its descendants) are injected into a targeted tissue or are injected systemically.

Polynucleotide therapy methods can be directed from any suitable promoter (e.g., the human cytomegalovirus (CMV), simian virus 40 (SV40), or metallothionein promoters), and regulated by any appropriate mammalian regulatory element or intron (e.g. the elongation factor 1a enhancer/promoter/intron structure). For example, if desired, enhancers known to preferentially direct gene expression in specific cell types can be used to direct the expression of a nucleic acid. The enhancers used can include, without limitation, those that are characterized as tissue- or cell-specific enhancers. Alternatively, if a genomic clone is used as a therapeutic construct, regulation can be mediated by the cognate regulatory sequences or, if desired, by regulatory sequences derived from a heterologous source, including any of the promoters or regulatory elements described above.

The resulting cells can be grown under conditions similar to those for unmodified cells, whereby the modified cells can be expanded and used for a variety of purposes.

Kits

The presently disclosed subject matter provides kits for inducing and/or enhancing an immune response and/or treating and/or preventing a cancer or a pathogen infection in a subject. In certain embodiments, the kit comprises an effective amount of presently disclosed cells or a pharmaceutical composition comprising thereof. In certain embodiments, the kit comprises a sterile container; such containers can be boxes, ampules, bottles, vials, tubes, bags, pouches, blister-packs, or other suitable container forms known in the art. Such containers can be made of plastic, glass, laminated paper, metal foil, or other materials suitable for holding medicaments. In certain non-limiting embodiments, the kit includes an isolated nucleic acid molecule encoding a presently disclosed HR template.

If desired, the cells and/or nucleic acid molecules are provided together with instructions for administering the cells or nucleic acid molecules to a subject having or at risk of developing a cancer or pathogen or immune disorder. The instructions generally include information about the use of the composition for the treatment and/or prevention of a cancer or a pathogen infection. In certain embodiments, the instructions include at least one of the following: description of the therapeutic agent; dosage schedule and administration for treatment or prevention of a neoplasia, pathogen infection, or immune disorder or symptoms thereof; precautions; warnings; indications; counter-indications; over-dosage information; adverse reactions; animal pharmacology; clinical studies; and/or references. The instructions may be printed directly on the container (when present), or as a label applied to the container, or as a separate sheet, pamphlet, card, or folder supplied in or with the container. The resulting cells can be grown under conditions similar to those for unmodified cells, whereby the modified cells can be expanded and used for a variety of purposes.

Exemplary Embodiments

A. In certain non-limiting embodiments, the presently disclosed subject matter provides for a cell, comprising an exogenous T cell receptor (TCR), and an exogenous CD8.

A1. The foregoing of A, wherein the exogenous CD8 comprises at least one monomer.

A2. The foregoing cell of A1, wherein the at least one monomer of the exogenous CD8 comprises an extracellular domain, a transmembrane domain, an intracellular domain, fragments thereof, or combinations thereof.

A3. The foregoing cell of A2, wherein the extracellular domain comprises a CD8α extracellular domain or a CD8β extracellular domain.

A4. The foregoing cell of A2 or A3, wherein the transmembrane a CD8α transmembrane domain or a CD8β transmembrane domain.

A5. The foregoing cell of A2-A4, wherein the intracellular domain comprises a CD8α intracellular domain or a CD8β intracellular domain.

A6. The foregoing cell of A2-A4, wherein the intracellular domain comprises a CD4 intracellular domain.

A7. The foregoing cell of A1-A5, wherein the at least one monomer comprises a CD8α extracellular domain, a CD8α transmembrane domain, and a CD8α intracellular domain.

A8. The foregoing cell of A1-A5, wherein the at least one monomer comprises a CD8β extracellular domain, a CD8β transmembrane domain, and a CD8β intracellular domain.

A9. The foregoing cell of A1-A5, wherein the at least one monomer comprises a CD8α extracellular domain, a CD8α transmembrane domain, and a CD8β intracellular domain.

A10. The foregoing cell of A1-A6, wherein the at least one monomer comprises a CD8α extracellular domain, a CD8α transmembrane domain, and a CD4 intracellular domain.

A11. The foregoing cell of A1-A10, wherein the at least one monomer comprises a signal peptide.

A12. The foregoing cell of A11, wherein the signal peptide is a CD8 signal peptide.

A13. The foregoing cell of A2-A12, wherein the extracellular domain comprises the amino acid sequence set forth in SEQ ID NO: 140, or SEQ ID NO: 145.

A14. The foregoing cell of A2-A13, wherein the transmembrane domain comprises the amino acid sequence set forth in SEQ ID NO: 141, or SEQ ID NO: 146.

A15. The foregoing cell of A2-A14, wherein the intracellular domain comprises the amino acid sequence set forth in SEQ ID NO: 142, SEQ ID NO: 147, or SEQ ID NO: 148.

A16. The foregoing cell of A11-A15, wherein the signal peptide comprises the amino acid sequence set forth in SEQ ID NO: 139, or SEQ ID NO: 144.

A17. The foregoing cell of A-A16, wherein the exogenous CD8 comprises a 2A sequence.

A18. The foregoing cell of A-A17, wherein the exogenous CD8 comprises a linker.

A19. The foregoing cell of A18, wherein the linker comprises the amino acid sequence set forth in SEQ ID NO: 137.

A20. The foregoing cell of A-A19, wherein the exogenous CD8 comprises a protease cleavage site.

A21. The foregoing cell of A-A20, wherein the protease cleavage site is a Furin cleavage site.

A22. The foregoing cell of A-A21, wherein the exogenous TCR is a patient derived TCR.

A23. The foregoing cell of A-A22, wherein the exogenous TCR comprises a signal sequence, a first and second 2A sequence, and a TCR polypeptide sequence.

A24. The foregoing cell of A-A23, wherein the exogenous TCR recognizes a cancer antigen.

A25. The foregoing cell of A24, wherein the cancer antigen is a neoantigen.

A26. The foregoing cell of A24, wherein the cancer antigen is a patient specific antigen.

A27. The foregoing cell of A-A26, wherein the cell is a primary cell.

A28. The foregoing cell of A-A26, wherein the cell is a patient-derived cell.

A29. The foregoing cell of A-A26, wherein the cell is a lymphocyte.

A30. The foregoing cell of A-A26, wherein the cell is a T cell.

A31. The foregoing cell of A-A26, wherein the cell if a young T cell.

A32. The foregoing cell of A31, wherein the cell is CD45RA+, CD62L+, CD28+, CD95−, CCR7+, and CD27+.

A33. The foregoing cell of A31, wherein the cell is CD45RA+, CD62L+, CD28+, CD95+, CD27+, CCR7+.

A34. The foregoing cell of A31, wherein the cell is CD45RO+, CD62L+, CD28+, CD95+, CCR7+, CD27+, CD127+.

A35. The foregoing cell of A-A34, further comprising a gene modification to enhance cell persistence and/or enhances memory cell differentiation A36. The foregoing cell of A-A35, wherein killing activity of the cell is increased between about 10% to about 500% as compared to killing activity of a cell that does not have the exogenous CD8.

A37. The foregoing cell of A-A36, wherein proliferation of the cell upon binding of the TCR to the antigen is increased between about 10% to about 500% as compared to proliferation of a cell that does not have the exogenous CD8.

A38. The foregoing cell of A-A37, wherein secretion of pro-inflammatory cytokine upon binding of the TCR to the antigen by the cell is increased between about 10% to about 500% as compared to secretion by a cell that does not have the exogenous CD8.

A39. The foregoing cell of A-A38, wherein LCK affinity of the cell is increased between about 10% to about 500% as compared to LCK affinity of a cell that does not have the exogenous CD8.

A40. The foregoing cell of A-A39, wherein persistence of the cell is increased between about 10% to about 500% as compared to persistence of a cell that does not have the exogenous CD8.

A41. The foregoing cell of A-A40, wherein tumor infiltration ability of the cell is increased between about 10% to about 500% as compared to tumor infiltration ability of a cell that does not have the exogenous CD8.

A42. The foregoing cell of A-A41, wherein the exogenous TCR is a CD8-dependent TCR.

A43. The foregoing cell of A-A41, wherein the exogenous TCR is a CD8-independent TCR.

A44. The foregoing cell of A-A43, wherein the exogenous CD8 is encoded by a CD8 Construct 1, a CD8 Construct 2, a CD8 Construct 3, or a CD8 Construct 4.

A45. The foregoing cell of A-A43, wherein the exogenous CD8 comprises: a CD8α extracellular domain, a CD8α transmembrane domain, and a CD8α intracellular domain; a CD8α extracellular domain, a CD8α transmembrane domain, a CD8α intracellular domain, a CD8β extracellular domain, a CD8β transmembrane domain, and a CD8β intracellular domain; a CD8α extracellular domain, a CD8α transmembrane domain, and aCD8β intracellular domain; or a CD8α extracellular domain, a CD8α transmembrane domain, and a CD4 intracellular domain.

A46. The foregoing cell of A-A43, wherein the exogenous CD8 comprises: a CD8α signal peptide (SEQ ID NO:139), a CD8α extracellular domain (SEQ ID NO:140), a CD8α transmembrane domain (SEQ ID NO:141), and a CD8α intracellular domain (SEQ ID NO: 142); a CD8α signal peptide (SEQ ID NO:139), a CD8α extracellular domain (SEQ ID NO:140), a CD8α transmembrane domain (SEQ ID NO:141), a CD8α intracellular domain (SEQ ID NO: 142), a CD8β signal peptide (SEQ ID NO:144), a CD8β extracellular domain (SEQ ID NO:145), a CD8β transmembrane domain (SEQ ID NO:146), and a CD8β intracellular domain (SEQ ID NO: 147); a CD8α signal peptide (SEQ ID NO:139), a CD8α extracellular domain (SEQ ID NO:140), a CD8α transmembrane domain (SEQ ID NO:141), and a CD8β intracellular domain (SEQ ID NO: 147); or a CD8α signal peptide (SEQ ID NO:139), a CD8α extracellular domain (SEQ ID NO:140), a CD8α transmembrane domain (SEQ ID NO:141), and a CD4 intracellular domain (SEQ ID NO: 148).

B. In certain non-limiting embodiments, the presently disclosed subject matter provides for a method of modifying a cell, the method comprising introducing into the cell a homologous recombination (HR) template nucleic acid sequence, wherein the HR template comprises first and second homology arms homologous to first and second target nucleic acid sequences, a TCR gene sequence positioned between the first and second homology arms, and a CD8 gene sequence positioned between the first and the second homology arms, and recombining the HR template nucleic acid into an endogenous locus of the cell.

B1. The foregoing method of B, wherein the HR template comprises a first 2A-coding sequence positioned upstream of the CD8 gene sequence, a second 2A-coding sequence positioned downstream of the CD8 gene sequence and upstream of the TCR gene sequence, and a third 2A-coding sequence positioned downstream of the TCR gene sequence; wherein the first, second, and third 2A-coding sequences code for the same amino acid sequence and are codon-diverged relative to each other.

B2. The foregoing method of B or B1, wherein the HR template comprises a sequence coding for the amino acid sequence Gly Ser Gly positioned immediately upstream of the first, second, and/or third 2A-coding sequences.

B3. The foregoing method of B1 or B2, wherein the HR template further comprises a sequence coding for a Furin cleavage site positioned upstream of the first, second, and/or third 2A-coding sequences.

B4. The foregoing method of B-B3, wherein the HR template further comprises a sequence encoding a signal sequence positioned immediately upstream of the TCR gene sequence and/or the CD8 gene sequence.

B5. The foregoing method of B-B4, wherein the HR template comprises a second TCR sequence positioned between the third 2A-coding sequence and the second homology arm.

B6. The foregoing method of B5, wherein the HR template comprises a sequence encoding a first signal sequence positioned immediately upstream the first TCR gene sequence; and a sequence encoding a second signal sequence positioned immediately upstream of the second TCR gene sequence.

B7. The foregoing method of B-B6, wherein the HR template comprises a second CD8 gene sequence positioned between the first CD8 gene sequence and the second 2A-coding sequence.

B8. The foregoing method of B7, wherein a 2A coding sequence is positioned between the first and second CD8 gene sequence.

B9. The foregoing method of B7 or B8, wherein a sequence coding for the amino acid sequence Gly Ser Gly is positioned between the first and second CD8 gene sequences.

B10. The foregoing method of B7-B9, wherein a sequence coding for a Furin cleavage site is positioned between the first and second CD8 gene sequences.

B11. The foregoing method of B-B10, wherein the CD8 gene sequence comprises a sequence encoding an extracellular domain, a sequence encoding an intracellular domain, a sequence encoding an intracellular domain, fragments thereof, or combinations thereof.

B12. The foregoing method of B11, wherein the sequence encoding an extracellular domain comprises a sequence encoding a CD8α extracellular domain or a CD8β extracellular domain.

B13. The foregoing method of B11 or B12, wherein the sequence encoding a transmembrane domain comprises a sequence encoding a CD8α transmembrane domain or a CD8β transmembrane domain.

B14. The foregoing method of B11-B13, wherein the sequence encoding an intracellular domain comprises a sequence encoding a CD8α intracellular domain or a CD8β intracellular domain.

B15. The foregoing method of B11-B14, wherein the sequence encoding an intracellular domain comprises a sequence encoding a CD4 intracellular domain.

B16. The foregoing method of B11-B15, wherein the CD8 gene sequence comprises a sequence encoding a CD8α extracellular domain, a CD8α transmembrane domain, and a CD8α intracellular domain.

B17. The foregoing method of B11-B15, wherein the CD8 gene sequence comprises a sequence encoding a CD8β extracellular domain, a CD8β transmembrane domain, and a CD8β intracellular domain.

B18. The foregoing method of B11-B15, wherein the CD8 gene sequence comprises a sequence encoding a CD8α extracellular domain, a CD8α transmembrane domain, and a CD8β intracellular domain.

B19. The foregoing method of B11-B15, wherein the CD8 gene sequence comprises a sequence encoding a CD8α extracellular domain, a CD8α transmembrane domain, and a CD4 intracellular domain.

B20. The foregoing method of B7-B19, wherein the HR template comprises a sequence encoding a first signal sequence positioned immediately upstream the first CD8 gene sequence; and a sequence encoding a second signal sequence positioned immediately upstream of the second CD8 gene sequence.

B21. The foregoing method of B4-B20, wherein the signal sequence is a CD8 signal sequence, a human growth hormone signal sequence, fragments thereof, or combinations thereof.

B22. The foregoing method of B-B21, wherein the first and second homology arms of the HR template are each from about 300 bases to about 2,000 bases in length.

B23. The foregoing method of B-B22, wherein the first and second homology arms of the HR template are each from about 600 bases to about 2,000 bases in length.

B24. The foregoing method of B-B23, wherein the exogenous TCR is a patient derived TCR.

B25. The foregoing method of B-B24, wherein the exogenous TCR comprises a signal sequence, a first and second 2A sequence, and a TCR polypeptide sequence.

B26. The foregoing method of B-B25, wherein the exogenous TCR recognizes a cancer antigen.

B27. The foregoing method of B26, wherein the cancer antigen is a neoantigen.

B28. The foregoing method of B26, wherein the cancer antigen is a patient specific antigen.

B29. The foregoing method of B-B28, wherein the HR template is non-viral.

B30. The foregoing method of B-B29, wherein the HR template is a circular DNA.

B31. The foregoing method of B-B29, wherein the HR template is a linear DNA.

B32. The foregoing method of B-B31, wherein the introducing occurs via electroporation.

B33. The foregoing method of B-B32, wherein the recombining comprises cleavage of the endogenous locus by a nuclease; and recombination of the HR template nucleic acid sequence into the endogenous locus by homology directed repair.

B34. The foregoing method of B33, wherein the nuclease is a Clustered Regularly Interspaced Short Palindromic Repeats (CRISPR) family nuclease, or derivative thereof.

B35. The foregoing method of B34, further comprising a gRNA.

B36. The foregoing method of B-B35, wherein the process further comprises culturing the cell.

B37. The foregoing method of B36, wherein the culturing is conducted in the presence of at least one cytokine.

B38. The foregoing method of B36 or B37, wherein the culturing is conducted in the presence of IL2, IL7, IL15, or any combination thereof.

B39. The foregoing method of B36 or B37, wherein the culturing is conducted in the presence of IL7 and IL15.

B40. The foregoing method of B-B39, further comprising a gene modification to enhance cell persistence and/or enhances memory cell differentiation.

B41. The foregoing method of B-B40, wherein the cell is a primary cell.

B42. The foregoing method of B-B40, wherein the cell is a patient-derived cell.

B43. The foregoing method of B-B40, wherein the cell is a lymphocyte.

B44. The foregoing method of B-B40, wherein the cell is a T cell.

B45. The foregoing method of B-B40, wherein the cell is a young T cell.

B46. The foregoing method of B45, wherein the cell is CD45RA+, CD62L+, CD28+, CD95−, CCR7+, and CD27+.

B47. The foregoing method of B45, wherein the cell is CD45RA+, CD62L+, CD28+, CD95+, CD27+, CCR7+.

B48. The foregoing method of B45, wherein the cell is CD45RO+, CD62L+, CD28+, CD95+, CCR7+, CD27+, CD127+.

B49. The foregoing method of B-B48, wherein killing activity of the cell is increased between about 10% to about 500% as compared to killing activity of a cell that does not have the CD8 gene sequence.

B50. The foregoing method of B-B49, wherein proliferation of the cell upon binding of the TCR to the antigen is increased between about 10% to about 500% as compared to proliferation of a cell that does not have the CD8 gene sequence.

B51. The foregoing method of B-B50, wherein secretion of pro-inflammatory cytokine upon binding of the TCR to the antigen by the cell is increased between about 10% to about 500% as compared to secretion by a cell that does not have the CD8 gene sequence.

B52. The foregoing method of B-B51, wherein LCK affinity of the cell is increased between about 10% to about 500% as compared to LCK affinity of a cell that does not have the CD8 gene sequence.

B53. The foregoing method of B-B52, wherein persistence of the cell is increased between about 10% to about 500% as compared to persistence of a cell that does not have the CD8 gene sequence.

B54. The foregoing method of B-B53, wherein tumor infiltration ability of the cell is increased between about 10% to about 500% as compared to tumor infiltration ability of a cell that does not have the CD8 gene sequence.

B55. The foregoing method of B-B54, wherein the TCR gene encodes a CD8-dependent TCR.

B56. The foregoing method of B-B54, wherein the TCR gene encodes a CD8-independent TCR.

B57. The foregoing method of B-B56, wherein the CD8 gene sequence is encoded by a CD8 Construct 1, a CD8 Construct 2, a CD8 Construct 3, or a CD8 Construct 4.

B58. The foregoing method of B-B56, wherein the CD8 gene sequence comprises: a CD8α extracellular domain, a CD8α transmembrane domain, and a CD8α intracellular domain; a CD8α extracellular domain, a CD8α transmembrane domain, a CD8α intracellular domain, a CD8β extracellular domain, a CD8β transmembrane domain, and a CD8β intracellular domain; a CD8α extracellular domain, a CD8α transmembrane domain, and a CD8β intracellular domain; or a CD8α extracellular domain, CD8α transmembrane domain, CD4 intracellular domain.

B59. The foregoing method of B-B56, wherein the CD8 gene sequence comprises: a CD8α signal peptide (SEQ ID NO:139), a CD8α extracellular domain (SEQ ID NO:140), a CD8α transmembrane domain (SEQ ID NO:141), and a CD8α intracellular domain (SEQ ID NO: 142); a CD8α signal peptide (SEQ ID NO:139), a CD8α extracellular domain (SEQ ID NO:140), a CD8α transmembrane domain (SEQ ID NO:141), a CD8α intracellular domain (SEQ ID NO: 142), a CD8β signal peptide (SEQ ID NO:144), a CD8β extracellular domain (SEQ ID NO:145), a CD8β transmembrane domain (SEQ ID NO:146), and a CD8β intracellular domain (SEQ ID NO: 147); a CD8α signal peptide (SEQ ID NO:139), a CD8α extracellular domain (SEQ ID NO:140), a CD8α transmembrane domain (SEQ ID NO:141), and a CD8β intracellular domain (SEQ ID NO: 147); or a CD8α signal peptide (SEQ ID NO:139), a CD8α extracellular domain (SEQ ID NO:140), a CD8α transmembrane domain (SEQ ID NO:141), and a CD4 intracellular domain (SEQ ID NO: 148).

C. In certain non-limiting embodiments, the presently disclosed subject matter provides for a cell modified by the method of B-B57.

D. In certain non-limiting embodiments, the presently disclosed subject matter provides for a composition comprising an effective amount of a cell of A-A46 or a cell of C.

D1. The foregoing composition of D, wherein the composition is a pharmaceutical composition that further comprises a pharmaceutically acceptable excipient.

D2. The foregoing composition of D or D1, wherein the composition is administered to a patient in need thereof for the treatment of cancer.

D3. The foregoing composition of D-D2, wherein the composition comprises a cryopreservation agent.

D4. The foregoing composition of D-D3, wherein the composition comprises serum albumin. D5. The foregoing composition of D-D4, wherein the composition comprises Plasma-Lyte A, HSA, and CryoStor CS10.

E. In certain non-limiting embodiments, the presently disclosed subject matter provides for a method of treating cancer in a subject in need thereof, the method comprising administering a therapeutically effective amount of a cell of A-A46, a cell of claim C, or a composition of D-D5.

E1. The foregoing method of E, wherein prior to administering the therapeutically effective amount of cells, a non-myeloablative lymphodepletion regimen is administered to the subject.

E2. The foregoing method of E or E1, wherein the cancer is a solid tumor.

E3. The foregoing method of E or E1, wherein the cancer is liquid tumor.

E4. The foregoing method of E2, wherein the solid tumor is selected from the group consisting of melanoma, thoracic cancer, lung cancer, ovarian cancer, breast cancer, pancreatic cancer, head and neck cancer, prostate cancer, gynecological cancer, central nervous system cancer, cutaneous cancer, HPV+ cancer, esophageal cancer, thyroid cancer, gastric cancer, hepatocellular cancer, cholangiocarcinomas, renal cell cancers, testicular cancer, sarcomas, and colorectal cancer.

E5. The foregoing method of E3, wherein the liquid tumor is selected from the group consisting of follicular lymphoma, leukemia, and multiple myeloma.

F. In certain non-limiting embodiments, the presently disclosed subject matter provides for a kit comprising a cell of A-A46, reagents for performing the method of B-B57, a cell of C, or a composition of D-D5.

F1. The foregoing kit of F, wherein the kit further comprises written instructions for treating a cancer.

G. In certain non-limiting embodiments, the presently disclosed subject matter provides for a cell, comprising: an exogenous T cell receptor (TCR); and an exogenous CD8, comprising: a CD8α extracellular domain, a CD8α transmembrane domain, a CD8α intracellular domain; a CD8α extracellular domain, a CD8α transmembrane domain, a CD8α intracellular domain, a CD8β extracellular domain, a CD8β transmembrane domain, and a CD8β intracellular domain; a CD8α extracellular domain, a CD8α transmembrane domain, and a CD8β intracellular domain; or a CD8α extracellular domain, a CD8α transmembrane domain, and a CD4 intracellular domain.

H. In certain non-limiting embodiments, the presently disclosed subject matter provides for a cell, comprising: an exogenous T cell receptor (TCR); and an exogenous CD8, comprising: a CD8α signal peptide (SEQ ID NO:139), a CD8α extracellular domain (SEQ ID NO:140), a CD8α transmembrane domain (SEQ ID NO:141), and a CD8α intracellular domain (SEQ ID NO: 142); a CD8α signal peptide (SEQ ID NO:139), a CD8α extracellular domain (SEQ ID NO:140), a CD8α transmembrane domain (SEQ ID NO:141), a CD8α intracellular domain (SEQ ID NO: 142), a CD8β signal peptide (SEQ ID NO:144), a CD8β extracellular domain (SEQ ID NO:145), a CD8β transmembrane domain (SEQ ID NO:146), and a CD8β intracellular domain (SEQ ID NO: 147); a CD8α signal peptide (SEQ ID NO:139), a CD8α extracellular domain (SEQ ID NO:140), a CD8α transmembrane domain (SEQ ID NO:141), and a CD8β intracellular domain (SEQ ID NO: 147); or a CD8α signal peptide (SEQ ID NO:139), a CD8α extracellular domain (SEQ ID NO:140), a CD8α transmembrane domain (SEQ ID NO:141), and a CD4 intracellular domain (SEQ ID NO: 148).

I. In certain non-limiting embodiments, the presently disclosed subject matter provides for a method of modifying a cell, the method comprising: introducing into the cell a homologous recombination (HR) template nucleic acid sequence, wherein the HR template comprises: first and second homology arms homologous to first and second target nucleic acid sequences; a TCR gene sequence positioned between the first and second homology arms; a CD8 gene sequence positioned between the first and the second homology arms; and recombining the HR template nucleic acid into an endogenous locus of the cell, wherein the CD8 gene sequence comprises: a CD8α extracellular domain, a CD8α transmembrane domain, and a CD8α intracellular domain; a CD8α extracellular domain, a CD8α transmembrane domain, a CD8α intracellular domain, a CD8β extracellular domain, a CD8β transmembrane domain, and a CD8β intracellular domain; a CD8α extracellular domain, a CD8α transmembrane domain, and a CD8β intracellular domain; or a CD8α extracellular domain, a CD8α transmembrane domain, and a CD4 intracellular domain.

J. In certain non-limiting embodiments, the presently disclosed subject matter provides for a method of modifying a cell, the method comprising: introducing into the cell a homologous recombination (HR) template nucleic acid sequence, wherein the HR template comprises: first and second homology arms homologous to first and second target nucleic acid sequences; a TCR gene sequence positioned between the first and second homology arms; a CD8 gene sequence positioned between the first and the second homology arms; and recombining the HR template nucleic acid into an endogenous locus of the cell, wherein the CD8 gene sequence comprises: a CD8α signal peptide (SEQ ID NO:139), a CD8α extracellular domain (SEQ ID NO:140), a CD8α transmembrane domain (SEQ ID NO:141), and a CD8α intracellular domain (SEQ ID NO: 142); a CD8α signal peptide (SEQ ID NO:139), a CD8α extracellular domain (SEQ ID NO:140), a CD8α transmembrane domain (SEQ ID NO:141), a CD8α intracellular domain (SEQ ID NO: 142), a CD8β signal peptide (SEQ ID NO:144), a CD8β extracellular domain (SEQ ID NO:145), a CD8β transmembrane domain (SEQ ID NO:146), and a CD8β intracellular domain (SEQ ID NO: 147); a CD8α signal peptide (SEQ ID NO:139), a CD8α extracellular domain (SEQ ID NO:140), a CD8α transmembrane domain (SEQ ID NO:141), and a CD8β intracellular domain (SEQ ID NO: 147); or a CD8α signal peptide (SEQ ID NO:139), a CD8α extracellular domain (SEQ ID NO:140), a CD8α transmembrane domain (SEQ ID NO:141), and a CD4 intracellular domain (SEQ ID NO: 148).

K. In certain non-limiting embodiments, the presently disclosed subject matter provides for a composition comprising a cell, wherein the cell comprises an exogenous T cell receptor (TCR) and an exogenous CD8, wherein the exogenous CD8 comprises: a CD8α extracellular domain, a CD8α transmembrane domain, and a CD8α intracellular domain; a CD8α extracellular domain, a CD8α transmembrane domain, a CD8α intracellular domain, a CD8β extracellular domain, a CD8β transmembrane domain, and a CD8β intracellular domain; a CD8α extracellular domain, a CD8α transmembrane domain, and a CD8β intracellular domain; or a CD8α extracellular domain, a CD8α transmembrane domain, and a CD4 intracellular domain.

L. In certain non-limiting embodiments, the presently disclosed subject matter provides for a composition comprising a cell, wherein the cell comprises an exogenous T cell receptor (TCR) and an exogenous CD8, wherein the exogenous CD8 comprises: a CD8α signal peptide (SEQ ID NO:139), a CD8α extracellular domain (SEQ ID NO:140), a CD8α transmembrane domain (SEQ ID NO:141), and a CD8α intracellular domain (SEQ ID NO: 142); a CD8α signal peptide (SEQ ID NO:139), a CD8α extracellular domain (SEQ ID NO:140), a CD8α transmembrane domain (SEQ ID NO:141), a CD8α intracellular domain (SEQ ID NO: 142), a CD8β signal peptide (SEQ ID NO:144), a CD8β extracellular domain (SEQ ID NO:145), a CD8β transmembrane domain (SEQ ID NO:146), and a CD8β intracellular domain (SEQ ID NO: 147); a CD8α signal peptide (SEQ ID NO:139), a CD8α extracellular domain (SEQ ID NO:140), a CD8α transmembrane domain (SEQ ID NO:141), and a CD8β intracellular domain (SEQ ID NO: 147); or a CD8α signal peptide (SEQ ID NO:139), a CD8α extracellular domain (SEQ ID NO:140), a CD8α transmembrane domain (SEQ ID NO:141), and a CD4 intracellular domain (SEQ ID NO: 148).

M. In certain non-limiting embodiments, the presently disclosed subject matter provides for a method of treating cancer in a subject in need thereof, the method comprising administering a therapeutically effective amount of a cell, wherein the cell comprises an exogenous T cell receptor (TCR) and an exogenous CD8, wherein the exogenous CD8 comprises: a CD8α extracellular domain, a CD8α transmembrane domain, and a CD8α intracellular domain; a CD8α extracellular domain, a CD8α transmembrane domain, a CD8α intracellular domain, a CD8β extracellular domain, a CD8β transmembrane domain, and a CD8β intracellular domain; a CD8α extracellular domain, a CD8α transmembrane domain, and a CD8β intracellular domain; or a CD8α extracellular domain, a CD8α transmembrane domain, and a CD4 intracellular domain.

N. A method of treating cancer in a subject in need thereof, the method comprising administering a therapeutically effective amount of a cell, wherein the cell comprises an exogenous T cell receptor (TCR) and an exogenous CD8, wherein the exogenous CD8 comprises: a CD8α signal peptide (SEQ ID NO:139), a CD8α extracellular domain (SEQ ID NO:140), a CD8α transmembrane domain (SEQ ID NO:141), and a CD8α intracellular domain (SEQ ID NO: 142); a CD8α signal peptide (SEQ ID NO:139), a CD8α extracellular domain (SEQ ID NO:140), a CD8α transmembrane domain (SEQ ID NO:141), a CD8α intracellular domain (SEQ ID NO: 142), a CD8β signal peptide (SEQ ID NO:144), a CD8β extracellular domain (SEQ ID NO:145), a CD8β transmembrane domain (SEQ ID NO:146), and a CD8β intracellular domain (SEQ ID NO: 147); a CD8α signal peptide (SEQ ID NO:139), a CD8α extracellular domain (SEQ ID NO:140), a CD8α transmembrane domain (SEQ ID NO:141), and a CD8β intracellular domain (SEQ ID NO: 147); or a CD8α signal peptide (SEQ ID NO:139), a CD8α extracellular domain (SEQ ID NO:140), a CD8α transmembrane domain (SEQ ID NO:141), and a CD4 intracellular domain (SEQ ID NO: 148).

EXAMPLES

The following are examples of methods and compositions of the invention. It is understood that various other embodiments may be practiced, given the general description provided above.

Example 1. Generation of NeoTCR Products

Neoepitope-specific TCRs identified by the imPACT Isolation Technology described in PCT/US2020/17887 (which is herein incorporated by reference in its entirety) were used to generate homologous recombination (HR) DNA templates. These HR templates were transfected into primary human T cells in tandem with site-specific nucleases (see FIGS. 1A-1C). The single-step non-viral precision genome engineering resulted in the seamless replacement of the endogenous TCR with the patient's neoepitope-specific TCR, expressed by the endogenous promoter. The TCR expressed on the surface is entirely native in sequence.

The precision of neoTCR-T cell genome engineering was evaluated by Targeted Locus Amplification (TLA) for off-target integration hot spots or translocations, and by next generation sequencing based off-target cleavage assays and found to lack evidence of unintended outcomes.

As shown in FIGS. 1A-1C, constructs containing genes of interest were inserted into endogenous loci. This was accomplished with the use of homologous repair templates containing the coding sequence of the gene of interest flanked by left and right HR arms. In addition to the HR arms, the gene of interest was sandwiched between 2A peptides, a protease cleavage site that is upstream of the 2A peptide to remove the 2A peptide from the upstream translated gene of interest, and signal sequences (FIG. 1B). Once integrated into the genome, the gene of interested expression gene cassette was transcribed as single messenger RNA. During the translation of this gene of interest in messenger RNA, the flanking regions were unlinked from the gene of interest by the self-cleaving 2A peptide and the protease cleavage site was cleaved for the removal of the 2A peptide upstream from the translated gene of interest (FIG. 1C). In addition to the 2A peptide and protease cleavage site, a gly-ser-gly (GSG) linker was inserted before each 2A peptide to further enhance the separation of the gene of interest from the other elements in the expression cassette.

It was determined that P2A peptides were superior to other 2A peptides for Cell Products because of its efficient cleavage. Accordingly, two (2) P2A peptides and codon divergence were used to express the gene of interest without introducing any exogenous epitopes from remaining amino acids on either end of the gene of interest from the P2A peptide. The benefit of the gene edited cell having no exogenous epitopes (i.e., no flanking P2A peptide amino acids on either side of the gene of interest) is that immunogenicity is drastically decreased and there is less likelihood of a patient infused with a Cell Product containing the gene edited cell to have an immune reaction against the gene edited cell.

As described in PCT/US/2018/058230, NeoTCRs were integrated into the TCRα locus of T cells. Specifically, a homologous repair template containing a NeoTCR coding sequence flanked by left and right HR Arms was used. In addition, the endogenous TCRβ locus was disrupted leading to the expression of only TCR sequences encoded by the NeoTCR construct. The general strategy was applied using circular HR templates as well as with linear templates.

The target TCRα locus (Cα) is shown along with the plasmid HR template, and the resulting edited sequence and downstream mRNA/protein products in FIGS. 1B and 1C. The target TCRα locus (endogenous TRAC) and its CRISPR Cas9 target site (horizontal stripe, cleavage site designated by arrow) are shown (FIGS. 1A-1C). The circular plasmid HR template with the polynucleotide encoding the NeoTCR is located between left and right homology arms ("LHA" and "RHA" respectively). The region of the TRAC introduced by the HR template that was codon optimized is shown (vertical stripe). The TCRβ constant domain was derived from TRBC2, which is indicated as being functionally equivalent to TRBC1. Other elements in the NeoTCR cassette include: 2A=2A ribosome skipping element (by way of non-limiting example, the 2A peptides used in the cassette are both P2A sequences that are used in combination with codon divergence to eliminate any otherwise occurring non-endogenous epitopes in the translated product); P=protease cleavage site upstream of 2A that removes the 2A tag from the upstream TCRβ protein (by way of non-limiting example the protease cleavage site can be a furin protease cleavage site); SS=signal sequences (by way of non-limited example the protease cleavage site can be a human growth hormone signal sequence). The HR template of the NeoTCR expression gene cassette includes two flanking homology arms to direct insertion into the TCRα genomic locus targeted by the CRISPR Cas9 nuclease RNP with the TCRα guide RNA. These homology arms (LHA and RHA) flank the neoE-specific TCR sequences of the NeoTCR expression gene cassette. While the protease cleavage site used in this example was a furin protease cleavage site, any appropriate protease cleavage site known to one of skill in the art could be used. Similarly, while HGH was the signal sequence chosen for this example, any signal sequence known to one of skill in the art could be selected based on the desired trafficking and used.

Once integrated into the genome (FIG. 1C), the NeoTCR expression gene cassette is transcribed as a single messenger RNA from the endogenous TCRα promoter, which still includes a portion of the endogenous TCRα polypeptide from that individual T cell (FIG. 1C). During ribosomal polypeptide translation of this single NeoTCR messenger RNA, the NeoTCR sequences are unlinked from the endogenous, CRISPR-disrupted TCRα polypeptide by self-cleavage at a P2A peptide (FIG. 1C). The encoded NeoTCRα and NeoTCRβ polypeptides are also unlinked from each other through cleavage by the endogenous cellular human furin protease and a second self-cleaving P2A sequence motifs included in the NeoTCR expression gene cassette (FIG. 1C). The NeoTCRα and NeoTCRβ polypeptides are separately targeted by signal leader sequences (derived from the human growth hormone, HGH) to the endoplasmic reticulum for multimer assembly and trafficking of the NeoTCR protein complexes to the T cell surface. The inclusion of the furin protease cleavage site facilitates the removal of the 2A sequence from the upstream TCRβ chain to reduce potential interference with TCRβ function. Inclusion of a gly-ser-gly linker before each 2A (not shown) further enhances the separation of the three polypeptides.

Additionally, three repeated protein sequences are codon diverged within the HR template to promote genomic stability. The two P2A are codon diverged relative to each other, as well as the two HGH signal sequences relative to each other, within the TCR gene cassette to promote stability of the introduced NeoTCR cassette sequences within the genome of the ex vivo engineered T cells. Similarly, the re-introduced 5' end of TRAC exon 1 (vertical stripe) reduces the likelihood of the entire cassette being lost over time through the removal of intervening sequence of two direct repeats.

In addition to NeoTCR Products, this method can be used for any CD8 Product.

In-Out PCR was used to confirm the precise target integration of the NeoE TCR cassette. Agarose gels show the results of a PCR using primers specific to the integration cassette and site generate products of the expected size only for cells treated with both nuclease and DNA template (KOKI and KOKIKO), demonstrating site-specific and precise integration.

Furthermore, Targeted Locus Amplification (TLA) was used to confirm the specificity of targeted integration. Cross-linking, ligation, and use of primers specific to the NeoTCR insert were used to obtain sequences around the site(s) of integration. The reads mapped to the genome are binned in 10 kb intervals. Significant read depths were obtained only around the intended site the integration site on chromosome 14, showing no evidence of common off-target insertion sites.

Antibody staining for endogenous TCR and peptide-HLA staining for neoTCR revealed that the engineering results in high frequency knock-in of the NeoTCR, with some TCR- cells and few WT T cells remaining. Knock-in is evidenced by neoTCR expression in the absence of an exogenous promoter. Engineering was carried out multiple times using the same neoTCR with similar results. Therefore, efficient and consistent expression of the NeoTCR and knockout of the endogenous TCR in engineered T cells was achieved.

Example 2. Generation of CD8 Product 1

Figure 11A:
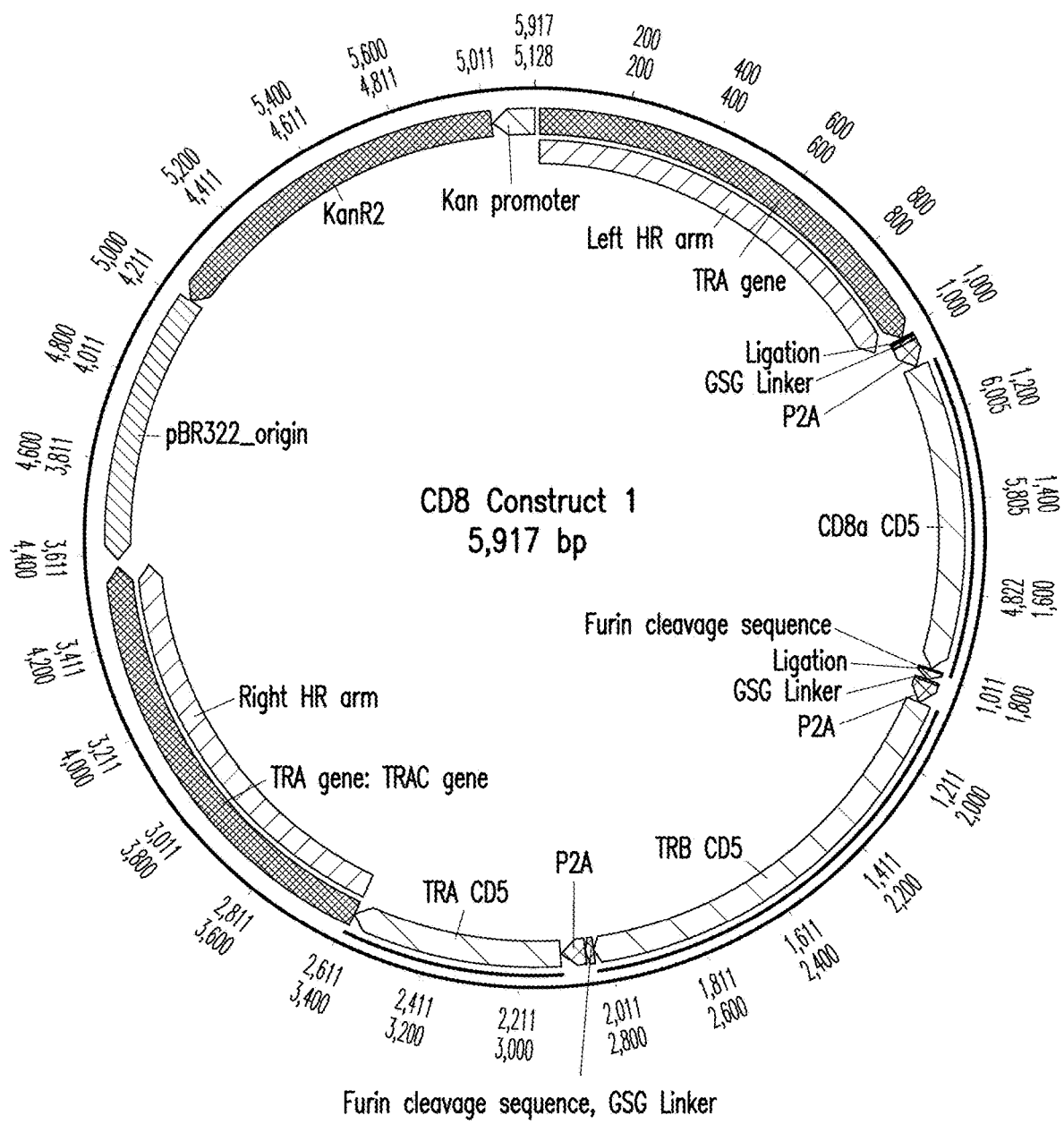
FIGS. 11A-11D.

T cell Isolation and Editing. CD4 and CD8 T cells were isolated from healthy donor PBMCs using the Miltenyi Prodigy or Miltenyi MACS separation columns according to the manufacturers' instructions. Positively-selected CD4 and CD8 T cells (using Miltenyi antibodies and isolation column) were used fresh or cryopreserved in 1% human serum albumin (Gemini), 49% plasmalyte (Baxter), and 50% CS10 (Sigma). Cryopreserved cells were thawed, washed in TexMACS (Miltenyi)+10% human AB serum (Valley Biomedical), and seeded at a density of 2×106 cells per mL in TexMACS+3% human AB serum (culture medium). One day after thaw, or immediately if used fresh, the cells were washed and re-seeded at a density of 1.46×106 cells per mL in culture medium+12.5 ng/mL IL7+12.5 ng/mL 11, 15+1:17.5 ratio of TransACT T cell activation reagent (all reagents from Miltenyi) by volume. Two days after activation, T cells were electroporated with i) a plasmid for the production of a NeoTCR Product (see, e.g., FIG. 1B) or ii) a CD8 Construct 1 (e.g., consisting of the coding sequence of CD8α flanked by P2A sites upstream of the neoTCR beta and alpha sequences and gRNA-Cas9 RNPs targeting the TCR alpha and beta loci; see, e.g., FIG. 2A). An exemplary expression construct of CD8 Construct 1 is shown in FIG. 11A. T cells were electroporated using the Lonza X-unit in 100 μL cuvettes and program EO-115. T cells are expanded in culture medium supplemented with 12.5 ng/mL IL7+12.5 ng/mL IL15. Supplemented medium was exchanged every 2-3 days until the end of study, 13 days after activation.

comPACT and comPACT-Dextramer preparation. Neoantigen-specific peptide-HLA complex polypeptides (each a "comPACT") were prepared according to the method as described in PCT/US2019/025415, hereby incorporated by reference in its entirety. A comPACT-dextramer complex was made for the labeling of neoTCR expressing T cells. Biotinylated comPACT protein was incubated with a streptavidin-conjugated fluorophore for 10 min at room temperature (RT). Biotin-40-dextran (NANOCS) was added to the mixture and incubated at RT for an additional 10 minutes. The comPACT-Dextramer was stored at 4° C.

Confirmation of comPACT binding to neoTCR edited T cells. T cells were stained for flow cytometry. Cells were first stained with viability dye for 20 minutes at 4° C., then washed and stained with the comPACT-dextramer for 10 minutes at 4° C. Surface antibodies (anti-CD8α, anti-CD8β, anti-CD4) were added to the suspension of cells and comPACT-dextramer, and the cells are incubated for an additional 20 minutes at 4° C. Cells were then washed and fixed in intracellular fixation buffer (BD Biosciences). All cells were acquired on an Attune NxT Flow Cytometer (ThermoFisher Scientific) and data analyzed with either FCS Express or FlowJo.

Cytometric Bead Array (CBA). Streptavidin coated plates (Eagle Biosciences) were washed 3 times with wash buffer (PBS supplemented with 1% BSA and 0.05% tween20) and then coated with comPACTs at different concentrations ranging from 100-0.01 ng/well. Wells with no comPACT and wells coated with mismatched comPACT were used as controls. The plates were incubated for 2 hr at room temperature, washed three times with wash buffer, and then washed three times with TexMACS supplemented with 3% human AB serum to remove the tween20. T cells were given two washes with TexMACS supplemented with 3% human AB serum and resuspended at 1 million cells/mL in TexMACS supplemented with 3% human AB serum and 1× penicillin-streptomycin solution. T cells were plated onto the comPACT coated plate at 100 μL/well and incubated at 37° C., 5% CO2. After 24h the supernatant was collected, and the cytokine concentrations were analyzed using the BD Cytometric Bead Array (CBA) Human Th1/Th2 Cytokine Kit II (Catalog No. 551809) following the manufacturer's protocol. Capture beads were mixed with culture supernatant, incubated with the detection reagent for 3 hr at RT protected from light, washed, and resuspended in wash buffer. Samples were assayed on an Attune NxT Flow Cytometer and data analyzed with FlowJo. The EC50 represents the concentration of cognate comPACT that elicits 50% of the maximum response and is calculated utilizing a least-squares fit of IFNγ secretion over a range of comPACT concentrations.

Intracellular Staining. T cells were stained for flow cytometry on the indicated days. T cells are first stained with viability dye for 20 minutes at 4° C., then washed and incubated with surface antibodies (anti-CD8α, anti-CD8β, anti-CD4) for an additional 20 minutes at 4° C. T cells are then washed and permeabilized for intracellular staining. T cells are stained with anti-2A peptide or with anti-IFNγ, anti-TNF, or anti-IL2 in permeabilization buffer for 20 minutes at 4° C. T cells are fixed in intracellular fixation buffer (BD Biosciences). Samples are assayed on an Attune NxT Flow Cytometer (ThermoFisher Scientific) and data analyzed with either FCS Express or FlowJo.

T cell Proliferation Assay. Edited CD4 and CD8 T cells are labeled with the e450 proliferation dye (eBioscience) according to the manufacturer's instructions. Labeled cells were stimulated on comPACT coated plates with a range of concentrations as described above. T cells were harvested over 48-96 hours and analyzed for proliferation as measured by dilution of the e450 dye.

T cell Killing Assay. HLA-matched cell lines were pulsed with the cognate neoantigen peptide or mismatched peptide for 1 h at 37° C., 5% CO2. The cells were washed 3 times with media to remove any unbound peptide and then co-cultured with edited CD4 and CD8 T cells that are labeled with the e450 proliferation dye described above. Co-cultures were incubated for 48 h at 37° C. with 5% CO2 before harvest. Cells were washed and stained with a fixable viability dye to determine killing efficiency. The e450 proliferation dye was used to distinguish edited T cells from target cells.

Generation and Validation of CD8 Product 1. An expression construct consisting of the coding sequence (CDS) of CD8α flanked by P2A sites upstream of the neoTCR beta and alpha sequences is synthesized. Briefly, the CDS of human CD8α is synthesized with a GSG-linker and P2A site upstream and flanked with restriction sites. The neoTCR expression vector of interest and the synthesized CD8α construct were incubated with restriction enzymes and ligated together to create the final HDR construct. The CD8 Construct 1 was electroporated along with gRNA-Cas9 RNPs targeting the TCRα and β loci. Model neoTCRs known to bind dextramer among CD8 T cells but not CD4 T cells (e.g. TCR097) were used to demonstrate that expression of the CD8α transgene enables these TCRs to bind dextramer among CD4 T cells.

To test the efficiency of the gene transfer and expression of CD8α on the surface of CD4 T cells, engineered CD4 T cells were stained with anti-CD8α antibodies and surface expression of the transgene is confirmed by flow cytometry as described above. NeoTCRs known to bind dextramer among CD8 T cells only (e.g., TCR 097) were used to demonstrate that expression of the CD8α transgene enables these TCRs to bind dextramer among CD4 T cells. See, FIGS. 13A, 13B, 14, 15A, and 15B. Furthermore, CD8α expression on wild type and genetically engineered CD8α T cells was assessed to determine whether the addition of the CD8α transgene increased surface levels of CD8α on CD8 T cells. CD4 T cells engineered to express the CD8α transgene were double-positive for CD4 and CD8α.

Figures 15A, 15B:
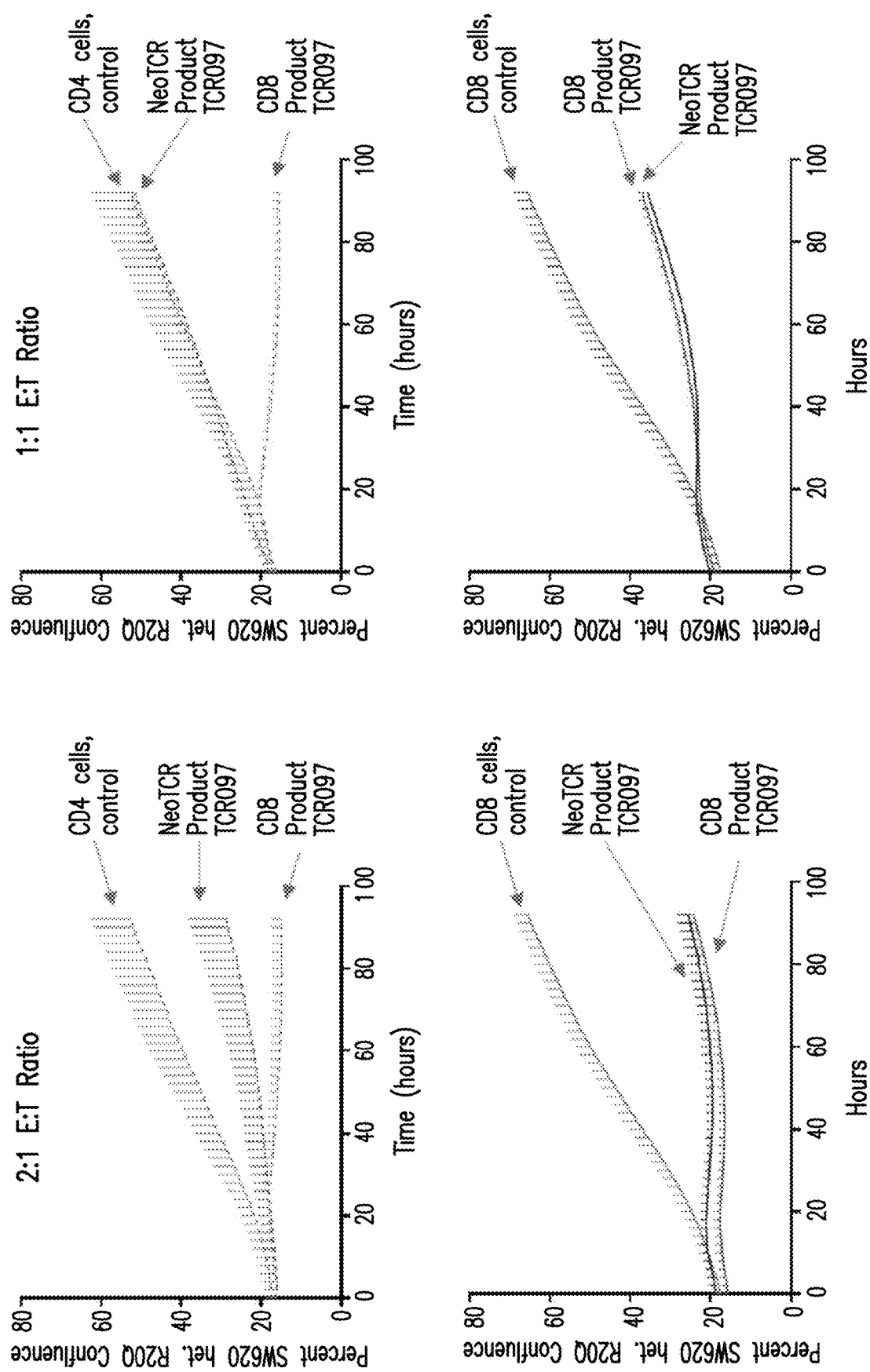
FIGS. 15A and 15B.

CD8 T cells were also engineered to express the CD8α transgene and characterized as described above. FIGS. 15A and 15B. Relative CD8α gene expression was also quantified via RT-qPCR and compared to control non-engineered CD8 T cells. CD8 T cells expressing the CD8α transgene had higher than endogenous levels of CD8α expression.

Effect of CD8 expression on T cell proliferation upon encounter of cognate antigen. Edited T cells were stained with a proliferation dye as described above. After staining, T cells were stimulated with a range of concentrations of cognate comPACT proteins. 48-72 hours later, T cells were harvested and stained with anti-CD4, anti-CD8, and anti-2A peptide as described above. Edited T cells were identified by 2A expression. Proliferation of the CD4 and CD8 T cells was determined by quantifying the dilution of the proliferative dye. NeoTCR-expressing T cells lacking the CD8α transgene were used as a negative control. NeoTCR CD4 T cells expressing the CD8α transgene proliferated in response to lower concentrations of cognate comPACT than CD4 T cells lacking CD8α expression.

Effect of CD8α expression on cytokine production upon encounter of cognate antigen. In addition to proliferation, effector cytokine production via intracellular cytokine staining was measured. In this assay, NeoTCR Products and CD8 Product 1 were be stimulated with various concentrations of cognate comPACT for 5 hours in the presence of brefeldin A. After stimulation, T cells were stained with anti-CD4 and anti-CD8α. Cells were be permeabilized and stained with anti-P2A peptide, anti-IFNγ, anti-TNF, and anti-IL2. NeoTCR CD4 T cells expressing the CD8α transgene produced effector cytokines in response to lower concentrations of cognate comPACT than neoTCR CD4 T cells lacking CD8α expression.

Effect of CD8α expression on killing activity upon encounter of cognate antigen. To assess effector function, edited CD4 and CD8 T cells were cultured with HLA-matched target cells pulsed with cognate peptide as described above. CD4 and CD8 T cells were edited separately to evaluate the ability of CD4 T cells expressing CD8α to kill target cells. NeoTCR CD4 T cells expressing the CD8α transgene killed a greater fraction of target cells presenting cognate peptide than neoTCR CD4 T cells lacking CD8α expression.

Example 3. Generation of CD8 Product 2

CD4 T cells engineered to express CD8α lack CD8β expression. However, CD8β has a higher affinity for LCK (Irie et al., 1998, J. Immunol, 161(1), 183-191). Therefore, T cells were edited to co-express CD8β with CD8α (i.e., a CD8 Product 2). An additional construct containing CD8β flanked by P2A sites, CD8α flanked by P2A sites, followed by the TRB and TRA alleles as previously described is generated. CD4 and CD8 T cells expressing CD8α and CD8β are evaluated using the same assays described above.

Figure 11B:
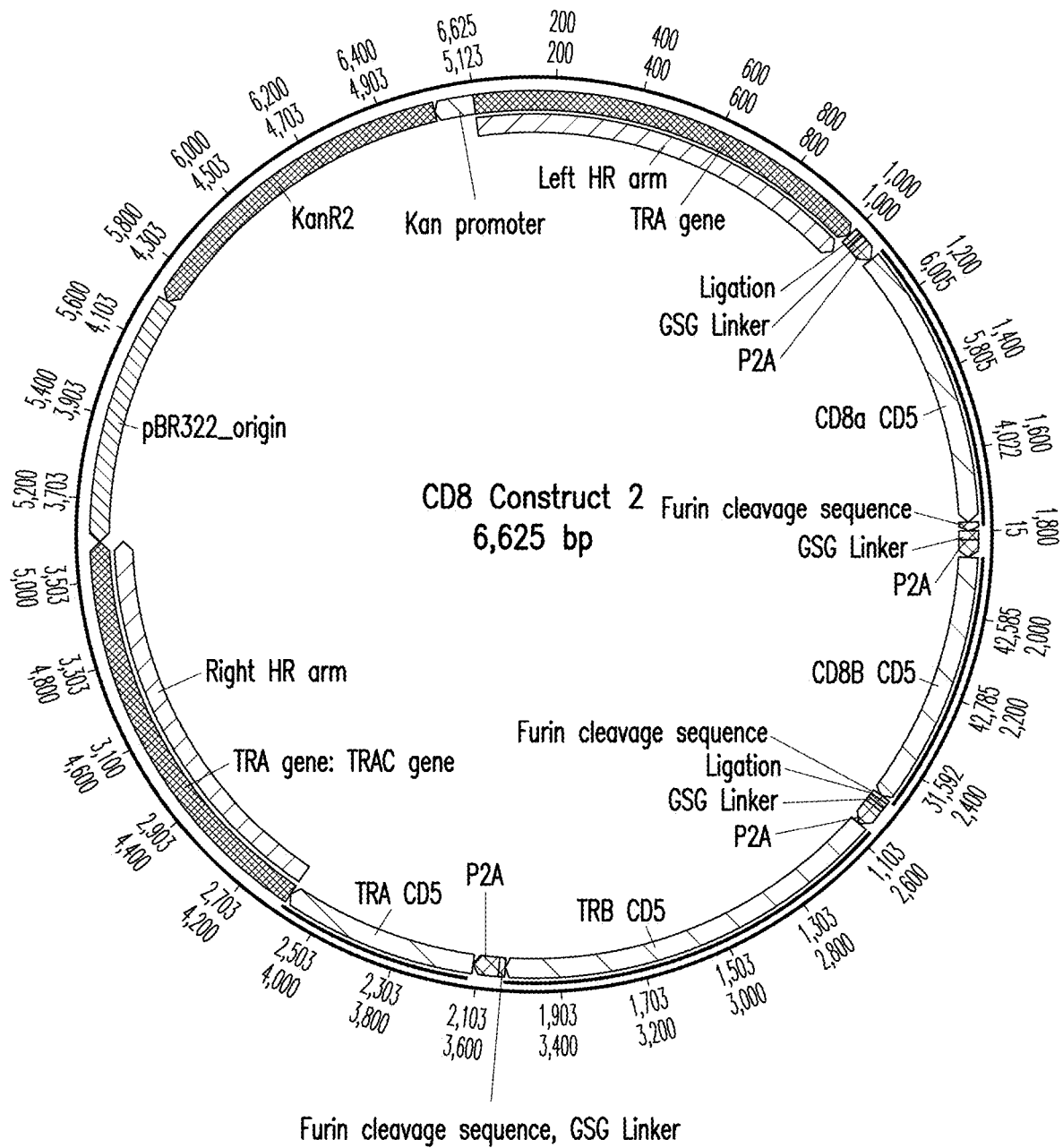

An exemplary expression construct with the CD8α and CD8 β sequences is shown in FIG. 11B.

CD8β expression was also assessed in the edited CD4 T cells. NeoTCR CD4 T cells expressing the CD8α and CD8β transgenes proliferated in response to lower concentrations of cognate comPACT than CD4 T cells expressing CD8α transgene alone. NeoTCR CD4 T cells expressing the CD8α and CD8β transgenes also produced effector cytokines in response to lower concentrations of cognate comPACT than neoTCR CD4 T cells expressing the CD8α transgene alone. And neoTCR CD4 T cells expressing the CD8α and CD8β transgenes killed a greater fraction of target cells presenting cognate peptide than neoTCR CD4 T cells expressing CD8α transgene alone.

Example 4. Generation of Chimeric CD8α and CD8β Constructs and CD8 Products 3 and 4

Figure 11C:
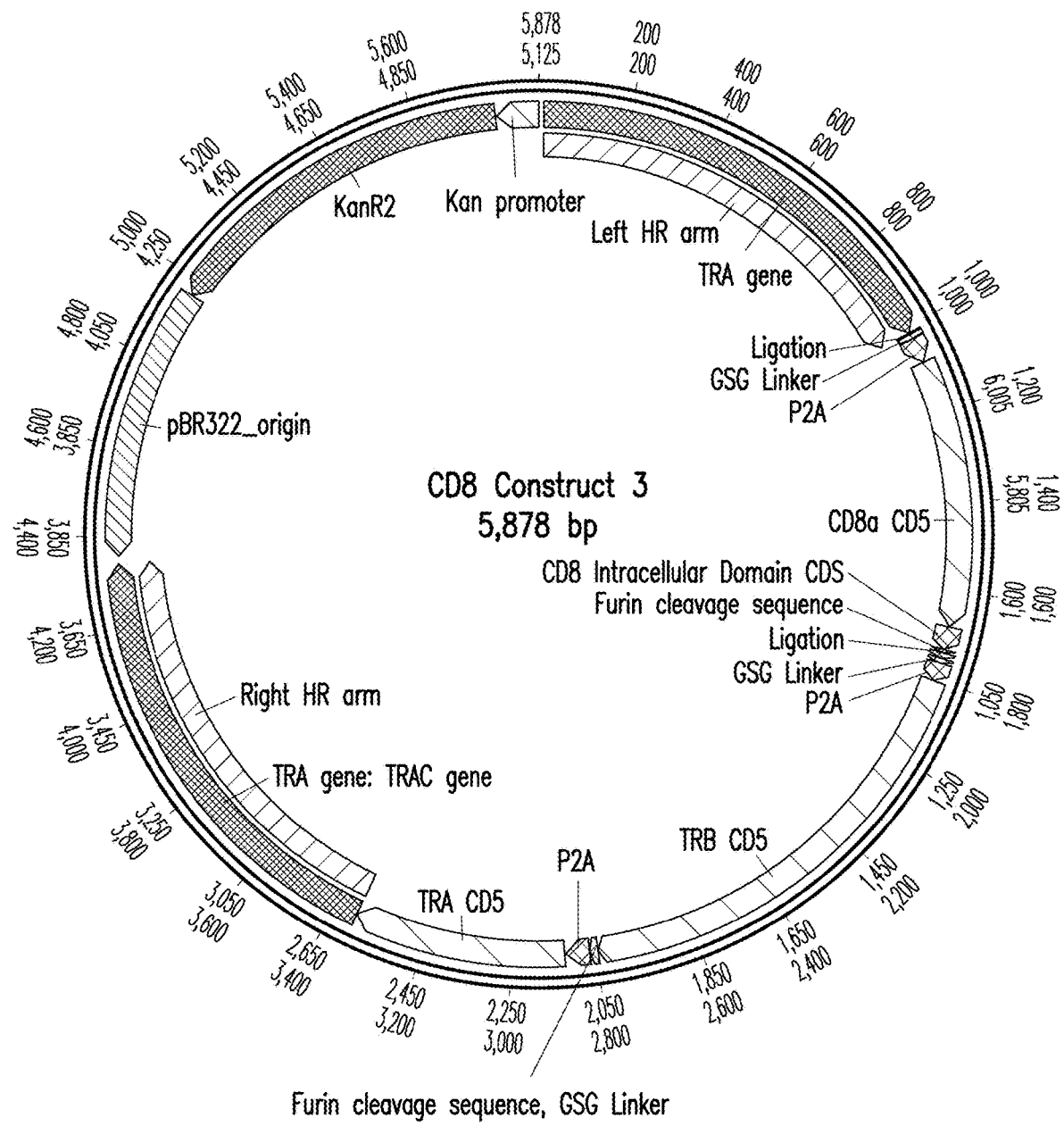

To ensure efficient editing of the T cells and expression of the neoTCR, chimeric proteins made up of the coding sequences for the extracellular and transmembrane domains of CD8α linked to the intracellular domain of CD8β were generated. An exemplary expression construct with the extracellular and transmembrane domains of CD8α linked to the intracellular domain of CD8β sequences is (i.e., a CD8 Product 3) shown in FIG. 11C.

Figure 11D:
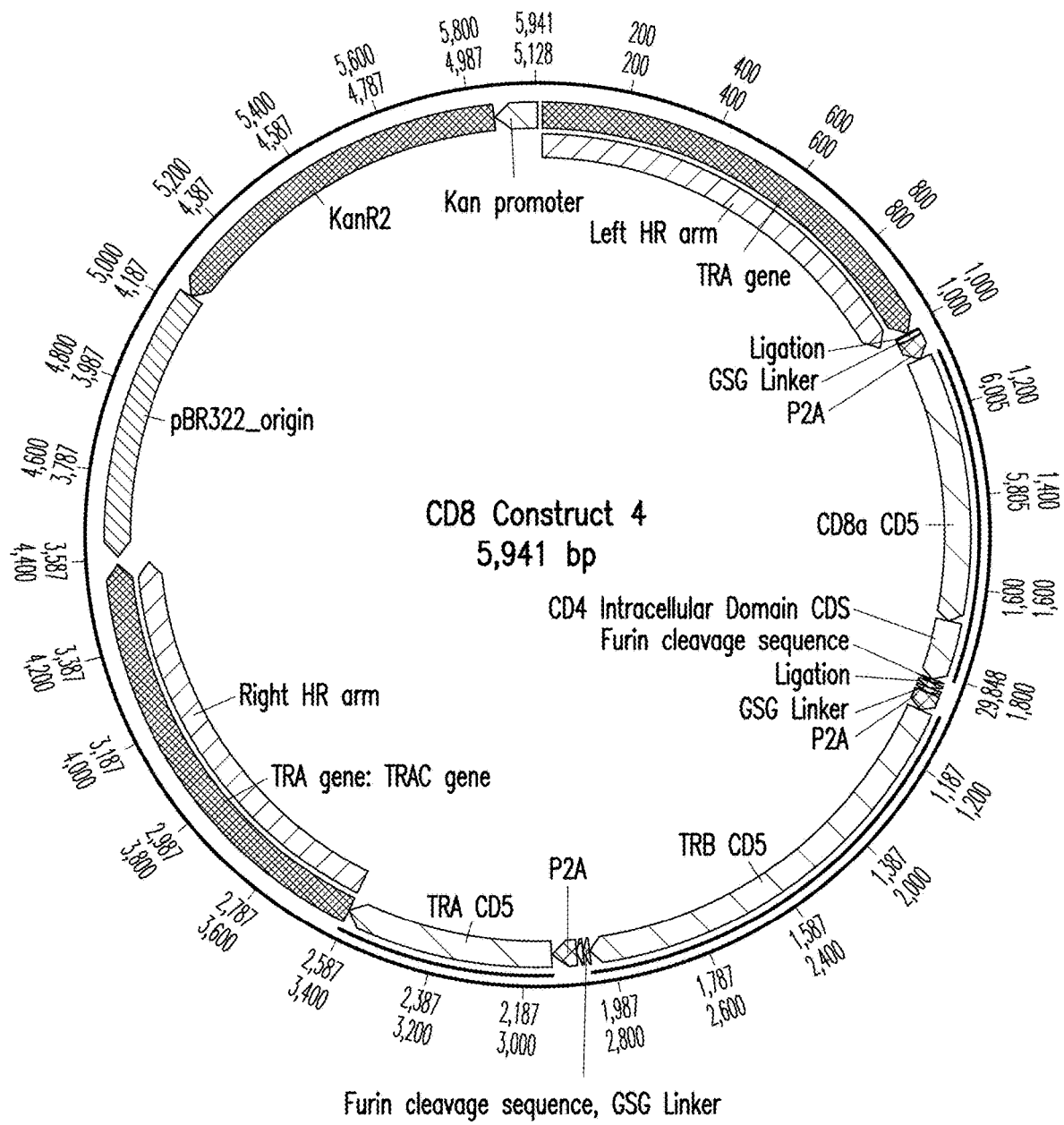
Figure 12:
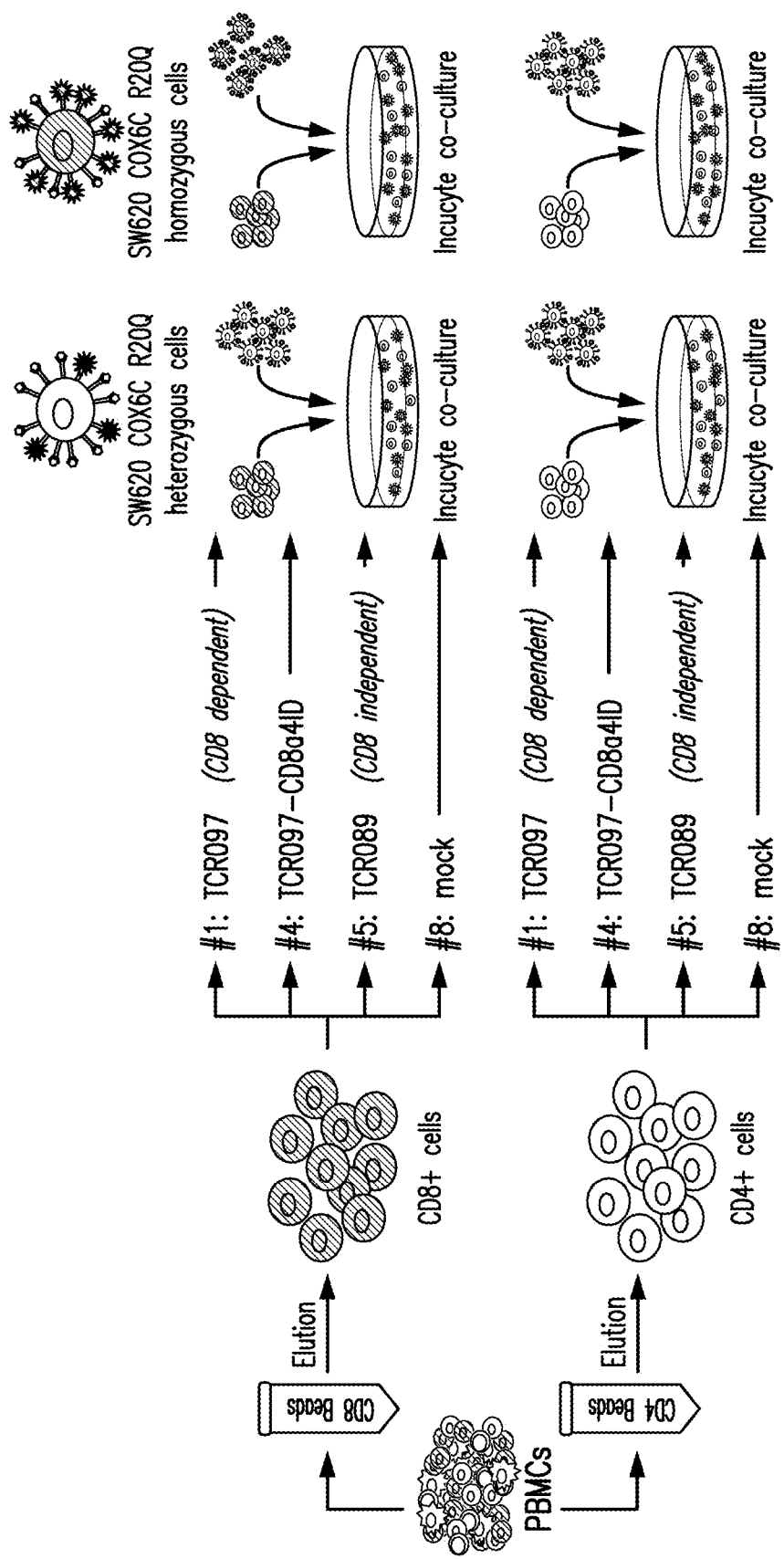
FIG. 12.

Furthermore, the intracellular domain of CD4 has an even higher affinity for LCK than CD8 (Irie et al., 1998). Therefore, a second chimeric protein was generated containing the coding sequences for the extracellular and transmembrane domains of CD8α linked to the intracellular domain of CD4. An exemplary expression construct with the extracellular and transmembrane domains of CD8α linked to the intracellular domain of CD4 sequences (i.e., a CD8 Product 4) is shown in FIG. 11D.

CD4 and CD8 T cells expressing the CD8 Products 3 and 4 were evaluated using the same assays described above.

NeoTCR CD4 T cells expressing the CD8α-CD8β-ID transgene proliferated in response to lower concentrations of cognate comPACT than CD4 T cells expressing CD8α transgene alone. NeoTCR CD4 T cells expressing the CD8α-CD8β-ID transgene produced effector cytokines in response to lower concentrations of cognate comPACT than neoTCR CD4 T cells expressing the CD8α transgene alone. NeoTCR CD4 T cells expressing the CD8α-CD8β-ID transgene killed a greater fraction of target cells presenting cognate peptide than neoTCR CD4 T cells expressing CD8α-CD8β-ID transgene.

NeoTCR CD4 T cells expressing the CD8α-CD4-ID transgene proliferated in response to lower concentrations of cognate comPACT than neoTCR CD4 T cells expressing CD8α-CD8β-ID transgene. NeoTCR CD4 T cells expressing the CD8α-CD4 transgene produced effector cytokines in response to lower concentrations of cognate comPACT than neoTCR CD4 T cells expressing the CD8α-CD8β-ID transgene.

NeoTCR CD4 T cells expressing the CD8α-CD4-ID transgene killed a greater fraction of target cells presenting cognate peptide than neoTCR CD4 T cells expressing CD8α-CD8β-ID transgene. NeoTCR CD8 T cells expressing the CD8α-CD4-ID transgene proliferated in response to lower concentrations of cognate comPACT than neoTCR CD8 T cells lacking the transgene. NeoTCR CD8 T cells expressing the CD8α-CD4 transgene produced effector cytokines in response to lower concentrations of cognate comPACT than neoTCR CD8 T cells lacking the transgene. NeoTCR CD8 T cells expressing the CD8α-CD4-ID transgene killed a greater fraction of target cells presenting cognate peptide than neoTCR CD8 T cells lacking the transgene.

Example 5. CD8 Products have Increased Sensitivity to neoE-HLA Target Recognition and Trigger Pro-Inflammatory and Cytotoxic Function MHC-I neoTCRs were cloned from neoE-specific T cells captured from the blood of a patient with colorectal cancer. Healthy donor CD8 and CD4 T cells were precision genome engineered to express the cloned MHC-I neoTCRs alone or to include engineering of ectopic CD8 co-receptors in the gene-edited T cells. Flow cytometric analysis was used to evaluate surface expression of neoTCRs and ectopic CD8 co-receptors (i.e., the CD8 and CD4 components of the CD8 Constructs 1-4), respectively. Rescue of neoTCR binding among CD4 T cells for lower affinity, CD8-dependent neoTCRs was observed. Importantly, in response to stimulation with cognate antigen, CD107a and intracellular IFNγ staining revealed 10-100-fold increases in the sensitivity of MHC-I neoTCR-induced effector functions by CD4 T cells, with no effect on specificity. No change in functionality or sensitivity was seen on CD8 T cells by the expression of additional CD8 co-receptor.

These results demonstrate that simultaneous precision genome engineering of the CD8 co-receptor together with CD8-dependent MHC-I neoTCRs into CD4 T cells (i.e., CD8 Products 1-4) significantly increases their sensitivity to neoE-HLA target recognition as well as triggering pro-inflammatory and cytotoxic function, yet without compromising antigen-specificity.

Example 6. Generation and Design of CD8 Products that have Varying LCK Affinities As described herein, four classes of CD8 Products were generated:
1. CD8α homodimer (CD8 Construct 1)
2. CD8α-P2A-CD8β (CD8 Construct 2)
3. CD8α with CD8β intracellular domain (CD8 Construct 3)
4. CD8α homodimer with CD4 intracellular domain (CD8 Construct 4)

Figure 10:
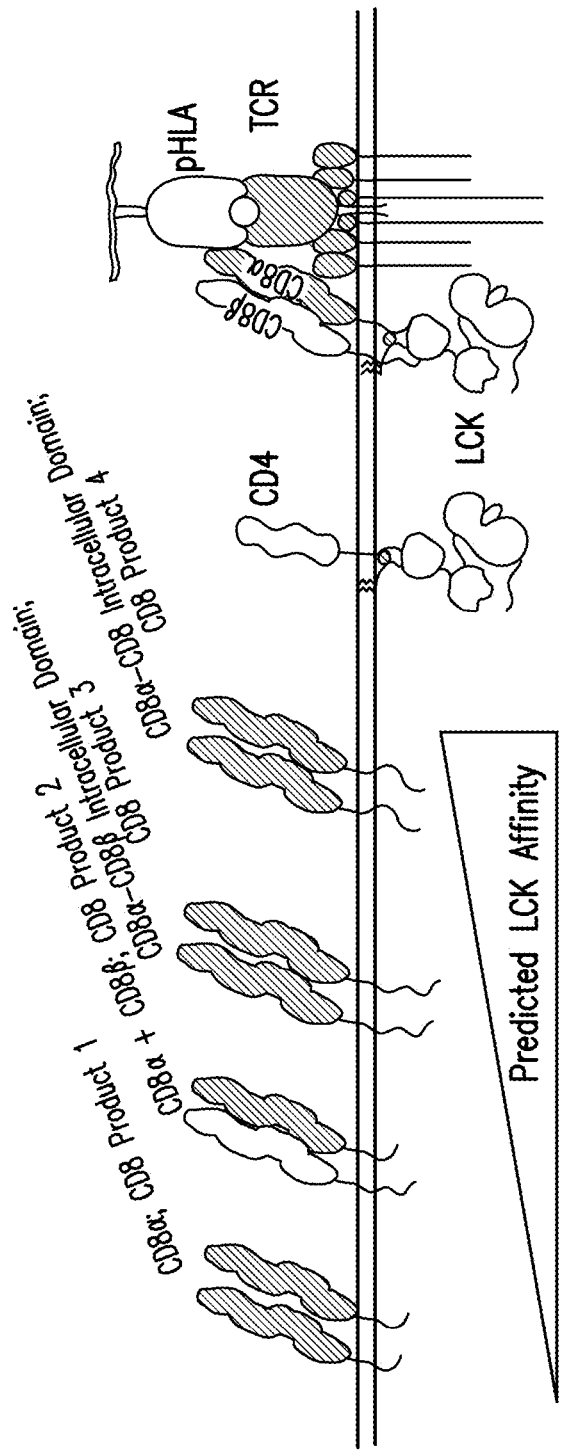
FIG. 10.

As shown in FIG. 10, these CD8 Constructs and resulting CD8 Products were designed to allow for varying degrees of LCK affinity. As predicted, CD8 Product 1 was shown to have the lowest LCK affinity, followed by CD8 Product 2, CD8 Product 3, and CD8 Product 4 (in that order with CD8 Product 4 having the highest LCK affinity.

Based on the high affinity of CD8 Product 4, this product was used in cell killing assays to exemplify the increased cell killing ability of CD8 Products 1-4 compared to NeoTCR Products.

Figure 13A:
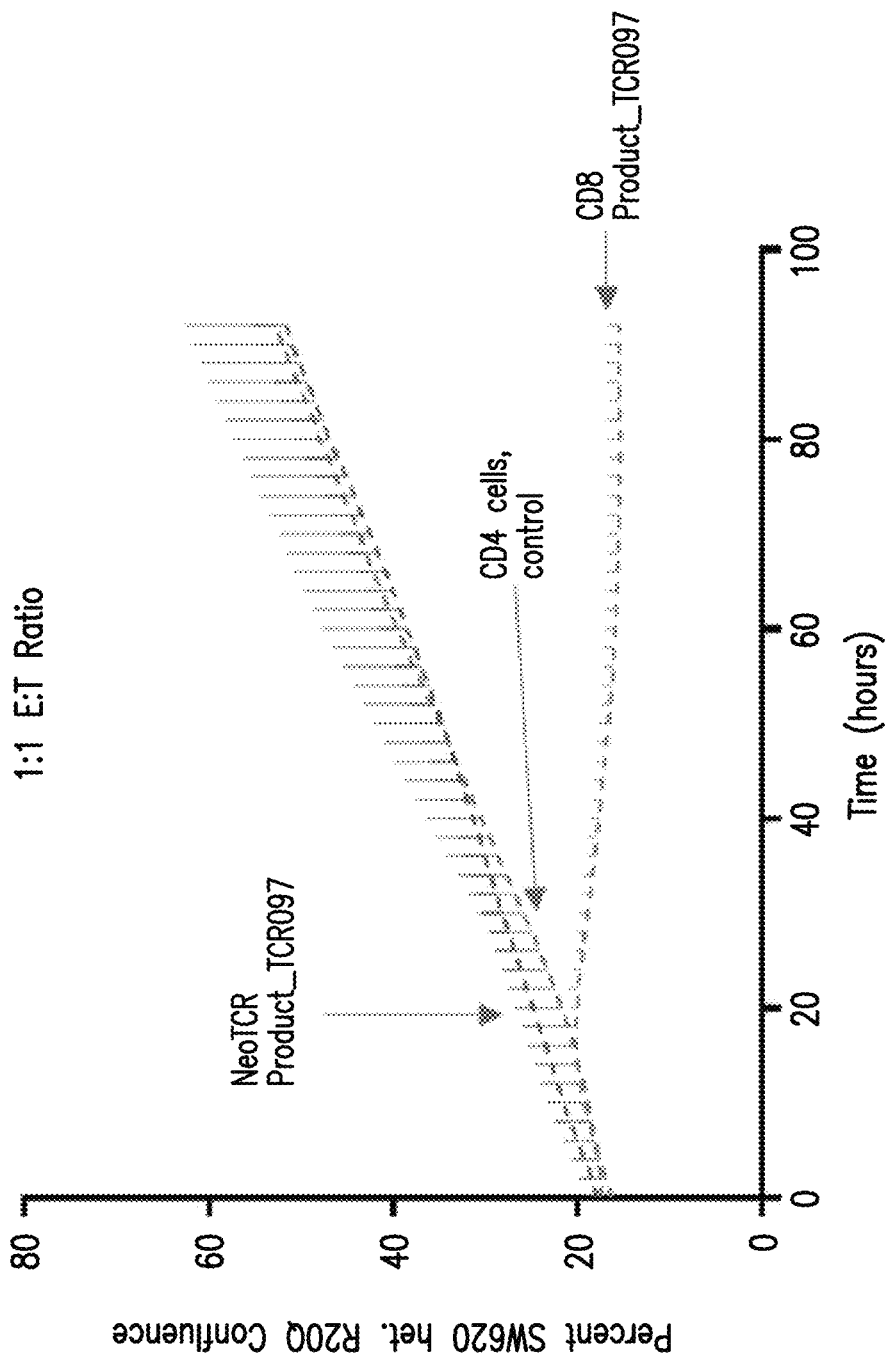
FIGS. 13A and 13B.
Figure 13B:
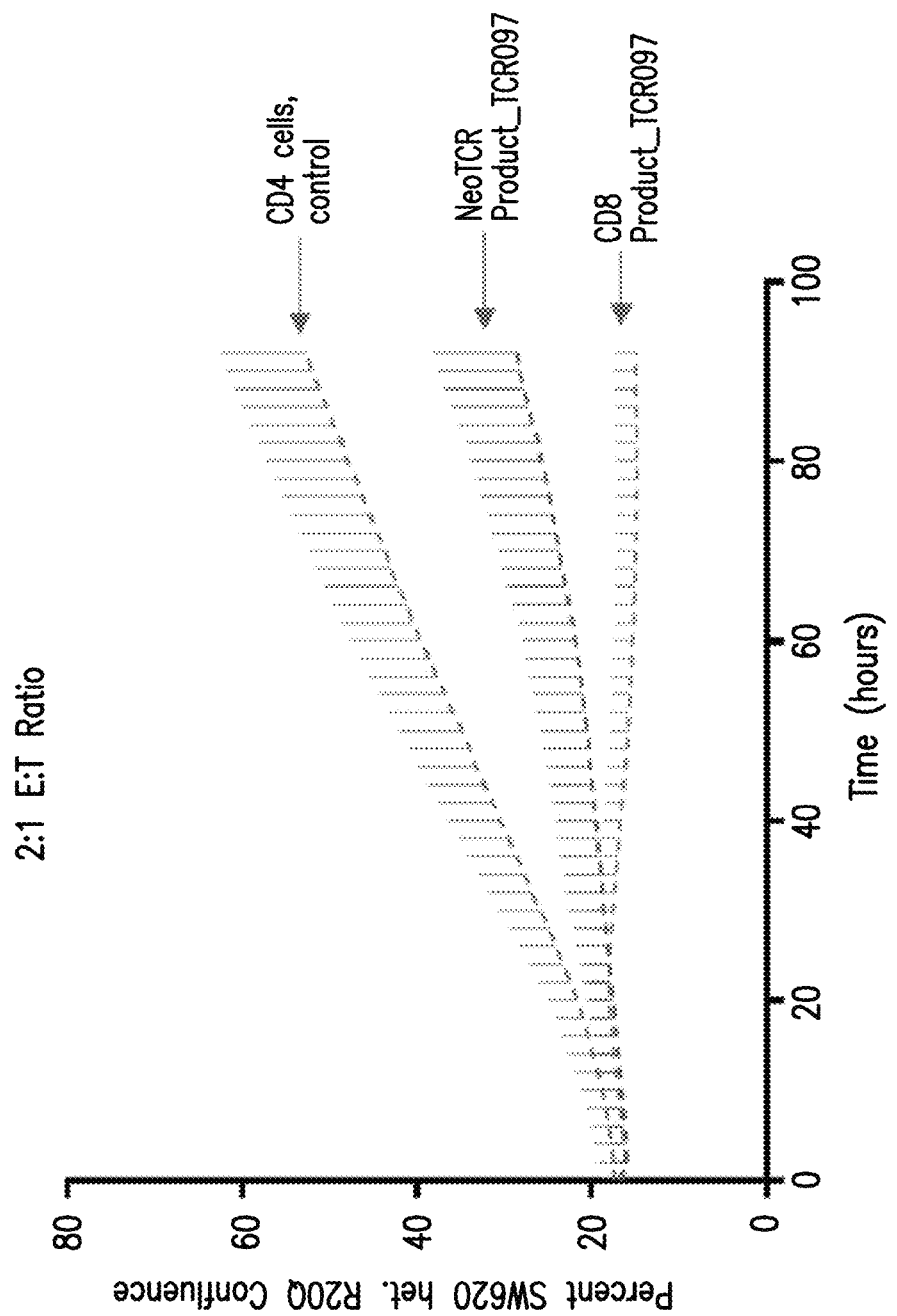
Figure 14:
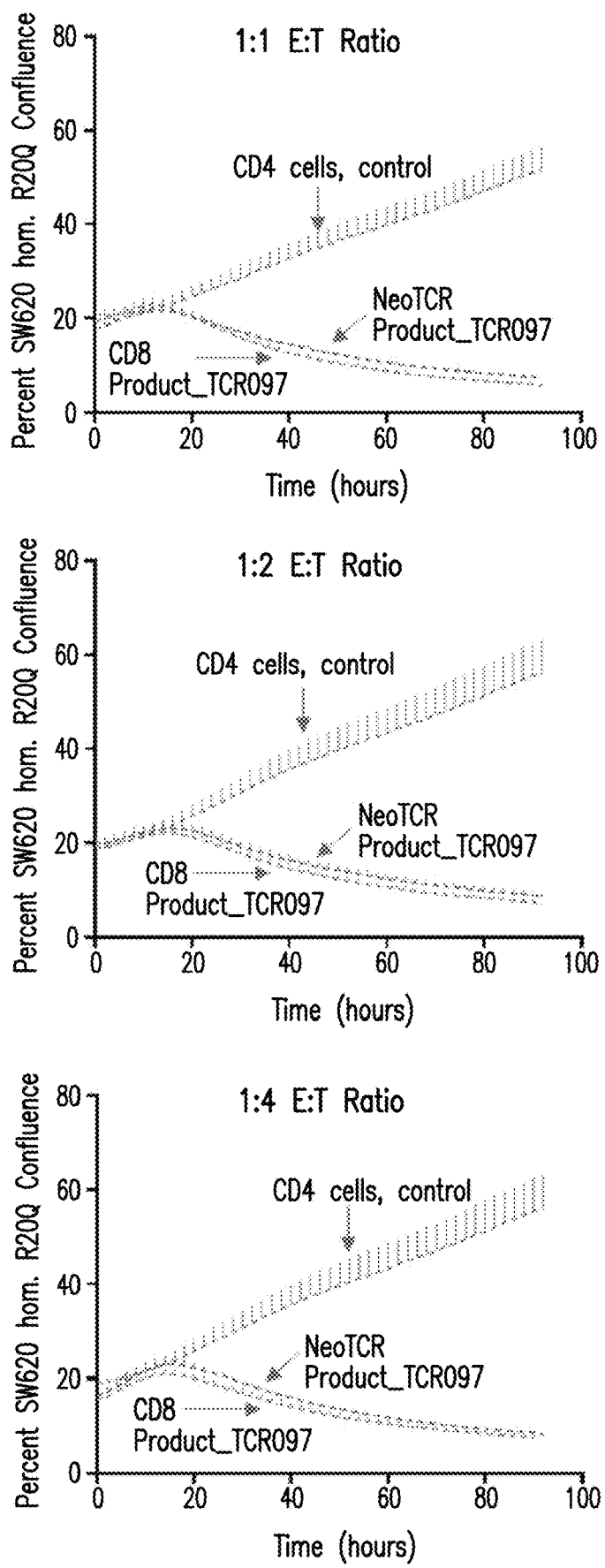
FIG. 14.

CD4+ T cells were engineered as described herein to express the CD8 Product 4 (with TCR097 as the NeoTCR in the product) described in FIGS. 2D and 3D. SW620 cell lines that were engineered to heterologously express the R20Q mutation (the cognate antigen to TCR097). The CD8 Product 4 expressing NeoTCR097 was combined with the SW620 heterologous cells. As shown in FIGS. 13A and 13B, the CD8 Product 4 provided substantially better killing of the cognate antigen expressing SW620 cells than the NeoTCR Product also expressing the TCR097. The experiment shown in FIG. 13A was done with an E:T ratio of 1:1 and as shown in the graph, the NeoTCR Product expressing TCR097 did not show any efficacy at killing of the cognate antigen expressing SW620 cells. The experiment shown in FIG. 13B was done with an E:T ratio of 2:1 and while the NeoTCR Product expressing TCR097 showed some ability to kill the cognate antigen expressing SW620 cells, it was clear from the experiment that the CD8 Product 4 expressing the TCR097 had superior efficacy.

The same engineered CD4+ cells that were used in the experiment above with data provided in FIGS. 13A and 13B, were also tested on SW620 cell lines that were engineered to homozygously express the R20Q mutation. In this experiment, the high expression of the cognate antigen was able to compensate for the low affinity NeoTCR097 and both the NeoTCR Product expressing TCR097 and the CD8 Product 4 expressing the TCR097 showed efficacy at killing the SW620 cells. However, the high expression of the cognate antigen in the homozygous SW620 cells is not physiologically relevant and this experiment serves to highlight the ability to rescue NeoTCR Products with low affinity TCRs that cannot effectively engage with and kill tumor cells by further engineering them to also include a CD8α homodimer with CD4 intracellular domain (i.e., a CD8 Product 4).

As a final control and proof of the efficacy of the CD8 Products, CD8 T cells were also transfected to express the NeoTCR097 and a CD8α homodimer with CD4 intracellular domain (i.e., a CD8 Product 4 using CD8 T cells instead of CD4 T cells). As shown in the top graphs in FIGS. 15A and 15B, the CD8 Product 4 provided substantially better killing of the SW620 cells than the NeoTCR Product when the products were made from CD4 T cells. However, when the CD8 Product 4 and NeoTCR Product were made from CD8 T cells (the bottom graphs in FIGS. 15A and 15B) the ability of the NeoTCR Product was rescued because of the endogenous CD8 expression in the CD8 T cells. While no overlay of the graphs is shown, it is also of note that the CD8 Product 4 in CD4 T cells shown the top graphs in FIGS. 15A and 15B, appear to have better efficacy than the CD8 Product 4 in CD8 T cells in the bottom two graphs; suggesting a superior ability of the CD8 Products described herein to engage with the cognate antigens of tumor cells leading to tumor death and effective treatment of patients with cancer in need of treatment.

Figure 16:
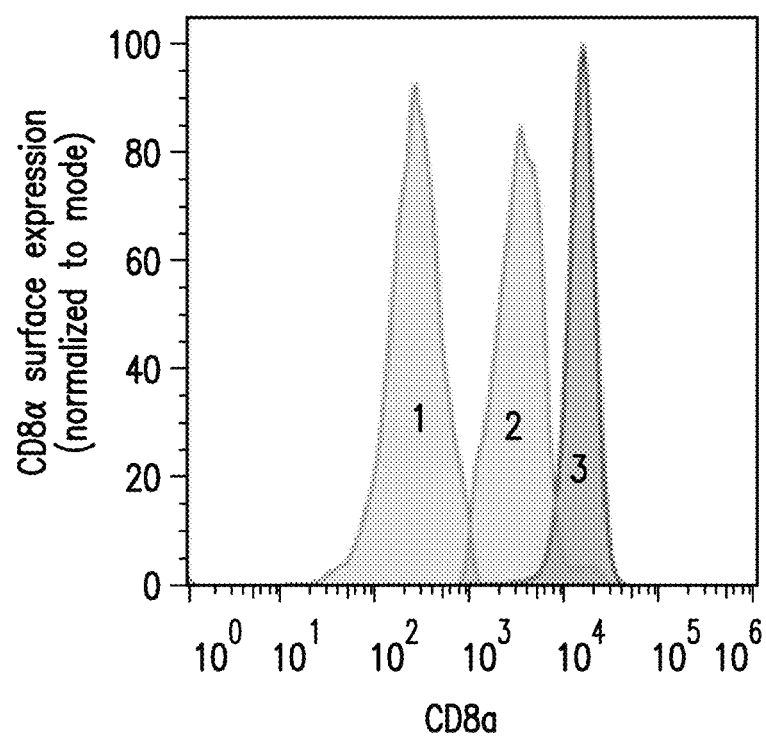
FIG. 16.

Example 6. CD8 Products have Increased CD4 T Cell Sensitivity while Maintaining NeoTCR Sensitivity In order to confirm that the CD8 Constructs expressed properly, CD8 Products 1, 2, 3, and 4 were tested to determine surface expression of CD8α. It was shown that each of CD8 Products 1, 2, 3, and 4 exhibited normal CD8α surface expression. Representative data from CD8 Product 4 is shown in FIG. 16.

Figures 17A, 17B:
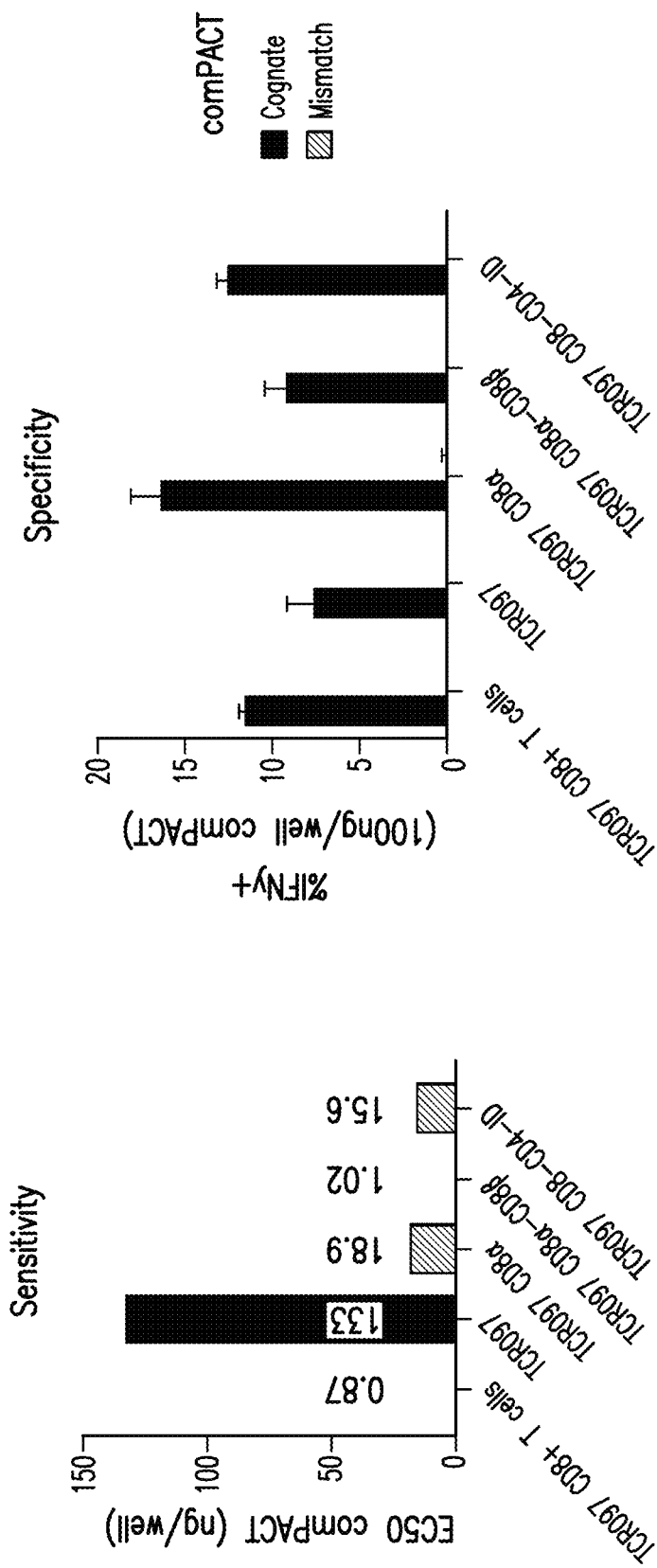
FIGS. 17A and 17B.
Figure 18:
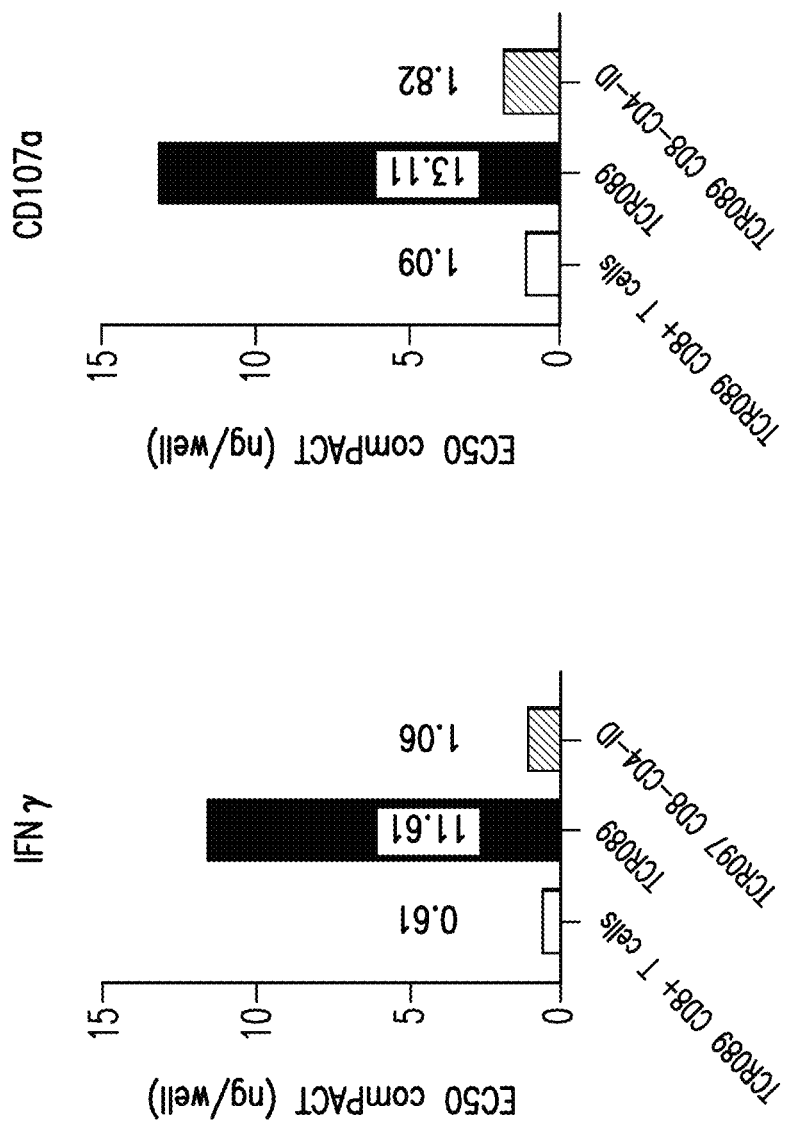
FIG. 18.

It was also important to determine how the CD8 Constructs affected CD4 T cell sensitivity and specificity for the cognate antigen of the expressed NeoTCR in the CD8 Products. Sensitivity experiments were performed and it was shown that CD8 Products 1-4 exhibited an increased CD4 T cell sensitivity (FIG. 17A). Specificity experiments were also performed on CD8 Products 1-4. CD8 Products 1, 2, 3, and 4 were made with NeoTCR097. Experiments were performed to test the CD8 Products 1, 2, 3, and 4 (expressing NeoTCR097) to assess the specificity of these products to the cognate antigen to NeoTCR097. As shown in FIG. 17B, CD8 Products 1, 2, 3, and 4 (expressing NeoTCR097) were specific for the cognate antigen to NeoTCR097 and showed no activity when exposed to a mismatched antigen. The specificity was determined by INFγ and CD107 production which are evidence of T cell activation. Thus, the CD8 Products described herein have an increased sensitivity to CD4 T cells and maintain their specificity to cognate antigen to the expressed NeoTCR compared to NeoTCR Products expressing the same NeoTCR.

Lastly, experiments were performed to investigate the impact the CD8 Constructs have on CD8-dependent and CD8-independent NeoTCRs. It was expected that CD8-dependent NeoTCRs would show an increased sensitivity to cognate antigen because the CD8 Cells would be engineered to express CD8α and that CD8-independent NeoTCRs would not show an increased sensitivity because of the independent nature of the NeoTCR. However, it was shown that NeoTCR Products 1, 2, 3, and 4 surprisingly increased the sensitivity of CD8-dependent (e.g., NeoTCR097) and CD8- independent (e.g., NeoTCR089) NeoTCRs. Accordingly, it was shown that the CD8 Constructs 1, 2, 3, and 4 can improve NeoTCR engagement and T cell killing of tumor cells with cognate NeoTCR antigens for all NeoTCRs regardless of whether they are CD8-dependent or CD8-independent.

While the present invention has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention.

All publications, patent applications, patents, and other references mentioned herein are incorporated by reference in their entirety. In case of conflict, the present specification, including definitions, will control. In addition, section headings, the materials, methods, and examples are illustrative only and not intended to be limiting.

What is claimed is:

1. A method of modifying a cell, the method comprising:
   a) introducing into the cell a non-viral homologous recombination (HR) template nucleic acid sequence, wherein the HR template comprises:
      i) first and second homology arms homologous to first and second target nucleic acid sequences;
      ii) a TCR gene sequence positioned between the first and second homology arms;
      iii) a CD8 gene sequence positioned between the first and the second homology arms, wherein the CD8 gene sequence encodes:
         1) a CD8α signal peptide, a CD8α extracellular domain, a CD8α transmembrane domain, and a CD8β intracellular domain; or
         2) a CD8α signal peptide, a CD8α extracellular domain, a CD8α transmembrane domain, and a CD4 intracellular domain; and
   b) recombining the HR template nucleic acid into an endogenous locus of the cell.

2. The method of claim 1, wherein the CD8 gene sequence encodes:
   a) a CD8α signal peptide set forth in SEQ ID NO:139, a CD8α extracellular domain set forth in SEQ ID NO: 140, a CD8α transmembrane domain set forth in SEQ ID NO: 141, and a CD8β intracellular domain set forth in SEQ ID NO: 147; or
   b) a CD8α signal peptide set forth in SEQ ID NO: 139, a CD8α extracellular domain set forth in SEQ ID NO: 140, a CD8α transmembrane domain set forth in SEQ ID NO: 141, and a CD4 intracellular domain set forth in SEQ ID NO: 148.

3. The method of claim 1, wherein the HR template comprises:
   a) a first 2A-coding sequence positioned upstream of the CD8 gene sequence, a second 2A-coding sequence positioned downstream of the CD8 gene sequence and upstream of the TCR gene sequence, and a third 2A-coding sequence positioned downstream of the TCR gene sequence, wherein the first, second, and third 2A-coding sequences code for the same amino acid sequence and are codon-diverged relative to each other;
   b) a sequence coding for the amino acid sequence Gly Ser Gly positioned immediately upstream of the first, second, and/or third 2A-coding sequences; and
   c) a sequence coding for a Furin cleavage site positioned upstream of the first, second, and/or third 2A-coding sequences.

4. The method of claim 1, wherein the HR template comprises a second TCR sequence positioned between the third 2A-coding sequence and the second homology arm.

5. The method of claim 4, wherein the HR template comprises:
   a) a sequence encoding a first signal sequence positioned immediately upstream the first TCR gene sequence; and
   b) a sequence encoding a second signal sequence positioned immediately upstream of the second TCR gene sequence.

6. The method of claim 1, wherein the first and second homology arms of the HR template are each from about 300 bases to about 2,000 bases in length.

7. The method of claim 1, wherein the exogenous TCR is a patient derived TCR.

8. The method of claim 1, wherein the introducing occurs via electroporation.

9. The method of claim 1, wherein the recombining comprises:
   a) cleavage of the endogenous locus by a Cas9/gRNA ribonucleoprotein nuclease; and
   b) recombination of the HR template nucleic acid sequence into the endogenous locus by homology directed repair.

10. The method of claim 1, further comprising culturing the cell in the presence of IL2, IL7, IL15, or a combination thereof.

11. The method of claim 1, wherein the CD8 gene sequence is encoded by a CD8 Construct 3, or a CD8 Construct 4.

* * * * *